US007241444B2

(12) United States Patent
Goetsch et al.

(10) Patent No.: US 7,241,444 B2
(45) Date of Patent: Jul. 10, 2007

(54) ANTI-IGF-IR ANTIBODIES AND USES THEREOF

(75) Inventors: Liliane Goetsch, Ayze (FR); Nathalie Corvaia, Saint Julien en Genevois (FR); Olivier Leger, Annemasse (FR); Alain Duflos, Labruguiere (FR); Jean-François Haeuw, Beaumont (FR); Alain Beck, Collonges-Sous-Salene (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 133 days.

(21) Appl. No.: 10/735,916

(22) Filed: Dec. 16, 2003

(65) Prior Publication Data

US 2005/0084906 A1 Apr. 21, 2005

Related U.S. Application Data

(63) Continuation-in-part of application No. PCT/FR03/00178, filed on Jan. 20, 2003.

(30) Foreign Application Priority Data

| Jan. 18, 2002 | (FR) | ................... 02 00653 |
| Jan. 18, 2002 | (FR) | ................... 02 00654 |
| May 7, 2002 | (FR) | ................... 02 05753 |
| Jul. 11, 2003 | (FR) | ................... 03 08538 |

(51) Int. Cl.
| *C07K 16/28* | (2006.01) |
| *C12P 21/08* | (2006.01) |
| *A61K 39/395* | (2006.01) |
| *A61K 39/00* | (2006.01) |
| *G01N 33/53* | (2006.01) |

(52) U.S. Cl. ............... 424/130.1; 424/133.1; 424/134.1; 424/135.1; 424/141.1; 424/143.1; 425/7.1; 425/810; 530/387.1; 530/387.3; 530/381.22; 530/391.3

(58) Field of Classification Search ............ 530/387.1, 530/387.3, 388.22, 391.3; 424/130.1, 133.1, 424/134.1, 135.1, 136.1, 143.1, 178.1; 435/810
See application file for complete search history.

(56) References Cited

U.S. PATENT DOCUMENTS

| 5,608,039 A | * | 3/1997 | Pastan et al. ............ 530/387.3 |
| 5,891,996 A | * | 4/1999 | Mateo de Acosta del Rio et al. ............ 530/387.3 |
| 5,935,821 A | * | 8/1999 | Chatterjee et al. ......... 435/69.6 |
| 6,068,841 A | * | 5/2000 | Seino et al. ............ 424/145.1 |
| 6,180,370 B1 | * | 1/2001 | Queen et al. ............ 435/69.6 |
| 6,235,883 B1 | * | 5/2001 | Jakobovits et al. ..... 530/388.22 |
| 6,300,064 B1 | * | 10/2001 | Knappik et al. ............... 435/6 |
| 6,342,219 B1 | * | 1/2002 | Thorpe et al. ............ 424/145.1 |

FOREIGN PATENT DOCUMENTS

| JP | 3018541 | 1/2000 |
| WO | WO 96/40210 A1 | 12/1996 |
| WO | WO 01/88138 A1 | 11/2001 |
| WO | WO 02/053596 A2 | 7/2002 |

OTHER PUBLICATIONS

Janway et al, p. 3:1-3:3, in Immunobiology, 1994.*
Traxler et al, J Pharm Belg 52(2): 88-96, 1997.*
Ciardiello et al, Clinical Cancer Research 5: 909-916, Apr. 1999.*
Baselga et al, Semin Oncol 26(4 suppl 12): 78-83, Aug. 1999, abstract only.*
Rodeck et al, J Cell Biochem 35(4): 315-20, Dec. 1987.*
Bartucci et al., "Differential Insulin-like Growth Factor I Receptor Signaling and Function in Estrogen Receptor (ER)-positive MCF-7 and ER-negative MDA-MB-231 Breast Cancer Cells", Cancer Research, Sep. 15, 2001, pp. 65747-6754, vol. 61.
Putz et al., "Epidermal Growth Factor (EGF) Receptor Blockade Inhibits the Action of EGF, Insulin-like Growth Factor I, and a Protein Kinase A Activator on the Mitogen-activated Protein Kinase Pathway in Prostate Cancer Cell Lines", Cancer Research, Jan. 1, 1999, pp. 227-233, vol. 59.
Coppola et al., "A Functional Insulin-Like Growth Factor I Receptor is Required for the Mitogenic and Transforming Activites of the Epidermal Growth Factor Receptor", Molecular and Cellular Biology, Jul. 1994, pp. 4588-4595, vol. 14, No. 7, American Society for Microbiology.
Cheatham et al., "Insulin Action and the Insulin Signaling Network", Endocrine Reviews, 1995, pp. 117-142, vol. 16, No. 2, The Endocrine Society.
Singer et al., "Optimal Humanization of 1B4, and Anti-CD18 Murine Monoclonal Antibody, is Achieved by Correct Choice of Human V-Region Framework Sequences", The Journal of Immunology, Apr. 1, 1993, pp. 2844-2857, vol. 150, No. 7, The American Association of Immunologists.

(Continued)

*Primary Examiner*—Christina Chan
*Assistant Examiner*—Phuong Huynh
(74) *Attorney, Agent, or Firm*—Buchanan, Ingersoll & Rooney, PC

(57) ABSTRACT

The present invention relates to novel antibodies capable of binding specifically to the human insulin-like growth factor I receptor IGF-IR and/or capable of specifically inhibiting the tyrosine kinase activity of said IGF-IR receptor, especially monoclonal antibodies of murine, chimeric and humanized origin, as well as the amino acid and nucleic acid sequences coding for these antibodies. The invention likewise comprises the use of these antibodies as a medicament for the prophylactic and/or therapeutic treatment of cancers overexpressing IGF-IR or any pathology connected with the overexpression of said receptor as well as in processes or kits for diagnosis of illnesses connected with the overexpression of the IGF-IR receptor. The invention finally comprises products and/or compositions comprising such antibodies in combination with anti-EGFR antibodies and/or compounds and/or anti-cancer agents or agents conjugated with toxins and their use for the prevention and/or the treatment of certain cancers.

17 Claims, 39 Drawing Sheets

OTHER PUBLICATIONS

Pastorino et al., "Doxorubicin-loaded Fab' Fragments of Anti-disialoganglioside Immunoliposomes Selectively Inhibit the Growth and Dissemination of Human Neuroblastoma in Nude Mice" Cancer Research, Jan. 1, 2003, pp. 86-92, vol. 63.

Glennie et al., "Preparation and Performance of Bispecific F(ab'γ)$_2$ Antibody Containing Thioether-Linked Fab'γ Fragments", The Journal of Immunology, Oct. 1, 1987, pp. 2367-2374, vol. 139, No. 7, The American Association of Immunologists.

Bebbington et al., "High-Level Expression of a Recombinant Antibody from Myeloma Cells using a Glutamine Synthetase Gene as an Amplifiable Selectable Marker", Bio/Technology, Feb. 1992, pp. 169-175, vol. 10.

Amit et al., "Three-Dimensional Structure of an Antigen-Antibody Complex at 2.8 Å Resolution", Science, Aug. 15, 1986, pp. 747-753, vol. 233.

Caton et al., "Identical D Region Sequences Expressed by Murine Monoclonal Antibodies Specific for a Human Tumor-Associated Antigen", The Journal of Immunology, Mar. 1, 1990, pp. 1965-1968, vol. 144, No. 5, The American Association of Immunologists.

Chothia et al., "Canonical Structures for the Hypervariable Regions of Immunoglobulins", J. Mol. Biol., 1987, pp. 901-917, vol. 196, Academic Press Limited.

Chothia et al., "Conformations of immunoglobulin hypervarible regions", Nature, Dec. 1989, pp. 877-883, vol. 342, 21/28.

Sharon, "Structural Characterization of Idiotapes by using Antibody Variants Generated by Site-Directed Mutagenesis", The Journal of Immunology, Jun. 15, 1990, pp. 4863-4869, vol. 144, No. 12, The American Association of Immunologists.

Connolly, et al., "Regulation of DUI45 Human Prostate Cancer Cell Proliferation by Insulin-Like Growth Factors and its Interaction with the Epidermal Growth Factor Autocrine Loop", The Prostate, 1994, pp. 167-175, vol. 24, Wiley-Liss, Inc.

Kabat, et al., "Identical V Region Amino Acid Sequences and Segments of Sequences in Antibodies of Different Specificities", The Journal of Immunology, Sep. 1, 1991, pp. 1709-1719, vol. 147, No. 5, The American Association of Immunologists.

Laguzza et al., "New Antitumor Monoclonal Antibody-Vinca Conjugates LY203725 and Related Compounds: Design, Preparation, and Representative in Vivo Activity", J. Med. Chem., 1989, pp. 548-555, vol. 32, American Chemical Society.

Fisher et al., "Endometrial Cancer in Tamoxifen—Treated Breast Cancer Patients: Findings from the National Surgical Adjuvant Breast and Bowel Project (NSABP) B-14", Journal of the National Cancer Institute, Apr. 6, 1994, pp. 527-537, vol. 86, No. 7.

Guvakova et al., "Tamoxifen Interferes witht he Insulin-like Growth Factor I Receptor (IGF-IR) Signaling Pathway in Breast Cancer Cells", Cancer Research, Jul. 1, 1997, pp. 2606-2610, vol. 57.

Forbes, "The Control of Breast Cancer: The Role of Tamoxifen", Seminars in Oncology, Feb. 1997, pp. SI-5-SI-19, vol. 24, No. 1, Suppl 1.

Kullberg et al., "Tumor-Cell Targeted Epidermal Growth Factor Liposomes Loaded with Boronated Acridine: Uptake and Processing", Pharmaceutical Research, Feb. 2003, pp. 229-236, vol. 20, No. 2, Plenum Publishing Corporation.

Suresh et al., "[17] Bispecific Monoclonal Antibodies from Hybrid Hybridomas", Methods in Enzymology, 1986, pp. 210-228, vol. 121, Academic Press, Inc.

Monfar et al., "Activation of pp70/85 S6 Kinases in Interluken-2-Responsive Lymphoid Cells is Mediated by Phosphatidylinositol 3-Kinase and Inhibited by Cyclic AMP", Molecular and Cellular Biology, Jan. 1995, pp. 326-337, vol. 15, No. 1, American Society for Microbiology.

Yamada et al., "Role of the Transmembrane Domain and Flanking Amino Acids in Internalization and Down-Regulation of the Insulin Receptor", The Journal of Biological Chemistry, Feb. 17, 1995, pp. 3115-3122, vol. 270, No. 7, The American Society for Biochemistry and Molecular Biology, Inc.

Ciardiello, "Epidermal Growth Factor Receptor Tyrosine Kinase Inhibitors as Anticancer Agents", Drugs, 2000, pp. 25-32, 60 Suppl. 1, Adis International Limited.

Petersen et al., "The Human Immune Response to KS1/4-desacetylvinblastine (LY256787) and KS1/4-desacetylvinblastine hydrazide (LY203728) in single and multiple dose clinical studies", Cancer Research, 1991, pp. 2286-2290, vol. 51, Issue 9, American Association for Cancer Research (Abstract only).

Laviola et al., "The Adapter Protein Grb10 Associates Preferentially with the Insulin Receptor as Compared with the IGF-I Receptor in Mouse Fibroblasts", J. Clin. Invest., Mar. 1997, pp. 830-837, vol. 99, No. 5, The American Society for Clinical Investigation, Inc.

Masquelier et al., "Amino Acid and Depeptide Derivatives of Daunorubicin. 1. Synthesis, Physiocochemical Properties, and Lysosomal Digestion", J. Med. Chem., 1980, pp. 1166-1170, vol. 23, American Chemical Society.

Mariette et al., "Nucleotide Sequence Analysis of the $V_L$ and $V_H$ Domains of Five Human IgM Directed to Lamin B", Arthritis & Rheumatism, Sep. 1993, pp. 1315-1324, vol. 36, No. 9, American College of Rheumatology.

Hailey et al., "Neutralizing Anti-Insulin-like Growth Factor Receptor 1 Antibodies Inhibit Receptor Function and Induce Receptor Degradation in Tumor Cells," Molecular Cancer Therapeutics, Dec. 2002, pp. 1349-1353, vol. 1.

Krause-Berthier et al., "Histology and Sensitivity to Anticancer Drugs of Two Human Non-Small Cell Lung Carcinomas Implanted in the Pleural Cavity of Nude Mice", Clinical Cancer Research, Jan. 2000, pp. 297-304, vol. 6.

Schneck et al., "Disposition of murine monoclonal antibody vinca conjugate (KS1/4-DAVLB) in patients with adenocarcinomas", Clin Pharmacol Ther., Jan. 1990, pp. 36-41, vol. 47, No. 1.

Ojima et al., "Tumor-Specific Novel Taxoid-Monoclonal Antibody Conjugates", J. Med. Chem., 2002, pp. 5620-5623, vol. 45, American Chemical Society.

Sharon, "Structural correlates of high antibody affinity: Three engineered amino acid substitutions can increase the affinity of an anit-*p*-azophenylarsonate antibody 200-fold", Proc. Natl. Acad. Sci./Immunology, Jun. 1990, pp. 4814-4817, vol. 87.

Burrow et al., "Expression of Insulin-Like Growth Factor Receptor, IGF-1, and IGF-2 in Primary and Metastatic Osteosarcoma", Journal of Surgical Oncology, 1998, pp. 21-27, vol. 69, Wiley-Liss, Inc.

Petruzzi et al., "Prior Cocaine Exposure in Different Environments Affects the Behavioral Responses of Mouse Dams", Pharmacology Biochemistry and Behavior, 1997, pp. 541-547, vol. 56, No. 3, Elsevier Science Inc.

Myers et al., "Common and Distinct Elements in Insulin and PDGF Signaling", Annals New York Academy of Sciences, pp. 369-387.

Valentinis et al., "Growth and Differentiation Signals by the Insulin-like Growth Factor 1 Receptor in Hemopoietic Cells are Mediated through Different Pathways", The Journal of Biological Chemistry, Apr. 30, 1999, pp. 12423-12430, vol. 274, No. 18, The American Society for Biochemistry and Molecular Biology, Inc.

Salomon et al., "Epidermal growth factor-related peptides and their receptors in human malignancies", Critical Reviews in Oncology/Hermatology, 1995, pp. 283-232, vol. 19, Elsevier Science Ireland Ltd.

Lee et al., "Enhancement of Insulin-Like Growth Factor Signaling in Human Breast Cancer: Estrogen Regulation of Insulin Receptor Substrate-1 Expression in Vitro and in Vivo", Molecular Endocrinology, 1999, pp. 787-796, vol. 10, No. 5, The Endocrine Society.

Kuehne et al., "Syntheses of 20'-Deoxyvinblastine, 20'-Deoxyleurosidine, 20'-Deoxyvincovaline, 20'-*epi*-20'-Deoxyvincovaline, and 20'-Deoxyvincristine and its 20'-Epimer through Racemic and Enantioselectively Generated Intermediates. New Syntheses of *D/E-cis* and *trans*-Ψ-Vincadifformines and *D/E-cis* and -*trans*-20-*epi*-Ψ-Vincadifformines", J. Org. Chem., 1989, pp. 3407-3420, vol. 54, 1989 American Chemical Society.

Duflos et al., "Novel Aspects of Natural and Modified *Vinca* Alkaloids", Curr. Med. Chem. —Anti-Cancer Agents, 2002, pp. 55-70, vol. 2, Bentham Science Publishers Ltd.

Beech et al., "Insulin-like growth factor-I receptor antagonism results in increased cytotoxicity of breast cancer cells to doxorubicin and taxol", Oncology Reports, 2001, pp. 325-329, vol. 8.

Railo et al., "The Prognostic Value of Insulin-like Growth Factor-I in Breast Cancer Patients. Results of a Follow-up Study on 126 Patients", European Journal of Cancer, 1994, pp. 307-311, vol. 30A, No. 3, Elsevier Science Ltd.

Wraight et al., "Reversal of epidermal hyperproliferation in psoriasis by insulin-like growth factor I receptor antisense oligonucleotides", Nature Biotechnology, May 2000, pp. 521-526, vol. 18.

Harding et al., "Immunogencity and pharmacokinetic attributes of poly(ethyleneglycol)-grafter immunoliposomes", Biochimica et Biophysica Acta, 1997, pp. 181-192, vol. 1327, Elsevier Science B.V.

Pietrzkowski et al., "Constitutive Expression of Insulin-like Growth Factor 1 and Insulin-like Growth Factor 1 Receptor Abrogates All Requirements for Exogenouse Growth Factors", Cell Growth & Differentiaton, Apr. 1992, pp. 199-205, vol. 3.

Zenni et al., "*Streptococcus pneumoniae* colonization in the young child: Association with otitis media and resistance to penicillin", The Journal of Pediatrics, Oct. 1995, pp. 533-537, Mosby-Year Books, Inc.

Jones et al., "Rapid PCR-Cloning of Full-Length Mouse Immunoglobulin Variable Regions", Bio/Technology, Jan. 1991, pp. 88-89, vol. 9.

Alessi et al., "Characterization of a 3-phosphoinositide-dependant protein kinase which phosphorylates and activates protein kinase Bα", Current Biology, Mar. 19, 1997, pp. 261-269, vol. 7, No. 4, Current Biology, Ltd.

Alessi et al., "3-Phosphoinositide-dependant protein kinase-1 (PDK1): structural and functional homology with the *Drosophilia* DSTPK61 kinase", Current Biology, Sep. 18, 1997, pp. 776-789, vol. 7, No. 10, Current Biology, Ltd.

Cavestri et al., "Access to rehavilitation facilities in an unselected hospital population affected by acute stroke", Ital. J. Neurol. Sci., Oct. 1996, pp. 9-16, vol. 18.

Sell et al., "Effect of a Null Mutation of the Insulin-Like Growth Factor I Receptor Gene on Growth and Transformation of Mouse Embryo Fibroblasts", Molecular and Cellular Biology, Jun. 1994, pp. 3604-3612, vol. 14, No. 6.

Sell et al., "Simian virus 40 large tumor antigen is unable to transform mouse embryonic fibroblasts lacking type 1 insulin-like growth factor receptor", Proc. Natl. Acad. Sci. USA/Cell Biology, Dec. 1993, pp. 11217-11221, vol. 90.

Sachdev et al., "A Chimeric Humanized Single-Chain Antibody against the Type I Insulin-like Growth Factor (IGF) Receptor Renders Breast Cancer Cells Refractory to the Mitogenic Effects of IGF-I", Cancer Research, Feb. 1, 2003, pp. 627-635, vol. 53.

Staerz et al., "Hybrid hybridoma producing a bispecific monoclonal antibody that can focus effector T-cell activity", Proc. Natl. Acad. Sci. USA/Immunology, Mar. 1986, pp. 1453-1457, vol. 83.

Morrione et al., "Failure of the Bovine Papillomavirus to Transform Mouse Embryo Fibroblasts with a Targeted Disruption of the Insulin-Like Growth Factor I Receptor Genes", Journal of Virology, Sep. 1995, pp. 5300-5303, vol. 69, No. 9, American Society for Microbiology.

Mountain et al., "Engineering Antibodies for Therapy", Biotechnology and Genetic Engineering Reviews, Dec. 1992, pp. 1-142, vol. 10, Intercept Ltd., UK.

Smith et al., "Comparison of Biosequences", Advances in Applied Mathematics, 1981, pp. 482-489, vol. 2, Academic Press, Inc.

Needleman et al., "A General Method Applicable to the Search for Similarities in the Amino Acid Sequence of Two Proteins", J. Mol. Biol. 1970, pp. 443-453, vol. 48.

Carter, "Improving The Efficacy of Antibody-Based Cancer Therapies", Nature Reviews, Nov. 2001, pp. 118-129, vol. 1.

Pearson et al., "Improved tools for biological sequence comparison", Proc. Natl. Acad. Sci. USA, Apr. 1988, pp. 2444-2448, vol. 85.

Herbst et al., "Epidermal Growth Factor Receptors as a Target for Cancer Treatment: The Emerging Role of IMC-C225 in the Treatment of Lung and Head and Neck Cancers", Seminars in Oncology, Feb. 2002, pp. 27-36, vol. 29, No. 1, Suppl. 1, Elsevier Science (USA).

Benson et al., "Information Disclosure, Subject Understanding, and Informed Consent in Psychiatric Research", Law and Human Behavior, 1988, pp. 455-475, vol. 12, No. 4, Plenium Publishing Corporation.

Benson et al., "Trends in the Social Control of Medical and Psychiatric Research", pp. 1-47.

Cirulli et al., "Sexual segregation in infant mice: behavioral and neuroendocrine response to *d*-amphetamine administration", Psychopharmacology, 1997, pp. 140-152, vol. 134, Springer-Verlag.

Arteaga et al., "Blockade of the Type I Somatomedin Receptor Inhibits Growth of Human Breast Cancer Cells in Athymic Mice", J. Clin. Invest., Nov. 1989, pp. 1418-1423, vol. 84, The American Society for Clinical Investigation, Inc.

Holliger et al., "Engineering antibodies for the clinic", Cancer and Metastasis Reviews, 2000, pp. 411-419, vol. 18, Kluwer Academic Publishers, Netherlands.

King et al., "Heath Teaching for People with Disabilities", Home Healthcare Nurse, 1995, pp. 52-58, vol. 13, No. 6, Lippincott-Raven Publishers.

Grothey et al., "The role of Insulin-Like Growth Factor I and its receptors in cell growth, transformation, apoptosis, and chemoresistance in solid tumors", J. Cancer Res. Clin. Oncol., 1999, pp. 166-173, vol. 125, Springer-Verlag.

Garnett, "Targeted drug conjugates: principles and progress", Advanced Drug Delivery Reviews, 2001, pp. 171-216, vol. 53, Elsevier Science B.V.

Roth et al., "Electroconvulsive Therapy in a Patient with Mania, Parkinsonism, and Tardive Dyskinesia", Convulsive Therapy, 1988, pp. 92-97, vol. No. 1, Raven Press, Ltd, New York.

Pagani et al., "The Management of Tetralogy of Fallot with Pulmonary Atresia and Diminutive Pulmonary Arteries", The Journal of Thoracic and Cardiovascular Surgery, 1999, pp. 1521-1533, vol. 110, No. 5, Mosby-Year Book, Inc.

Cheatham et al., A Meta-Analysis of Selective *Versus* Routine Nasogastric Decompression After Elective Laparotomy, Annals of Surgery, 1995, pp. 469-478, vol. 221, No. 5, J. B. Lippincott Company.

Tatusova et al., "BLAST 2 Sequences, a new tool for comparing protein and nucleotide sequences", FEMS Microbiology Letters, 1999, pp. 247-250, vol. 174, Elsevier Science B.V.

Park et al., "Generation and Characterization of a novel tetravalent bispecific antibody that binds to hepatitis B virus surface antigens", Molecular Immunology, 2001, pp. 1123-1130, vol. 37, Elsevier Science Ltd.

Ammirati et al., "The Endolymphatic Sac: Microsurgical Topographic Anatomy", Neurosurgery, Feb. 1995, pp. 416-419, vol. 36, No. 2.

Surmacz et al., "Type I Insulin-Like Growth Factor Receptor Function in Breast Cancer", Breast Cancer Research and Treatment, 1998, pp. 225-267, vol. 47, Kluwer Academic Publishers, Netherlands.

Hakam et al., "Expression of Insulin-Like Growth Factor 1 Receptor in Human Colorectal Cancer", Human Pathology, 1999, pp. 1128-1133, vol. 30, No. 10, W.B. Saunders Company.

Hurwitz et al., "Inhibition of tumor growth by poly(ethylene glycol) derivatives of anti-ErbB2 antibodies", Cancer Immunol Immunother, 2000, pp. 226-234, vol. 49, Springer-Verlag.

Lu et al., "Insulin-Like Growth Factor I Receptor Signaling and Resistance to Trastuzumab (Herceptin)", Journal of the National Cancer Institute, Dec. 19, 2001, pp. 1852-1857, vol. 93, No. 24, Oxford University Press.

Li et al., "Single-chain antibodies against human Insulin-Like Growth Factor I receptor: expression, purification, and effect on tumor growth", Cancer Immunol Immunother, 2000, pp. 243-253, vol. 49, Springer-Verlag.

Cheatham et al., "Structural and functional analysis of $pp70^{S6K}$", proc. Natl. Acad. Sci/Cell Biology, Dec. 1995, pp. 11696-11700, vol. 92.

Chang et al., "Insulin Stimulation of Mitogen-activated Protein Kinases, $p90^{rsk}$, and p70 S6 Kinase in Skeletal Muscle of Normal and Insulin-resistant Mice", The Journal of Biological Chemistry, Dec. 15, 1995, pp. 29928-29935, vol. 270, No. 50, The American Society for Biochemistry and Molecular Biology, Inc.

* cited by examiner

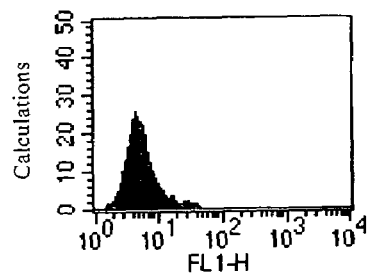
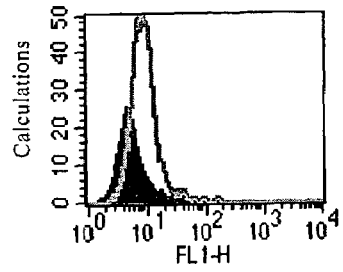
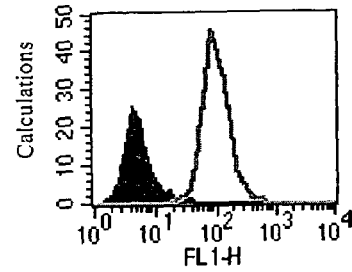
FIGURE 3A    FIGURE 3B    FIGURE 3C
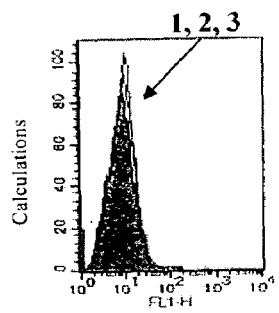
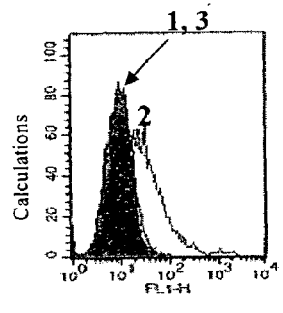
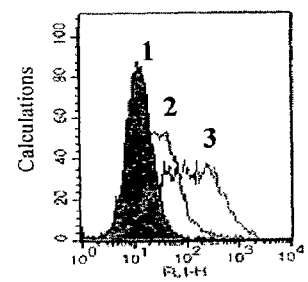
Nontransfected cells    IGF-IR+ cells    IR+ cells
FIGURE 4A    FIGURE 4B    FIGURE 4C

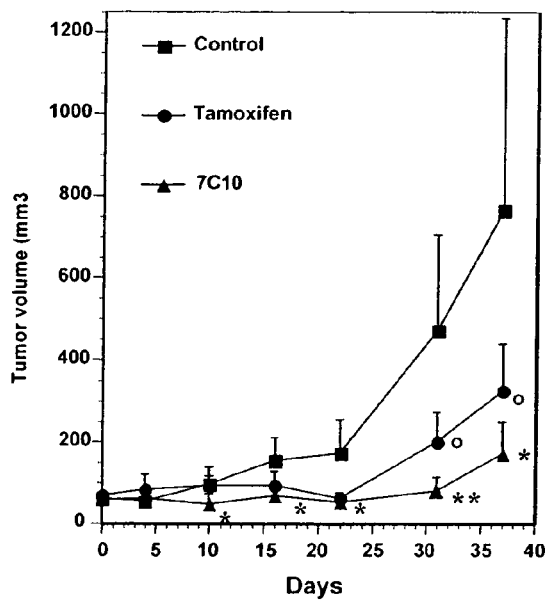
FIGURE 7
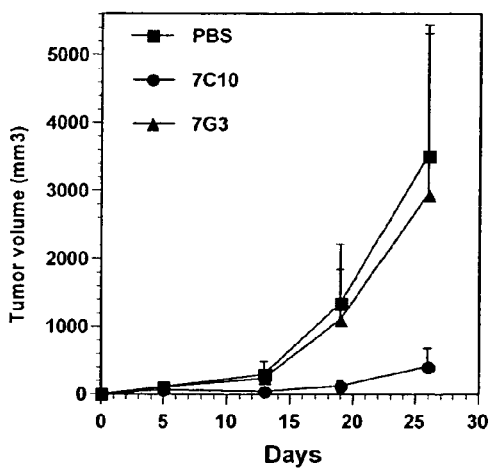 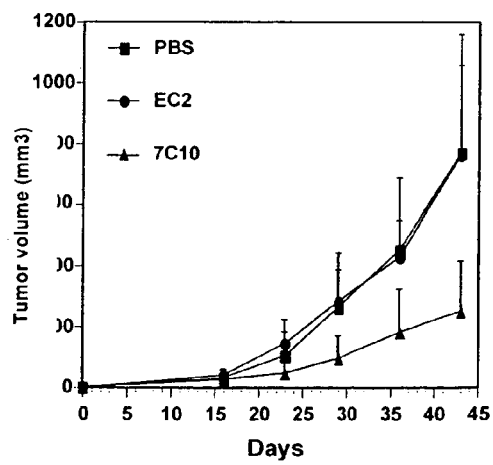
FIGURE 8A
FIGURE 8B

```
    ATGAAGTTGCCTGTTAGGCTGTTGGTGCTGATGTTCTGGATTCCTGCTTCCAGAAGTGAT
  1 ---------+---------+---------+---------+---------+---------+ 60
    TACTTCAACGGACAATCCGACAACCACGACTACAAGACCTAAGGACGAAGGTCTTCACTA
    ATGAAGTTGCCTGTTAGGCTGTTGGTGCT
         oligo MKV-1        L   M   F   W   I   P   A   S   R   S   D   -
                            3' end      leader peptide GTTTTGATGACCCAAATTCCACTCTCCCTGCCTGTCAGTCTTGGAGATCAAGCCTCCATC
 61 ---------+---------+---------+---------+---------+---------+ 120
    CAAAACTACTGGGTTTAAGGTGAGAGGGACGGACAGTCAGAACCTCTAGTTCGGAGGTAG V   L   M   T   Q   I   P   L   S   L   P   V   S   L   G   D   Q   A   S   I   -

TCTTGCAGATCTAGTCAGAGCATTGTACATAGTAATGGAAACACCTATTTACAATGGTAC
121 ---------+---------+---------+---------+---------+---------+ 180
    AGAACGTCTAGATCAGTCTCGTAACATGTATCATTACCTTTGTGGATAAATGTTACCATG

S   C   R   S   S   Q   S   I   V   H   S   N   G   N   T   Y   L   Q   W   Y   -
                 CDR 1

CTGCAGAAACCAGGTCAGTCTCCAAAGCTCCTGATCTACAAAGTTTCCAACCGACTTTAT
181 ---------+---------+---------+---------+---------+---------+ 240
    GACGTCTTTGGTCCAGTCAGAGGTTTCGAGGACTAGATGTTTCAAAGGTTGGCTGAAATA

L   Q   K   P   G   Q   S   P   K   L   L   I   Y   K   V   S   N   R   L   Y   -
                                                 CDR 2

GGGGTCCCAGACAGGTTCAGTGGCAGTGGATCAGGGACAGATTTCACACTCAAGATCAGC
241 ---------+---------+---------+---------+---------+---------+ 300
    CCCCAGGGTCTGTCCAAGTCACCGTCACCTAGTCCCTGTCTAAAGTGTGAGTTCTAGTCG

G   V   P   D   R   F   S   G   S   G   S   G   T   D   F   T   L   K   I   S   -

AGCGTGGAGGCTGAGGATCTGGGAGTTTATTACTGCTTTCAAGGTTCACATGTTCCGTGG
301 ---------+---------+---------+---------+---------+---------+ 360
    TCGCACCTCCGACTCCTAGACCCTCAAATAATGACGAAAGTTCCAAGTGTACAAGGCACC

S   V   E   A   E   D   L   G   V   Y   Y   C   F   Q   G   S   H   V   P   W   -
                                             CDR 3
                                                                         GG
    ACGTTCGGTGGAGGCACCAAGCTGGAAATCAAACGGGCTGATGCTGCACCAACTGTATCC
361 ---------+---------+---------+---------+---------+---------+ 420
    TGCAAGCCACCTCCGTGGTTCGACCTTTAGTTTGCCCGACTACGACGTGGTTGACATAGG

T   F   G   G   G   T   K   L   E   I   K
         MKC oligo
    TAGAAGGGTGGTAGGTCA
    ATCTTCCCACCATCCAGT
421 ---------+-------- 438
    TAGAAGGGTGGTAGGTCA
```

FIGURE 14

```
            ATGATGGTGTTAAGTCTTCTGTACCTCTTGACAGCCATTCCTGGTATCCTGTCTGATGTA
       1    ---------+---------+---------+---------+---------+---------+  60
            TACTACCACAATTCAGAAGACATGGACAACTGTCGGTAAGGACCATAGGACAGACTACAT
MHV-12      ATGATGGTGTTAAGTCTTCTGTACCT
MHV-8       ATGAGAGTGCTGATTCTTTTGTG
                                      L  L  T  A  I  P  G  I  L  S  D  V   -
                                      ‾‾‾‾‾‾‾‾‾‾‾‾‾‾‾‾‾‾‾‾‾‾‾‾‾‾‾‾‾
                                      3' end    leader peptide
            CAGCTTCAGGAGTCAGGACCTGGCCTCGTGAAACCTTCTCAGTCTCTGTCTCTCACCTGC
       61   ---------+---------+---------+---------+---------+---------+  120
            GTCGAAGTCCTCAGTCCTGGACCGGAGCACTTTGGAAGAGTCAGAGACAGAGAGTGGACG

Q  L  Q  E  S  G  P  G  L  V  K  P  S  Q  S  L  S  L  T  C   -

TCTGTCACCGGCTACTCCATCACCGGTGGTTATTTATGGAACTGGATCCGGCAGTTTCCA
      121   ---------+---------+---------+---------+---------+---------+  180
            AGACAGTGGCCGATGAGGTAGTGGCCACCAATAAATACCTTGACCTAGGCCGTCAAAGGT

S  V  T  G  Y  S  I  T  G  G  Y  L  W  N  W  I  R  Q  F  P   -
                                    ‾‾‾‾‾‾‾‾‾‾‾‾‾‾
                                       CDR 1
            GGAAACAAACTGGAGTGGATGGGCTACATAAGCTACGACGGTACCAATAACTACAAACCA
      181   ---------+---------+---------+---------+---------+---------+  240
            CCTTTGTTTGACCTCACCTACCCGATGTATTCGATGCTGCCATGGTTATTGATGTTTGGT

G  N  K  L  E  W  M  G  Y  I  S  Y  D  G  T  N  N  Y  K  P   -
                                    ‾‾‾‾‾‾‾‾‾‾‾‾‾‾‾‾‾‾‾‾‾‾‾‾‾‾‾‾‾
                                             CDR 2
            TCTCTCAAAGATCGAATCTCCATCACTCGTGACACATCTAAGAACCAGTTTTTCCTGAAG
      241   ---------+---------+---------+---------+---------+---------+  300
            AGAGAGTTTCTAGCTTAGAGGTAGTGAGCACTGTGTAGATTCTTGGTCAAAAAGGACTTC

S  L  K  D  R  I  S  I  T  R  D  T  S  K  N  Q  F  F  L  K   -
            ‾‾‾‾‾‾‾‾‾‾‾‾‾‾
            TTGAATTCTGTGACTAATGAAGACACAGCTACATATTACTGTGCAAGATACGGTAGGGTC
      301   ---------+---------+---------+---------+---------+---------+  360
            AACTTAAGACACTGATTACTTCTGTGTCGATGTATAATGACACGTTCTATGCCATCCCAG

L  N  S  V  T  N  E  D  T  A  T  Y  Y  C  A  R  Y  G  R  V   -
                                                            ‾‾‾‾‾‾‾‾
                                                              CDR 3
                                                            GGG
            TTCTTTGACTACTGGGGCCAAGGCACCACTCTCACAGTCTCCTCAGCCAAAACGACACCC
      361   ---------+---------+---------+---------+---------+---------+  420
            AAGAAACTGATGACCCCGGTTCCGTGGTGAGAGTGTCAGAGGAGTCGGTTTTGCTGTGGG

F  F  D  Y  W  G  Q  G  T  T  L  T  V  S  S
            ‾‾‾‾‾‾‾‾
              oligo MHC-1
            GGTAGACAGATAGGTGAC
            CCATCTGTCTATCCACTG
      421   ---------+-------- 438
            GGTAGACAGATAGGTGAC
```

FIGURE 15

```
                        3      7                            CDR 1
7C10 VL mouse   DVLMTQIPLSLPVSLGDQASISC  RSSQSIVHSNGNTYLQ
DRB1-4.3        ......T................  ................E
C94-5B11'CL     ......T................  ................E
Kabat sgII mouse..V...T................  .....L..........E CDR 2
7C10 VL mouse   WYLQKPGQSPKLLIY  KVSNRLY  GVPDRFSGSGSGTDFTL
DRB1-4.3        ...............  .....FS  .................
C94-5B11'CL     ...............  .....FS  .................
Kabat sgII mouse...............  .....FS  .................

77                  CDR 3
7C10 VL mouse   KISSVEAEDLGVYYC  FQGSHVPWT  FGGGTKLEIK
DRB1-4.3        ...R...........  .......F.  ...S....D..
C94-5B11'CL     ...R...........  .........  ..........
Kabat sgII mouse...R...........  ...T...Y.  ..........
```

```
                                              CDR 1
7C10 VL mouse    DVLMTQIPLSLPVSLGDQASISC  RSSQSIVHSNGNTYLQ
GM607            .IV...S......TP.EP.....  .....LL....YN..D
DPK15/A19        .IV...S......TP.EP.....  .....LL....YN..D
Kabat sgII hu    .IV...S......TP.EP.....  .....LL..D.XX..X CDR 2
7C10 VL mouse    WYLQKPGQSPKLLIY  KVSNRLY  GVPDRFSGSGSGTDFTLK
GM607            ..........Q....  LG...AS  ..................
DPK15/A19        ..........Q....  LG...AS  ..................
Kabat sgII hu    ..........Q....  L....AS  ..................

CDR 3
7C10 VL mouse    ISSVEAEDLGVYYC  FQGSHVPWT  FGGGTKLEIK
GM607            ..R.....V.....  M.ALQT.Q.  ..Q...V...
DPK15/A19        ..R.....V.....  M.ALQT.
Kabat sgII hu    ..R.....V.....  M.ALQX.R.  ..Q...V...
```

FIGURE 18

```
                                                    CDR 1
7C10 VL mouse          DVLMTQIPLSLPVSLGDQASISC  RSSQSIVHSNGNTYLQ
GM 607                 .IV...S......TP.EP.....  .....LL....YN..D
7C10 VL Humanized 1    ..V...S......TP.EP.....  ................
7C10 VL Humanized 2    .IV...S......TP.EP.....  ................

CDR 2
7C10 VL mouse          WYLQKPGQSPKLLIY  KVSNRLY  GVPDRFSGSGSGTDFTL
GM 607                 ..........Q....  LG...AS  .................
7C10 VL Humanized 1    ..........Q....  .......  .................
7C10 VL Humanized 2    ..........Q....  .......  .................

CDR 3
7C10 VL mouse          KISSVEAEDLGVYYC  FQGSHVPWT  FGGGTKLEIK
GM 607                 ...R.....V.....  M.ALQT.Q.  ..Q...V...
7C10 VL Humanized 1    ...R.....V.....  .........  ..Q...V...
7C10 VL Humanized 2    ...R.....V.....  .........  ..Q...V...
```

FIGURE 19

```
                MluI
                 |
    GTCAGAACGCGTGCCGCCACCATGAAGTTGCCTGTTAGGCTGTTGGTGCTGATGTTCTGG
  1 ---------+---------+---------+---------+---------+---------+ 60
    CAGTCTTGCGCACGGCGGTGGTACTTCAACGGACAATCCGACAACCACGACTACAAGACC

M  K  L  P  V  R  L  L  V  L  M  F  W  -
                                      Peptide leader
    TTTCCTGCTTCCAGCAGTGATGTTGTGATGACTCAGTCTCCACTCTCCCTGCCCGTCACC
 61 ---------+---------+---------+---------+---------+---------+ 120
    AAAGGACGAAGGTCGTCACTACAACACTACTGAGTCAGAGGTGAGAGGGACGGGCAGTGG
                                  2
     F  P  A  S  S  S  D  V  V  M  T  Q  S  P  L  S  L  P  V  T  -

CCTGGAGAGCCGGCCTCCATCTCCTGCAGGTCTAGTCAGAGCATTGTACATAGTAATGGA
121 ---------+---------+---------+---------+---------+---------+ 180
    GGACCTCTCGGCCGGAGGTAGAGGACGTCCAGATCAGTCTCGTAACATGTATCATTACCT
                                                    CDR 1
     P  G  E  P  A  S  I  S  C  R  S  S  Q  S  I  V  H  S  N  G  -
                  KpnI
                    |
    AACACCTATTTGCAATGGTACCTGCAGAAGCCAGGGCAGTCTCCACAGCTCCTGATCTAT
181 ---------+---------+---------+---------+---------+---------+ 240
    TTGTGGATAAACGTTACCATGGACGTCTTCGGTCCCGTCAGAGGTGTCGAGGACTAGATA

N  T  Y  L  Q  W  Y  L  Q  K  P  G  Q  S  P  Q  L  L  I  Y  -

AAAGTTTCTAATCGGCTTTATGGGGTCCCTGACAGGTTCAGTGGCAGTGGATCAGGCACA
241 ---------+---------+---------+---------+---------+---------+ 300
    TTTCAAAGATTAGCCGAAATACCCCAGGGACTGTCCAAGTCACCGTCACCTAGTCCGTGT
            CDR 2
     K  V  S  N  R  L  Y  G  V  P  D  R  F  S  G  S  G  S  G  T  -

GATTTTACACTGAAAATCAGCAGAGTGGAGGCTGAGGATGTTGGGGTTTATTACTGCTTT
301 ---------+---------+---------+---------+---------+---------+ 360
    CTAAAATGTGACTTTTAGTCGTCTCACCTCCGACTCCTACAACCCCAAATAATGACGAAA

D  F  T  L  K  I  S  R  V  E  A  E  D  V  G  V  Y  Y  C  F  -

CAAGGTTCACATGTTCCGTGGACGTTCGGCCAAGGGACCAAGGTGGAAATCAAACGTGAG
361 ---------+---------+---------+---------+---------+---------+ 420
    GTTCCAAGTGTACAAGGCACCTGCAAGCCGGTTCCCTGGTTCCACCTTTAGTTTGCACTC
            CDR 3
     Q  G  S  H  V  P  W  T  F  G  Q  G  T  K  V  E  I  K
    BamHI
      |
    TGGATCCTCTGCG
421 ---------+--- 433
    ACCTAGGAGACGC
```

FIGURE 20

```
         MluI
           |
    GTCAGAACGCGTGCCGCCACCATGAAGTTGCCTGTTAGGCTGTTGGTGCTGATGTTCTGG
  1 ---------+---------+---------+---------+---------+---------+ 60
    CAGTCTTGCGCACGGCGGTGGTACTTCAACGGACAATCCGACAACCACGACTACAAGACC

M  K  L  P  V  R  L  L  V  L  M  F  W  -
                                 Leader peptide
    TTTCCTGCTTCCAGCAGTGATATTGTGATGACTCAGTCTCCACTCTCCCTGCCCGTCACC
 61 ---------+---------+---------+---------+---------+---------+ 120
    AAAGGACGAAGGTCGTCACTACAACACTACTGAGTCAGAGGTGAGAGGGACGGGCAGTGG
                         2
    F  P  A  S  S  S  D  I  V  M  T  Q  S  P  L  S  L  P  V  T  -

CCTGGAGAGCCGGCCTCCATCTCCTGCAGGTCTAGTCAGAGCATTGTACATAGTAATGGA
121 ---------+---------+---------+---------+---------+---------+ 180
    GGACCTCTCGGCCGGAGGTAGAGGACGTCCAGATCAGTCTCGTAACATGTATCATTACCT
                                             CDR 1
    P  G  E  P  A  S  I  S  C  R  S  S  Q  S  I  V  H  S  N  G  -
                          KpnI
                           |
    AACACCTATTTGCAATGGTACCTGCAGAAGCCAGGGCAGTCTCCACAGCTCCTGATCTAT
181 ---------+---------+---------+---------+---------+---------+ 240
    TTGTGGATAAACGTTACCATGGACGTCTTCGGTCCCGTCAGAGGTGTCGAGGACTAGATA

N  T  Y  L  Q  W  Y  L  Q  K  P  G  Q  S  P  Q  L  L  I  Y  -

AAAGTTTCTAATCGGCTTTATGGGGTCCCTGACAGGTTCAGTGGCAGTGGATCAGGCACA
241 ---------+---------+---------+---------+---------+---------+ 300
    TTTCAAAGATTAGCCGAAATACCCCAGGGACTGTCCAAGTCACCGTCACCTAGTCCGTGT
            CDR 2
    K  V  S  N  R  L ·Y  G  V  P  D  R  F  S  G  S  G  S  G  T  -

GATTTTACACTGAAAATCAGCAGAGTGGAGGCTGAGGATGTTGGGGTTTATTACTGCTTT
301 ---------+---------+---------+---------+---------+---------+ 360
    CTAAAATGTGACTTTTAGTCGTCTCACCTCCGACTCCTACAACCCCAAATAATGACGAAA

D  F  T  L  K  I  S  R  V  E  A  E  D  V  G  V  Y  Y  C  F  -

CAAGGTTCACATGTTCCGTGGACGTTCGGCCAAGGGACCAAGGTGGAAATCAAACGTGAG
361 ---------+---------+---------+---------+---------+---------+ 420
    GTTCCAAGTGTACAAGGCACCTGCAAGCCGGTTCCCTGGTTCCACCTTTAGTTTGCACTC
            CDR 3·
    Q  G  S  H  V  P  W  T  F  G  Q  G  T  K  V  E  I  K
  BamHI
    |
    TGGATCCTCTGCG
421 ---------+--- 433
    ACCTAGGAGACGC
```

FIGURE 21

```
                                17              27      CDR 1
7C10 VH       DVQLQESGPGLVKPSQSLSLTCSVTGYSIT   GGYLWN  WIRQ
AN03'CL       ..............................  S..Y..  ....
Kabat sgI(A)  E........S......T.........D...  S..WN.  ....

CDR 2
7C10 VH       FPGNKLEWMG  YISYDGTNNYKPSLKD  RISITRDTSKNQFFL
AN03'CL       ..........  ..N...N...N....N  ...............
Kabat sgI(A)  ..........  ....S.STY.N....S  ............Y..

84          CDR 3
7C10 VH       KLNSVTNEDTATYYCAR  YGRV-FFDY   WGQGTTLTVSS
AN03'CL       ......T..........  E.YGY....   ...........
Kabat sgI(A)  Q.....T..........  G.YGYG...   ......V....
```

FIGURE 22

```
                            Rch 1              30    CDR 1   Rch 2
7C10 VH mouse     DVQLQESGPGLVKPSQSLSLTCVTGYSIT    GGYLWN   WIRQ
human Kabat sgII  Q.................T.....T.S.G.VS  SYWS..   ....
human VH FUR1'CL  Q.................ET....T.S....S  S..Y.S   ....
human Germline    Q.................ET....T.S....S  S..Y.S   ....

Rch 2   48      CDR 2       67  71   Rch 3
7C10 VH mouse     FPGNKLEWMG  YISYDGTNNYKPSLKD   RISITRDTSKNQFFL
human Kabat sgII  P..KG...I.  R.Y.S.STX.N....S   .VT.SV.......S.
human VH FUR1'CL  P..KG...I.  SMFHS.SSY.N....S   .VT.SV.......S.
human Germ-line   P..KG...I.  S.YHS.STY.N....S   .VT.SV.......S.

Rch 3             CDR 3           Rch 4
7C10 VH mouse     KLNSVTNEDTATYYCAR   YGRVFFDY         WGQGTTLTVSS
human Kabat sgII  ..S...AA...V.....   ELPGGYDV         .....LV....
human VH FUR1'CL  Q.R...AA...V.....   GRYCSSTSCNWFDP   .....LV....
human Germline    ..S...AA...V.....
```

FIGURE 23

```
                            30  CDR 1              48
7C10 VH mouse    DVQLQESGPGLVKPSQSLSLTCSVTGYSIT GGYLWN WIRQFPGNKLEWMG
human germline   Q..............ET.....T.S....S S..Y.G ....P..KG...I.
VH Humanized 1   Q..............ET.....T.S....  ......  ....P..KG.....
VH Humanized 2   Q..............ET.....T.S....  ......  ....P..KG...I.
VH Humanized 3   Q..............ET.....T.S....S ......  ....P..KG...I.

CDR 2          67  71
7C10 VH mouse    YISYDGTNNYKPSLKD RISITRDTSKNQFFLKLNSVTNEDTATYYCAR
human germline   S.FHS.SSY.N....S .VT.SV.......S...S...AA...V.....
VH Humanized 1   ................ ..T.S.........S...S...AA...V.....
VH Humanized 2   ................ .VT.S.........S...S...AA...V.....
VH Humanized 3   ................ .VT.SV........S...S...AA...V.....

CDR 3
7C10 VH mouse    YGRVFFDY WGQGTTLTVSS
human germline
VH Humanized 1   ........ .....LV....
VH Humanized 2   ........ .....LV....
VH Humanized 3   ........ .....LV....
```

FIGURE 24

```
MluI
     |
     GTCAGAACGCGTGCCGCCACCATGAAAGTGTTGAGTCTGTTGTACCTCTTGACAGCCATT
  1  ---------+---------+---------+---------+---------+---------+  60
     CAGTCTTGCGCACGGCGGTGGTACTTTCACAACTCAGACAACATGGAGAACTGTCGGTAA

M   K   V   L   S   L   L   Y   L   L   T   A   I   -
                                       Leader peptide
     CCTGGTATCCTGTCTCAGGTGCAGCTTCAGGAGTCGGGCCCAGGACTGGTGAAGCCTTCG
 61  ---------+---------+---------+---------+---------+---------+ 120
     GGACCATAGGACAGAGTCCACGTCGAAGTCCTCAGCCCGGGTCCTGACCACTTCGGAAGC P   G   I   L   S   Q   V   Q   L   Q   E   S   G   P   G   L   V   K   P   S   -

GAGACCCTGTCCCTCACCTGCACTGTCTCTGGTTACTCCATCACCGGTGGTTATTTATGG
121  ---------+---------+---------+---------+---------+---------+ 180
     CTCTGGGACAGGGAGTGGACGTGACAGAGACCAATGAGGTAGTGGCCACCAATAAATACC
                                              30              CDR 1
      E   T   L   S   L   T   C   T   V   S   G   Y   S   I   T   G   G   Y   L   W   -

AACTGGATACGGCAGCCCCCAGGGAAGGGACTGGAGTGGATGGGGTATATCAGCTACGAC
181  ---------+---------+---------+---------+---------+---------+ 240
     TTGACCTATGCCGTCGGGGGTCCCTTCCCTGACCTCACCTACCCCATATAGTCGATGCTG
                                                 48
      N   W   I   R   Q   P   P   G   K   G   L   E   W   M   G   Y   I   S   Y   D   -
             KpnI
              |
     GGTACCAATAACTACAAACCCTCCCTCAAGGATCGAATCACCATATCACGTGACACGTCC
241  ---------+---------+---------+---------+---------+---------+ 300
     CCATGGTTATTGATGTTTGGGAGGGAGTTCCTAGCTTAGTGGTATAGTGCACTGTGCAGG
                CDR 2                            67              71
      G   T   N   N   Y   K   P   S   L   K   D   R   I   T   I   S   R   D   T   S   -

AAGAACCAGTTCTCCCTGAAGCTGAGCTCTGTGACCGCTGCGGACACTGCAGTGTATTAC
301  ---------+---------+---------+---------+---------+---------+ 360
     TTCTTGGTCAAGAGGGACTTCGACTCGAGACACTGGCGACGCCTGTGACGTCACATAATG

K   N   Q   F   S   L   K   L   S   S   V   T   A   A   D   T   A   V   Y   Y   -

TGTGCGAGATACGGTAGGGTCTTCTTTGACTACTGGGGCCAGGGAACCCTGGTCACCGTC
361  ---------+---------+---------+---------+---------+---------+ 420
     ACACGCTCTATGCCATCCCAGAAGAAACTGATGACCCCGGTCCCTTGGGACCAGTGGCAG
                      CDR 3
      C   A   R   Y   G   R   V   F   F   D   Y   W   G   Q   G   T   L   V   T   V   -

BamHI
              |
     TCCTCAGGTGAGTGGATCCTCTGCG
421  ---------+---------+----- 445
     AGGAGTCCACTCACCTAGGAGACGC

```
          MluI
           |
     GTCAGAACGCGTGCCGCCACCATGAAAGTGTTGAGTCTGTTGTACCTCTTGACAGCCATT
  1  ---------+---------+---------+---------+---------+---------+  60
     CAGTCTTGCGCACGGCGGTGGTACTTTCACAACTCAGACAACATGGAGAACTGTCGGTAA

M   K   V   L   S   L   L   Y   L   L   T   A   I    -
                                       Leader peptide
     CCTGGTATCCTGTCTCAGGTGCAGCTTCAGGAGTCGGGCCCAGGACTGGTGAAGCCTTCG
 61  ---------+---------+---------+---------+---------+---------+ 120
     GGACCATAGGACAGAGTCCACGTCGAAGTCCTCAGCCCGGGTCCTGACCACTTCGGAAGC P   G   I   L   S   Q   V   Q   L   Q   E   S   G   P   G   L   V   K   P   S   -

GAGACCCTGTCCCTCACCTGCACTGTCTCTGGTTACTCCATCACCGGTGGTTATTTATGG
121  ---------+---------+---------+---------+---------+---------+ 180
     CTCTGGGACAGGGAGTGGACGTGACAGAGACCAATGAGGTAGTCGCCACCAATAAATACC
                                              30        CDR 1
      E   T   L   S   L   T   C   T   V   S   G   Y   S   I   T   G   G   Y   L   W   -

AACTGGATACGGCAGCCCCCAGGGAAGGGACTGGAGTGGATCGGGTATATCAGCTACGAC
181  ---------+---------+---------+---------+---------+---------+ 240
     TTGACCTATGCCGTCGGGGGTCCCTTCCCTGACCTCACCTAGCCCATATAGTCGATGCTG
                                          48
      N   W   I   R   Q   P   P   G   K   G   L   E   W   I   G   Y   I   S   Y   D   -

KpnI
         |
     GGTACCAATAACTACAAACCCTCCCTCAAGGATCGAGTCACCATATCACGTGACACGTCC
241  ---------+---------+---------+---------+---------+---------+ 300
     CCATGGTTATTGATGTTTGGGAGGGAGTTCCTAGCTCAGTGGTATAGTGCACTGTGCAGG
                 CDR 2                      67            71
      G   T   N   N   Y   K   P   S   L   K   D   R   V   T   I   S   R   D   T   S   -

AAGAACCAGTTCTCCCTGAAGCTGAGCTCTGTGACCGCTGCGGACACTGCAGTGTATTAC
301  ---------+---------+---------+---------+---------+---------+ 360
     TTCTTGGTCAAGAGGGACTTCGACTCGAGACACTGGCGACGCCTGTGACGTCACATAATG

K   N   Q   F   S   L   K   L   S   S   V   T   A   A   D   T   A   V   Y   Y   -

TGTGCGAGATACGGTAGGGTCTTCTTTGACTACTGGGGCCAGGGAACCCTGGTCACCGTC
361  ---------+---------+---------+---------+---------+---------+ 420
     ACACGCTCTATGCCATCCCAGAAGAAACTGATGACCCCGGTCCCTTGGGACCAGTGGCAG
                      CDR 3
      C   A   R   Y   G   R   V   F   F   D   Y   W   G   Q   G   T   L   V   T   V   -

BamHI
           |
     TCCTCAGGTGAGTGGATCCTCTGCG
421  ---------+---------+----- 445
     AGGAGTCCACTCACCTAGGAGACGC

```
        MluI
         |
    GTCAGAACGCGTGCCGCCACCATGAAAGTGTTGAGTCTGTTGTACCTCTTGACAGCCATT
  1 ---------+---------+---------+---------+---------+---------+ 60
    CAGTCTTGCGCACGGCGGTGGTACTTTCACAACTCAGACAACATGGAGAACTGTCGGTAA

M   K   V   L   S   L   L   Y   L   L   T   A   I    -
                                        Leader peptide
    CCTGGTATCCTGTCTCAGGTGCAGCTTCAGGAGTCGGGCCCAGGACTGGTGAAGCCTTCG
 61 ---------+---------+---------+---------+---------+---------+ 120
    GGACCATAGGACAGAGTCCACGTCGAAGTCCTCAGCCCGGGTCCTGACCACTTCGGAAGC P   G   I   L   S   Q   V   Q   L   Q   E   S   G   P   G   L   V   K   P   S    -

GAGACCCTGTCCCTCACCTGCACTGTCTCTGGTTACTCCATCAGCGGTGGTTATTTATGG
121 ---------+---------+---------+---------+---------+---------+ 180
    CTCTGGGACAGGGAGTGGACGTGACAGAGACCAATGAGGTAGTCGCCACCAATAAATACC
                                            30           CDR 1
     E   T   L   S   L   T   C   T   V   S   G   Y   S   I   S   G   G   Y   L   W    -

AACTGGATACGGCAGCCCCCAGGGAAGGGACTGGAGTGGATCGGGTATATCAGCTACGAC
181 ---------+---------+---------+---------+---------+---------+ 240
    TTGACCTATGCCGTCGGGGGTCCCTTCCCTGACCTCACCTAGCCCATATAGTCGATGCTG
                                          48
     N   W   I   R   Q   P   P   G   K   G   L   E   W   I   G   Y   I   S   Y   D    -
        KpnI
         |
    GGTACCAATAACTACAAACCCTCCCTCAAGGATCGAGTCACCATATCAGTGGACACGTCC
241 ---------+---------+---------+---------+---------+---------+ 300
    CCATGGTTATTGATGTTTGGGAGGGAGTTCCTAGCTCAGTGGTATAGTCACCTGTGCAGG
            CDR 2                          67           71
     G   T   N   N   Y   K   P   S   L   K   D   R   V   T   I   S   V   D   T   S    -

AAGAACCAGTTCTCCCTGAAGCTGAGCTCTGTGACCGCTGCGGACACTGCAGTGTATTAC
301 ---------+---------+---------+---------+---------+---------+ 360
    TTCTTGGTCAAGAGGGACTTCGACTCGAGACACTGGCGACGCCTGTGACGTCACATAATG

K   N   Q   F   S   L   K   L   S   S   V   T   A   A   D   T   A   V   Y   Y    -

TGTGCGAGATACGGTAGGGTCTTCTTTGACTACTGGGGCCAGGGAACCCTGGTCACCGTC
361 ---------+---------+---------+---------+---------+---------+ 420
    ACACGCTCTATGCCATCCCAGAAGAAACTGATGACCCCGGTCCCTTGGGACCAGTGGCAG
                    CDR 3
     C   A   R   Y   G   R   V   F   F   D   Y   W   G   Q   G   T   L   V   T   V    -

BamHI
                |
    TCCTCAGGTGAGTGGATCCTCTGCG
421 ---------+---------+----- 445
    AGGAGTCCACTCACCTAGGAGACGC

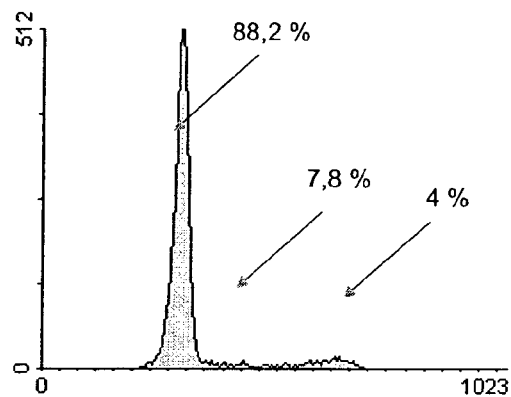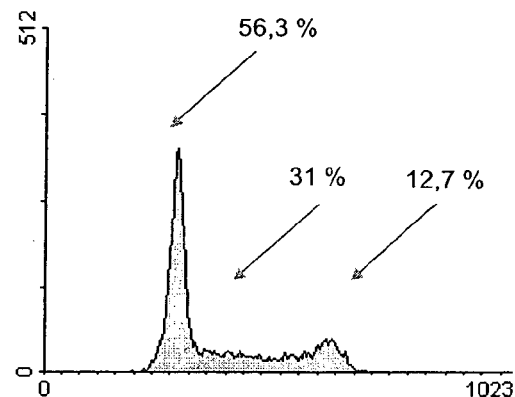
FIGURE 33A  FIGURE 33B
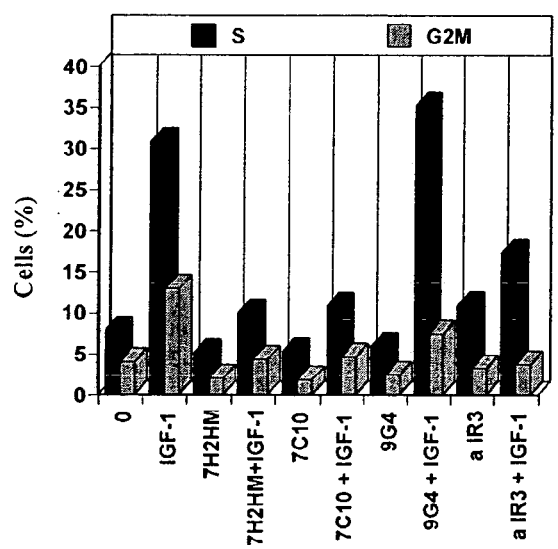
FIGURE 33C

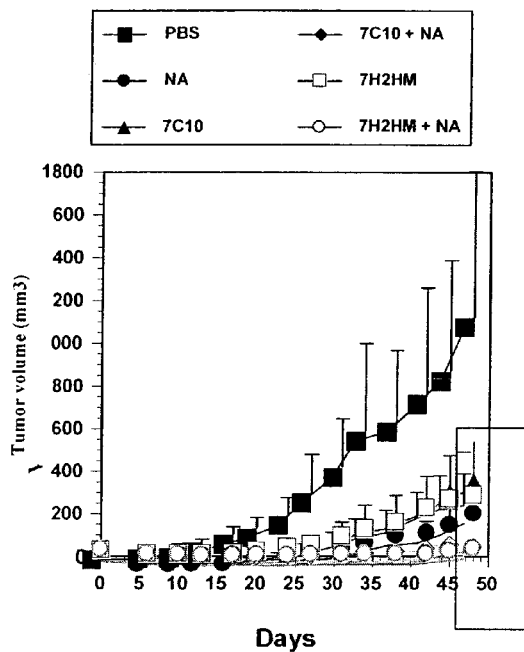
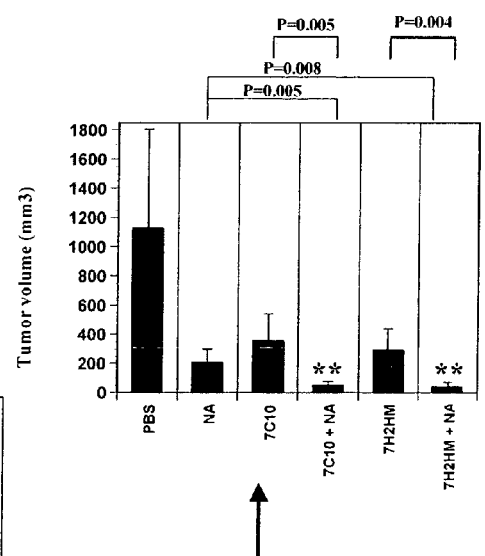
FIGURE 35A  FIGURE 35B
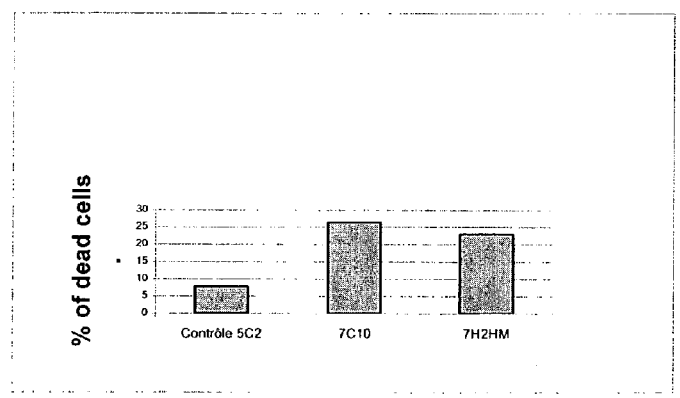
FIGURE 36

FIGURE 40A
IGF-I 50 ng/ml
0    0    9G4   7C10  IgG17H2HM 1H7
TyrP
IGF-1R
IGF-I 50 ng/ml
FIGURE 40B
0    0    9G4   7C10  IgG17H2HM  1H7
TyrP
IRS-I
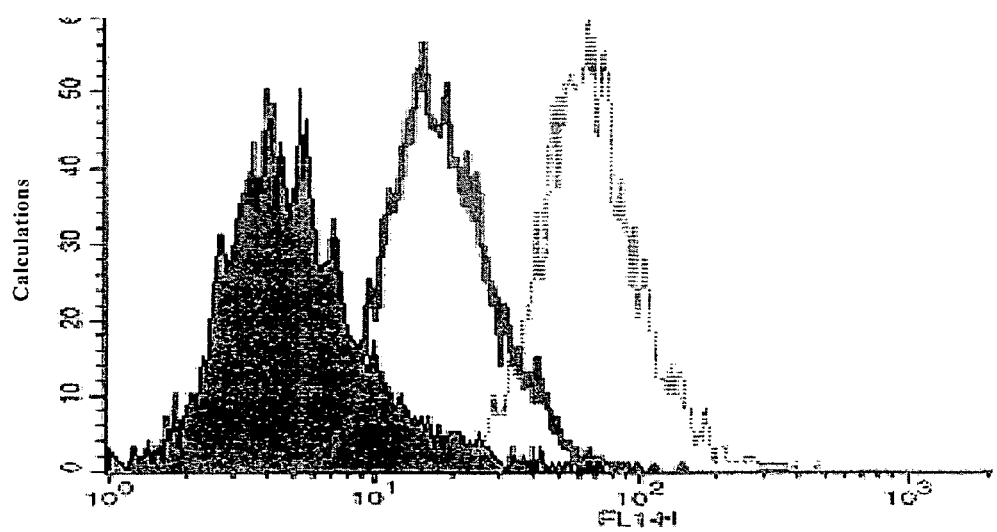
FIGURE 41

ANTI-IGF-IR ANTIBODIES AND USES THEREOF

This application is a continuation-in-part of PCT/FR03/00178 filed in France on Jan. 20, 2003, which claims priority from FR 0200653 filed in France on Jan. 18, 2002, FR 0200654 filed in France on Jan. 18, 2002 and FR 0205753 filed in France on May 7, 2002, the entire contents of which are hereby incorporated by reference. The present application claims priority under 35 U.S.C. § 119 to FR 0308538 filed in France on Jul. 11, 2003, the entire contents of which is hereby incorporated by reference.

BACKGROUND

The present invention relates to novel antibodies capable of binding specifically to the human insulin-like growth factor I receptor IGF-IR and/or capable of specifically inhibiting the tyrosine kinase activity of said IGF-IR receptor, especially monoclonal antibodies of murine, chimeric and humanized origin, as well as the amino acid and nucleic acid sequences coding for these antibodies. The invention) likewise comprises the use of these antibodies as a medicament for the prophylactic and/or therapeutic treatment of cancers overexpressing IGF-IR or any pathology connected with the overexpression of said receptor as well as in processes or kits for diagnosis of illnesses connected with the overexpression of the IGF-IR receptor. The invention finally comprises products and/or compositions comprising such antibodies in combination with anti-EGFR antibodies and/or compounds and/or anti-cancer agents or agents conjugated with toxins and their use for the prevention and/or the treatment of certain cancers.

The insulin-like growth factor I receptor called IGF-IR is a receptor with tyrosine kinase activity having 70% homology with the insulin receptor IR. IGF-IR is a glycoprotein of molecular weight approximately 350,000. It is a heterotetrameric receptor of which each half-linked by disulfide bridges—is composed of an extracellular a-subunit and of a transmembrane β-subunit (see FIG. 1). IGF-IR binds IGF I and IGF II with a very high affinity (Kd #1 nM) but is equally capable of binding to insulin with an affinity 100 to 1000 times less. Conversely, the IR binds insulin with a very high affinity although the ICFs only bind to the insulin receptor with a 100 times lower affinity. The tyrosine kinase domain of IGF-IR and of IR has a very high sequence homology although the zones of weaker homology respectively concern the cysteine-rich region situated on the a-subunit and the C-terminal part of the β-subunit. The sequence differences observed in the a-subunit are situated in the binding zone of the ligands and are therefore at the origin of the relative affinities of IGF-IR and of IR for the IGFs and insulin respectively. The differences in the C-terminal part of the β-subunit result in a divergence in the signalling pathways of the two receptors; IGF-IR mediating mitogenic, differentiation and antiapoptosis effects, while the activation of the IR principally involves effects at the level of the metabolic pathways (Baserga et al., Biochim. Biophys. Acta, 1332: F105–126, 1997; Baserga R., Exp. Cell. Res., 253: 1–6, 1999).

The cytoplasmic tyrosine kinase proteins are activated by the binding of the ligand to the extracellular domain of the receptor. The activation of the kinases in its turn involves the stimulation of different intra-cellular substrates, including IRS-1, IRS-2, Shc and Grb 10 (Peruzzi F. et al., J. Cancer Res. Clin. Oncol., 125:166–173, 1999). The two major substrates of IGF-IR are IRS and Shc which mediate, by the activation of numerous effectors downstream, the majority of the growth and differentiation effects connected with the attachment of the IGFs to this receptor (FIG. 2). The availability of substrates can consequently dictate the final biological effect connected with the activation of the IGF-IR. When IRS-1 predominates, the cells tend to proliferate and to transform. When Shc dominates, the cells tend to differentiate (Valentinis B. et al.; J. Biol. Chem. 274:12423–12430, 1999). It seems that the route principally involved for the effects of protection against apoptosis is the phosphatidyl-inositol 3-kinases (PI 3-kinases) route (Prisco M. et al., Horm. Metab. Res., 31:80–89, 1999; Peruzzi F. et al., J. Cancer Res. Clin. Oncol., 125:166–173, 1999).

The role of the IGF system in carcinogenesis has become the subject of intensive research in the last ten years. This interest followed the discovery of the fact that in addition to its mitogenic and antiapoptosis properties, IGF-IR seems to be required for the establishment and the maintenance of a transformed phenotype. In fact, it has been well established that an overexpression or a constitutive activation of IGF-IR leads, in a great variety of cells, to a growth of the cells independent of the support in media devoid of fetal calf serum, and to the formation of tumors in nude mice. This in itself is not a unique property since a great variety of products of overexpressed genes can transform cells, including a good number of receptors of growth factors. However, the crucial discovery which has clearly demonstrated the major role played by, IGF-IR in the transformation has been the demonstration that the R-cells, in which the gene coding for IGF-IR has been inactivated, are totally refractory to transformation by different agents which are usually capable of transforming the cells, such as the E5 protein of bovine papilloma virus, an overexpression of EGFR or of PDGFR, the T antigen of SV 40, activated ras or the combination of these two last factors (Sell C. et al., Proc. Natl. Acad. Sci., USA, 90: 11217–11221, 1993; Sell C. et al., Mol. Cell. Biol., 14:3604–3612, 1994; Morrione A. J., Virol., 69:5300–5303, 1995; Coppola D. et al., Mol. Cell. Biol., 14:4588–4595, 1994; DeAngelis T et al., J. Cell. Physiol., 164:214–221, 1995).

IGF-IR is expressed in a great variety of tumors and of tumor lines and the IGFs amplify the tumor growth via their attachment to IGF-IR. Other arguments in favor of the role of IGF-IR in carcinogenesis come from studies using murine monoclonal antibodies directed against the receptor or using negative dominants of IGF-IR. In effect, murine monoclonal antibodies directed against IGF-IR inhibit the proliferation of numerous cell lines in culture and the growth of tumor cells in vivo (Arteaga C. et al., Cancer Res., 49:6237–6241, 1989 Li et al., Biochem. Biophys. Res. Com., 196:92–98, 1993; Zia F et al., J. Cell. Biol., 24:269–275, 1996; Scotlandi K et al., Cancer Res., 58:4127–4131, 1998). It has likewise been shown in the works of Jiang et al. (Oncogene, 18:6071–6077, 1999) that a negative dominant of IGF-IR is capable of inhibiting tumor proliferation.

SUMMARY

The object of the present invention is to be able to have available a murine monoclonal antibody, preferably a chimerized or humanized antibody, which will recognize IGF-IR specifically and with great affinity. This antibody will interact little or not at all with the IR receptor on insulin. Its attachment will be able to inhibit in vitro the growth of tumors expressing IGF-IR by interacting principally with the signal transduction pathways activated during IGF1/IGF-IR and IGF2/IGF-IR interactions. This antibody will be able to be active in vivo on all the types of tumors expressing IGF-IR including estrogen-dependent tumors of the breast and tumors of the prostate, which is not the case for the anti-IGF-IR monoclonal antibodies (written MAb or MAB) currently available. In effect, αIR3, which refers to the domain of IGF-IR, totally inhibits the growth of estrogen-dependent tumors of the breast (MCF-7) in vitro but is without effect on the corresponding model in vivo (Arteaga C. et al., J. Clin. Invest. 84:1418–1423, 1989). In the same way, the scFv-Fc fragment derived from the murine monoclonal 1H7 is only weakly active on the tumor of the breast MCF-7 and totally inactive on an androgen-independent tumor of the prostate (Li S. L. et al., Cancer Immunol. Immunother., 49:243–252, 2000).

In a surprising manner, the inventors have demonstrated a chimeric antibody (called C7C10) and two humanized antibodies respectively called h7C10 humanized form 1 and h7C10 humanized form 2, derivatives of the murine monoclonal antibody 7C10, recognising IGF-IR and corresponding to all of the criteria stated above, that is to say to a nonrecognition of the receptor on the insulin, to an in vitro blockage of the IGF1 and/or IGF2 proliferation induced but likewise to the in vivo inhibition of the growth of different tumors expressing IGF-IR among which are an osteosarcoma and a non-small cell lung tumor but likewise and more particularly the estrogen-dependent tumor of the breast MCF-7 and an androgen-independent tumor of the prostate DU-145. In the same way, and in a surprising manner, the intensity of inhibition of the tumor growth of MCF-7 cells in vivo by the antibody 7C10 is comparable, or even significantly superior, to that observed with Lamoxifen, one of the reference compounds in the treatment of estrogen-dependent tumors of the breast. Furthermore, it has been shown that these antibodies inhibit the phosphorylation of the tyrosine of the beta chain of IGF-IR and of IRS1, the first substrate of the receptor. Moreover, it has likewise been established that these antibodies cause the internalization of said receptor and its degradation contrary to what is usually observed with natural ligands which allow the rapid recycling of the receptor on the surface of the cells. It has been possible to characterize these antibodies by their peptidic and nucleic sequence, especially by the sequence of their regions determining their complementarity (CDR) for IGF-IR.

Thus, according to a first embodiment, a subject of the present invention is an isolated antibody, or one of its functional fragments, said antibody or one of its said fragments being capable of binding specifically to the human insulin-like growth factor I receptor and, if necessary, preferably moreover capable of inhibiting the natural attachment of the ligands IGF1 and/or IGF2 of IGF-IR and/or capable of specifically inhibiting the tyrosine kinase activity of said IGF-IR receptor, characterized in that it comprises a light chain comprising at least one complementarity determining region CDR chosen from the CDRs of amino acid sequence SEQ ID Nos. 2, 4 or 6, or at least one CDR whose sequence has at least 80%, preferably 85%, 90%, 95% and 98% identity, after optimum alignment, with the sequence SEQ ID Nos. 2, 4 or 6, or in that it comprises a heavy chain comprising at least one CDR chosen from the CDRs of amino acid sequence SEQ ID Nos. 8, 10 and 12, or at least one CDR whose sequence has at least 80%, preferably 85%, 90%, 95% and 98% identity, after optimum alignment, with the sequence SEQ ID No. 8, 10 and 12.

DETAILED DESCRIPTION

In the present description, the terms "to bind" and "to attach" have the same meaning and are inter-changeable.

In the present description, the terms polypeptides, polypeptide sequences, peptides and proteins attached to antibody compounds or to their sequence are interchangeable.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

By CDR region or CDR, it is intended to indicate the hypervariable regions of the heavy and light chains of the immunoglobulins as defined by Kabat et al. (Kabat et al., Sequences of proteins of immunological interest, 5th Ed., U.S. Department of Health and Human Services, NIH, 1991, and later editions). 3 heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

By "percentage of identity" between two nucleic acid or amino acid sequences in the sense of the present invention, it is intended to indicate a percentage of nucleotides or of identical amino acid residues between the two sequences to be compared, obtained after the best alignment (optimum alignment), this percentage being purely statistical and the differences between the two sequences being distributed randomly and over their entire length. The comparisons of sequences between two nucleic acid or amino acid sequences are traditionally carried out by comparing these sequences after having aligned them in an optimum manner, said comparison being able to be carried out by segment or by "comparison window". The optimum alignment of the sequences for the comparison can be carried out, in addition to manually, by means of the local homology algorithm of Smith and Waterman (1981) [Ad. App. Math. 2:482], by means of the local homology algorithm of Neddleman and Wunsch (1970) [J. Mol. Biol. 48: 443], by means of the similarity search method of Pearson and Lipman (1988) [Proc. Natl. Acad. Sci. USA 85:2444], by means of computer software using these algorithms (GAP, BESTFIT, FASTA and TFASTA in the Wisconsin Genetics Software Package, Genetics Computer Group, 575 Science Dr., Madison, Wis., or else by BLAST N or BLAST P comparison software).

The percentage of identity between two nucleic acid or amino acid sequences is determined by comparing these two sequences aligned in an optimum manner and in which the nucleic acid or amino acid, sequence to be compared can comprise additions or deletions with respect to the reference sequence for an optimum alignment between these two sequences. The percentage of identity is calculated by determining the number of identical positions for which the nucleotide or the amino acid residue is identical between the two sequences, by dividing this number of identical positions by the total number of positions in the comparison window and by multiplying the result obtained by 100 in order to obtain the percentage of identity between these two sequences.

For example, it is possible to use the BLAST program, "BLAST 2 sequences" (Tatusova et al., "Blast 2 sequences—a new tool for comparing protein and nucleotide sequences", FEMS Microbiol Lett. 1/4:247–250) available on the world wide web at ncbi.nlm.nig.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

By amino acid sequence having at least 80%, preferably 85%, 90%, 95% and 98% identity with a reference amino acid sequence, those having, with respect to the reference sequence, certain modifications, in particular a deletion, addition or substitution of at least one amino acid, a truncation or an elongation are preferred. In the case of a substitution of one or more consecutive or nonconsecutive amino acid(s), the substitutions are preferred in which the substituted amino acids are replaced by "equivalent" amino acids. The expression "equivalent amino acids" is aimed here at indicating any amino acid capable of being substituted with one of the amino acids of the base structure without, however, essentially modifying the biological activities of the corresponding antibodies and such as will be defined later, especially in the examples.

These equivalent amino acids can be determined either by relying on their structural homology with the amino acids which they replace, or on results of comparative trials of biological activity between the different antibodies capable of being carried out.

By way of example, mention is made of the possibilities of substitution capable of being carried out without resulting in a profound modification of the biological activity of the corresponding modified antibody. It is thus possible to replace leucine by valine or isoleucine, aspartic acid by glutamic acid, glutamine by asparagine, arginine by lysine, etc., the reverse substitutions being naturally envisageable under the same conditions.

The antibodies according to the present invention are preferably specific monoclonal antibodies, especially of murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495–497, 1975).

The monoclonal antibodies according to the invention can be obtained, for example, from an animal cell immunized against the IGF-IR receptor, or one of its fragments containing the epitope specifically recognized by said monoclonal antibodies according to the invention. Said IGF-IR receptor, or one of its said fragments, can especially be produced according to the usual working methods, by genetic recombination starting with a nucleic acid sequence contained in the cDNA sequence coding for the IGF-IR receptor or by peptide synthesis starting from a sequence of amino acids comprised in the peptide sequence of the IGF-IR receptor.

The monoclonal antibodies according to the invention can, for example, be purified on an affinity column on which the IGF-IR receptor or one of its fragments containing the epitope specifically recognized by said monoclonal antibodies according to the invention has previously been immobilized. More particularly, said monoclonal antibodies can be purified by chromatography on protein A and/or G, followed or not followed by ion-exchange chromatography aimed at eliminating the residual protein contaminants as well as the DNA and the LPS, in itself followed or not followed by exclusion chromatography on Sepharose gel in order to eliminate the potential aggregates due to the presence of dimers or of other multimers. In an even more preferred manner, the whole of these techniques can he used simultaneously or successively.

Chimeric or humanized antibodies are likewise included in antibodies according to the present invention.

By chimeric antibody, it is intended to indicate an antibody which contains a natural variable (light chain and heavy chain) region derived from an antibody of a given species in combination with the light chain and heavy chain constant regions of an antibody of a species heterologous to said given species.

The antibodies or their fragments of chimeric type according to the invention can be prepared by using the techniques of genetic recombination, for example, the chimeric antibody can be produced by cloning a recombinant DNA containing a promoter and a sequence coding for the variable region of a nonhuman, especially murine, monoclonal antibody according to the invention and a sequence coding for the constant region of human antibody. A chimeric antibody of the invention encoded by such a recombinant gene will be, for example, a mouse-man chimera, the specificity of this antibody being determined by the variable region derived from the murine DNA and its isotype determined by the constant region derived from the human DNA. For the methods of preparation of chimeric antibodies, it is possible, for example, to refer to the document Verhoeyon et al. (Bioassays, 8:74, 1988).

By humanized antibody, it is intended to indicate an antibody which contains CDR regions derived from an antibody of nonhuman origin, the other parts of the antibody molecule being derived from one (or from several) human antibodies. Moreover, some of the residues of the segments of the skeleton (called FR) can be modified in order to conserve the affinity of the binding (Jones et al., Nature, 321:522–525, 1986; Verhoeyon et al., Science, 239:1534–1536, 1988; Riechmann et al., Nature, 332:323–327, 1988).

The humanized antibodies according to the invention or their fragments can be prepared by techniques known to the person skilled in the art (such as, for example, those described in the documents Singer et al., J. Immun. 150: 2844–2857, 1992; Mountain et al., Biotechnol. Genet. Eng. Rev., 10: 1–142, 1992; or Bebbington et al., Bio/Technology, 10:169–175, 1992) Such humanized antibodies according to the invention are preferred for their use in in vitro diagnostic methods, or in vivo prophylactic and/or therapeutic treatment.

By functional fragment of an antibody according to the invention, it is intended to indicate in particular an antibody, fragment, such as Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of sequence SEQ ID No. 2, 4, 6, 8, 10 or 12 according to the invention, and, especially, in that it is capable of exerting in a general manner an even partial activity of the antibody from which it is descended, such as in particular the capacity to recognize and to bind to the IGF-IR receptor, and, if necessary, to inhibit the activity of tie IGF-IR receptor.

Preferably, said functional fragments will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100 in a more preferred manner to at least 1/10 of that of the antibody from which it is descended, with respect to the IGF-IR receptor.

Such a functional fragment will contain at the minimum 5 amino acids, preferably 10, 15, 25, 50 and 100 consecutive amino acids of the sequence of the antibody from which it is descended.

Preferably, these functional fragments will be fragments of Fv, scFv, Fab, F(ab')$_2$, F(ab'), scFv-Fc type or diabodies, which generally have the same specificity of binding as the antibody from which they are descended. According to the present invention, antibody fragments of the invention can be obtained starting from antibodies such as described above by methods such as digestion by enzymes, such as pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

In a more preferred manner, the invention comprises the antibodies, or their functional fragments, according to the present invention, especially chimeric or humanized antibodies, obtained by genetic recombination or by chemical synthesis.

In a preferred embodiment, a subject of the invention is an antibody, or one of its functional fragments, according to the invention, characterized in that it comprises a heavy chain comprising at least one CDR of sequence SEQ ID No. 12 or a sequence having at Least 80% identity after optimum alignment with the sequence SEQ ID No. 12.

Among the six short CDR sequences, the third CDR of the heavy chain (CDRII3) has a greater size variability (greater diversity essentially due to the mechanisms of arrangement of the genes which give rise to it). It can be as short as 2 amino acids although the longest size known is 26. Functionally, CDRH3 plays a role in part in the determination of the specificity of the antibody (Sogal et al., PNAS, 71:4298–4302, 1974; Amit et al., Science, 233:747–753, 1986; Chothia et al., J. Mol. Biol., 196:901–917, 1987; Chothia et al., Nature, 342:877–883, 1989; Caton et al., J. Immunol., 144:1965–1968, 1990; Sharon et al., PNAS, 87:4814–4817, 1990; Sharon et al., J. Immunol., 144:4.863–4869, 1990; Kabat et. al., J. Immunol., 147: 1709–1719, 1991).

It is known that only a low percentage of the amino acids of the CDRs contribute to the construction of an antibody binding site, but these residues must be maintained in a very specific tridimensional conformation.

In a more preferred manner, the present invention relates to an antibody or one of its functional fragments, according to the invention, characterized in that it comprises a heavy chain comprising at least two of the three CDRs or the three CDRs of sequence SEQ ID Nos. 8, 10 and 12, or at least two of three CDRs or three CDRs of sequence respectively having at least 80% identity after optimum alignment with the sequence SEQ ID No. 8, 10 and 12.

In a likewise preferred embodiment, a subject of the invention is an antibody or one of its functional fragments, according to the invention, characterized in that it comprises a light chain comprising at least one CDR chosen from the CDRs of sequence SEQ ID No. 2, 4 or 6, or a CDR whose sequence has at least 80% identity after optimum alignment with the sequence SEQ ID No. 2, 4 or 6.

In a more preferred embodiment, a subject of the invention is an antibody or one of its functional fragments according to the invention, characterized in that it comprises a light chain comprising at least two of the three CDRs or the three CDRs of sequence SEQ ID Nos. 2, 4 and 6, or at least two of three CDRs or three CDRs of sequence respectively having at least 80% identity after optimum alignment with the sequence SEQ ID No. 2, 4 and 6.

In a more preferred manner, the antibody or one of its functional fragments according to the invention is characterized in that it comprises a heavy chain comprising the three CDRs of sequence SEQ ID Nos. 8, 10 and 12, or three CDRs of sequence respectively having at least 80% of identity after, optimum alignment with the sequence SEQ ID No. 8, 10 and 12 and in that it moreover comprises a light chain comprising the three CDRs of sequence SEQ. ID Nos. 2, 4 and 6, or three CDRs of sequence respectively having at least 80% of identity after optimum alignment with the sequence SEQ ID No. 2, 4 and 6.

According to another aspect, a subject of the present invention is an antibody or one of its functional fragments, according to the invention, characterized in that it does not attach or it does not attach in a significant manner to the human insulin receptor IR.

In a preferred manner, said functional fragments according to the present invention will be chosen from the fragments Fv, scFv, Fab, (Fab')$_2$, Fab', scFv-Fc or diabodies, or any functional fragment whose half-life would have been increased by a chemical modification, especially by PEGylation, or by incorporation in a liposome.

According to another aspect, the invention relates to a murine hybridoma capable of secreting a monoclonal antibody according to the present invention, especially the hybridoma of murine origin such as deposited at the Collection National de Culture De Microorganism (CNCM, National. Center of Microorganism Culture) (Institut Pasteur, 25, rue du Cocteur Roux, F-75724 PARIS Cedex 15, France) on Sep. 19, 2001 under the number I-2717.

The monoclonal-antibody here called 7C10, or one of its functional fragments, characterized in that said antibody is secreted by the hybridoma deposited at the CNCM on Sep. 19, 2001 under the number I-2717 is, of course, part of the present invention.

In a particular embodiment, the present invention relates to a murine antibody, or one of its functional fragments, according to the invention, characterized in that said antibody comprises a light chain of sequence comprising the amino acid sequence SEQ ID No. 54, or a sequence having at least 80% identity after optimum alignment with the sequence SEQ ID No. 54, or/and in that it comprises a heavy chain of sequence comprising the amino acid sequence. SEQ ID No. 69, or a sequence having at least 80% identity after optimum alignment with the sequence SEQ ID No. 69.

According to a likewise particular aspect, the present invention relates to a chimeric antibody, or one of its functional fragments, according to the invention, characterized in that said antibody moreover comprises the light chain and heavy chain constant regions derived from an antibody of a species heterologous to the mouse, especially man, and in a preferred manner in that the light chain and heavy chain constant regions derived from a human antibody are respectively the kappa and gamma-1, gamma-2 or gamma-4 region.

According to a likewise particular aspect, the present invention relates to a humanized antibody or one of its functional fragments, according to the invention, characterized in that said antibody comprises a light chain and/or a heavy chain in which the skeleton segments FR1 to FR4 (such as defined below in examples 12 and 13, in tables 5 and 6) of said light chain and/or heavy chain are respectively derived from skeleton segments FR1 to FR4 of human antibody light chain and/or heavy chain.

According to a preferred embodiment, the humanized antibody or one of its functional fragments, according to the present invention is characterized in that said humanized antibody comprises a light chain comprising the amino acid sequence SEQ ID No. 61 or 65, or a sequence having at least 80% identity after optimum alignment with the sequence SEQ ID No. 61 or 65, or/and in that it comprises a heavy chain comprising the amino acid sequence SEQ ID No. 75, 79 or 83, or a sequence having at least 80% idontity after optimum alignment with the sequence SEQ ID No. 75, 79 or 83.

Preferably, the humanized antibody, or one of its functional fragments, according to the invention is characterized in that said humanize antibody comprises a light chain comprising the amino acid sequence SEQ ID No. 65, and in that it comprises a heavy chain of sequence comprising the amino acid sequence SEQ ID No. 79 or 83, preferably SEQ ID No. 83.

According to a novel aspect, the present invention relates to an isolated nucleic acid, characterized in that it is chosen from the following nucleic acids:
a) a nucleic acid, DNA or RNA, coding for an antibody, or one of its functional fragments, according to the invention;
b) a complementary nucleic acid of a nucleic acid such as defined in a); and
c) a nucleic acid of at least 18 nucleotides capable of hybridizing under conditions of great stringency with at least one of the CDRs of nucleic acid sequence SEQ ID No. 1, 3, 5, 7, 9 or 11, or with a sequence having at least 80%, preferably 85%, 90%, 95n and 98%, identity after optimum alignment with the sequence SEQ ID No. 1, 3, 5, 7, 9 or 11.

By nucleic acid, nucleic or nucleic acid sequence, polynucleotide, oligonucleotide, polynucleotide sequence, nucleotide sequence, terms which will be employed indifferently in the present invention, it is intended to indicate a precise linkage of nucleotides, which are modified or unmodified, allowing a fragment or a region of a nucleic acid to be defined, containing or not containing unnatural nucleotides, and being able to correspond just as well to a double-stranded DNA, a single-stranded DNA as to the transcription products of said DNAs.

It must also be understood here that the present invention does not concern the nucleotide sequences in their natural chromosomal environments that is to say in the natural state. It concerns sequences which have been isolated and/or purified, that is to say that they have been selected directly or indirectly, for example by copy, their environment having been at least partially modified. It is thus likewise intended to indicate here the isolated nucleic acids obtained by genetic recombination by means, for example, of host cells or obtained by chemical synthesis.

By nucleic sequences having a percentage of identity of at least 80%, preferably 85%, 90%, 95% and 98%, after optimum alignment with a preferred sequence, it is intended to indicate the nucleic sequences having, with respect to the reference nucleic sequence, certain modifications such as, in particular, a deletion, a truncation, an elongation, a chimeric fusion and/or a substitution, especially point substitution. It preferably concerns sequences in which the sequences code for the same amino acid sequences as the reference sequence, this being connected to the degeneracy of the genetic code, or complementary sequences which are capable of hybridizing specifically with the reference sequences, preferably under conditions of high stringency, especially such as defined below.

A hybridization under conditions of high stringency signifies that the temperature conditions and ionic strength conditions are chosen in such a way that they allow the maintenance of the hybridization between two fragments of complementary DNA. By way of illustration, conditions of high stringency of the hybridization step for the purposes of defining the polynucleotide fragments described above are advantageously the following.

The DNA-DNA or DNA-RNA hybridization is carried out in two steps: (1) prehybridization at 42° C. for 3 hours in phosphate buffer (20 mM, pH 7.5) containing 5×SSC (1×SSC corresponds to a 0.15 M NaCl+0.015 M sodium citrate solution), 50% of formamide, 7% of sodium dodecyl sulfate (SOS), 10× Denhardt's, 5% of dextran sulfato and 1% of salmon sperm DNA; (2) actual hybridization for 20 hours at a temperature dependent on the size of the probe (i.e.: 42° C., for a probe size >100 nucleotides), followed by 2 washes of 20 minutes at 20° C. in 2×SSC+2% of SDS, 1 wash of 20 minutes at 20° C. in 0.1×SSC+0.1% of SDS. The last wash is carried out in 0.1×SSC+0.1% of SDS for 30 minutes at 60° C. for a probe size >100 nucleotides. The hybridization conditions of high stringency described above for a polynucleotide of defined size can be adapted by the person skilled in the art for oligonucleotides of greater or smaller size, according to the teaching of Sambrook et al., (1989, Molecular cloning: a laboratory manual. 2nd Ed. Cold Spring Harbor).

The invention likewise relates to a vector comprising a nucleic acid according to the present invention.

The invention aims especially at cloning and/or expression vectors which contain a nucleotide sequence according to the invention.

The vectors according to the invention preferably contain elements, which allow the expression and/or the secretion of the nucleotide sequences in a determined host cell. The vector must therefore contain a promoter, signals of initiation and termination of translation, as well as appropriate regions of regulation of transcription. It must be able to be maintained in a stable manner in the host cell and can optionally have particular signals which specify the secretion of the translated protein. These different elements are chosen and optimized by the person skilled in the art as a function of the host cell used. To this effect, the nucleotide sequences according to the invention can be inserted into autonomous replication vectors in the chosen host, or be integrative vectors of the chosen host.

Such vectors are prepared by methods currently used by the person skilled in the art, and the resulting clones can be introduced into an appropriate host by standard methods, such as lipofection, electroporation, thermal shock, or chemical methods.

The vectors according to the invention are, for example, vectors of plasmidic or viral origin. They are useful for transforming host cells in order to clone or to express the nucleotide sequences according to the invention.

The invention, likewise comprises the host cells transformed by or comprising a vector according to the invention.

The host cell can be chosen from prokaryotic or eukaryotic systems, for example bacterial cells but likewise yeast cells or animal cells, in particular mammalian cells. It is likewise possible to use insect cells or plant cells.

The invention likewise concerns animals, except man, which comprise at least one cell transformed according to the invention.

According to another aspect, a subject of the invention is a process for production of an antibody, or one of its functional fragments according to the invention, characterized in that it comprises the following stages:
a) culture in a medium and appropriate culture conditions of a host cell according to the invention; and
b) the recovery of said antibodies, or one of their functional fragments, thus produced starting from the culture medium or said cultured cells.

The cells transformed according to the invention can be used in processes for preparation of recombinant polypeptides according to the invention. The processes for preparation of a polypeptide according to the invention in recombinant form, characterized, in that they employ a vector and/or a cell transformed by a vector according to the invention, are themselves comprised in the present invention. Preferably, a cell transformed by a vector according to the invention is cultured under conditions which allow the expression of said polypeptide and said recombinant peptide is recovered.

As has been said, the host cell can be chosen from prokaryotic or eukaryotic systems. In particular, it is possible to identify nucleotide sequences according to the invention, facilitating secretion in such a prokaryotic or eukaryotic system. A vector according to the invention carrying such a sequence can therefore advantageously be used for the production of recombinant proteins, intended to be secreted. In effect, the purification of these recombinant proteins of interest will be facilitated by the fact that they are present in the supernatant of the cell culture rather than in the interior of the host cells.

It is likewise possible to prepare the polypeptides according to the invention by chemical synthesis. Such a preparation process is likewise a subject of the invention. The person skilled in the art knows the processes of chemical synthesis, for example the techniques employing solid phases (see especially Steward et al., 1984, Solid phase peptide synthesis, Pierce Chem. Company, Rockford, Ill., 2nd ed., (1984)) or techniques using partial solid phases, by condensation of fragments or by a classical synthesis in solution. The polypeptides obtained by chemical synthesis and being able to contain corresponding unnatural amino acids are likewise comprised in the invention.

The antibodies, or one of their functional fragments, capable of being obtained by a process according to the invention are likewise comprised in the present invention.

According to a second embodiment, the present invention concerns an antibody according to the invention such as described further above, characterized in that it is, moreover, capable of binding specifically to the human epidermal growth factor receptor EGFR and/or capable of specifically inhibiting the tyrosine kinase activity of said EGFR receptor.

In a general manner, the growth factors are small proteins involved in the regulation of the proliferation and of the differentiation of normal cells. Some of these growth factors likewise play an important role in the initiation and the maintenance of cell transformation, being able to function as autocrine or paracrine factors. This is especially the case, in addition to the IGF1 described further above, for the epidermal growth factor EGF, which seems particularly involved in the appearance of the tumor phenotype, the progression of tumors and the generation of metastases.

EGF and IGF1 exert their action through the intermediary of their respective receptor here called EGFR and IGF-IR. It concerns in the two cases membrane receptors with tyrosine kinase activity whose overexpression is described in numerous cancers. It must, however, be noted that the interaction of these two receptors is not clearly established and that the studios carried out by various teams in this connection give contradictory results as to the collaboration of these two receptors.

Studies carried out on prostate tumor cells show that the interruption of the autocrine loop EGF/EGFR by an anti-EGFR monoclonal antibody (here called "MAB" or "MAb") is manifested by a complete loss of the response of the DU145 cells to IGF1 (Connolly J. M. and Rose D. P., Prostate, April 24(4):167–75, 1994; Putz T. et al., Cancer Res., Jan. 1, 59(1):227–33, 1999). These results would suggest that a blockage of the receptor for the EGF would be sufficient in order to obtain a total inhibition of the transformation signals generated by the activation of the two receptors (EGFR and IGF-IR). On the other hand, other studies (Pietrzkowski et al., Cell Growth Differ, Apr., 3(4): 199–205, 1992; Coppola et al., Mol Cell Biol., July, 14(7): 4588–95, 1994) have shown that an over-expression of EGFR necessitates the presence of a functional IGF-IR in order to exert its mitogenic and transformant potential, although IGF-IR does not necessitate, for its part, the presence of functional EGFR in order to mediate its action. This second series of studies would be more in agreement with a strategy tending preferentially to block IGF-IR with the aim of simultaneously affecting the two receptors.

In a surprising manner, the inventors have, firstly, demonstrated that a coinhibition of the attachment of the IGF1 and/or IGF2 to the IGF-IR receptor and of the attachment of the EGF to the EGFR receptor allows a significant synergy of action of these two actions to be obtained against the in vivo tumor growth in nude mice carrying a tumor expressing these two receptors. One of the more probable hypotheses which is able to explain this synergy of action is that the two growth factors EGF and IGF1 (and/or IGF2) themselves act in synergy in the transformation of normal cells to cells with tumoral character and/or in the growth and/or the proliferation of tumor cells for certain tumors, especially for those overexpressing the two receptors EGFR and IGF-IR and/or having an overactivation of the transduction signal mediated by these two receptors, in particular at the level of the tyrosine kinase activity of these receptors.

According to a preferred aspect of this embodiment, the invention concerns an antibody such as described further above, characterized in that it consists of a bispecific antibody comprising a second motif specifically inhibiting the attachment of the EGF to the EGFR and/or specifically inhibiting the tyrosine kinase activity of said EGFR receptor.

The term "second motif" is intended to indicate above especially a sequence of amino acids comprising a fragment capable of specifically binding to EGFR, in particular a CDR region of a variable chain of an anti-EGFR antibody, or, one of the fragments of this CDR region of sufficient length in older to exert this specific binding, or else several CDR regions of an anti-EGFR antibody.

The bispecific or bifunctional antibodies form a second generation of monoclonal antibodies in which two different variable regions are combined in the same molecule (Hollinger and Bohlen 1999 Cancer and metastasis rev. 18: 411–419). Their use has been demonstrated both in the diagnostic field and in the therapy field from their capacity to recruit new effector functions or to target several molecules on the surface of tumor cells. These antibodies can be obtained by chemical methods (Glennie M J et al. 1987 J. Immunol. 139, 2367–2375; Repp R. et al. 1995 J. Hemat. 377–382) or somatic methods (Staerz U. D. and Bevan M. J. 1986 PNAS 83, 1453–1457; Suresh M. R. et al. 1986 Method Enzymol. 121: 210–228) but likewise and preferentially by genetic engineering techniques which allow the heterodimerization to be forced and thus facilitate the process of purification of the antibody sought (Merchand et al. 1998 Nature Biotech. 16:677–681).

These bispecific antibodies can be constructed as entire IgG, as bispecific Fab'2, as Fab'PEG or as diabodies or else as bispecific scFv but likewise as a tetravalent bispecific antibody or two attachment sites are present for each antigen targeted (Park et al. 2000 Mol. Immunol. 37 (18):1123–30) or its fragments as described further above.

In addition to an economic advantage from the fact that the production and the administration of a bispecific antibody are less onerous than the production of two specific antibodies, the use of such bispecific antibodies has the advantage of reducing the toxicity of the treatment. This is because the use of a bispecific antibody allows the total quantity of circulating antibodies to be reduced and, consequently, the possible toxicity.

In a preferred embodiment of the invention, the bispecific antibody is a bivalent or tetravalent antibody.

In practice, the interest in using a tetravalent bispecific antibody is that it has a greater avidity in comparison with a bivalent antibody on account of the presence of two attachment sites for each target, respectively IGF-IR and EGFR in the present invention.

In a similar manner to the selection of the functional fragments of the anti-IGF-IR antibody described above, said second motif is selected from the fragments Fv, Fab, F(ab')$_2$, Fab', scFv, scFv-Fc and tho diabodies, or any form whose half-life would have been increased like the pegylated fragments such as Fv-PEG, scFv-PEG, Fab-PEG, F(ab')$_2$-PEG or Fab'-PEG. According to an even more preferred aspect of the invention, said second anti-EGFR motif is descended from the mouse monoclonal antibody 225, its mouse-man chimeric derivative C225, or a humanized antibody derived from this antibody 225.

According to yet another aspect, a subject of the invention is an antibody, or one of its functional fragments, according to the invention as a medicament, preferably a humanized antibody such as defined above. Antibody, for the remainder of the present description, must be understood as an anti-IGE-IR antibody as well as a bispecific anti-IGF-IR/EGFR antibody.

The invention likewise concerns a pharmaceutical composition comprising by way of active principle a compound consisting of an antibody, or one of its functional fragments according to the invention, preferably mixed with an excipient and/or a pharmaceutically acceptable vehicle.

According to yet another embodiment, the present invention likewise concerns a pharmaceutical composition such as described further above which comprises a second compound chosen from the compounds capable of specifically inhibiting the attachment of the EGF to the human epidermal growth factor receptor EGFR and/or capable of specifically inhibiting the tyrosine kinase activity of said EGFR receptor.

In a preferred aspect of the invention, said second compound is chosen from the isolated anti-EGFR antibodies, or their functional fragment, capable of inhibiting by competition the attachment of the EGF to the EGFR. More particularly, said anti-EGFR antibody is chosen from the monoclonal, chimeric or humanized anti-EGFR antibodies, or their functional fragments. Even more particularly, said functional fragments of the anti-EGFR antibody are chosen from the fragments Fv, Fab, F(ab')$_2$, Fab', scFv-Fc or diabodies, or any fragment whose half-life would have been increased, like pegylated fragments. Said antibody can consist, in an even more preferred manner, of the mouse monoclonal antibody 225, its mouse-man chimeric derivative C225 (also called IMC-C225) or a humanized antibody derived from this antibody 225.

Another complementary embodiment of the invention consists in a composition such as described above which comprises, moreover, as a combination product for simultaneous, separate or sequential use, a cytotoxic/cytostatic agent and/or an inhibitor of the tyrosine kinase activity respectively of the receptors for IGF-I and/or for EGF.

"Simultaneous use" is understood as meaning the administration of the two compounds of the composition according to the invention in a single and identical pharmaceutical form.

"Separate use" is understood as meaning the administration, at the same time, or the two compounds of the composition according to the invention in distinct pharmaceutical forms.

"Sequential use" is understood as meaning the successive administration of the two compounds of the composition according to the invention, each in a distinct pharmaceutical form.

In a general fashion, the composition according to the invention considerably increases the efficacy of the treatment of cancer. In other words, the therapeutic effect of the anti-IGF-IR antibody according to the invention is potentiated in an unexpected manner by the administration of a cytotoxic agent. Another major subsequent advantage produced by a composition according to the invention concerns the possibility of using lower efficacious doses of active principle, which allows the risks of appearance of secondary effects to be avoided or to he reduced, in particular the effects of the cytotoxic agent.

In addition, this composition according to the invention would allow the expected therapeutic effect to be attained more rapidly.

In a particularly preferred embodiment, said composition as a combination product according to the invention is characterized in that said cytotoxic/cytostatic agent is chosen from the agents interacting with DNA, the antimetabolites, the topoisomerase I or II inhibitors, or else the spindle inhibitor or stabilizer agents or else any agent capable of being used in chemotherapy. Such cytotoxic/cytostatic agents, for each of the aforesaid classes of cytotoxic agents, are, for example, cited in the 2001 edition of VIDAL, on the page devoted to the compounds attached to the cancerology and hematology column "Cytotoxics", these cytotoxic compounds cited with reference to this document are cited here as preferred cytotoxic agents.

In a particularly, preferred embodiment, said composition as a combination product according to the invention is characterized in that said cytotoxic agent is coupled chemically to said antibody for simultaneous use.

In a particularly preferred embodiment, said composition according to the invention is characterized in that said cytotoxic/cytostatic agent is chosen from the spindle inhibitor or stabilizer agents, preferably vinorelbine and/or vinflunine and/or vincristine.

Immunoliposomes are liposomes capable of vehicling compounds, such as cytotoxic and/or cytostatic agents, such as described above, and of addressing them to tumour cells by means of antibodies or of antibody fragments attached to their surface. The antibodies or antibody fragments used are directed against antigens overexpressed at the surface of tumour cells and/or surface antigens the expression of which is restricted to tumour cells. They are preferably directed against tyrosine kinase receptors, and more particularly against the receptors for IGF-I, EGF or else VEGF. A preferred antibody is a monoclonal or polyclonal, preferably monoclonal, or, even humanized, antibody which will recognize the IGF-IR specifically and with high affinity. Even more preferably, this antibody consists of the antibody which is the subject of the present invention.

The use of immunoliposomes for inhibiting tumour cell growth has been described in the literature. By way of example, mention may be made of the immunoliposomes which target proteins, such as ErbB2 (Hurwitz E. et al., Cancer Immunol. Immunother, 49:226–234, 2000; Park J. W. et al., Clinical Cancer Res., 8:1172–1181, 2002) or EGFR (Harding J. A. et al., Biochim. Biophys. Acta, 1327: 181–192, 1997), or glycolipids such as the ganglioside GD2 (Pastorino F. et al., Cancer Res., 63:86–92, 2003).

Immunoliposomes combine the advantages of liposomes and of immunoconjugates. Liposomes in fact make it possible to encapsulate cytotoxic and/or cytostatic agents and thus to protect them against degradation. They also have the advantage of decreasing the toxicity of the vehiculed agents and of reducing the side effects that they induce. They may thus allow the use of agents which are much more toxic than the agents conventionally used in anticancer chemotherapies. The conjugation of antibodies or of antibody fragments to the surface of liposomes has the advantage of thus providing a system for specific targeting and addressing of the cytotoxic agent encapsulated in the liposome. In addition, unlike immunoconjugates, since the vehiculed agent is not covalently coupled to the antibody or to the antibody fragment, it will be completely active as soon as it is introduced into the target cell.

The antibodies or antibody fragments may be attached, without any limitation, covalently to the surface of the liposomes using conventional methods of bioconjugation. The coupling of these antibodies or of the fragments will be carried out on the lipids or lipids carrying a PEG which have been inserted into the liposomal membrane. In the case of a PEG-lipid, the coupling will be carried out on the PEG in the distal position with respect to the lipid. Liposomes carrying PEG groups (PEG-grafted liposomes) have the advantage of having longer half-lives than "naked" liposomes. By way of example, mention may be made of coupling of the antibody or of the fragment, via thiol groups, to the activated lipids or PEG-lipids exhibiting maleimide or bromoacetyl groups. The thiol groups for this type of coupling may come from 2 sources. They may be free cysteine residues introduced into a recombinant fragment of the antibody of interest, for example Fab' or scFv fragments with an additional cysteine residue, or released after enzymatic hydrolysis of the antibody of interest and controlled reduction, which is the case, for example, during the preparation of Fab' fragments from complete antibodies. Complete antibodies can also be coupled, after controlled oxidation of the oligosaccharides carried by the heavy chains, to lipids or PEG-lipids exhibiting free amine or hydrazide groups.

Since tumour cells overexpressing the IGF-IR generally possess the property of also overexpressing EGFR, it could also prove to be advantageous to claim bispecific immunoliposomes for targeting both the IGF-IR and the EGFR. Similarly, monospecific liposomes to the surface of which would be grafted one of the ligands for these two receptors, IGF-I, IGF-2 or EGF, or bispecific liposomes, would make it possible to target the same tumour cells overexpressing one of these receptors or both. This approach has been described for the EGFR (Kullberg E. B. et al., Pharm. Res., 20:229–236, 2003) but not for the IGF-IR.

Such immunoliposomes having antibodies anti-IGR-IR, or fragments thereof, attached covalently to the surface of the liposomes, are comprised in the present invention.

Method for the treatment of cancer wherein such immunoliposomes are administrated to patient in need of such treatment, forms also part of the present invention.

In order to facilitate the coupling between said cytotoxic agent and said antibody according to the invention, it is especially possible to introduce spacer molecules between the two compounds to be coupled, such as poly(alkylene) glycols like polyethylene glycol, or else amino acids, or, in another embodiment, to use active derivatives of said cytotoxic agents into which would have been introduced functions capable of reacting with said antibody according to the invention. These coupling techniques are well known to the person skilled in the art and will not be expanded upon in the present description.

In another preferred embodiment, said inhibitor of the tyrosine kinase activity of the receptors for IGR-I and/or for EGF is selected from the group consisting of derived natural agents, dianilinophthalimides, pyrazolo- or pyrrolopyridopyrimidines or else quinazilines. Such inhibitory agents are well known to the person skilled in the art and described in the literature (Ciardiello F., Drugs 2000, Suppl. 1, 25–32).

Other inhibitors of EGFR can, without any limitation, consist of tile anti-EGFR monoclonal antibodies C225 and 22Mab (ImClone Systems Incorporated), ABX-EGF. (Abgenix/Cell Genesys), EMD-7200 (Merck KgaA) or the compounds ZD-1834, ZD-1838 and ZD-1839 (AstraZeneca) PKT-166 (Novartis), PKI-166/CGP-75166 (Novartis), PTK /87 (Novartis), CP 701 (Cephalon), leflunomide (Pharmacia/ Sugen), CI-1033 (Warner-Lambert Parke-Davis), CI-1033/ PD 183, 805 (Warner-Lambert Parke-Davis), CL-387, 785 (Wyeth-Ayerst), BBR-1611 (Boehringer Mannheim GmbH/ Roche), Naamidine A (Bristol-Myers Squibb), RC-3940-II (Pharmacia), BIBX-1382 (Boehringer Ingelheim), OLX-103 (Merck & Co), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer. Center), WHI-P97 (Parker Hughes Cancer Center), GW-282974 (Glaxo), KT-8391 (Kyowa Hakko) or the "EGFR Vaccine" (York Medical/Centro de Immunologia Molecular).

According to yet another embodiment of the invention, the composition such as described above can likewise comprise another antibody compound directed against the extracellular domain of the HER2/neu receptor, as a combination product for simultaneous, separate or sequential use, intended for the prevention and for the treatment of cancer, especially the cancers overexpressing said HER2/neu receptor and the receptor IGF-IR and/or EGFR, such as especially cancer of the breast.

Reference can be made especially to the publications of Albanell et al. (J. of, the National Cancer Institute, 93(24): 1830–1831, 2001) and of Lu et al. (J. of the National Cancer Institute, 93(24):1852–1857, 2001) justifying the unexpected interest in combining an anti-HER2/neu antibody with an anti-IGF-IR antibody according to the present invention.

In a particular manner, said anti-HER2/neu antibody of the composition according to the invention is the antibody called Trastuzumab (also called Herceptin).

The invention relates, in another aspect, to a composition characterized in that one, at least, of said antibodies, or one of their functional fragments, is conjugated with a cell toxin and/or a radioelement.

Preferably, said toxin or said radioelement is capable of inhibiting at least one cell activity of cells expressing the IGF-IR and/or EGFR receptor, in a more preferred manner capable of preventing the growth or the proliferation of said cell, especially of totally inactivating said cell.

Preferably also, said toxin is an enterobacterial toxin, especially Pseudomonas exotoxin A.

The radioelements (or radioisotopes) preferably conjugated to the antibodies employed for the therapy are radioisotopes which emit gamma rays and preferably iodine$^{131}$, yttrium$^{90}$, gold$^{199}$, palladium$^{100}$, copper$^{67}$, bismuth$^{217}$ and antimony$^{211}$. The radioisotopes which emit beta and alpha rays can likewise be used for the therapy.

By toxin or radioelement conjugated to at least one antibody, or one of its functional fragments, according to the invention, it is intended to indicate any means allowing said toxin or said radioelement to bind to said at least one antibody, especially by covalent coupling between the two compounds, with or without introduction of a linking molecule.

Among the agents allowing binding in a chemical (covalent), electrostatic or noncovalent manner of all or part of the components of the conjugate, mention may particularly be made of benzoquinone, carbodiimide and more particularly EDC (1-ethyl-3-[3-dimethyl-aminopropyl]-carbodiimide hydrochloride), dimaleimide, dithiobis-nitrobenzoic acid (DTNB), N-succinimidyl S-acetyl thio-acetate (SATA), the bridging agents having one or more phenylazide groups reacting with the ultraviolets (U.V.) and preferably N-[-4-(azidosalicylamino)butyl]-3'-(2'-pyridyldithio)-propionamide (APDP), N-succinimid-yl 3-(2-pyridyldithio)propionate (SPDP), 6-hydrazino-nicotinamide (HYNIC).

Another form of coupling, especially for the radioelements, can consist in the use of a bifunctional ion chelator.

Among these chelates, it is possible to mention the chelates derived from EDTA (ethylenediaminetetraacetic acid) or from DTPA (diethylenetriaminepentaacetic acid) which have been developed for binding metals, especially radioactive metals, and immunoglobulins. Thus, DTPA and its derivatives can be substituted by different groups on the carbon chain in order to increase the stability and the rigidity of the ligand-metal complex (Krejcarek et al. (1977.); Brechbiel et al. (1991); Gansow (1991); U.S. Pat. No. 4,831,175).

For example diethylenetriaminepentaactic acid (DTPA) and its derivatives, which have been widely used in medicine and in biology for a long time either in their free form, or in the form of a complex with a metallic ion, have the remarkable characteristic of forming stable chelates with metallic ions and of being coupled with proteins of therapeutic or diagnostic interest such as antibodies for the development of radioimmunoconjugates in cancer therapy (Meases et al., (1984); Gansow et al. (1990)).

Likewise preferably, said at least one antibody forming said conjugate according to the invention is chosen from its functional fragments, especially the fragments amputated of their Fc component such as the scFv fragments.

The present invention moreover comprises the use of the composition according to the invention for the preparation of a medicament.

More particularly, according to another embodiment, the invention concerns the use of an antibody, or one of its functional fragments, and/or of a composition for the preparation of a medicament intended for the prevention or for the treatment of an illness induced by an overexpression and/or an abnormal activation of the IGF-IR and/or EGFR receptor, and/or connected with a hyperactivation of the transduction pathway of the signal mediated by the interaction of the 1-IGF1 or IGF2 with IGF-IR and/or of EGF with EGFR and/or HER2/neu.

In the present specification, by the object of the invention "use of a product or a composition for the preparation of a medicament intended for the prevention or for the treatment of a disease", it is also comprised "a method of preventing or treatment of such disease comprising the administration of said product or composition in a patient in need of such treatment"

Preferably, said use according to the invention is characterized in that the administration of said medicament does not induce or induces only slightly secondary effects connected with inhibition of the insulin receptor IR, that is to say inhibition of the interaction of the IR receptor with its natural ligands due to the presence of said medicament, especially by a competitive inhibition (connected with the attachment of said medicament to the IR.

The present invention moreover comprises the use of an antibody, or one of its functional fragments, preferably humanized, and/or of a composition according to the invention for the preparation of a medicament in tended to inhibit the transformation of normal cells into cells with tumoral character, preferably IGF-dependent, especially IGF1- and/or IGF2-dependent and/or EGF-dependent and/or HER2/neu-dependent cells.

The present invention likewise relates to the use of an antibody, or one of its functional fragments, preferably humanized, and/or of a composition according to the invention for the preparation of a medicament intended to inhibit the growth and/or the proliferation of tumor cells, preferably IGF-dependent, especially IGF1- and/or IGF2-dependent and/or EGF-dependent and/or estrogen-dependent, and/or HER2/neu-dependent cells.

In a general manner, a subject of the present invention is the use of an antibody, or one of its functional fragments, preferably humanized, and/or of a composition according to the invention, for the preparation of a medicament intended for the prevention or for the treatment of cancer preferably, expressing IGF-IR and/or EGFR, and/or of cancer preferably having a hyperactivation of the transduction pathway of the signal mediated by the interaction of IGF1 or IGF2 with IGF-IR, such as, for example, the overexpression of IRS1 and/or of EGF with EGFR.

The subject of the present invention is likewise the use of an antibody, or one of its functional fragments, preferably humanized, and/or of a composition according to the invention, for the preparation of a medicament intended for the prevention or for the treatment of psoriasis, psoriasis whose epidermal hyperproliferation can be connected with the expression or the overexpression of IGF-IR and/or EGFR, and/or with the hyperactivation of the transduction pathway of the signal mediated by the interaction of IGF-IR with its natural ligands (Wraight C. J. et al. Nat. Biotechnol., 2000, 18(5):521–526. Reversal of epidermal hyperproliferation in psoriasis by insulin-like growth factor I receptor antisense oligonucleotides) and/or of EGFR with its natural ligands.

Among the cancers which can be prevented and/or treated, prostate cancer, osteosarcomas, lung cancer, breast cancer, endometrial cancer or colon cancer or any other cancer overexpressing IGF-IR is preferred.

According to yet another aspect, a subject of the present invention is a method of diagnosis, preferably in vitro, of illnesses connected with an overexpression or an underexpression, preferably an overexpression, of the ICF-IR and/or EGFR receptor starting from a biological sample in which the abnormal presence of IGF-IR and/or EGFR receptor is suspected, characterized in that said biological sample is contacted with an antibody, or one of its functional fragments, according to the invention, it being possible for said antibody to be, if necessary, labeled.

Preferably, said illnesses connected with the overexpression of the IGF-IR and/or EGFR receptor in said diagnosis method will be cancers.

Said antibody, or one of its functional fragments, can be present in the form of an immunoconjugate or of a labeled antibody so as to obtain a detectable and/or quantifiable signal.

The antibodies labeled according to the invention, or their functional fragments include, for example, antibodies called immunoconjugates which can be conjugated, for example, with enzymes such as peroxidase, alkaline phosphatase, α-D-galactosidase, glucose oxydase, glucose amylase, carbonic anhydrase, acetylcholinesterase, lysozyme, malate dehydrogenase or glucose 6-phosphate dehydrogenase or by a molecule such as biotin, digoxygenin or 5-bromodeoxyuridine. Fluorescent labels can be likewise conjugated to the antibodies or to their functional fragments according to the invention and especially include fluorescein and its derivatives, fluorochrome, rhodamine and its derivatives, GFP (GFP for "Green Fluorescent Protein"), dansyl, umbelliferone etc. In such conjugates, the antibodies of the invention or their functional fragments can be prepared by methods known to the person skilled in tho art. They can be coupled to the enzymes or to the fluorescent labels directly or by the intermediary of a spacer group or of a linking group such as a polyaldehyde, like glutaraldehyde, ethylenediaminetetraacetic acid (EDTA), diethylene-triaminepentaacetic acid (DPTA), or in the presence of coupling agents such as those mentioned above for the therapeutic conjugates. The conjugates containing labels of fluorescein type can be prepared by reaction with an isothiocyanate.

Other conjugates can likewise include chemoluminescent labels such as luminol and the dioxetanes, bio-luminescent labels such as luciferase and luciferin, or else radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121}$, tellurium$^{122m}$, tellurium$^{125m}$, thulium$^{165}$, thulium$^{167}$, thulium$^{168}$, fluorine$^{18}$, yttrium$^{199}$, iodine$^{131}$, The methods known to the person skilled in the art existing for coupling the therapeutic radioisotopes to the antibodies either directly or via a chelating agent such as EDTA, DTPA mentioned above can be used for the radioelements which can be used in diagnosis. It is likewise possible to mention labeling with Na[I$^{125}$] by the chloramine T method [Hunter W. M. and Greenwood F. C. (1962) Nature 194:495] or else With technetium$^{99m}$ by the technique of Crockford et al. (U.S. Pat. No. 4,424,200) or attached via DTPA as described by Hnatowich (U.S. Pat. No. 4,479,930).

Thus, the antibodies, or their functional fragments, according to the invention can be employed in a process for the detection and/or the quantification of an overexpression or of an underexpression, preferably an overexpression, of the IGF-IR and/or EGFR receptor in a biological sample, characterized in that it comprises the following steps:

a) the contacting of the biological sample with an antibody, or one of its functional fragments, according to the invention; and
b) the demonstration of the IGF-IR and/or EGFR/antibody complex possibly formed.

In a particular embodiment, the antibodies, or their functional fragments, according to the invention, can be employed in a process for the detection and/or the quantification of the IGF-IR and/or EGFR receptor in a biological sample, for the monitoring of the efficacy of a prophylactic and/or therapeutic treatment of IGF- and/or EGF-dependent cancer or else of psoriasis.

More generally, the antibodies, or their functional fragments, according to the invention can be advantageously employed in any situation where the expression of the IGF-IR and/or EGFR receptor must be observed in a qualitative and/or quantitative manner.

Preferably, the biological sample is formed by a biological fluid, such as serum, whole blood, cells, a tissue sample or biopsies of human origin.

Any procedure or conventional test can be employed in order to carry out such a detection and/or dosage. Said test can be a competition or sandwich test, or any test known to the person skilled in the art dependent on the formation of an immune complex of antibody-antigen type. Following the applications according to the invention, the antibody or one of its functional fragments can be immobilized or labeled. This immobilization can be carried out on numerous supports known to the person skilled in the art. These supports can especially include glass, polystyrene, poly-propylene, polyethylene, dextran, nylon, or natural or modified cells. These supports can be either soluble or insoluble.

By way of example, a preferred method brings into play immunoenzymatic processes according to the ELISA technique, by immunofluorescence, or radio-immunoassay (RIA) technique or equivalent.

Thus, the present invention likewise comprises the kits or sets necessary for carrying out a method of diagnosis of illnesses induced by an overexpression or an underexpression of the IGF-IR and/or EGFR receptor or for carrying out a process for the detection and/or the quantification of an overexpression or of an underexpression of the IGF-IR and/or EGFR receptor in a biological sample, preferably an overexpression of said receptor, characterized in that said kit or set comprises the following elements:
a) an antibody, or one of its functional fragments, according to the invention;
b) optionally, the reagents for the formation of the medium favorable to the immunological reaction;
c) optionally, the reagents allowing the demonstration of IGF-IR and/or EGFR/antibody complexes produced by the immunological reaction.

The invention moreover relates to the, use of a composition as a combination product according to the invention, for the preparation of a medicament intended for the prevention or for the treatment of cancer, especially cancers for which said cytotoxic agent or said anti-HER2/neu antibody is generally prescribed and, especially, for which cancers the tumor cells express or overexpress the IGF-IR and/or EGFR receptor.

A subject of the invention is likewise the use of an antibody according to the invention for the preparation of a medicament intended for the specific targeting of a biologically active compound to cells expressing or overexpressing the IGF-IR and/or EGFR receptor.

It is intended here by biologically active compound to indicate any compound capable of modulating, especially of inhibiting, cell activity, in particular their growth, their proliferation, transcription or gene translation.

A subject of the invention is also an in vivo diagnostic reagent comprising an antibody according to the invention, or one of its functional fragments, preferably labeled, especially radiolabeled, and its use in medical imaging, in particular for the detection of cancer connected with the expression or the overexpression by a cell of the IGF-IR and/or EGFR receptor.

The invention likewise relates to a composition as a combination product or to an anti-IGF-IR and/or EGFR/toxin conjugate or radioelement, according to the invention, as a medicament.

Preferably, said composition as a combination product or said conjugate according to the invention will be mixed with an excipient and/or a pharmaceutically acceptable vehicle.

In the present description, pharmaceutically acceptable vehicle is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Preferably, these compounds will be administered by the systemic route, in particular by the intravenous route, by the intramuscular, intradermal, intraperitoneal or subcutaneous route, or by the oral route. In a more preferred manner, the composition comprising the antibodies according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

For the first time, data illustrating the recognition of IGF-IR and Insulin/IGF-I hybrid receptor by the same monoclonal antibody able to inhibit specifically, in vitro and in vivo, the tumoral growth, thus allowing to treat cancer, more particularly breast cancer, able to conjointly express the two receptor types are shown in the present example (see particularly example 26). Actually, the capacity of 7C10 and h7C10 to recognize and/or inhibit the tyrosine kinase activity of IGF-IR and Insulin/IGF-I receptor allow to avoid the escape of tumor consequent upon the expression of this hybrid receptor. Such an antibody could be an innovative therapeutic compound of a essential interest for the treatment of cancer.

Cancer pathologies are characterized by an uncontrolled cellular growth. In several cancer, growth factors are specifically binding with their receptors and then transmit growth, transformation and/or survival signals to the tumoral cell. The growth factor receptors over-expression at the tumoral cell surface is largely described (Solomon D S et al., Crit. Rev. Oncol. Hematol. 1995. 19: 183 ; Burrow S. et al., J. Surg. Oncol., 1998. 69 21 ; Hakam A. et al. Hum. Pathol, 1999. 30: 1128 ; Railo M. J. et al., Eur. J. Cancer, 1994. 30: 307 ; Happerfield L. C. et al., J. Pathol., 1997. 183: 412). This over-expression, leading to a direct perturbation of cellular growth regulation mechanisms, can also affect the Cell sensibility to induced apoptose by classical chemotherapies or radiotherapies.

During last few years, it has been show that the targeting of growth factor receptors, like EGF-R (for Epidermal growth factor receptor) or Her2/neu over-expressed on the tumoral cell surface, with respectively humanized (herceptin®) or chimeric (C225) antibodies results in an significant inhibition of the tumoral growth on patients and in a significant increase of the efficacity of classical chemotherapy treatments (Carter P. Nature Rev. Cancer, 2001. 1(2): 118; Hortobagyi G. N. Semin. Oncol., 2001. 28: 43; Herbst R. S. et al. Semin. Oncol., 2202. 29: 27). Other receptors like IGF-IR (for Insulin like growth factor receptor) or VEGF-R (for vascular endothelial growth factor receptor) have been identified as potential target in several preclinical studies.

More particularly, IGF-IR is part of the tyrosine kinase receptors. It shows a high homology with the Insulin receptor (IR) which exist under two isoforms A and B.

The IGF-IR and IR are tetrameric glycoproteins composed of two extracellular α- and two transmembrane β-subunits linked by disulfide bonds. Each α-Subunit, containing the ligand-binding site is approximately 130- to 135-kDa, whereas each β-subunit containing the tyrosine kinase domain is approximately 90- to 95-kDa. These receptors share more than 50% overall amino acid sequence similarity and 84% similarity in the tyrosine kinase domain. After ligand binding, phosphorylated receptors recruit and phosphorylate docking proteins, including the insulin receptor substrate-1 protein family (IRS1), Gab1 and Shc (Avruch 1998, Roth et al. 1988, White 1998, Laviola et al. 1997, Cheatham et al. 1995), leading to the activation of different intracellular mediators. Although both the IR and IGF-IR similarly activate major signalling pathways, differences exist in the recruitment of certain docking proteins and intracellular mediators between both receptors (Sasaoka et al. 1996, Nakae et al. 2001, Dupont and Le Roith 2001, Koval et al. 1998). These differences are the basis for the predominant metabolic effects elicited by IR activation and the predominant mitogenic, transforming and anti-apoptotic effects elicited by IGF-IR activation (De Meyts et al. 1995, Singh et al. 2000, Prisco et al. 1999, Kido et al. 2001). Insulin binds with high affinity to the IR (100-fold higher than to the IGF-IR), whereas insulin-like growth factors (IGF-I and IGF-2) bind to the IGF-IR with 100-fold higher affinity than to the IR.

The human IR exists in two isoforms, IR-A and IR-B, generated by alternative splicing of the IR gene that either excludes or includes 12 amino acid residues encoded by a small exon (exon 11) at the carboxy-terminus of the IR α-subunit. Thee relative abundance of IR isoforms is regulated by tissue specific and unknown factors (Moller et al. 1989, Mosthaf et al. 1990). IR-B is the predominant IR isoform in normal adult tissues (adipose tissue, liver and muscle) that are major target tissues for the metabolic effects of insulin (Moller et al. 1989, Mosthaf et al. 1990). IR-A is the predominant isoform in fetal tissues and mediates fetal growth in response to IGF-2 (Frasca et al. 1999), as also suggested by genetic studies carried out in transgenic mice (DeChiara et al 1990, Louvi et al,. 1997). Moreover, when cells transform and become malignant, dedifferentiation is often associated with an increased IR-A relative abundance (Pandini et al. 2002).

Given the high degree of homology, the insulin and IGF-I half-receptors (composed of one α- and one β-subunit) can heterodimerize, leading to the formation of insulin/IGF-I hybrid receptors (Hybrid-Rs) (Soos et al. 1990, Kasuya et al. 1993, Seely et al. 1995, Bailyes et al. 1997).

Both IR isoforms are equally able to form hybrids with IGF-IR. Hybrid-RsA and Hybrid-RsB, however, have different functional characteristics. Hybrid-RsB has reduced affinity for IGF-I and especially for IGF-2. In contrast, Hybrid-RsA has a high affinity for IGF-I and bind also IGF-2 and insulin at a physiological concentration range. The expression of Hybrid-RsA up-regulates the IGF system by two different mechanisms i) binding (with high affinity) and activation by both IGF-I and IGF-2 (which do not occur with the Hybrid-RsB), ii) activation of the IGF-IR pathway after insulin binding. Insulin binding lo Hybrid-RsA phosphorylates the ICF-IR β-subunit and activates an IGF-IR-specific substrate (CrkII) so that Hybrid-RsA shifts insulin to IGF-IR signaling (Pandini et al. 2002).

In several tissues, like liver, spleen or placenta, hybrid-Rs are more represented than IGF-IR (Bailyes. et al. 1997); As tumor tissues overexpress both IGF-IR and IR-A (Frasca et al. 1999, Sciacca et al. 1999, Veila. et al. 2001), Hybrid-RsA may also be overexpressed in a variety of human malignancies, including thyroid and breast cancers providing a selective growth advantage to malignant cells able to respond by a type IGF-IR signalisation following a stimulation by IGF-I and/or IGF-2 but also by insulin at physiological concentrations (Bailyes et al. 1997, Pandini et al. 1999, Belfiore et al. 1999, Frasca et al. 1999, Sciacca et al. 1999, Vella et al. 2001).

The realisation of such "therapeutic tools" able to block in the same time the two receptors is of particular interest as they swill allow to avoid the escape phenomena mediated by the expression in a same tumor of IGF-IR and hybrid receptors.

The present invention allows to jointly block the Insulin/IGF-I receptor and IGF-IR activity by generating a compound, and more particularly an antibody, of high affinity able to bind to said two receptors and also to block their activation by IGF-I, IGF-II or Insulin.

The present invention also deals with the use of an isolated antibody, according to the present invention, or a fragment thereof, said antibody or fragment being able to bind to i) human IGF-IR and/or to inhibit the natural binding of its ligands IGF-I and/or IGF-II, and/or also able to inhibit specifically the tyrosine kinase activity of said IGF-IR and ii) insulin/IGF-I hybrid receptors, and/or to inhibit the natural binding of their ligands IGF-I, IGF-II and/or Insulin, and/or also able to specifically inhibit the tyrosine kinase activity of said Insulin/IGF-I receptors.

More particularly, in a preferred embodiment, said antibody is characterized in that it comprises the sequences of the 7C10 and h17C10 antibodies anti-IGF-IR, and fragment thereof, of the present invention, notably the antibodies anti-IGF-IR according to the present invention having a light chain comprising at least a CDR region selected in the group consisting in SEQ ID No. 2, 4 or 6 (or at least a CDR with at least 80% of homology after optimal alignment with SEQ ID No. 2, 4 or 6), and/or a heavy chain comprising at least a CDR region selected in the group consisting in SEQ ID No. 8, 10 or 12 (or at least a CDR with at least 80% of homology after optimal alignment with SEQ ID No. 8, 10 or 12).

According to another preferred embodiment, said antibody is used for cancer therapy, more particularly breast cancer therapy.

Actually, it is known that breast tumoral cells specifically present on their surface IGF-IR but also a great number of Insulin receptor and, as a consequence, a great number of Insulin/IGF-I Hybrid receptors (Frasca et al. 1999, Sciacca et al. 1999, Vella et al. 2001).

The antibody, or fragments thereof, could be use alone or in association with another antibody able to target another growth factor implied in, the proliferation or dissemination of tumoral cells. It could also be used in association with a chemotherapeutic agent or another tyrosine kinase inhibitor in co-administration or in the form of an immuno-conjugate, said agent being chemical, biological and/or natural. Fragments of said antibody could also be use in bispecific antibodies obtained by recombinant mechanisms or biochemical coupling, and then associating the specificity of the above described antibody with the specificity of other antibodies able to recognise other receptors involved in the proliferation, the angiogenese or any other mechanisms involved in the tumoral development.

Particular aspect of the present invention: Cytotoxic and/or cytostatic active agent coupled to an addressing system, particularly to the antibodies 7C10, C7C10 or h7C10, or fragment thereof, according to the present invention capable of binding specifically to the human insulin-like growth factor-1 receptor IGF-IR and Insulin/IGF-I hybrid receptor The present invention relates also to novel compounds comprising a cytotoxic and/or cytostatic active agent coupled to an addressing systems. More particularly, the present invention relates to a compound comprising a Vinca alkaloid coupled to an antibody capable of binding specifically to the human insulin-like growth factor-1 receptor IGF-IR and/or capable of specifically inhibiting the tyrosine kinase activity of said IGF-IR receptor, in particular a monoclonal antibody of murine, chimeric, primatized, humanized and human origin. The invention also relates to the mode of coupling of the elements of said compound and also comprises the use of these compounds as a medicinal product for the prophylactic and/or therapeutic treatment of cancer, more particularly of cancers overexpressing IGF-IR, or of any pathological condition associated with overexpression of said receptor.

Currently, along with surgery and radiotherapy, chemotherapy represents one of the most effective means of combating cancer. Many cytotoxic and/or cytostatic agents have been isolated or synthesized and make it possible to destroy or reduce, if not definitively, at least significantly, the tumour cells. However, the toxic activity of these agents is not limited to tumour cells, and the non-tumour cells are also effected and can be destroyed. More particularly, side effects are observed on rapidly renewing cells, such as haematopoietic cells or cells of the epithelium, in particular of the mucous membranes. By way of illustration, the cells of the gastrointestinal tract are largely effected by the use of cytotoxic agents.

One of the aims of the present invention is also to be able to provide a compound which makes it possible to limit the side effects on normal cells while at the same time conserving a high cytotoxicity on tumour cells.

According to an original approach, the applicant, rather than developing new molecules, has sought to overcome the problem of toxicity of known molecules by limiting to tumour cells the access of said molecules. To do this, the applicant has developed an antibody-type addressing system for targeting only tumour cells.

One of the advantages of this approach is to be able to use known cytotoxic agents which are well defined in pharmacological and pharmacokinetic terms. In addition, it is then possible to use strong cytotoxic agents which until now have been neglected in favour of cytotoxic agents which are less strong but which have a better therapeutic index (and therefore exhibit, fewer side effects).

Another advantage lies in the use of an antibody, i.e. of a product of biological origin which does not add any toxicity to that of the cytotoxic agent. In addition, as will be subsequently developed, the choice of the antibody makes it possible to accumulate with the action of the cytotoxic agent its own biological activity.

The applicant has demonstrated that the use of a Vinca alkaloid coupled to an addressing device is of value in chemotherapy.

According to a first aspect, a subject of the present invention is a compound comprising at least one molecule of active agent coupled to an addressing system, said at least one molecule of active agent being a strong cytotoxic and/or cytostatic compound chosen from Vinca alkaloids, and said addressing system being a polyclonal or monoclonal antibody, which may be bispecific, or a functional fragment thereof, capable of targeting, preferably specifically, tumour cells.

An advantage of a compound according to the invention is that the active agent is directly brought to the target cells by the antibody and, besides the fact that it does not degrade the other cells, its biological activity is not decreased.

One of the advantages associated with using antibodies as an addressing system is that it is possible to couple several active agents to them, thus increasing the efficacy of the compound. Specifically, since the compound is brought directly to the target cells, the fact that there are several active agents will not lead to an increase in side effects, but only to an increase in the desired in situ effect on the tumour cells.

By way of non-limiting examples of targeting antibodies which can be used according to the invention, mention may be made, without any limitation, of the CeaVac antibodies directed against colorectal tumour cells, and the Y Theragyn/pemtumomab and OvaRex antibodies directed against ovarian tumour cells.

The present invention relates to a compound as described above, which comprises from 1 to 50 molecules of active agent, preferably from 1 to 10, and better still from 1 to 6. The choice of the number of molecules of, active agent depends, inter alia, on the molecular weight of each of the elements. For example, by way of indication, for an antibody of IgG1 type with a molecular weight of 150 000 Da, it is preferred to couple from 4 to 6 molecules of vinblastine with a molecular weight of 900 Da (Petersen et al., Cancer Res., 1991, 51:2286). If the antibody is conjugated with too large an amount of cytotoxic agents, there is a risk that said agents will mask the recognition site for the antigen and decrease its activity.

In practice, the compound which is the subject of the invention is used as a medicinal product, and more particularly as an medicinal product intended for the treatment of cancer.

The present invention differs from the prior art not only in the sense that the choice of the antibody is aimed at targeting tumour cells as described above, but also in that said antibody exhibits an intrinsic activity on the tumour cells.

According to another embodiment of the invention, the compound as described above is also capable of inhibiting tumour cell proliferation and/or apoptotic function restoration by blocking transduction signals, the progression of cells in the cell cycle and/or membrane-bound receptor availability (phenomena of internalization and of degradation of said receptor), or of reverting an apoptosis-resistant phenotype in the case of an antibody directed against the IGF-IR, insofar as it is widely described that overexpression of this receptor confers on tumour cells a means of withstanding apoptosis and in particular apoptosis induced by chemotherapy compounds (Beech D. J. et al., Oncology reports, 2001, 8:325–329; Grothe A. et al., J. Cancer Res. clin Oncol., 1999, 125:166–173). Another mechanism of action of the compound as described above may be associated with the Fc portion of the antibody, if a whole antibody is used, and may consist of the setting up of effector mechanisms such as ADCC (antibody-dependent cellular cytotoxicity) and CDC (complement-dependent cytotoxicity).

By way of non-limiting example of antibodies, mention may be made of, Avastin/Bevacizumab which acts on colorectal cancers by interfering with tumour angiogenesis, Rituxan/rituximab, the activity of which is mainly related, to the effector functions of the molecule, and in particular ADCC, and also Herceptin/Lrastuzumab which acts by inhibition of signal transduction end inhibition of cell progression in the cell cycle, and also, in large part, by initiating ADCC mechanisms.

Vinca alkaloids correspond to the family of natural compounds of which vinblastine, vincristine, anhydrovinblastine and leurosine, which are present in considerable amounts in plants, are demonstrative examples.

The term "Vinca alkaloids" should also be understood to mean all the derivatives present in small amounts, such as deoxyvinblastine or leurosidine, taken by way of non-limiting examples. It should also be understood to mean derivatives of natural structure but which are obtained by synthesis, such as, without any limitation, anhydrovinblastine.

The term "Vinca alkaloid" should also be understood to mean all the compounds derived from these natural compounds by chemical or biochemical modification in one or more steps. These modifications may affect the "vindoline" component or the "velbanamine" component or both components simultaneously. The Vinca alkaloids, as such, are known to those skilled in the art (Antitumor Bisindole Alkaloids from Catharanthus roseus (L.)). The Alkaloids, Brossi A. et al., M. Ed. Academic Press Inc. San Diego, vol. 37, 1990; Jacquesy J. C. et al., Biomedical Chemistry: Applying Chemical Principles to the Understanding and Treatment of Disease, edited by Torrence, P. F., John Wiley and Sons Inc.: New York, 2000, pp. 227–246;, Fahy J. et al., J. Current Pharm. Des., 2001, 7:1181–97; Duflos A et al., Novel Aspects of Natural and Modified Vinca Alkaloids, Curr. Med. Chem.—Anti-Cancer Agents, 2002, 2:55–70).

The preferred derivatives according to the present invention are those which exhibit a pharmacological advantage established by virtue of cytotoxicity assays or activity assays on certain specific targets, such as tubulin, or which have demonstrated advantages in in vivo tests on animals. Among these compounds, mention may be made of the derivatives currently used in anticancer chemotherapy: vinblastine, vincristine, vindesine and vinorelbine, and also the derivatives which have demonstrated an advantage in clinical studies, such as vinepidine, vinfosiltine, vinzolidine and vinflunine.

The invention is therefore partly based on the choice of an original cytotoxic agent without any bias from the prior art.

More particularly, a subject of the present invention is a compound as described above, in which said Vinca alkaloid is selected from vinblastine, deoxyvinblastine, deoxyleurosidine, vincristine; vindesine, vinorelbine, vinepidine, vinfosiltine, vinzolidine and vinflunine.

The subject of the invention has, more specifically, been demonstrated and exemplified using deoxyvinblastine and its 4'-S isomer, commonly known as deoxyleurosidine.

The structure of each of these two compounds has been described for many years, but their pharmacological activity is considered to be moderate or weak (Neuss N. et al., Tetrahedron Letters, 1968, No. 7, pp 783–7; U.S. Pat. No. 4,143,041, Eli Lilly and Company, Filed Nov. 25, 1977; and recently, Kuehne M. E. et al., J. Org. Chem., 1989, 54, 14:3407–20; Kuehne M. E., Org. Biomol. Chem., 2003 1:2120–36). Their real advantage as a compound with unquestionable antitumour pharmacological activity has never been described and demonstrated by in vivo experiments on murine tumour models.

The present invention therefore relates to a compound as described above, in which said vinca alkaloid is (4'-R) deoxyvinblastine and/or (4'-S) deoxyleurosidine.

The greater activity of these two derivatives has been demonstrated against P388 murine leukaemia grafted intravenously on day 0. The compound is administered intraperitoneally in a single dose on day 1. The protocol for this test is described by Kruczynski A. et al., Cancer Chemotherapy and Pharmacology, 1998, volume 41, pages 437 to 447.

Conventionally, the in vivo activity of cytotoxic compounds is expressed by the T/C at a dose expressed in mg per kg. The T/C corresponds to the ratio, multiplied by 100, of the median of the survival time of the treated animals to the median of the survival time of the control animals.

By way of example, for cytotoxic agents used to date, the maximum activity of vinblastine sulphate is expressed at tile dose of 5 mg/kg, with T/C=143. The maximum, activity of vincristine sulphate is expressed at the doses of 1.25 and 2.5 mg/kg, with T/C=143 in both cases.

Unexpectedly, the maximum activity of deoxyvinblastine ditartrate is expressed at the dose of 20 mg/kg, with T/C=214 and the maximum activity of deoxyleurosidine ditartrate is expressed at the dose 2.5 mg/kg, with T/C−200.

In view of these results, the present invention therefore relates to the use of (4'-R) deoxyvinblastine and/or (4'-S) deoxyleurosidine, collectively referred to as deoxyvinblastine in the remainder of the description, for treating cancer.

According to a preferred form, as described above, the present invention envisages the coupling of deoxyvinbiastine to a compound of the monoclonal or polyclonal, preferably monoclonal, antibody type.

More particularly, as will subsequently be described, a preferred antibody making up the compound which is the subject of the present invention is a monoclonal or polyclonal, preferably monoclonal, antibody which will recognize the IGF-IR specifically and with high affinity, and which will have the ability to inhibit the growth of tumours, more particularly of tumours expressing the IGF-IR.

The cytoplasmic protein tyrosine kinases are activated by binding of the ligand to the extracellular domain of the receptor. Activation of the kinases leads, in turn, to stimulation of various intracellular substrates, including IRS-1, ISR-2, Shc and Grb 10 (Peruzzi F. et al., J. Cancer Res. Clin. Oncol., 125:166–173, 1999). The two major substrates for the IGF-IR are IRS and Shc, which mediate, by activation of many downstream effectors, most of growth and differentiation effects associated with the binding of IGFs to this receptor. Substrate availability can, consequently, dictate the final biological effect associated with activation of the IGF-IR. When IRS-1 predominates, the cells tend to proliferate and to transform. When Shc dominates, the cells tend to differentiate (Valentinis B. et al., J. Biol. Chem., 274: 12423–12430, 19999). It appears that the pathway mainly implicated for the effects of protection against apoptosis is the phosphatidylinositol 3-kinases (PI 3-kinases) pathway (Prisco M. et al., Horm. Metab. Res., 31:80–89, 1999; Peruzzi E. et al., J Cancer Res. Clin. Oncol., 125:166–173, 1999).

According to a preferred embodiment, a subject of the present invention is a compound as described above (cytotoxic and/or cytostatic active agent coupled to an addressing system), comprising an antibody capable of recognizing the IGF-IR specifically and with high affinity. This antibody will interact little or not at all with the insulin receptor IR. Its binding should inhibit, in vitro, the growth of tumours expressing the IGF-IR by interacting mainly with the signal transduction pathways activated during IGF1/IGF-IR and IGF2/IGF-IR interactions. This antibody should be active in vivo on all tumour types expressing the IGF-IR, including oestrogen-dependent breast tumours and prostate tumours, which is not the case for the anti-IGF-IR monoclonal antibodies (referred to as MAb or MAB) currently available. In fact, αIR3, which is a reference in the IGF-IR field, completely inhibits the growth of oestrogen-dependent breast tumours (MCF-7) in vitro, but has no effect on the corresponding in vivo model (Artega C. et al., J. Clin. Invest., 84:1418–1423, 1989). Similarly, the scFv-Fc fragment derived from the murine monoclonal 1H7 is only weakly active on the MCF-7 breast tumour and completely inactive on an androgen-independent prostate tumour (Li S. L. et al., Cancer Immunol. Immunother., 49:243–252, 2000).

According to a preferred embodiment, a subject of the present invention is a compound (cytotoxic and/or cytostatic active agent coupled to an addressing system) as described above, comprising an antibody, or one of its functional fragments, said antibody or one of its said fragments being capable of binding specifically to the human insulin-like growth factor-I receptor IGF-IR and, where appropriate, capable of inhibiting the natural binding of the IGF-IR ligands IGF1 and/or IGF2, and/or capable of specifically inhibiting the tyrosine kinase activity of said IGF-IR receptor.

Such a compound has a double advantage.

Firstly, it makes it possible, as described above, to bring the cytotoxic agent directly to tumour cells, more particularly tumour cells overexpressing the IGF-IR, and thus to decrease the side effects in normal cells.

Secondly, its mode of action is not limited to targeting. The compound which is the subject of the present invention cumulates the action of the cytotoxic agent which makes it possible to destroy the tumour cells and the action of the antibody which will inhibit the growth of tumour cells, preferably of tumour cells expressing the IGF-IR, by interacting with the signal transduction pathways, and will make it possible to decrease the resistance to apoptosis of cells overexpressing the receptor for IGF-I and, consequently, to improve the activity of chemotherapy drugs, part of the mechanism of action of which lies in the induction of apoptosis.

According to a preferred embodiment of the compound (cytotoxic and/or cytostatic active agent coupled to an addressing system) which is the subject of this particularly object of the present invention, the monoclonal antibody, or one of its functional fragments, is the 7C10, a C7C10 or a h7C10, or fragment thereof, or their derived antibodies, as described in the first part of the present specification directed to the antibodies anti-IGR-IR of the present invention In this respect, the applicant filed a French patent application FR 03/08538 on Jul. 11, 2003 for "Novel antitumour immunoconjugates". The content of this patent application is incorporated herein by way of reference.

Immunoliposomes containing such particular cytotoxic and/or cytostatic agents, such as described above, such as the vinca alkaloids, and of addressing them to tumour cells by means of antibodies or of antibody fragments attached to their surface are comprised in the present invention.

Method of treatment of cancer, particularly the preferred cancers cited above, comprising the administration of the present immunoliposomes forms also part of the present invention.

The antibodies or antibody fragments used are directed against antigens overexpressed at the surface of tumour cells and/or surface antigens the expression of which is restricted to tumour cells. They are preferably directed against tyrosine kinase receptors, and more particularly against the receptors for IGF-I, EGF or else VEGF. A preferred antibody is a monoclonal or polyclonal, preferably monoclonal, or even humanized, antibody which will recognize the IGF-IR specifically and with high affinity. Even more preferably, this antibody consists of the antibody anti-IGR-IR which is the subject of the present invention described in the first part of the specification.

According to another embodiment of the compound (cytotoxic and/or cytostatic active agent coupled to an addressing system) which is a subject of the present invention, the monoclonal antibody as described above is also capable of binding specifically to the human epidermal growth factor receptor, EGFR, and/or capable of specifically inhibiting the tyrosine kinase activity of said EGFR receptor.

According to a preferred aspect of this embodiment of the compound(cytotoxic and/or cytostatic active agent coupled to an addressing system), the coupled monoclonal antibody consists of a bispecific antibody comprising a second unit which specifically inhibits the binding of EGF to the EGFR and/or which specifically inhibits the tyrosine kinase activity of said EGFR receptor.

In a preferred embodiment of the invention, the bispecific antibody which can be used here for cytotoxic and/or cytostatic active agent coupled to an addressing system according to this invention is those as described in the first part of the present specification related to bispecific antibodies of the invention.

Another aspect of the invention concerns the mode of coupling between the antibody and the cytotoxic agent. Whatever the nature of the coupling, which may be direct or indirect, stable or labile, it should in no way impair the respective biological functions of the antibody and of the cytotoxic agent. It is clearly understood that any coupling satisfying this characteristic, and known to those skilled in the art, is included in the scope of the present patent application. In addition, the coupling, and more particularly the linkage used, must allow release of the deoxyvinblastine, in the 4-deacetylated or 3-acid, or 4-deacetylated and 3-acid, form, or in the form of one of these forms carrying all or part of said linkage used, in the target cells.

According to a preferred embodiment, the coupling is chemical coupling. More particularly, said chemical coupling is composed of an anchorage on the Vinca alkaloid, an anchorage on the antibody and a linkage connecting these two anchorages.

The term "linkage" should be understood to mean any structure capable of providing a bond of whatever possible nature between the two elements of the compound, namely a chemical molecule and an antibody.

In terms of the anchorage on the Vinca alkaloid, several possibilities are envisaged. Mention may, for example, be made of an anchorage on the alcohol function in the 4-position after deacetylation of the 4-acetoxy group of said Vinca alkaloid.

In another embodiment, the anchorage on the vinca alkaloid is effected on the acid function in the 3-position after deacetylation of the 4-acetoxy group and demethylation of the ester function in the 3-position of said Vinca alkaloid.

According to yet another embodiment of the invention, the anchorage on the Vinca alkaloid is effected on the acid function in the 3-position directly by reaction on the ester function in the 3-position of said Vinca alkaloid.

According to yet another embodiment of the invention, the anchorage on the vinca alkaloid is effected via an ester or thioester function on the hydroxyl function in the 3-position.

An additional embodiment consists in effecting the anchorage on the Vinca alkaloid via an amide function or an ester function or a hydrazide function on the acid function in the 4-position.

As regards the anchorage on the antibody, it should in no way denature the antibody, so as not to decrease its ability to recognize and interact with the tumour cells.

To do this, it is preferable for the anchorage on the antibody to be effected on the oligosaccharides, the lysines and/or the aspartic acid and glutamic acid residues.

The Vinca alkaloid may also be coupled on the carboxylic functions of the antibody, carried by the aspartic acid and glutamic acid residues of the antibody. For example, an amine, hydrazide or hydrazine derivative of the Vinca alkaloid will be coupled on these residues in the presence of a compound of carbodiimide type, such as N-(3-dimethylaminopropyl)-N'-ethylcarbodiimide (or EDAC).

In practice, it is even more preferable to effect the anchorage on the oligosaccharides present on the antibody. Specifically, there are no oligosaccharides in the recognition sites of the antibody and, as a result, there is no risk of impairing the recognition/biological activity capacities of said antibody. According to a preferred embodiment of the invention, the anchorage is effected on the oligosaccharides present on the asparagines (Asn) which are followed by a consensus sequence consisting of an amino acid and a serine or a threonine. For example, without any limitation, a preferred anchorage on the IgG1 antibody used in the invention is on Asn297.

A combined anchorage, i.e. an anchorage on oligosaccharides, lyines and/or aspartic acid and glutamic acid, is also covered.

An additional embodiment consists in greatly increasing the density of the Vinca alkaloid in order to attain 10 to 50 mol per mole of antibody. Mention may be made of the coupling of a hemisuccinate derivative of the Vinca alkaloid on a lysine polymer (Poly-L-Lys or Poly-D-Lys). The conjugate thus obtained is then coupled on the oligosaccharides of the antibody, oxidized beforehand with meta-periodate.

In another embodiment, a hydrazide derivative of the Vinca alkaloid may be coupled on a dextran oxidized beforehand with meta-periodate. The conjugate obtained is then coupled to the antibody via the lysine residues.

According to yet another embodiment, a hemisuccinate derivative of the Vinca alkaloid may be coupled on a dextran activated beforehand by controlled oxidation with meta-periodate and then substituted with a compound of diamide type. The conjugate obtained is then coupled on the lysine residues of the antibody.

According to a preferred embodiment of the invention, the anchorage on the antibody is effected by reaction of an amine function, a hydrazine function, a hydrazide function or an acid function which has been activated.

More particularly, the anchorage on the antibody is effected by reaction of an epoxide function or of a disulphide function, a sulphide function or an acid function which has been activated, with a nitrogen-containing residue or with a hydroxyl residue or with a thiol residue of said antibody.

Mention may also be made, in a nonlimiting manner, of other linkages which may also be used to covalently attach the Vinca alkaloids to the antibodies or to their functional fragments (Garnett et al., Adv. Drug Deliv. Rev., 2001, 171–216), such as aldehydes which make it possible to form Schiff bases, which can then be stabilized by reduction with sodium borohydride or cyanoborohydride; disulphides which have the advantage of being able to release the Vinca alkaloids inside the tumour cell by virtue of the intracytoplasmic reducing environment; more stable thioethers; more labile thioesters; linkages which are labile in acidic medium, which have the advantage of allowing release of the cytotoxic agent in the tumour, which is generally more acid, or during the passage from the endosome (pH 6.0 6.8) to the lysosome (pH 4.5 5.5), or else enzyme-degradable linkages which have the advantage of being stable in the serum and of releasing the cytotoxic agent in the intracellular medium of the tumour cell.

Mention may also be made of peptide sequences of the Ala Leu type, which can be cleaved by lysosomal hydrolases (Masquelier et al., J. Med. Chem., 1980, 23:1166–1170) or else linkages of the hydrazone type, such as those used in the gemtuzumab ozogamicin immunoconjugate used in the treatment of certain types of leukaemia and sold under the name Mylotarg (Hamann et al., Bioconjugate Chem., 2002, 13:47).

As described above, a preferred form of the invention uses a linkage which allows release, of the deoxyvinblastine in the tumour cells.

A first means for achieving this consists in using a linkage connecting the two anchorages which consists of a peptide chain. In fact, such a peptide linkage will be degraded/hydrolysed in the target cells by the enzymes of the endosomes and of the lysosomes.

According to another embodiment of the invention, the linkage connecting the two anchorages consists of a linear or branched carbon-based chain. In the latter case, it is envisaged that one or more aromatic, ethylenic or acetylenic groups and also one or more ketone, amide, ester, hydrazide, hydrazone, amine, ether, sulphide or disulphide groups are included in the carbon chain in a distinct or combined manner. For example, in the case of an attachment via a disulphide bridge, it is the reducing medium which will allow cleavage of the linkage and release of the deoxyvinblastine.

In all cases, only the linkage is destroyed in order to release the active principle, said active principle and the antibody themselves remaining intact.

According to yet another embodiment, there is no linkage, but the Vinca alkaloid is coupled directly with a nitrogen-containing residue or with a hydroxyl residue or with a thiol residue of the antibody.

The advantage of such a direct coupling lies in the absence of anchorage linkage and, consequently, in the absence of an immune reaction by the patient against this linkage. The appearance of anti-linkage antibodies secreted by the body in response to the intrusion of said linkage is thus, for example, avoided.

More particularly, the compound according to the invention is characterized in that the acid function in the 4-position of the Vinca alkaloid is coupled, via a hydrazide function, with an aldehyde residue of the antibody, generated beforehand.

The invention also relates to a pharmaceutical composition comprising, as active principle, a compound consisting of a Vinca alkaloid coupled to an antibody, or one of its functional fragments, according to the invention, to which a pharmaceutically acceptable excipient and/or vehicle is preferably added.

The present invention also comprises the use of the compound according to the invention for preparing a medicinal product.

More particularly, according to another embodiment, the invention relates to the use of a compound as described above and/or of a composition comprising such a compound, for preparing a medicinal product intended for the prevention or treatment of cancers, in particular cancers induced by overexpression and/or activation of the IGF-IR and/or EGFR receptor which is abnormal, and/or associated with hyperactivation of the signal transduction pathway mediated by the interaction of IGF1 or IGF2 with IGF-IR and/or of EGF with EGFR.

Among the cancers which may be prevented and/or treated, prostate cancer, osteosarcomas, lung cancer, breast cancer, endometrial cancer or colon cancer, or any other cancer overexpressing IGF-IR, is preferred.

Other characteristics and advantages of the invention appear in the continuation of the description with the examples and the figures whose legends are represented below.

LEGENDS TO THE FIGURES

FIG. 1: Schematic representation of IGF-IR.

FIG. 2: Scheme of the transduction of the signals mediated by IGF-IR during the attachment of IGFs.

FIGS. 3A, 3B and 3C: Recognition of native IGF-IR expressed on the surface of MCF-7 cells by the monoclonal antibody 7C10.

For this experiment, the MCF-7 cells are incubated with the 7C10 antibody or with a negative control antibody, then recovered with the aid of a fluorescent anti-species secondary antibody. The labeling is read on a FACS. The first histogram (FIG. 3A) corresponds to the MCF-7 cells alone. In the second histogram (FIG. 3B), the unshaded curve corresponds to the nonspecific labeling by a control isotype murine antibody. In the third histograin (FIG. 3C), the unshaded curve shows the recognition of IGF-TR by MAB 7C10.

FIGS. 4A, 4B and 4C: Labeling of Sf9 insect cells respectively expressing IGF-IR or IR.

FIG. 4A shows the labeling of nontransfected cells alone (1) or cells labeled with control commercial monoclonal antibodies respectively recognizing IGF-IR (2) or IR (3). In FIG. 4B, Sf9 cells uniquely expressing IGF-IR are labeled with aIR3 (2) or anti-IR(3), the peak (1) representing the single cells. In FIG. 4C, Sf9 cells uniquely expressing TR are labeled with an anti-IR (3) or aIR3 (2), the peak (1) representing the single cells.

FIG. 5: Inhibitor effect of 7C10 antibody on the proliferation of MCF-7 cells induced by IGF-I.

The MCF-7 cells are incubated in the presence of increasing concentrations of IGF1 in the presence or in the absence of the MAB to be tested. The cell proliferation is evaluated by following the incorporation of $^3$H thymidine. The commercial antibody aIR3 is used as a positive control of the experiment. The 7G3 is a murine anti-IGF-IR IgG1 without activity on proliferation and used as a control isotype.

FIGS. 6A, 6B and 6C:

FIG. 6A: in vivo effect of the monoclonal antibody 7C10 on the growth of MCF-7 tumors established in nude mice;

FIGS. 6B and 6C: figures respectively from publications of Arteaga et al. (J. Clin. Invest., 84, 1418–1423, 1989) and from Li et al. (Cancer Immunol. Immunother., 49, 243–252), and showing for FIG. 6B the effect of murine aIR3 (likewise written aIR3) and for FIG. 6C the effect of a recombinant scFv-Fc derived from the 1H7 antibody on tumor growth.

FIG. 7: Comparative study of the effect: of the MAb 7C10 and of tamoxifen on the growth in vivo of the tumor MCF-7.

FIGS. 8A, 8B and 8C: Study of the antitumor activity of the murine antibody 7C10 in different xenograft models of tumor cells in vivo.

FIG. 8A shows the results obtained on an osteosarcoma model SK-ES-1, FIG. 8B concerns an androgen-independent tumor of the prostate DU-145 and FIG. 8C a model of non-small cell tumor of the lung A549. In these three models, the treatment was carried out twice per week i.p. at a rate of 250 µg/dose/mouse. The curves-7G3, EC2 and 9G4 correspond respectively to three murine IgG1 used as an experiment control isotype in each of the models.

FIG. 9: Study of the antitumor effect of the MAb 7C10. compared to navelbine (vinorelbine) as well as the synergy of the two compounds on the growth in vivo of the line A549.

FIG. 10: Comparative activity of MAb aIR3, 7C10 and 1H7 on the IGF-2 proliferation induced by MICF-7 cells.

FIG. 11: Comparison of the murine 7C10 and chimeric C7C10 MAb for the inhibition of the IGF1 proliferation of MCF-7 cells in vitro. The antibody 9G4 is a murine IgG1 used as an experiment control isotype.

FIG. 12: Comparative effect of the 7C10 and h7C10 MAb (humanized 1, written here 7H2HM) on the in vitro model of IGF1-induced proliferation of MCF-7 cells.

FIG. 13: Effect of the 7C10 and h7C10 MAb (humanized 1, written here 7H2HM) on the transduction of the signal induced by IGF1. The first line of spots corresponds to the revelation, by an antiphospho-tyrosine antibody, of the phosphorylation of the inmunoprecipitatied β chain from the cells incubated in the presence of IGF1 alone or of IGF1 mixed with various antibodies to be tested. The 9G4 and the hIgG1 are respectively the control isotypes of the forms 7C10 and h7C10 (likewise written 7H2HM). The second line of spots corresponds to the revelation of the β chain and shows that the quantity deposited in all of the wells is perfectly equivalent.

FIG. 14: Sequence of the cDNA (SEQ ID No. 48), of its complementary strand (SEQ ID No. 50) and its translation into amino acids (SEQ ID No. 49), of the PCR fragment amplified from the mouse hybridoma 7C10 with the primers MKV-1 and MKC and which codes for the 3' end of the loader peptide and 7C10 VL.

FIG. 15: Sequence of the cDNA (SEQ ID No. 51), of its complementary strand (SEQ ID No. 53) and its translation into amino acids (SEQ ID No. 52), of the PCR fragment amplified from the mouse hybridoma 7C10 with the primers MHV-12 and MHC-1, or MHV-8 and MHC-1 and which codes for the 3' end of the leader peptide and 7C10 VH.

FIG. 16: Recognition of the IGF-I receptor by the chimeric antibody *7C10, likewise called C7C10 (supernatant of cos7-transfected cell culture).

FIG. 17: Comparison of the amino acid sequence of mouse 7C10 VL (SEQ ID No. 54) with cells of other mouse antibodies having the greatest sequence homology.

The numbering of the amino acids is that of Kabat et al. (1991). The residues in the framework regions (outside CDRs) which differ between 7C10 VL and Kabat mouse subgroup II (SEQ ID No: 57) are underlined. A dot indicates that the residue is identical at this position in comparison with the sequence of 7C10 VL. DRB1-4.3 (SEQ ID No. 55) represents the sequence of the light chain of an anti-human mouse antibody MHC CLASS TT B-Chain (access number in the Kabat databank is N011794). C94-5B11' CL (SEQ ID No. 56) represents the sequence of the light chain of a mouse antibody (access number in the Kabat databank is P019314).

FIG. 18: Comparison of amino acid sequences of mouse 7C10 VL (SEQ ID No. 54) with cells of human light chains belonging to Kabat human subgroup II (SEQ ID No. 60) and having the greatest sequence homology.

The amino acid sequences are aligned and compared with that of mouse 7C10 VL. A dot indicates that the residue is identical at this position in comparison with the sequence of 7C10 VL. GM607 (SEQ ID No. 58) represents the sequence of the kappa light chain secreted by the human lymphoblastoid line GM607 (Klobeck et al., Nucleic Acids Res., 12:6995–7006, 1984a and Klobeck et. al., Nature, 309: 73–76, 1984b, the access number in the Kabat databank is N011606). DPK15/A19 (SEQ ID No. 59) represents the sequence of the human V germinal line kappa II.

FIG. 19: Comparison of amino acid sequences of variable regions of the light chains (VL) of mouse 7C10 (SEQ ID No. 54), of human antibody GM 607 (SEQ ID No. 58) and of two versions of humanized 7C10 1 and 2 (SEQ ID Nos. 61 and 65).

The amino acid sequences are aligned and compared with that of mouse 7C10 VL. A dot indicates that the residue is identical at this position in comparison with the sequence of 7C10 VL. GM607 represents the sequence of the kappa light chain secreted by the human lymphoblastoid line GM607 (Klobeck et al., 1984a and 1984b, access number in the Kabat database: N011606).

FIG. 20: cDNA sequence (SEQ ID No. 62), its complementary strand (SEQ ID No. 64) and its translation into amino acids (SEQ ID No. 63), of the gene constructed by de novo assembly coding for the leader peptide and the humanized version 1 of 7C10 VL.

FIG. 21: cDNA sequence (SEQ ID No. 66), its complementary strand (SEQ ID No. 68) and its translation into amino acids (SEQ ID No. 67), of the gene constructed by de novo assembly coding for the leader peptide and the humanized version 2 of 7C10 VL.

FIG. 22: Comparison of the amino acid sequences of mouse 7C10 VH (SEQ ID No. 69) with those of human mouse heavy chains belonging to Rabat mouse subgroup I(A) and having the greatest sequence homology.

The numbering of the amino acids is that of Kabat et al. (1991). The residues in the framework regions (outside CDRs) which differ between 7C10 VF and Kabat mouse subgroup I(A) (SEQ ID No. 71) are underlined. A dot indicates that the residue is identical at this position in comparison with the sequence of mouse 7C10 VH. AN03'CL (SEQ ID No. 70) represents the sequence of the heavy chain of a mouse antibody (access number in the Kabat databank: P001289).

FIG. 23: Comparison of amino acid sequences of mouse 7C10 VH (SEQ ID No. 69) with those of human heavy chains belonging to the Kabat human subgroup II (SEQ ID No. 72) and having the greatest sequence homology.

The underlined residues are part of the canonical structures defined by Chothia e al. (1989). A dot indicates that the residue is identical at this position in comparison with the mouse 7C10 VH sequence. Human VH FUR1'CL (SEQ ID No. 73) represents the sequence of the heavy chain of a human anti-lamin B antibody IgM/K of autoimmune origin (Mariette et al., Arthritis and Rheumatism, 36:1315–1324, 1993; access number in Kabat: N020619). Human germline (SEQ ID No. 74) represents the sequence of the human germinal line 4.22 VII IV (Sanz et al., EMBO. J. 8:3741–3748, 1989).

FIG. 24: Comparison of the amino acid sequences of the variable regions of the heavy chains (VH) of mouse 7C10 (SEQ ID No. 69) and of the three versions humanized by CDR-grafting humanized VH 1, 2 and 3 (respectively SEQ ID Nos. 75, 79 and 8.3).

The numbering of the residues corresponds to that of Kabat. The sequences are aligned and compared with that of mouse 7C10 VH. A dot indicates that the residue is identical at this position in comparison with the sequence of mouse 7C10 VH.

FIG. 25: cDNA sequence (SEQ ID No. 76), its complementary strand (SEQ ID No. 78) and its translation into amino acids (SEQ ID No. 77), of the gene constructed by de novo assembly coding for the leader peptide and the humanized version 1 of 7C10 VH.

FIG. 26; cDNA sequence (SEQ ID No. 80), its complementary strand (SEQ ID No. 82) and its translation into amino acids (SEQ ID No. 81), of the gene constructed by de novo assembly coding for the leader peptide and the humanized version 2 of 7C10 VH.

FIG. 27: cDNA sequence (SEQ ID No. 84), its complementary strand (SEQ ID No. 86) and its translation into amino acids (SEQ ID No. 85), of the gene constructed by de novo assembly coding for the loader peptide and the humanized version 3 of 7C10 VH.

FIG. 28: Comparison of the recognition activity of the IGF-I receptor by the chimeric antibody 7C10 (called "C7C10") and its humanized version 1 (/C10 hum 1) in ELISA.

FIG. 29: Influence on the recognition activity of the IGR-I receptor of the humanized versions 1 and 2 of the light chain of the 7C10 antibody in ELISA.

FIG. 30: Comparison of the recognition activity of the IGF-I receptor by the chimeric antibody 7C10 and three humanized versions of the heavy chain (7C10 hum 1, 2 and 3) in combination with humanized 7C10 VL 2 in ELISA.

FIG. 31: Antitumor activity of the 7C10 antibody in an orthotopic model A549.

FIGS. 32A, 32B, 32C and 32D: Study of the ADCC observed at the level of A549 and MCF-7 cells cultured during 4 hours in the presence of the antibody 7H2HM. (respectively FIGS. 32C and 32D). The antibody h4D5 is used in parallel as an experiment positive control for the cells A549 and MCF-7 (respectively FIGS. 32A and 32B).

FIGS. 33A, 33B and 33C: Effects of the antibodies 7C10 and,7H2HM on the cell cycle of the MCF-7 cells.

FIG. 33A represents the proportion of MCF-7 cells in the G0/G1, S and CZ/M phase in the absence of IGF1, expressed as a significant percentage of total MCF-7 cells observed FIG. 33B represents the proportion of MCF-/ cells in the G0/G1, S and G2/M phase in the presence of IGF1, expressed as a percentage of total MCF-7 cells observed.

FIG. 33C represents the proportion of MCF-7 cells in the S (■) and G2/M (□) phase, expressed as a percentage of total MCF-7 cells observed, in the presence of the compounds indicated in the figure compared with a control sample in the absence of IGF1 ("0").

Figure 34A:
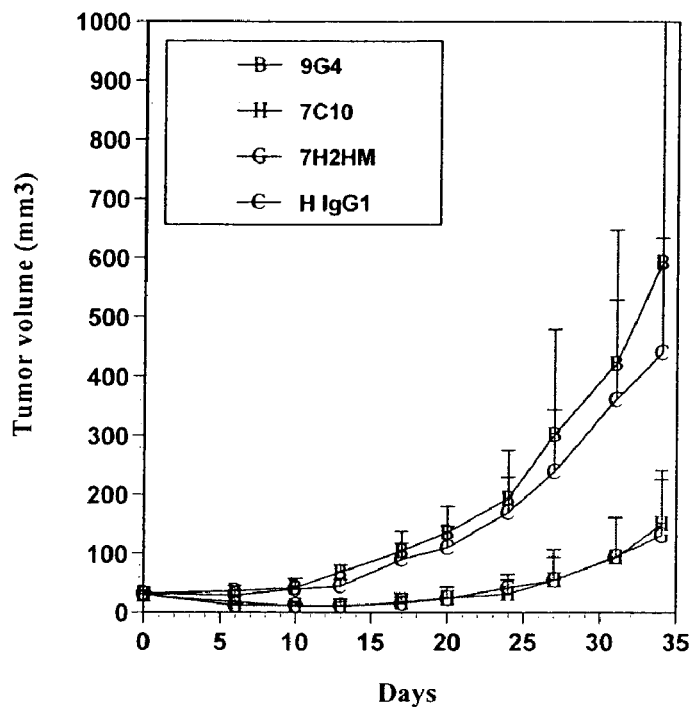
Figure 34B:
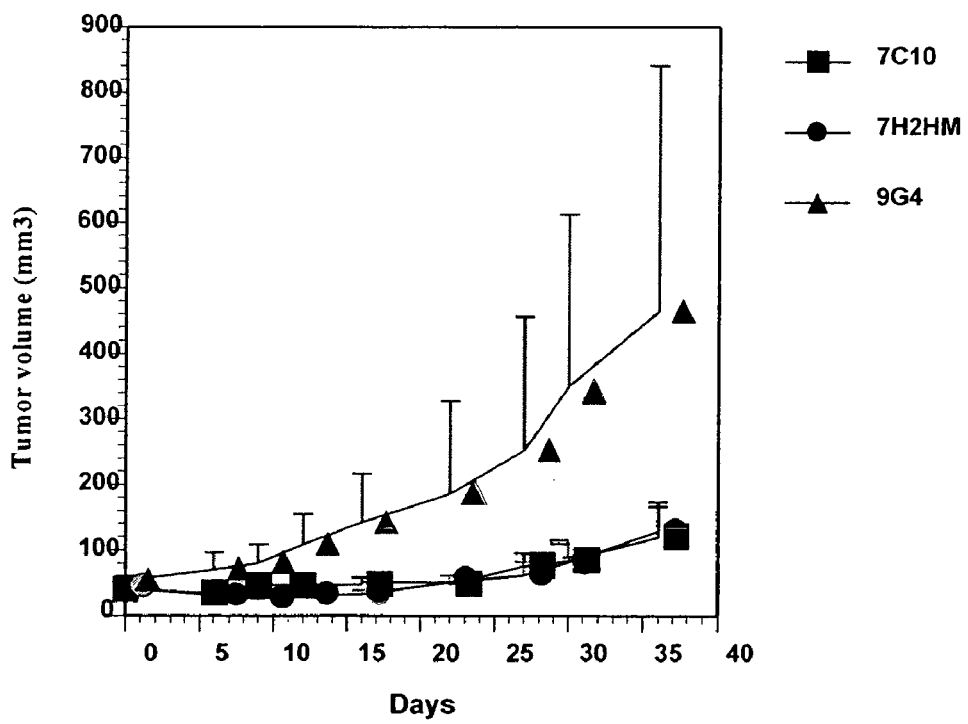

FIGS. 34A and 34B: Comparative effect of the antibodies 7C10 arid 7H2HM on the growth of A549 cells in vitro (FIG. 34A) and on the growth of MCF-7 cells in vivo (FIG. 34B).

FIGS. 35A and 35B: Study of the synergy of the antibody 7H2HM combined with navelbine (NA) oil the model A549 in vivo, compared with the control samples. FIG. 35A represents the development of the volume of the implanted tumor as a function of the treatment carried out starting from the commencement of the treatment and over approximately 50 days (FIG. 35A) FIG. 35B represents in a particular manner the results obtained for this development compared at approximately 48 days. In this figure, the results obtained with the antibody 7C10 have been introduced by way of comparison (the asterisks (*) correspond to the comparison control group/group (7C10+Na) or control group/group (7H2HM+Na) in a t-test).

FIG. 36: study of the effect of the antibodies 7C10 and 7H2HM on apoptosis.

This figure represents the potentiation of the effect of doxorubicin by the antibodies 7C10 and 7H2HM (doxorubicin 2 µg/ml).

FIGS. 37A to 37D: Demonstration by labeling in FACS of the presence of EGFR and of IGF-IR on the surface of A549 cells.

Figure 38:
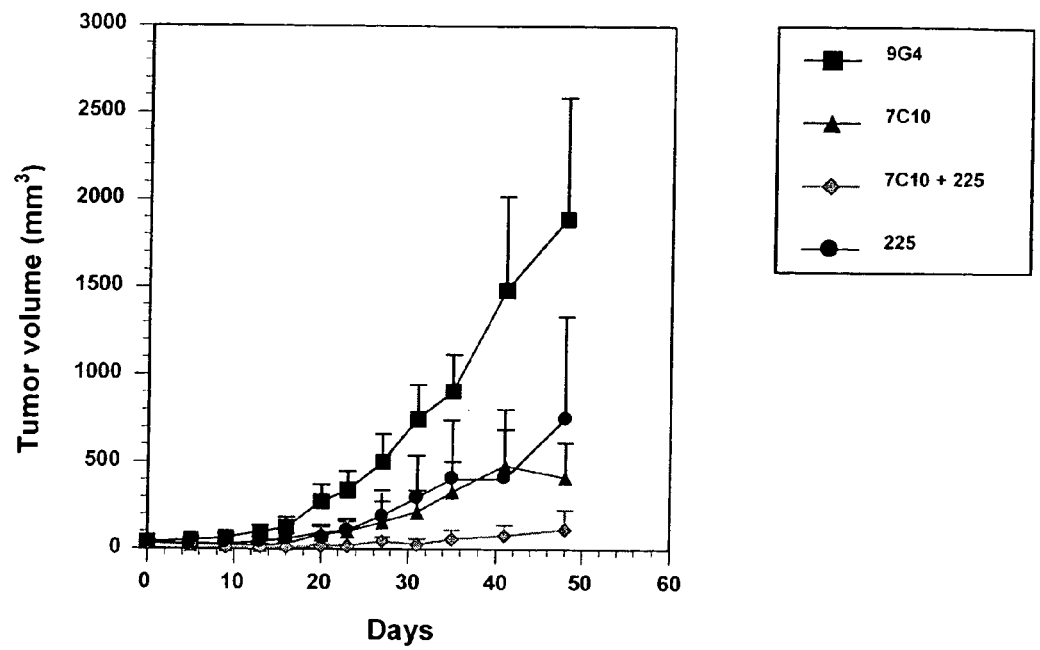

FIG. 38: Effect of a coadministration of the MAB 7C10 and 225 on the in vivo growth of the tumor A549.

Figure 39:
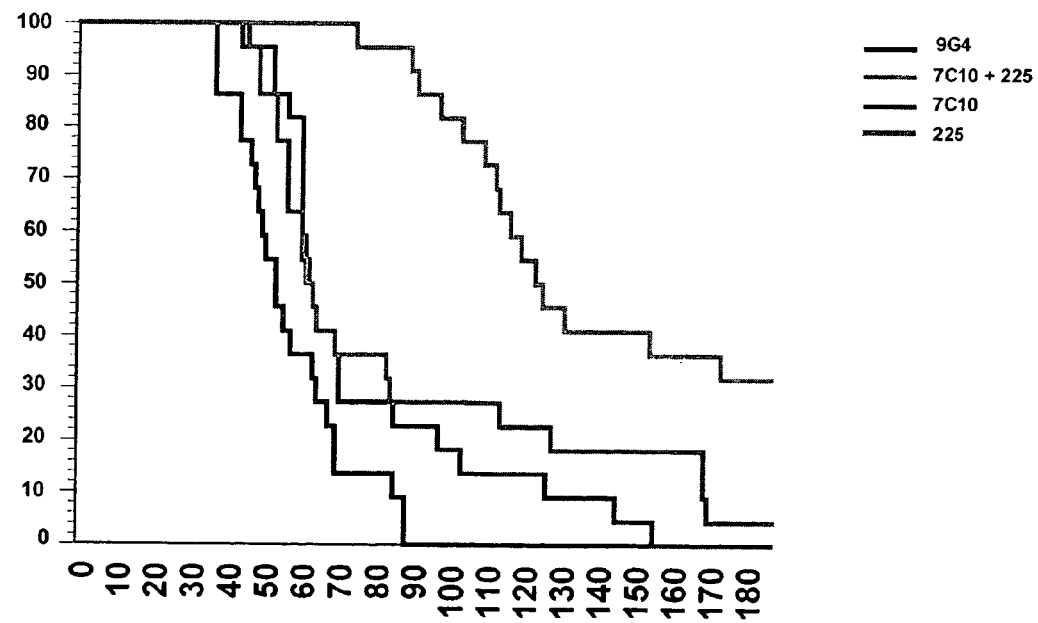

FIG. 39: Effect of a coadministration of the MAB 7C10 and 225 on the survival of mice orthotopically implanted with A549 cells.

FIGS. 40A and 40B: Demonstration of the inhibition of tyrosine phosphorylation of the beta chain of IGF-IR and of IRS-1 by the MAB 7C10 and 7H2HM.

FIG. 41: Demonstration of the induction of the internalization of IGF-IR by the MAB 7C10 and 7112HM.

Figure 42A:
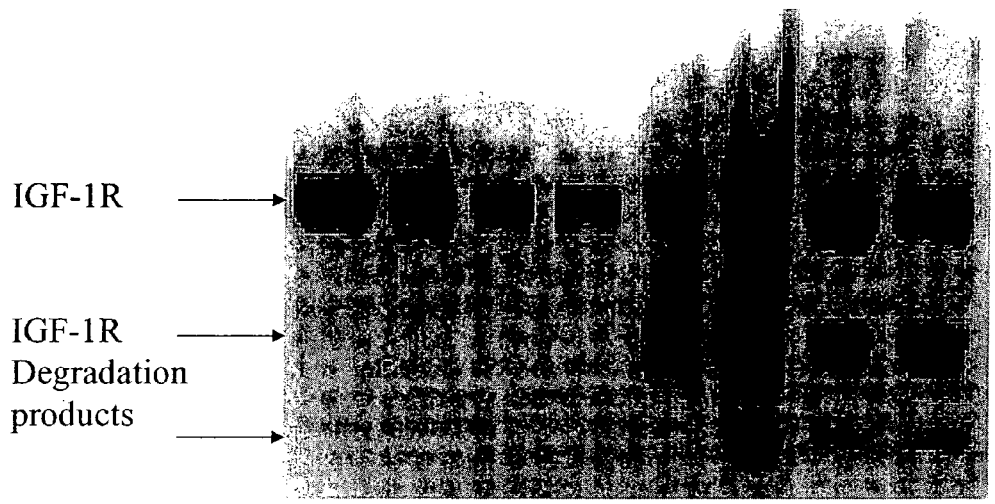
Figure 42B:
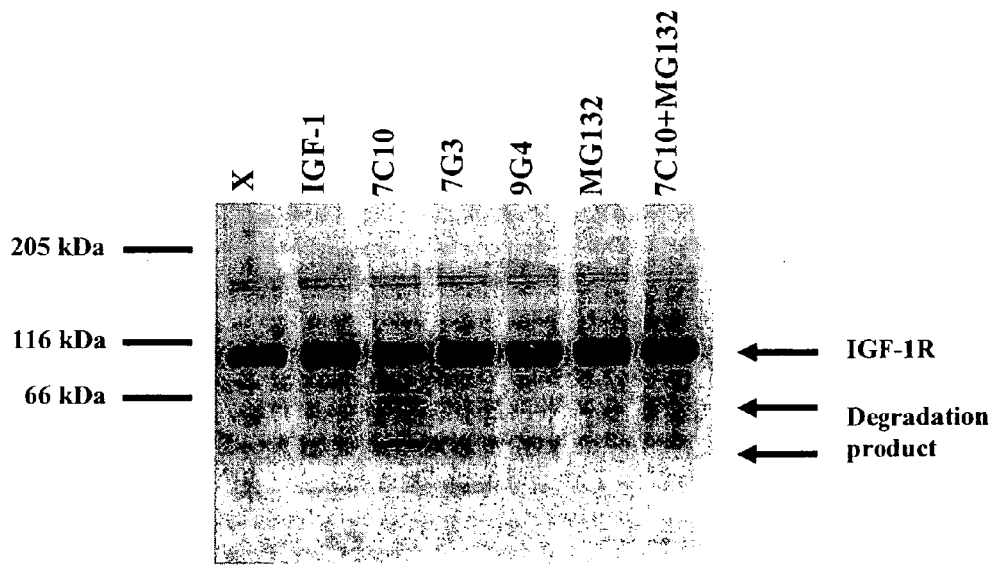
Figure 42C:
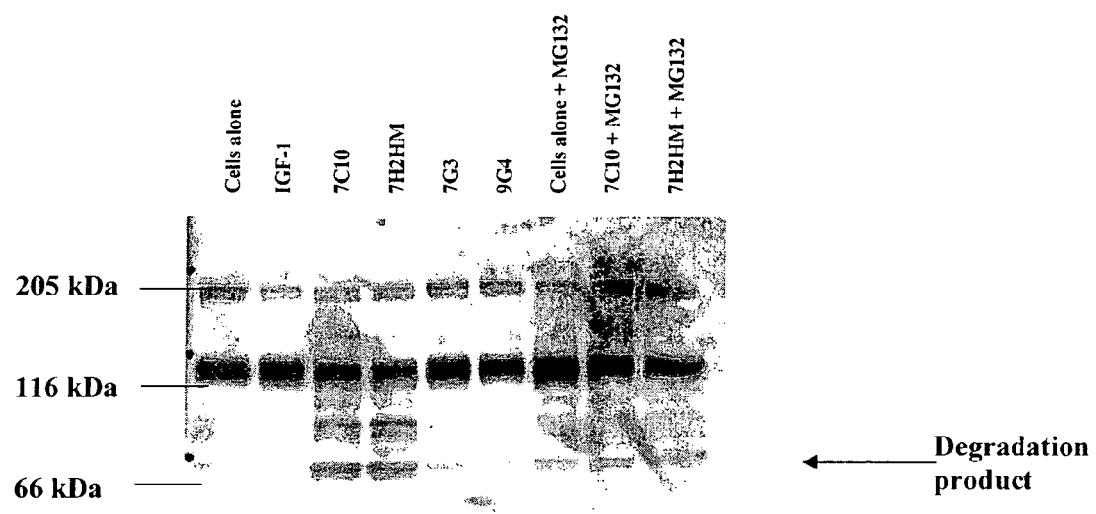

FIGS. 42A to 42C: Demonstration of the degradation of IGF-IR by the MAB 7C10 and 7112HM.

Figure 43A:
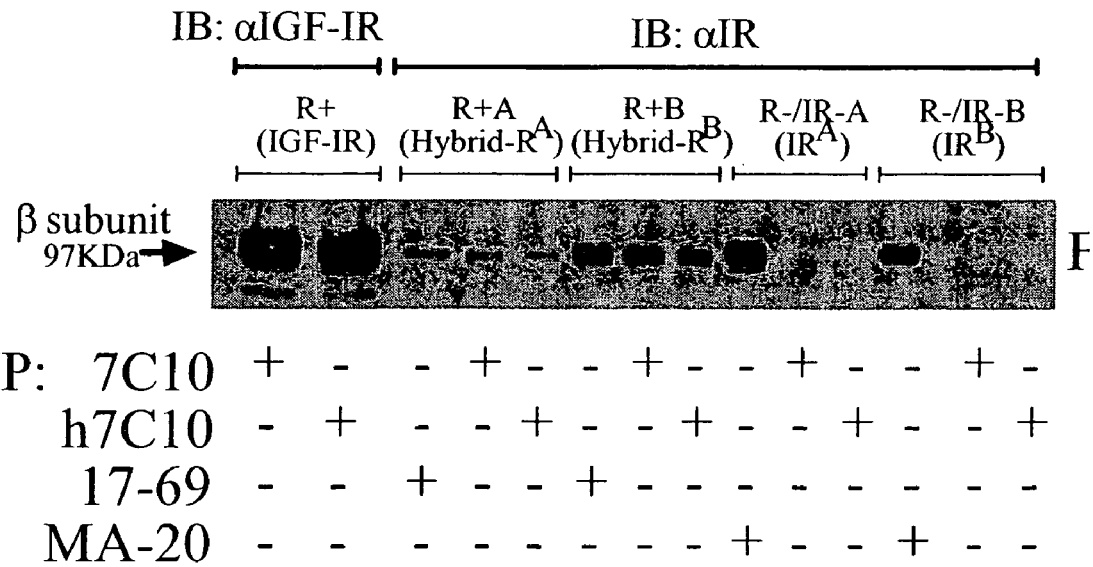
Figure 43B:
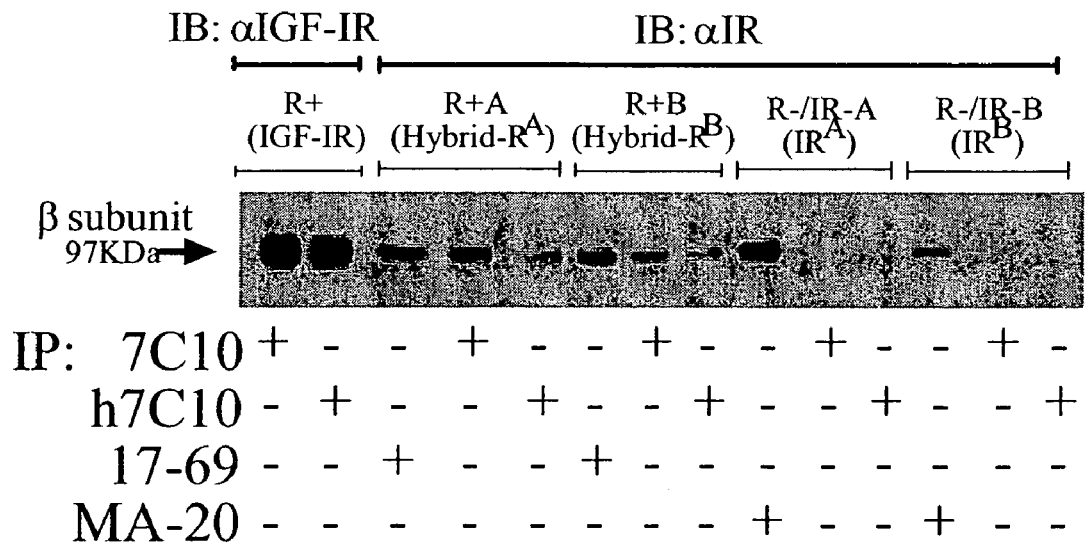

FIGS. 43A and 43B: Immuno-blotting with an anti-IGF-IR β-subunit and anti-IR β-subunit on filters containing cellular lysates obtained after immunoprecipitation and SDS-PAGE for two independent experiments (A and B).

Figure 44:
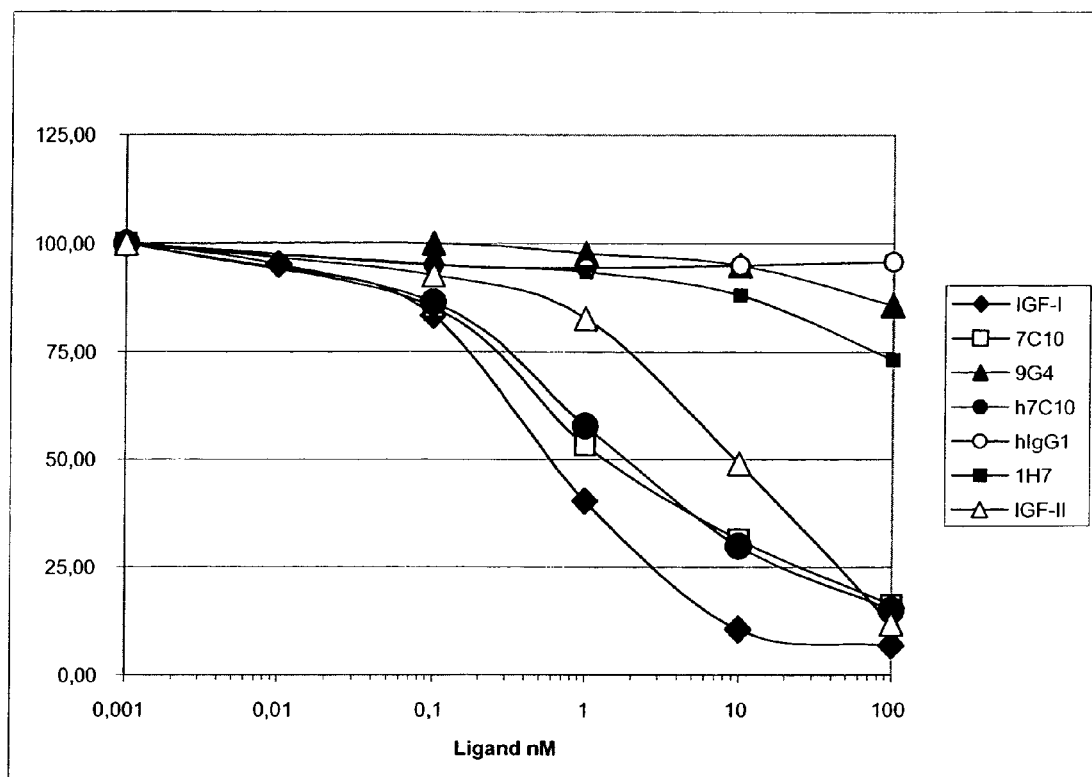

FIG. 44: Immunocapture of R+ cell lysates IGF-IR in Maxisorb plates coated with 17–69 antibody and binding by $^{125}$I-IGF-I in the absence or the presence of increasing concentrations of unlabeled ligand (IGF-I) or antibodies (7C10, h7C10, 1H7, 9G4).

Figure 45:
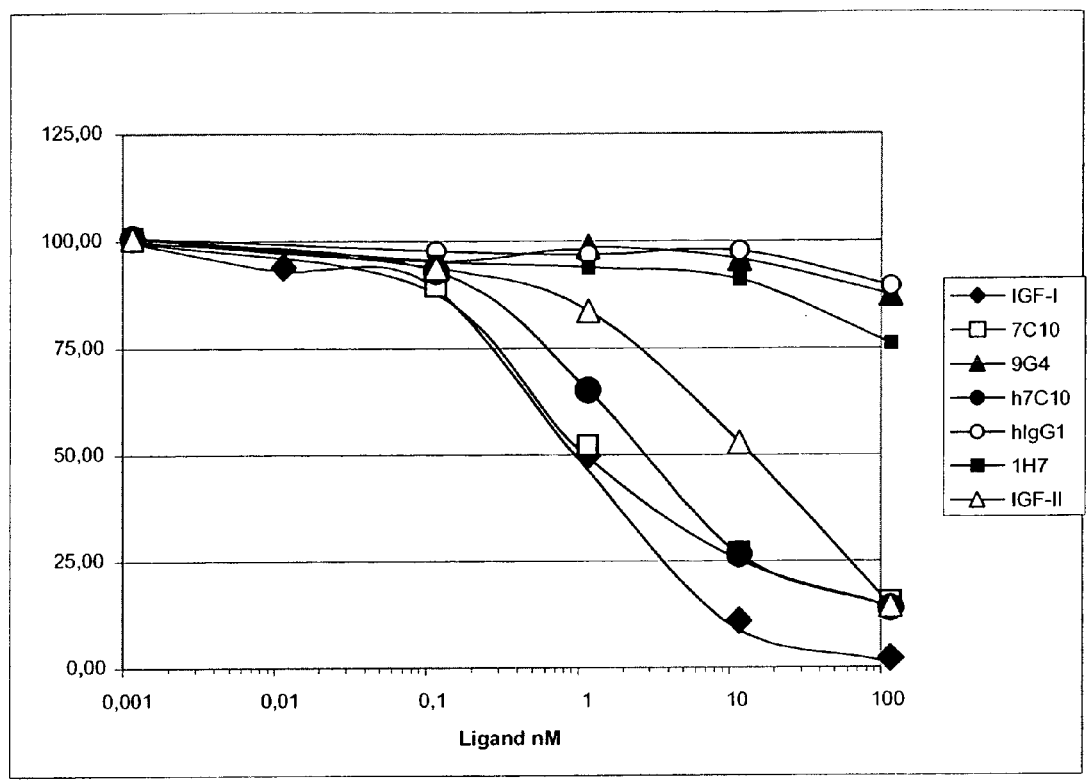

FIG. 45:. Immunocapture of R−/IR-A cell lysates Hybrid-R″ in Maxisorb plates coated with 83–7 antibody and binding by $^{125}$I-IGF-I in the absence or the presence of increasing concentrations of unlabeled ligand (IGF-T) or antibodies (7C10, h7C10, 1H7, 9G4).

Figure 46:
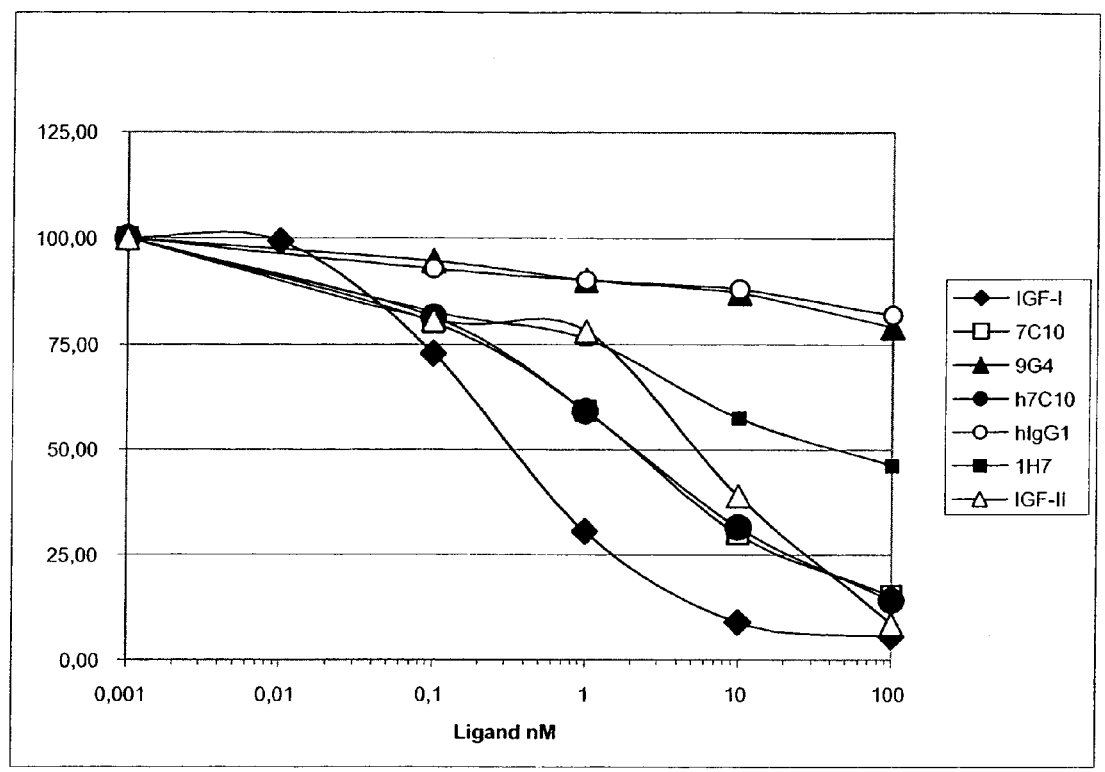

FIG. 46: Immunocapture of R−/IR-B cell lysates Hybrid-$R^B$ in Maxisorb plates coated with 83–7 antibody and binding by $^{125}$I-IGF-I in the absence or the presence of increasing concentrations of unlabeled ligand (IGF-I) or antibodies (7C10, h7C10, 1H7, 9G4).

Figure 47A:
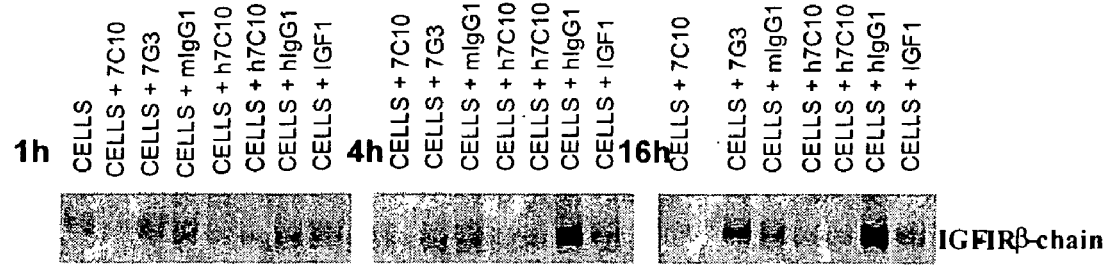
Figure 47B:
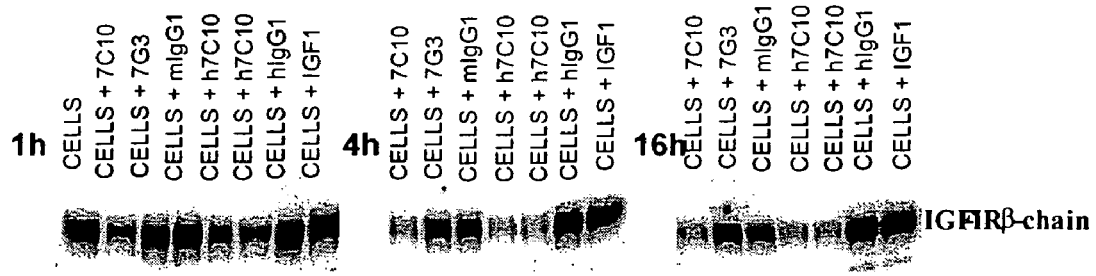

FIGS. 47A and 47B: Immuno-blatting analysis of antibody induced degradation of the IGF-IR in A549 (A) and MCF-7 (B) cells.

Figure 48:
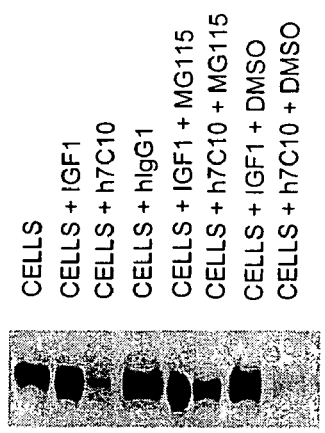

FIG. 48: Immuno-blotting analysis of antibody degradation pathway of TCF-IR in MCF-7 cells.

Figure 49:
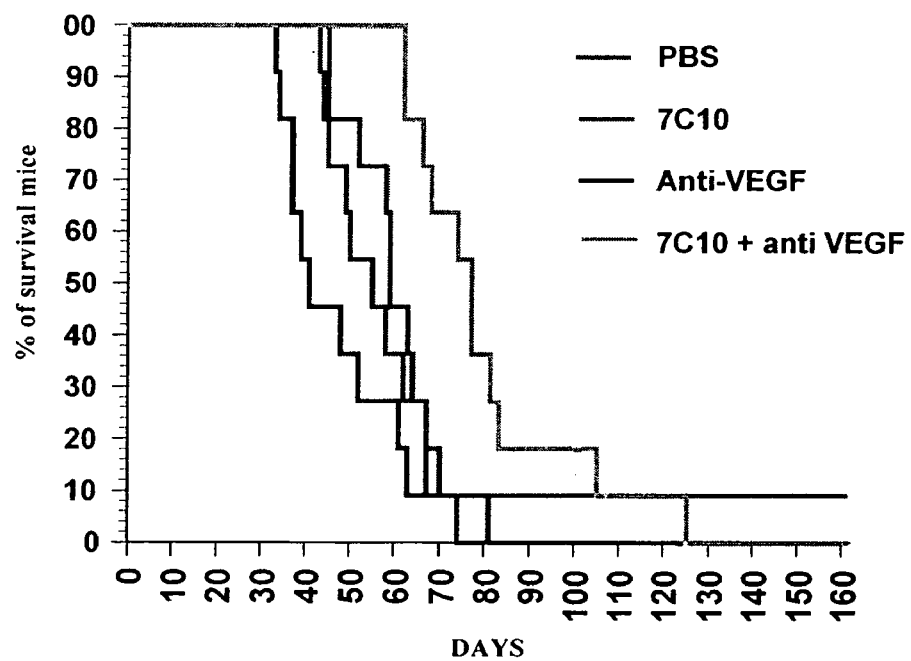

FIG. 49: Anti-tumoral activity of the murine antibody 7C10 co-administrated with an anti-VEGF antibody on mice orthopically implanted with A549 cells.

Figure 50:
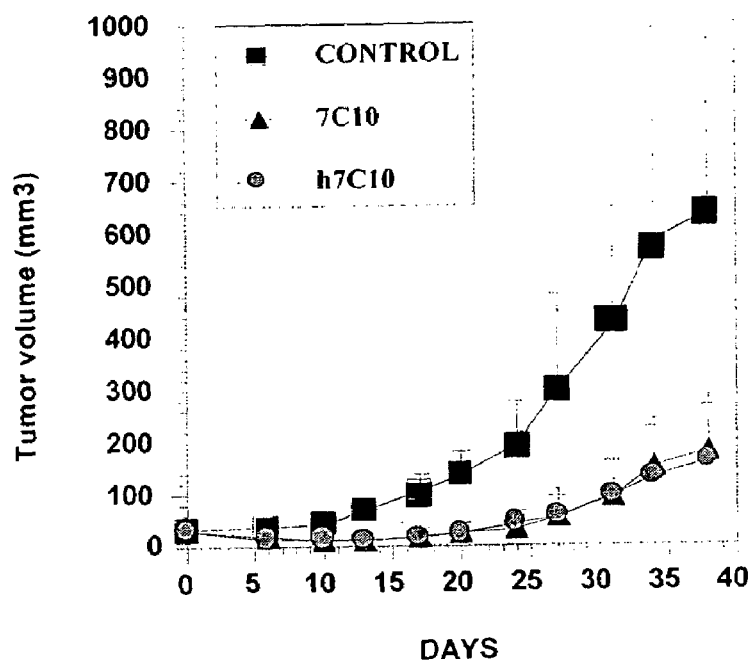
Figure 51:
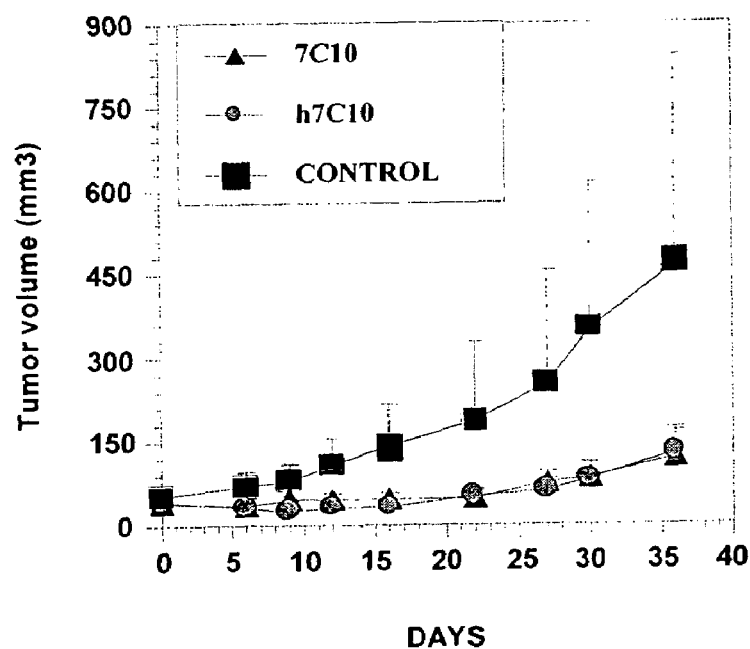

FIGS. 50 and 51: Comparison of the in vivo anti-tumoral activity of the 7C10 and h7C10 antibodies on the A549 (FIG. 50) and MCF-7 (FIG. 51) models.

Figure 52:
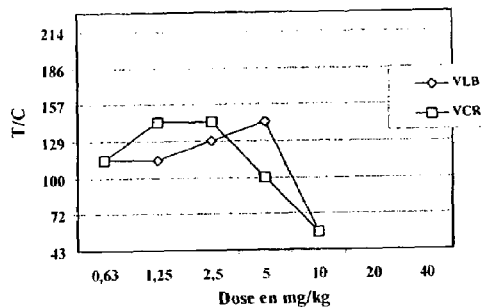
Figure 53:
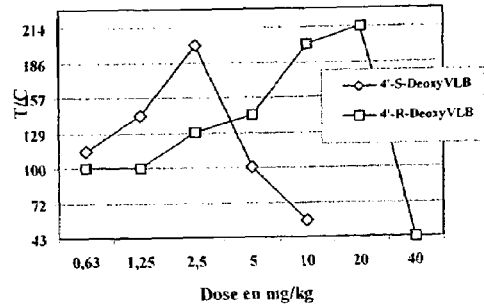

FIGS. 52 and 53: Comparison of the anti-leukaemia activity of vinblastine and vincristine (FIG. 52) and of 4'R and 4'S deoxyvinblastines (FIG. 53)

Figure 54:
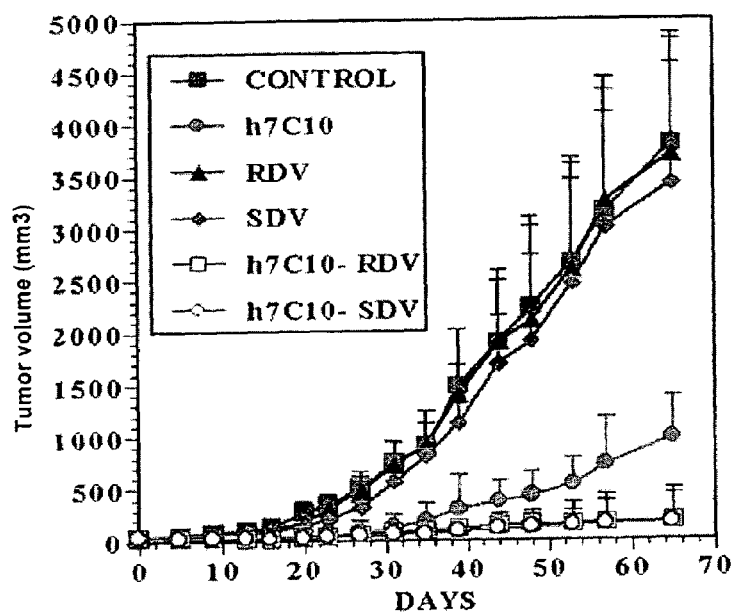

FIG. 54: In vivo antitumour activity of 4'R- and 4' S-deoxyvinblastines conjugated with IGR-IR antibodies on human tumours of various origins.

EXAMPLE 1

Generation and Selection of the Murine Monoclonal Antibody (MAb)

With the aim of generating MAb specifically directed against IGF-IR and not recognizing the IR, a protocol comprising 6 screening stages was envisaged.

It consisted in:
immunizing mice with recombinant IGF-IR, in order to generate hybridomas,
screening the culture supernatants by ELISA on the recombinant protein which served for immunization,
testing all the supernatants of hybridomas positive by ELISA on the native receptor overexpressed on the surface of MCF-7 tumor cells,
evaluating the supernatants of hybridomas positive in the two first screenings in terms of differential recognition of IGF-IR and of IR on insect cells infected with baculoviruses respectively expressing IGF-IR or IR,
verifying that the antibodies selected at this stage were capable of inhibiting in vitro the induced IGF1 proliferation of the MCF-7 cells,
ensuring the in vivo activity, in nude mice, of the candidate retained in terms of impact on the growth of the tumor MCF-7.

All of these different stages and results obtained will be briefly described below in example 1.

For the immunization stage, mice were injected twice, by the subcutaneous route, with 8 µg of recombinant IGF-IR. Three days before the fusion of the cells of the female rat with the cells of the murine myeloma Sp2OAg14, the mice were stimulated by an intravenous injection of 3 µg of the recombinant receptor. Fourteen days after the fusion, the supernatants of hybridomas were screened by ELISA, on plates sensitized by recombinant IGE-IR. The hybridomas whose supernatants were found positive were conserved and amplified before being tested on the FACScan so as to verify that the antibodies produced were likewise, capable of recognizing native IGF-IR. In order to do this, MCF-7 cells from an estrogen-dependent tumor of the breast overexpressing IGF-IR were incubated with each of the culture supernatants produced by the hybridomas selected in ELISA. The native/MAb receptor complexes on the surface of the cell were revealed by a secondary anti-species antibody coupled to a fluorochrome. FIGS. 3A to 3C show a histogram type obtained with the supernatant of the hybridoma /C10 (FIG. 3C) compared with a cell labeling alone+ secondary antibody (FIG. 3A) or with a labeling utilizing a control isotype (FIG. 3B)

At this stage of the selection, only the hybridomas secreting MAb at the same time recognizing the recombinant receptor and the native receptor were selected and cloned. The MAb secreted by these hybridomas were produced and then purified before being tested on the FACScan, according to the method described above, on Sf9 insect cells expressing IGF-IR or IR in order to eliminate the hybridomas at the same time recognizing the two receptors. FIG. 4A shows a total recovery of the histograms 1, 2, 3 respectively corresponding to the noninfected cells+secondary antibodies (1), to the noninfected cells labeled by aIR3+secondary antibodies (2) and to the noninfected cells labeled by an anti-IR antibody+secondary antibodies (3). This first result shows well the absence of IGF-IR and of IR detectable on the surface of these noninfected insect cells. FIG. 4B shows a labeling of infected cells by a baculovirus expressing IGF-IR. In this second figure, the aIR3, used as a positive control, labels well, as expected, the cells (peak 2), while the anti-IR (peak 3) is superimposed on the peak of single cells. Finally, in FIG. 4C, it is shown that the anti-IR labels well, as expected, the Sf9 cells expressing the IR (peak 3), but in an unexpected manner, the aIR3 described in the literature as specific for IGF-IR seems likewise to recognize the IR (peak 2).

The results obtained in this third screening system are summarized in table 1 and show the generation of an MAb: 7C10, satisfying the criteria of recognition of the IGF-IR and of nonrecognition of the IR. The isotyping of the Mab 7C10 has shown that it involves an IgG1.

TABLE 1

Comparative reactivity of MAb 7C10 on Sf9 insect cells expressing IGF-IR or IR

| | MFI (Mean fluorescence intensity) | | |
|---|---|---|---|
| | Noninfected cells | IGF1R + cells | IR + cells |
| Cells | 8 | 8 | 7 |
| Anti-IR | 4.6 | 9 | 91 |
| Anti-IGF-IR (aIR3) | 9 | 35 | 32 |
| EC2 | 8 | 13 | 11 |
| Anti-mouse FITC | 4.3 | 9 | 13 |
| UltraCulture medium | 9 | 10 | 11 |
| 15B9 | 7.5 | 25 | 77.8 |
| 9F5D | 8 | 41 | 40 |
| 13G5 | 7.8 | 37 | 24 |
| 7C10 | 8.6 | 49 | 13 |

The two last screenings provided for the selection of the MAb consisted in verifying that the latter was very capable of inhibiting the cell proliferation induced by the IGF-I in vitro and in vivo on the cell line MCF-7.

Figure 5:
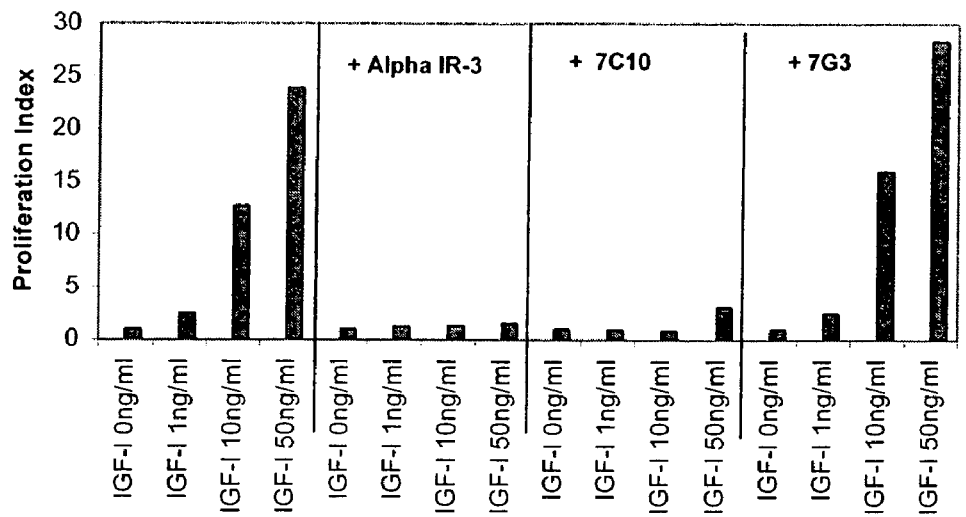

For the in vitro selection, the MCF-7 cells were inoculated, deprived of fetal calf serum, then incubated in the presence of increasing concentrations of IGF-I (from 1 to 50 ng/ml) in the presence or in the absence of the 7C10 antibody to be tested added to a final concentration of 10 µg/ml. In this experiment, the commercial aIR3 MAb was introduced as a positive control and the 7G3 MAb (isolated in parallel to the 7C10 and weakly recognizing the native receptor (MFI on the FACS of 50 compared with 200 for the MAb 7C10)) as a control isotype. The cell proliferation is estimated by following on the β counter the incorporation of tritiated thymidine by the cells. The results are expressed as a proliferative index. The data presented in FIG. 5 show that IGF1 is capable of stimulating in a dose-dependent manner the proliferation of the MCF-7 cells. The MAb aIR3, used as a positive control, completely inhibits the proliferation of the MCF-7 cells induced by the IGF-I. In the same manner, the MAb 7C10 significantly inhibits the growth of the MCF-7 cells induced by IGF-I. Finally, the MAb 7G3 used as an isotype control turns out well, as expected, without effect on the tumor cell growth in vitro of the MCF-7 cell.

Figure 6A:
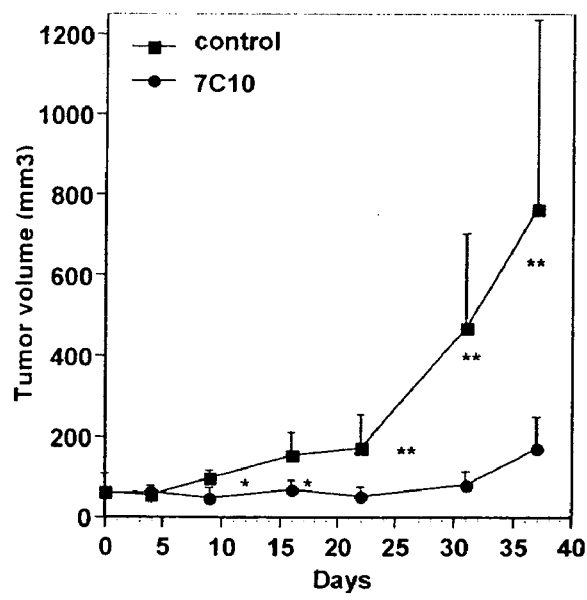
Figure 6B:
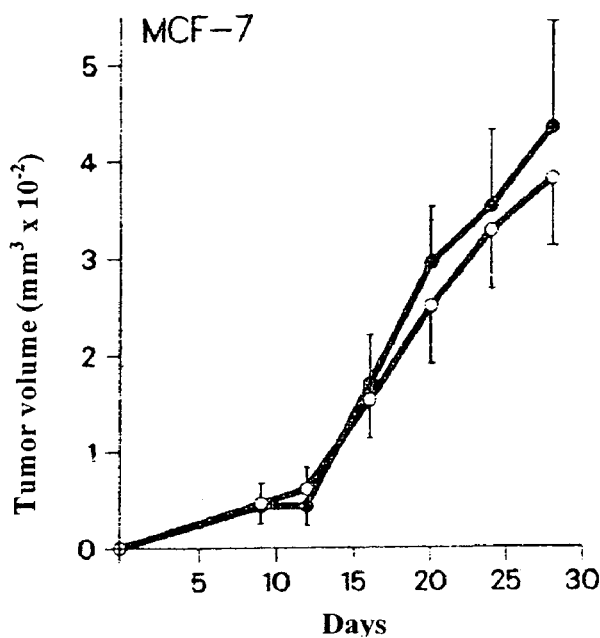
Figure 6C:
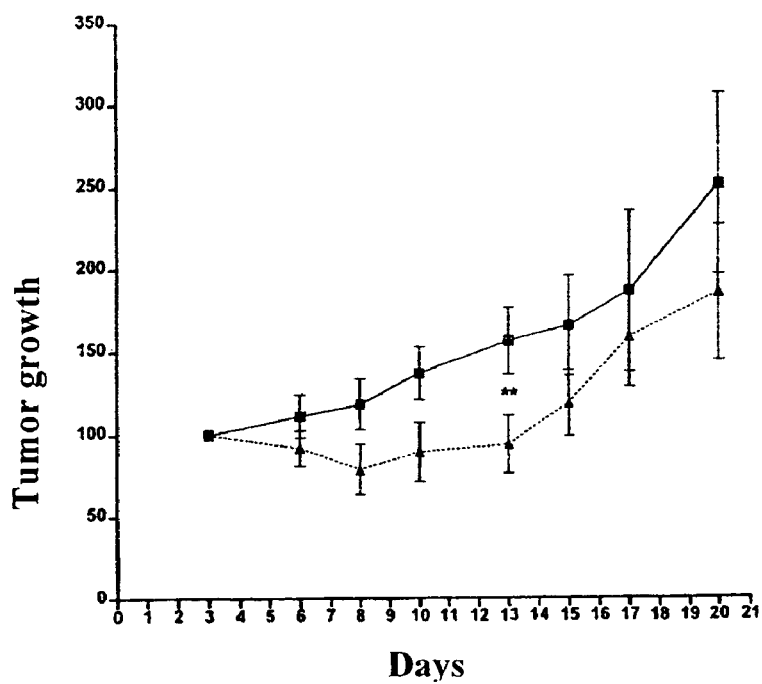

The in vivo selection was carried out in an established tumor model. In order to do this, nude mice received a subcutaneous implant of slow-release estrogen, indispensable for the taking of the tumor in a murine model. Twenty-four hours after implantation of the estrogens, $5.10^6$ MCF-7 cells are grafted onto the right flank of the mouse subcutaneously. Five days after this cell graft, the tumors are measurable and batches of 6 mice are formed at random. The treatment of the mice is carried out twice per week, during 5 to 6 weeks, at the dose of 250 µg/dose/mouse. In the control group, the mice are treated in the same fashion with a murine control isotype. The results presented in FIG. 6A show a very significant inhibition of the tumor growth induced by the antibody 7C10. This activity is particularly unexpected if reference is made to the data available concerning aIR3, always used as a reference in the domain of the receptor for IGF1, and known for not having any activity in vivo on the growth of estrogen-dependent tumors (see FIG. 6B). In the same way, compared with the results obtained with the recombinant antibody scFv-Fc derived from the murine MAb 1H7 (see FIG. 6C), the MAb 7C10 is much more efficacious in the in vivo inhibition of the growth of the MCF-7 cells.

EXAMPLE 2

Comparison of the Effect of 7C10 and of Tamoxifen on the In Vivo Growth of the Tumor MCF-7

With the aim of determining the effectiveness of the treatment by the antibody 7C10 in the context of estrogen-dependent cancer of the breast, 7C10 was compared with the tamoxifen compound currently used for the treatment of mammary carcinoma in the context of developed forms with local and/or metastatic progression and in the context of the prevention of recurrences (see VIDAL 2000, pages 1975–1976).

In hormone-dependent cancers of the breast, a significant correlation exists between the expression of the receptors for estrogens (ER) and that of the IGF-IR (Surmacz E. et al., Breast Cancer Res. Treat., February, 47(3) :255–267, 1998). Furthermore, it seems that the estrogens (E2) act in synergy with IGF3 (sometimes written IGF-I or IGFI) in order, to stimulate cell proliferation. It has in effect been shown that a treatment with E2 increases by approximately 10 times the mRNA level of IGF-IR as well as the expression level of the protein (Lee A. V. et al., Mol. Endocrinol., May, 13(5): 787–796, 1999). This increase is manifested by a significant increase in the phosphorylation of the IGF-IR. In addition, the E2 significantly stimulates the expression of IRS-1 ("IRS-1" for "Insulin Receptor Substrate-1") which is one of the substrates of the phosphorylated IGF-TR.

Tamoxifen has been widely used for many years in hormone therapy for the treatment of patients suffering from E2-dependent breast cancers (Forbes J. F., Semin. Oncol., February, 24 (1st Suppl. 1):S1–5-S1–19, 1997). This molecule enters into competition with the estradiol and inhibits the attachment of this to its receptor (Jordan V. C., Breast Cancer Res. Treat., 31(1):41–52, 1994). It has in addition been demonstrated that tamoxifen is capable of inhibiting the IGF-IR-dependent proliferation by inhibiting the expression of the receptor and its phosphorylation (Guvakova M. A. et al., Cancer Res., Jul. 1, 57(13):2606–2610, 1997). These data as a whole seem to indicate that IGF-IR is an important mediator of the proliferation induced by the E2/ER interaction.

The long-term use of tamoxifen is associated with a significant increase in the risk of endometrial cancer (Fisher et al., J. of National Cancer Institute, 86, 7:527–537, 1994; VIDAL 2000, 1975–1976) and of collateral recurrence of E2-independent cancer of the breast (Li C. I. et al., J. Natl. Cancer Inst., Jul. 4, 93(13) :1008–1013, 2001). In this context, a comparison of the in vivo antitumor effect of the antibody 7C10 and of tamoxifen has been carried out on the MCF-7 model so as to determine the part of the activity connected with IGF-IR in the mediated ER proliferation. In order to do this, $7.10^6$ MCF-7 cells were implanted sc (subcutaneously) in nude mice, 24 hours after implantation in these same mice of a grain of estradiol with prolonged release (0.72 mg/tablet liberated over 60 days), indispensable for the establishment of any E2-dependent human tumor in this animal species. Five days after this implantation, the tumors are measured and groups of 6 mice are formed. These groups are treated respectively with 1) the 7C10 antibody injected ip (intraperitoneally) at a rate of 250 µg/mouse, twice per week, 2) 10 µg of tamoxifen take(n in PBS containing 3% of hydroxypropyl-cellulose (HPC) ip or 3) the solvent in which the tamoxifen is taken up (hydroxypropylcellulose). The tamoxifen is administered daily for 4 weeks except at the weekend. The mice treated with tho MAb 7C10 likewise daily receive an injection of PBS with 3% HPC. A study was previously carried out in order to verify that the solvent alone is without influence on the tumor growth.

The results presented in FIG. 7 shown that the MAb 7C10 is capable of significantly inhibiting the growth of the tumor MCF-7 in vivo (the asterisks (*) correspond to the comparison control group/7C10 group in a t-test). In a surprising fashion, the antibody 7C10 seems to be significantly more efficacious than tamoxifen for the inhibition of the tumor growth (the circles (°) correspond to the comparison tamoxifen group/7C10 group in a t-test) suggesting that this type of treatment by MAB might be substituted for treatment with tamoxifen.

EXAMPLE 3

Figure 8C:
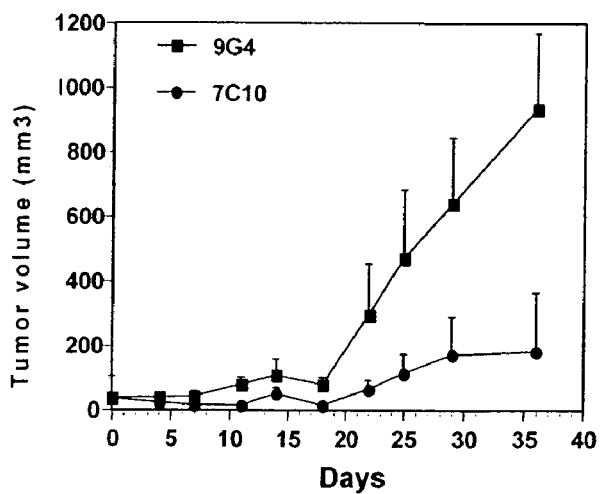

Demonstration of the Antitumor Activity of the MAb 7C10 In Vivo on Human Tumors of Different Origins a) In Vivo Activity of the Antibody 7C10 in Three Tumor Models In order to generalize the activity of the 7C10 antibody to other tumors expressing the receptor for IGF1, 7C10 was tested in vivo in an androgen-independent model of tumor of the prostate DU145 (likewise written DU-145), in an SKES-1 osteosarcoma model and in a model of non-small cell tumor of the lung A549. The protocol is comparable to that described above for MCF-7 and the results presented in FIGS. 8A to 8C show a significant activity of this MAB in the 3 tumor models. The activity observed in the model, of tumor of the prostate is to be noted very particularly inasmuch as the single chain scFv of the MAB 1H7 is without activity in an androgen-independent model of tumor of the prostate (Li et al., 2000).

b) In Vivo Activity of the Antibody 7C10 in an Orthotopic Model A549

Figure 31:
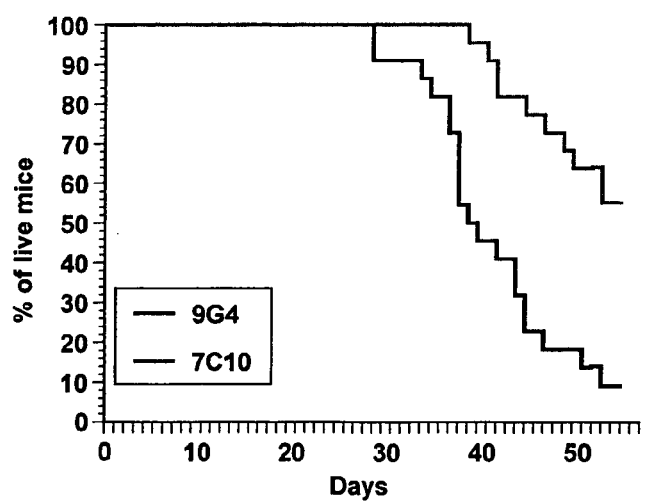
Figure 32A:
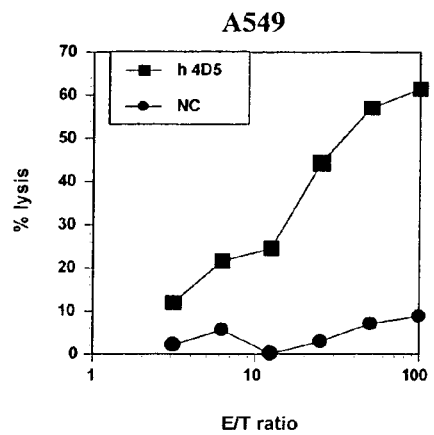
Figure 32B:
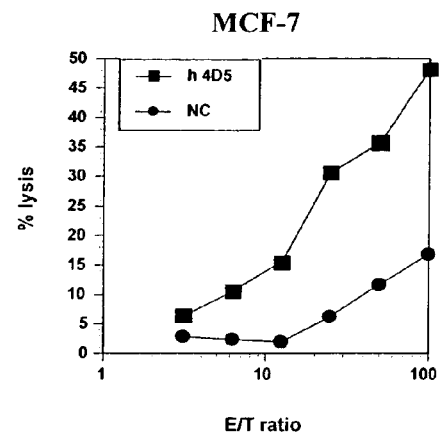
Figure 32C:
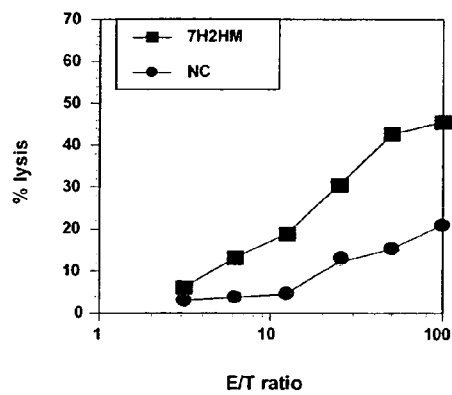
Figure 32D:
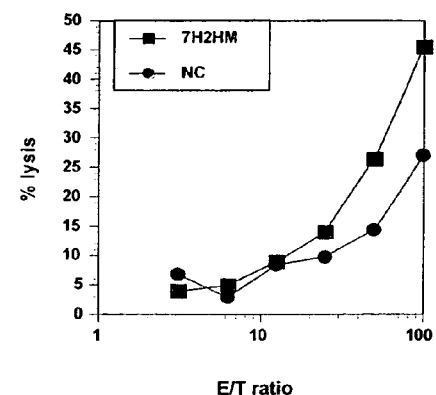

The conventional xenograft models as described above do not allow the study of drugs on metastatic dissemination. In effect, the tumors implanted s.c. (subcutaneously) remain localized at the sight of injection and are therefore not really a reflection of the situation in man. In order to evaluate our antibody in a model closer to reality, the A549 cells were implanted in an intrapleural location. This model, which is well described (Clin. Cancer Res. 2000 Jan.; 6(1) :297–304) allows a metastatic dissemination close to that observed in man to be observed, with mediastinal, pulmonary, cardiac and vertebral metastases. In the study which was carried out, $10^6$ A549 cells were injected intrapleurally into female nude mice. 7 days after implantation; the mice were divided into 2 batches of 22. One of these batches received a challenge dose of 500 µg/mouse and was then treated twice per week at a rate of 250 μg of 7C10/dose. The second batch was treated according to the same scheme with the control isotype 9G4. FIG. 31 shows a significant extension of survival in the mice treated with the MAB 7C10 indicating that this antibody is capable of having an action on metastatic dissemination.

EXAMPLE 4

Comparison of the MAb 7c10 with Navelbine In Vivo; Effect of a Coadministration of the Two Treatments Navelbine is a chemotherapy compound indicated in non-small cell cancer of the lung and in metastatic cancer of the breast. The comparative study of 7C10 and of navelbine and the possible synergy between the two products was studied on the tumor model A549. For this study, $5.10^6$ A549 cells were grafted subcutaneously on the right flank of the mouse. Five days after the cell graft, the tumors are measurable and the treatments with MAb and/or navelbine are commenced. The MAb dose is always 250 μg/dose/mouse, twice per week, intra-peritoneally. Concerning navelbine, it will be administered at the maximum dose tolerated by the mouse or 10 mg/kg, intraperitoneally. For this treatment three injections will be carried out at intervals of 7 days. During the coadministrations, the two products are mixed before injection.

Figure 9:
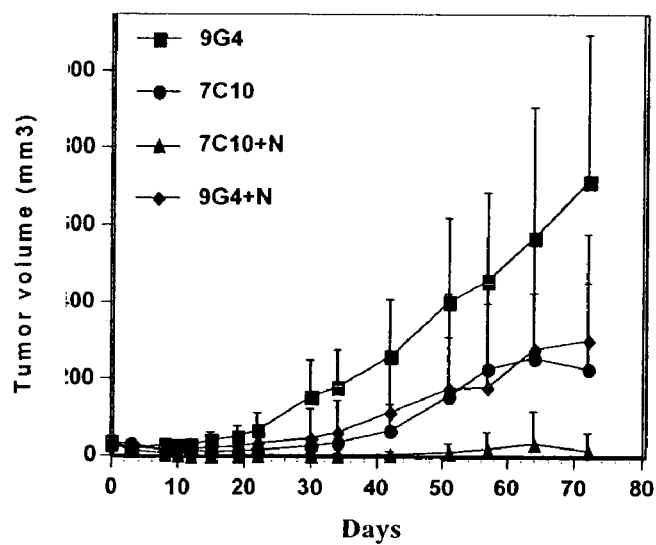

The results presented in FIG. 9 show in a surprising fashion that, in this model, the antibody 7C10 is as active as the conventional treatment with navelbine. A very significant synergy of the two products is likewise observed with five mice out of seven not having measurable tumors on day 72.

EXAMPLE 5

Study of the In Vitro Inhibition of the IGF2-Induced Growth of the MCF-7 Tumors

Figure 10:
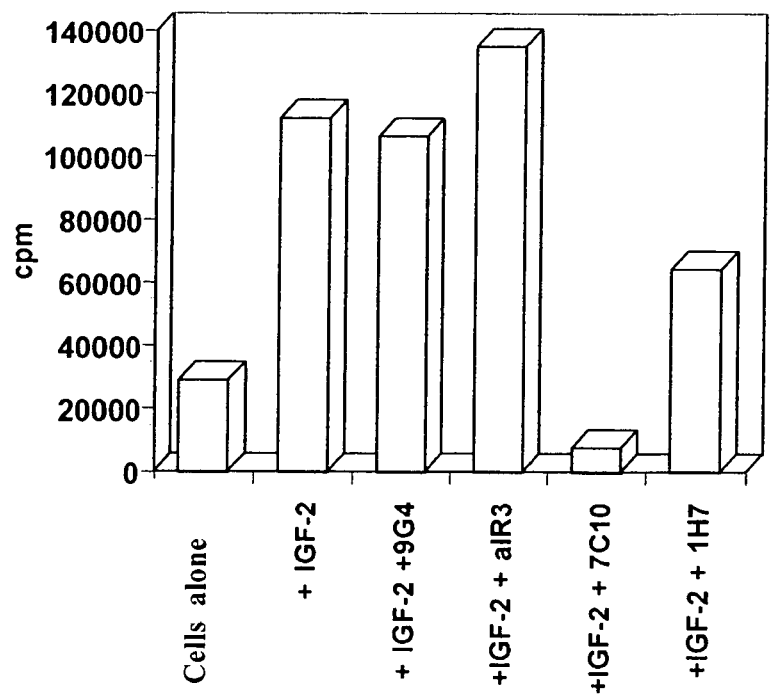

As indicated above, IGF-IR is overexpressed by numerous tumors but it has furthermore been described that in a good part of the cancers of the breast and of the colon especially, the proliferation signal is given to this receptor via IGF2 (sometimes written IGF-II or IGFII). It is therefore essential to ensure that the MAb 7C10 is likewise capable of inhibiting the IGF2 growth induced on the MCF-7 tumor in vitro. In order to do this, cells were inoculated into 96-well plates, deprived of fetal calf serum and stimulated by the addition of 200 ng of IGF2 per ml, final concentration, of medium, in the presence or in the absence of the MAb to be tested introduced at a concentration of 10 μg/ml. The results presented in FIG. 10 show that IGF2, like IGF1, significantly stimulates the growth of MCF-7 cells. The addition of a control isotype, 9G4, remains without effect on this stimulation. As already described by De Leon et al. (Growth Factors, 6:327–334, 1992), no effect is observed during the addition of the MAb aIR3. On the other hand, 7C10 totally inhibits the growth induced by IGF2. Its activity is significantly better than that of 1H7.

EXAMPLE 6

Biological Activity of the Choleric 7C10 (C7C10) and Humanized (h7C10) Antibodies 7C10 a) 7C10/C7C10 and 7C10/h7C10 comparison on the MCF-7 Model In Vitro

Figure 11:
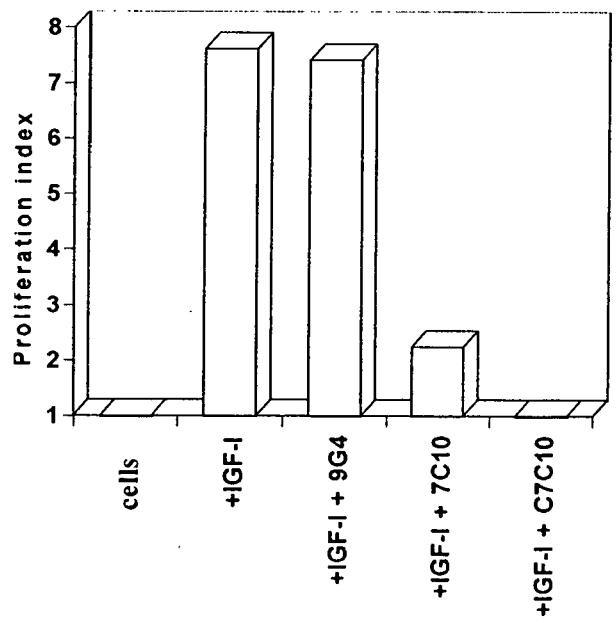
Figure 12:
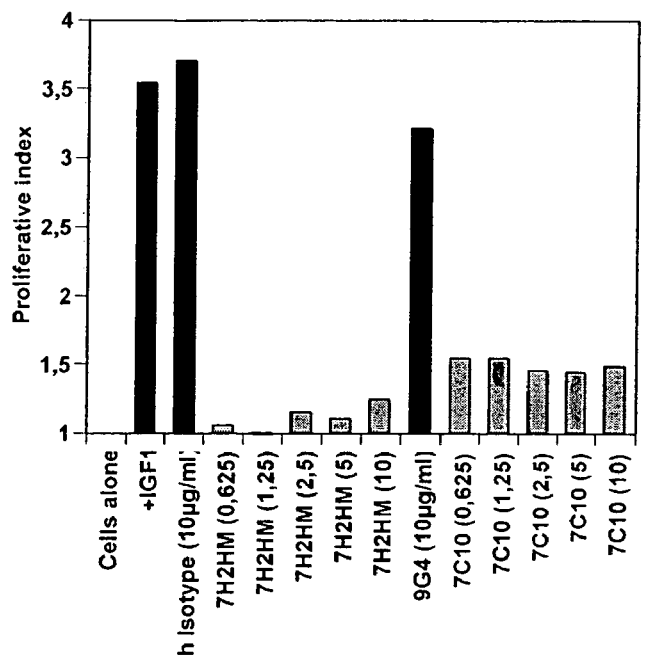
Figure 13:
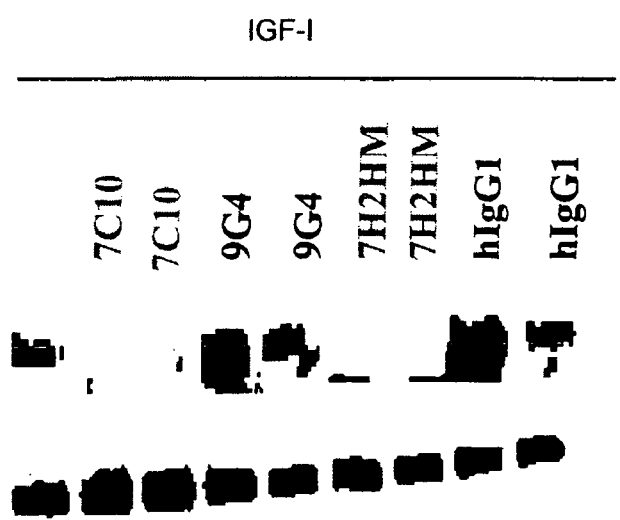

The chimeric form of the MAb 7C10 and the purified humanized form 1 (written here 7H2HM) were tested in vitro in the MCF-7 model as described above. The results presented respectively in FIGS. 11 and 12 show that these two forms have perfectly preserved their properties of inhibiting the IGF1-induced growth of the MCF-7 tumor.

b) Comparative Effect of the MAb 7C10 and h7C10 on the Transduction of the Signal Induced by the Attachment of IGF1 to its Receptor The activity of the inhibition of the IGF1 growth induced in vitro on the line MCF-/ ought to be the translation of an inhibition of the transduction of the signal mediated by IGF1 during the attachment of the MAb 7C10 to the receptor. In order to verify this hypothesis, MCF-7 cells were incubated with or without IGF1, in the presence or in the absence of the antibodies to be tested. After a short incubation time, the cells were lysed, the β chain immunoprecipitated and the phosphorylation of this subunit estimated with the aid of an antiphosphotyrosine kinase antibody. The results presented in FIG. 13 show that the attachment of the 7C10 or of the h7C10 significantly inhibits the phosphorylation of the subunit of IGF-IR contrary to an irrelevant murine (9G4) or human antibody (written IgG1 on the scheme).

c) Involvement of the 7H2HM Antibody in the Mechanisms of ADCC

The inhibition of the transduction of the signal described above in paragraph b) is the principal mechanism of action involved in the biological activity of the antibodies 7C10 and 7H2M. It is, however, probable that during its administration in man, the antibody 7H2HM, of isotype IgG1, is capable of inducing cell lysis by a mechanism of ADCC type (Antibody Dependent Cellular Cytotoxicity). In order to verify this point, NK (Natural Killer) cells coming from the peripheral blood of human donors are placed in the presence of A549 or MCF-7 cells previously incubated for 4 hours with 10 μg of 7H2HM antibody per $5.10^5$ cells and labeled with $^{51}$Cr (50 μg). In this experiment, herceptin (written h4D5 on FIGS. 32A and 32B) is used as an experiment positive control. FIGS. 32A to 32D show that, as expected, herceptin induces a significant ADCC on the two cells A549 and MCF-7 (see respectively FIGS. 32A and 32B) 7H2HM is likewise capable of inducing an ADCC on the A549 cells (see FIG. 32C), but this phenomenon is of smaller amplitude on the MCF-7 cells (see FIG. 32D).

d) Effects of the Antibodies 7C10 and 7H2HM on the Cell Cycle.

The inhibition of the cell growth observed in vitro on the line MCF-7 should be manifested by an effect on the cell cycle. In order to reply to this question, $4.10^5$ cells are inoculated into 6-well plates, 24 hours after inoculation, the calf serum is removed and IGF1 added in the presence or in the absence of the antibodies to be tested. After incubation for 24 hours, the cells are recovered for the study of the cell cycle. FIG. 33B demonstrates the effect of IGF1 on the entry into the cycle and the growth of the MCF-7 cells compared with the entry into the cycle and the growth of the MCF-7 cells in the absence of IGF1 (see FIG. 33A). After addition of the growth factor, a significant decrease in the G0/G1 phase (from 88.2% to 56.3%) to the benefit of the S (from 7.8% to 31%) and G2/M (from 4% to 12.7%) phases is observed. During the addition of the antibodies 7C10 and 7H2HM (see FIG. 33C), a significant inhibition of the entry into the cycle is observed. In it is to be noted that the murine antibody and its humanized homolog have a comparable activity on the cell cycle. The aIR3, introduced as a positive control, seems slightly less active than the 7C10 and the 7H2HM in this test. The antibody 9G4 used as a control isotype is without effect on the cell cycle.

e) Comparative Activity In Vivo of the Antibodies 7C10 and 7H2HM on the Model A549

In order to confirm the activity of the humanized antibody 7H2HM in vivo, the latter was compared with 7C10 in the model of non-small cell tumor of the lung A549. This experiment was carried out exactly as described above except for the dose of antibody which is 125 µg/dose twice per week in place of 250 µg/dose twice per week and that of the fact of the nonavailability of great quantities of 7H2HM. The antibody 9G4 was used as an isotype control for 7C10 and an irrelevant human immunoglobulin of isotype IgG1 (below called HIgG1) was used as a control for the humanized antibody 7H2HM.

FIG. 34A shows that there are no significant differences between the 9G4 and HIgG1 control curves. As expected, a significant inhibition of the tumor growth is observed with the murine antibody 7C10. Concerning the humanized antibody 7H2HM, the activity observed is of exactly the same intensity as that observed with its murine counterpart. This data, in addition to the observations described above in vitro, indicates that the humanization has not modified the properties of the antibody generated. On the other hand, in the xenograft models in the mouse, the activity of the humanized antibody seems to be integrally connected with a mechanism of inhibition of the transduction of the signal. In effect, if an ADCC part was in play in the inhibition of the tumor growth in the Nude mouse, a difference ought to be observed between the activity of the murine and humanized antibodies.

An in vivo experiment was likewise carried out on the MCF-7 breast tumor model and shows that, as expected, the antibody 7H2HM is perfectly comparable with the murine antibody 7C10 for the inhibition of the growth of this tumor in vivo (FIG. 34B).

f) Demonstration of a Synergy Between the 7H2HM and Navelbine

The protocol described in example 4 was repeated with the aim of reproducing the results obtained with 7C10 with its humanized homolog: the antibody 7H2HM.

The results presented in FIGS. 35A and 35B show that, as in the case of 7C10, a significant synergy is demonstrated between the humanized antibody 7H2HM and navelbine.

g) Effect of the Antibodies 7C10 and 7H2HM on the Apoptosis of MCF-7 Cells In Vitro As indicated above, IGF-IR is capable of conferring protection against apoptosis when it is overexpressed on the surface of cells. Furthermore, it has been demonstrated in these examples that the antibodies 7C10 and 7H2HM were capable of potentiating an active compound in chemotherapy. In order to test the power of the antibodies 7C10 and 7H2HM to induce apoptosis, and to explain in part their synergy potential with the chemotherapy, experiments were conducted on the MCF-7 cells in the presence or in the absence of doxorubicin, a medicament known to induce the apoptosis of this cell line in vitro. In these experiments, the MCF-7 cells are inoculated at $2.10^4/cm^2$ in Petri dishes and cultured for 24 h in RPMI without phenol red supplemented with 10% of fetal calf serum (FCS). The cells are then washed twice with PBS and put back into culture in medium with 0% FCS. They are allowed an adaptation time of 10 minutes at 37° C. before the addition of the antibodies at 10 µg/ml. After an extra 10 minutes, at 37° C., recombinant IGF-I (Sigma) is added to the culture medium to a final concentration of 50 ng/ml. The cells are left at 37° C. again for one hour in order to allow the attachment of the antibodies and of the IGF-I. Finally, the doxorubicin (Sigma) is added to the culture medium at 2 µg/ml and the cells are incubated for 24 hours at 37° C.

The experiments have likewise been conducted with navelbine at a concentration of 10 µg/ml.

The analysis of the cell viability is carried out by flow cytometric analysis after labeling with the annexin V-FITC (20 minutes, 4° C.) and DAPI (2 µg/ml) The percentage of dead cells considered is the labeled population Annexin +/DAPI+. The antibody 5C2 is used as a control isotype.

The results represented in FIG. 36 show that doxorubicin induces apoptosis in 8% of the MCF-7 cells. When the cells are treated conjointly with the antibody 7C10 and the doxorubicin a significant increase in cell death is observed. The same effect is shown with the antibody 7H2HM. The same type of results was observed when the antibody is combined with navelbine.

EXAMPLE 7

Cloning Strategy of Genes Coding for the Variable Regions of the Heavy and Light Chains of the Monoclonal Antibody (MAb) 7C10

The total RNA was extracted from $10^7$ cells of hybridomas secreting the antibody 7C10 by using the TRI REAGENT™ (according to the instructions given by the supplier, SIGMA, T9424). The first cDNA strand was synthesized with the aid of the 'First strand cDNA synthesis' kit of Amersham-Pharmacia (#27-9621-01, according to the instructions given by the supplier). For the two chains, the reaction was primed with the oligonucleotide Not I-d(T)18, comprised in the Kit.

The cDNA:mRNA hybrid thus obtained was used for the amplification by PCR of the genes coding for the heavy and light chains of the Mab 7C10. The PCR were carried out by using a combination of oligonucleotides specific for the heavy and light (Kappa) chains of mouse immunoglobulins. The primers corresponding to the 5' ends hybridize in the region corresponding to the signal peptides (Table 2 for heavy chains, Table 3 for light chains). These primers were compiled from a large number of mouse antibody sequences found in the databanks (Jones S. T. et al., Bio/Technology 9:88–89, 1991). The primers corresponding to the 3' ends hybridize in the constant regions of the heavy chains (CH1 domain of the subclass IgG1, not far from the V-C junction, MHC-1 primer Table 4) and light chains (Kappa domain not far from the V-C junction, MKC primer Table 4).

TABLE 2

Oligonucleotide primers for the 5' region of
the variable domains of the heavy chains of mouse
immunoglobulin (MHV) ("MHV" for "Mouse Heavy Variable")

| | | |
|---|---|---|
| MHV-1: | 5' ATGAAATGCAGCTGGGTCATSTTCTT 3' | (SEQ ID No. 13) |
| MHV-2: | 5' ATGGGATGGAGCTRTATCATSYTCTT 3' | (SEQ ID No. 14) |

TABLE 2-continued

Oligonucleotide primers for the 5' region of
the variable domains of the heavy chains of mouse
immunoglobulin (MHV) ("MHV" for "Mouse Heavy Variable")

| | | |
|---|---|---|
| MHV-3: | 5' ATGAAGWTGTGGTTAAACTGGGTTTT 3' | (SEQ ID No. 15) |
| MHV-4: | 5' ATGRACTTTCCGYTCAGCTTGRT 3' | (SEQ ID No. 16) |
| MHV-5: | 5' ATGGACTCCAGGCTCAATTTAGTTTT 3' | (SEQ ID No. 17) |
| MHV-6: | 5' ATGGCTGTCYTRGSGCTRCTCTTCTG 3' | (SEQ ID No. 18) |
| MHV-7: | 5' ATGGRATGGAGCKGGRTCTTTMTCTT 3' | (SEQ ID NO. 19) |
| MHV-8: | 5' ATGAGAGTGCTGATTCTTTTGTG 3' | (SEQ ID No. 20) |
| MHV-9: | 5' ATGGMTTGGGTGTGGAMCTTGCTATT 3' | (SEQ ID No. 21) |
| MHV-10: | 5' ATCGGCAGACTTACATTCTCATTCCT 3' | (SEQ ID No. 22) |
| MHV-11: | 5' ATGGATTTTGGGCTGATTTTTTTTATTG 3' | (SEQ ID No. 23) |
| MHV-12: | 5' ATGATGGTGTTAAGTCTTCTGTACCT 3' | (SEQ ID No. 24) |

NB KEY: R = A/G, Y = T/C, W = A/T, K = T/G, M = A/C, S = C/G.

TABLE 3

Oligonucleotide primers for the 5' region of
the variable domains of kappa (light) chains of mouse
immunoglobulin (MKV) ("MKV" for "Mouse Kappa Variable")

| | | |
|---|---|---|
| MKV-1: | 5' ATGAAGTTGCCTGTTAGGCTGTTGGTGCT 3' | (SEQ ID No. 25) |
| MKV-2: | 5' ATGGAGWCAGACACACTCCTGYTATGGGT 3' | (SEQ ID No. 26) |
| MKV-3: | 5' ATGAGTCTCCTCACTCAGGTCCT 3' | (SEQ ID No. 27) |
| MKV-4: | 5' ATGAGGRCCCCTGCTCAGWTTYTTGG 3' | (SEQ ID No. 28) |
| MKV-5: | 5' ATGGATTTWCAGGTGCAGATTWTCAGCTT 3' | (SEQ ID No. 29) |
| MKV-5A: | 5' ATGGATTTWCARGTGCAGATTWTCAGCTT 3' | (SEQ ID No. 30) |
| MKV-6: | 5' ATGAGGTKCYYTGYTSAGYTYCTGRG 3' | (SEQ ID No. 31) |
| MKV-7: | 5' ATGGGCWTCAAGATGGAGTCACA 3' | (SEQ ID No. 32) |
| MKV-8: | 5' ATGTGGGGAYCTKTTTYCMMTTTTTCAAT 3' | (SEQ ID No. 33) |
| MKV-9: | 5' ATGGTRTCCWCASCTCAGTTCCTT 3' | (SEQ ID NO. 34) |
| MKV-10: | 5' ATGTATATATGTTTGTTGTCTATTTC 3' | (SEQ ID No. 35) |
| MKV-11: | 5' ATGGAAGCCCCAGCTCAGCTTCTCTT 3' | (SEQ ID No. 36) |
| MKV-12A: | 5' ATGRAGTYWCAGACCCAGGTCTTYRT 3' | (SEQ ID No. 37) |
| MKV-12B: | 5' ATCGAGACACATTCTCAGGTCTTTGT 3' | (SEQ ID No. 38) |
| MKV-13: | 5' ATGGATTCACAGGCCCAGGTTCTTAT 3' | (SEQ ID No. 39) |

NB KEY: R = A/G, Y = T/C, W = A/T, K = T/G, M = A/C, S - C/G.

TABLE 4

Oligonucleotide primers for the 3' ends of the mouse $V_R$ and $V_L$ genes

Light chain (MKC):

5' ACTGGATGGTGGGAAGATGG 3'      (SEQ ID No. 40)

TABLE 4-continued

Oligonucleotide primers for the 3' ends of the mouse $V_R$ and $V_L$ genes

Constant region of the mouse Kappa domain:

```
  A   D   A   A   P   T   V   S   I   F   P   P   S   S   (SEQ ID No. 41)
 GCT GAT GCT CCA CCA ACT GTA TCC ATC TTC CCA CCA TCC AGT  (SEQ ID No. 42)
                         ||  ||| ||| ||| ||| ||| |||
             (MKC)       CC  ATC TTC CCA CCA TCC AGT      (SEQ ID No. 43)
```

Heavy chain (MHC-1)
5' CCAGTGGATACACAGATG 3'     (SEQ ID No. 44)
CH1 domain of mouse gamma-1 (IgG1 subclass):

```
  A   K   I   T   P   P   S   V   Y   P   L              (SEQ ID No. 46)
 GCC AAA ACG ACA CCC CCA TCT GTC TAT CCA CTG              (SEQ ID No. 45)
             ||| ||| ||| ||| ||| ||| |||
    (MHC-1)  CCC CCA TCT GTC TAT CCA CTG                  (SEQ ID No. 47)
```

EXAMPLE 9

Sequences of Immunoglobulins Cloned from the Mouse Hybridoma 7C10

By following the amplification strategy described above, PCR products corresponding to the variable regions of the heavy (VH) and light (VL) chains were cloned by using the "pGEM®-T Easy Vector Systems" (Promega). For 7C10 VL, PCR products were obtained with the MKC primer in combination with the MKV1 and MKV2 primers. For 7C10 VH, PCR products were obtained with the MHC-1 primer in combination with the MHV8 and MHV12 primers. A thorough sequencing of the PCR products cloned in the pGem-T easy vectors revealed two different sequences for the light chain and one unique sequence for the heavy chain.

a) Variable Region Isolated From the Oligo MKV1

The DNA sequence obtained is characteristic of a variable region of functional Ig. This novel sequence is therefore presumed to be that coding for 7C10 VL. The DNA (SEQ ID Nos. 48 and 50) and amino acid (SEQ ID No. 49) sequences of the cDNA coding for 7C10 VL are represented in FIG. 14.

b) Variable Region Isolated From the Oligo MKV2

The gene coding for this light chain comes from an aberrant mRNA transcript which is present in all the standard fusion partners derived from the original MOPC-21 tumor of which the mouse myeloma Sp2/Oag14, which was used in order to produce the 7C10 hybridoma, is part. This sequence contains an aberrant recombination between the V and J genes (deletion of four nucleotide bases involving a change in the reading frame) and a mutation of the invariable cysteine in position 23 to tyrosine. These changes suggest that this light chain would be nonfunctional although nevertheless transcribed to messenger RNA. The DNA sequence of this pseudo light chain is not shown.

c) Variable Region Isolated From the Oligos MHV8 and MHV12

The DNA sequences obtained with these two oligos are identical, apart from the sequence encoded by the oligo itself. This sequence is a novel sequence coding for a functional heavy chain presumed to be that of the monoclonal antibody 7C10. The DNA (SEQ ID Nos. 51 and 53) and amino acid (SEQ ID No. 52) sequences of the cDNA coding for 7C10 VH are represented in FIG. 15.

EXAMPLE 9

Construction of Chimeric Mouse-Man Genes

The chimeric antibody 7C10 was constructed so as to have the mouse 7C10 regions VL and VH connected to the human constant regions kappa and gamma-1, respectively. Oligos were used in order to modify the 5' and 3' ends of the sequences flanking the DNA coding for 7C10 VL and VH in order to allow their cloning in vectors for expression in mammalian cells. These vectors use the strong promoter HCMV in order effectively to transcribe the heavy and light chains of the chimeric antibody 7C10. On the other hand, these vectors likewise contain the replication origin of SV40 allowing an effective replication of the DNA and, as a consequence, as a transitory expression of the proteins in cos cells.

EXAMPLE 10

Expression and Evaluation of the Recognition Activity of the IGF-I Receptor of the Chimeric Antibody 7C10

The two plasmids containing the DNA coding for the chimeric 7C10 antibody were cotransfected in cos-7 cells (ATCC number CRL-1651) in order to study the transitory expression of the recombinant antibody. After incubation for 72 hours, the culture medium was removed, centrifuged in order to eliminate the cell debris and analyzed by the ELISA technique for the production of human IgG1 (see Example 16) and the recognition of the receptor for IGF-I (see Example 17).

The ELISA tests for measurement of concentrations of human IgG1/Kappa showed that the expression of the chimeric antibody 7C10 in the cos-7 cells was between 300 and 500 ng/mm, which is comparable to the values obtained with the majority of antibodies.

The ELISA tests for recognition of the receptor for IGF-I show that the chimeric antibody recognizes it specifically and with a good relative avidity (see FIGS. 3A, 3B and 3C). This provides the functional proof that the good VH and VL of the 7C10 antibody have been identified. In addition, this chimeric form of 7C10 appears as being an indispensable tool in the evaluation of the affinity of the humanized forms.

EXAMPLE 11

Molecular Modeling of the Variable Regions of the Mouse Antibody 7C10

In order to assist and to refine the humanization process by "CDR grafting", a molecular model of the VL and VH regions of the mouse antibody 7C10 was constructed. The model is based on the crystallographic structure of the heavy chain 1AY1 and of the light chain 2PCP.

EXAMPLE 12

Figures 16, 17:
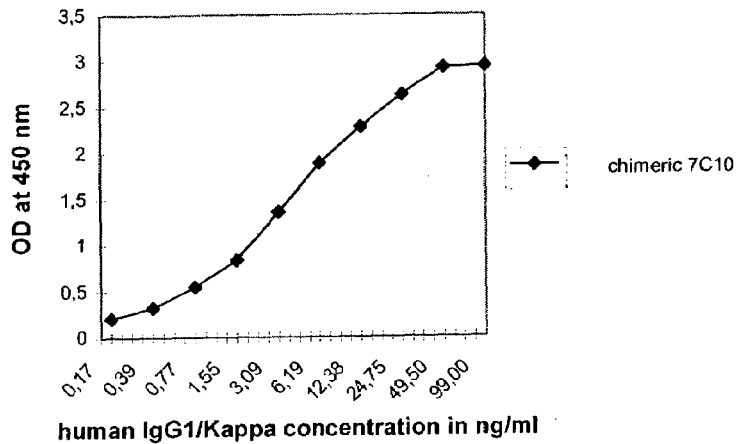

Process of Humanization by CDR Grafting of the Variable Region of the Light Chain of the Antibody 7C10 (7C10VL)

a) Comparison of the Amino Acid Sequence of 7C10 VL with All the Known Mouse VL Sequences As a preliminary step to humanization by CDR grafting, the amino acid sequence of 7C10 VL was first compared with all the mouse VL sequences present in the databank of Kabat (Internet address: ftp.ebi.ac.uk/pub/database/kabat/fasta format/, last update of data dates from 1999). 7C10 VL has thus been identified as belonging to the subgroup II of the Kappa light chains as defined by Kabat et al. (*In Sequences of proteins of immunological interest* (5 edn) NIH publication No. 91-3242, U.S. Department of Health and Human Services, Public Health Service, National Institutes of Health, Bethesda, 1991). The VL regions of monoclonal antibodies of mice having a sequence identity ranging up to 95% have been identified (DRB1-4.3 (SEQ ID No. 55): 95% and C94-5B11'CL (SEQ ID No. 56): 95%, see FIG. 17). In order to attempt to identify the out of the ordinary residues in the 7C10 VL sequence, the amino acid sequence of 7C10 VL (SEQ ID No. 54) was aligned with the consensus sequence of the subgroup II of the mouse kappa chains (SEQ ID No. 57) as defined by Kabat (see FIG. 17).

In the Kabat position number 3, the valine (V) normally present in the subgroup II of the Kappa light chains according to Kabat (71%) is replaced by a leucine (L) A leucine in this position is not rare since it is found, for example, in DRB1-4.3 and C94-5B11'CL. According to the molecular model, this residue does not seem to play a particular role. Consequently, the conservation of this residue in the humanized form will not be envisaged.

In the Kabat position number 7, the threonine (T) normally present in the subgroup II of the Kappa light chains according to Kabat (66%) is replaced by an iso-leucine (I). An isoleucine in this position is relatively rare since it is only found 15 times among all the mouse VL sequence known and never among human VL sequences. The molecular model shows that this residue (17) points toward the surface of the molecule but does not contact the CDRs (the residue of a CDR which is the closest would be the arginine in Kabat position number 42). In addition, it does not seem very probable that this residue 17 directly contacts the antigen. Consequently, the conservation of this residue in the humanized form will not be envisaged, at any rate at first.

In the Kabat position number 77, the arginine (R) normally present in the subgroup II of the Kappa light chains according to Kabat (95.5%) is replaced by a serine (S). A serine in this position is not rare.

b) Comparison of the Amino Acid Sequence of 7C10 VL with All the Known Human VL Sequences In order to identify the best human candidate for the "CDR grafting", the Kappa VL region of human origin having the greatest homology possible with 7C10 VL was sought. To this end, the amino acid sequence of mouse kappa 7C10 VL was compared with all the human Kappa VL sequences present in the database of Kabat. Mouse 7C10 VL had the greatest sequence homology with the human kappa VL regions of subgroup II as defined by Kabat et al, (1991). VH regions of monoclonal antibodies of human origin have been identified having a sequence identity ranging up to 75.9% (GM607 (SEd ID No. 58), see FIG. 18) over the whole of the 112 amino acids composing the variable region. A germinal line of human origin, DPK15/A19 (SEQ ID No. 59), having a sequence identity of 76% (see FIG. 18) was also identified, GM607 (Klobeck et al., 1984). GM607 was therefore chosen as a human sequence receptive of CDRs (according to the definition of Kabat) of mouse 7C10 VL. By comparing the GM607 sequences with that of the consensus sequence of the human subgroup II (SEQ ID No. 60) (FIG. 18), no particular residue in the framework regions (Rch) could be identified, indicating by the same fact that GM607 was a good candidate for CDR grafting.

c) Humanized Versions of 7C10 VL

The following stage in the humanization process consisted in joining the CDRs of mouse 7C10 VL to the framework regions (Rch) of the human light chain selected, G607 (Klobeck et al., 1984). At this stage of the process, the molecular model of the mouse Fv regions of 7C10 is particularly useful in the choice of the mouse residues to be conserved as being able to play a role either in the maintenance of the tridimensional structure of the molecule (canonical structure of tho CDRs, VH/VL interface, etc.) or in the binding to the antigen. In the Rchs, each difference between the mouse (7C10 VL) and human (GM607) amino acids was examined scrupulously (see Table 5). In addition, the particular residues in the mouse sequence 7C10 VL which were identified (see example 12.a) were taken into account if needed.

In the first version humanized by "CDR grafting" of 7C10 VL, human 1, a single change in the framework regions (Rch) of GM607 was carried out. This change concerns the residue 2 (nomenclature of Kabat) situated in Rch 1. This residue enters in effect into the composition of the canonical structure of the CDR 1 of 7C10 VL and could therefore be critical for maintaining this loop in its good conformation. The valine present in this position in the mouse 7C10 VL sequence is thus conserved in this same position in the humanized form (see Table 5 and FIG. 19 for the amino acid sequence (SEQ ID No. 61) and FIG. 20 for the DNA sequence (SEQ ID Nos. 62 and 64) and the amino acid sequence comprising the peptide signal (SEQ ID No. 63).

In the second version humanized by "CDR grafting" of 7C10 VL, human 2, no change in the Rchs of the human light chain GM607 has been made. All the residues of the Rchs are thus of human origin including the residue 2 which has therefore been mutated in order to replace the valine present in mouse 7C10 VL by an isoleucine found in this same position in the human light chain GM607 (see Table 5 and FIG. 19 for the amino acid sequence (SEQ ID No. 65) and FIG. 21 for the DNA sequence (SEQ ID Nos. 66 and 68) and the amino acid sequence comprising the peptide signal (SEQ ID No. 67)). This human form 2 is therefore totally humanized (apart from, of course, CDRs themselves) since all the residues of the Rchs are those of the light chain of human origin, CM607.

TABLE 5

Alignment of the amino acid sequences leading to the design of the remodeled human 7C10 $V_L$ regions

| Kabat | # | FR or CDR | Mouse light chain 7C10 | Human germinal line DPK15/A19 | GM 607 | Remodeled human 7C10 1 | Remodeled human 7C10 2 | Comments |
|---|---|---|---|---|---|---|---|---|
| 1 | 1 | FR1 | D | D | D | D | D | |
| 2 | 2 | | V* | I* | I* | V* | I* | Cano L1 4(16) Vernier zone |
| 3 | 3 | | L | V | V | V | V | |

TABLE 5-continued

Alignment of the amino acid sequences leading to the design of the remodeled human 7C10 V$_L$ regions

| Kabat | # | FR or CDR | Mouse light chain 7C10 | Human germinal line DPK15/A19 | GM 607 | Remodeled human 7C10 1 | Remodeled human 7C10 2 | Comments |
|---|---|---|---|---|---|---|---|---|
| 4 | 4 | I | M | M | M | M | M | Vernier zone |
| 5 | 5 | I | T | T | T | T | T | |
| 6 | 6 | I | Q | Q | Q | Q | Q | |
| 7 | 7 | I | I | S | S | S | S | |
| 8 | 8 | I | P | P | P | P | P | |
| 9 | 9 | I | L | L | L | L | L | |
| 10 | 10 | I | S | S | S | S | S | |
| 11 | 11 | I | L | L | L | L | L | |
| 12 | 12 | I | P | P | P | P | P | |
| 13 | 13 | I | V | V | V | V | V | |
| 14 | 14 | I | S | T | T | T | T | |
| 15 | 15 | I | L | P | P | P | P | |
| 16 | 16 | I | G | G | G | G | G | |
| 17 | 17 | I | D | E | E | E | E | |
| 18 | 18 | I | Q | P | P | P | P | |
| 19 | 19 | I | A | A | A | A | A | |
| 20 | 20 | I | S | S | S | S | S | |
| 21 | 21 | I | I | I | I | I | I | |
| 22 | 22 | I | S | S | S | S | S | |
| 23 | 23 | FR1 | C | C | C | C | C | |
| 24 | 24 | CDR1 | R | R | R | R | R | |
| 25 | 25 | I | S* | S* | S* | S* | S* | Cano L1 4(16) |
| 26 | 26 | I | S | S | S | S | S | |
| 27 | 27 | I | Q | Q | Q | Q | Q | |
| 27A | 28 | I | S | S | S | S | S | |
| 27B | 29 | I | I* | L* | L* | i* | i* | Cano L1 4(16) |
| 27C | 30 | I | V | L | L | i | I | |
| 27D | 31 | I | H | H | H | H | H | |
| 27E | 32 | I | S | S | S | S | S | |
| 28 | 33 | I | N | N | N | N | N | |
| 29 | 34 | I | G | G | G | G | G | |
| 30 | 35 | I | N | Y | Y | n | N | |
| 31 | 36 | I | T | N | N | t | T | |
| 32 | 37 | I | Y | Y | Y | Y | Y | |
| 33 | 38 | I | L* | L* | L* | L* | L* | Cano L1 4(16) |
| 34 | 39 | CDR1 | Q | D | D | q | Q | |
| 35 | 40 | FR2 | W | W | W | W | W | Vernier zone |
| 36 | 41 | I | Y | Y | Y | Y | Y | VH/VL inter Vernier zone |
| 37 | 42 | I | L | L | L | L | L | |
| 38 | 43 | I | Q | Q | Q | Q | Q | VL/VH inter |
| 39 | 44 | I | K | K | K | K | K | |
| 40 | 45 | I | P | P | P | P | P | |
| 41 | 46 | I | G | G | G | G | G | |
| 42 | 47 | I | Q | Q | Q | Q | Q | |
| 43 | 48 | I | S | S | S | S | S | |
| 44 | 49 | I | P | P | P | P | P | VL/VH inter (+) |
| 45 | 50 | I | K | Q | Q | Q | Q | |
| 46 | 51 | I | L | L | L | L | L | VL/VH inter Vernier zone |
| 47 | 52 | I | L | L | L | L | L | Vernier zone |
| 48 | 53 | I | I | I | I | I* | I* | Cano L2 1(7) Vernier zone |

TABLE 5-continued

Alignment of the amino acid sequences leading to the design of the remodeled human 7C10 V$_L$ regions

| Kabat | # | FR or CDR | Mouse light chain 7C10 | Human germinal line DPK15/A19 | GM 607 | Remodeled human 7C10 1 | Remodeled human 7C10 2 | Comments |
|---|---|---|---|---|---|---|---|---|
| 49 | 54 | FR2 | Y | Y | Y | Y | Y | Vernier zone |
| 50 | 55 | CDR2 | K | L | L | k | K | |
| 51 | 56 | | V* | G* | G* | v* | v* | Cano L2 1(7) |
| 52 | 57 | | S* | S* | S* | S* | S* | Cano L2 1(7) |
| 53 | 58 | | N | N | N | N | N | |
| 54 | 59 | | R | R | R | R | R | |
| 55 | 60 | | L | A | A | l | L | |
| 56 | 61 | CDR2 | Y | S | S | y | Y | |
| 57 | 62 | FR3 | G | G | G | G | G | |
| 58 | 63 | | V | V | V | V | V | |
| 59 | 64 | | P | P | P | P | P | |
| 60 | 65 | | D | D | D | D | D | |
| 61 | 66 | | R | R | R | R | R | |
| 62 | 67 | | F | F | F | F | F | |
| 63 | 68 | | S | S | S | S | S | |
| 64 | 69 | | G* | G* | G* | G* | G* | Cano L2 1(7) Vernier zone |
| 65 | 70 | | S | S | S | S | S | |
| 66 | 71 | | G | G | G | G | G | Vernier zone |
| 67 | 72 | | S | S | S | S | S | |
| 68 | 73 | | G | G | G | G | G | Vernier zone |
| 69 | 74 | | T | T | T | T | T | Vernier zone |
| 70 | 75 | | D | D | D | D | D | |
| 71 | 76 | | F* | F* | F* | F* | F* | Cano L1 4(16) Vernier zone |
| 72 | 77 | | T | T | T | T | T | |
| 73 | 78 | | L | L | L | L | L | |
| 74 | 79 | | K | K | K | K | K | |
| 75 | 80 | | I | I | I | I | I | |
| 76 | 81 | | S | S | S | S | S | |
| 77 | 82 | | S | R | R | R | R | |
| 78 | 83 | | V | V | V | V | V | |
| 79 | 84 | | E | E | E | E | E | |
| 80 | 85 | | A | A | A | A | A | |
| 81 | 86 | | E | E | E | E | E | |
| 82 | 87 | | D | D | D | D | D | |
| 83 | 88 | | L | V | V | V | V | |
| 84 | 89 | | G | G | G | G | G | |
| 85 | 90 | | V | V | V | V | V | |
| 86 | 91 | | Y | Y | Y | Y | Y | |
| 87 | 92 | | Y | Y | Y | Y | Y | VL/VH inter |
| 88 | 93 | FR3 | C | C | C | C | C | |
| 89 | 94 | CDR3 | F | M | M | f | F | VL/VH inter |
| 90 | 95 | | Q* | Q* | Q* | Q* | Q* | Cano L3 1(9) |
| 91 | 96 | | G | A | A | g | G | VL/VH inter |
| 92 | 97 | | S | L | L | s | S | |
| 93 | 98 | | H | Q | Q | h | H | |
| 94 | 99 | | V | T | T | v | V | |
| 95 | 100 | | P* | P* | P* | P* | P* | Cano L3 1(9) |
| 96 | 101 | | W | | | w | W | VL/VH inter (+) |
| 97 | 102 | CDR3 | T | | T | T | T | |

TABLE 5-continued

Alignment of the amino acid sequences leading to the design of the remodeled human 7C10 $V_L$ regions

| Kabat | # | FR or CDR | Mouse light chain 7C10 | Human germinal line DPK15/A19 | GM 607 | Remodeled human 7C10 1 | Remodeled human 7C10 2 | Comments |
|---|---|---|---|---|---|---|---|---|
| 98 | 103 | FR4 | F | | F | F | F | VL/VH inter (+) Vernier zone |
| 99 | 104 | | G | | G | G | G | |
| 100 | 105 | | G | | Q | Q | Q | |
| 101 | 106 | | G | | G | G | G | |
| 102 | 107 | | T | | T | T | T | |
| 103 | 108 | | K | | K | K | K | |
| 104 | 109 | | L | | V | V | V | |
| 105 | 110 | | E | | E | E | E | |
| 106 | 111 | | I | | I | I | I | |
| 107 | 112 | FR4 | K | | K | K | K | |

Legend:
The first column (Kabat) indicates the position of the amino acid residue according to Kabat et al. (1991);
the second column (#) indicates the position of the amino acid in the regular sequence;
the third column (RF or CDR) was made in order easily to identify the segments of the skeleton (FR1, FR2, FR3 and FR4) and the CDR segments (CDR1, CDR2 and CDR3) ("CDR" for "Complementarity-Determining Region") with the three CDRs separating the four FRs;
the fourth column (Mouse light chain 7C10) represents the amino acid sequence (SEQ ID No. 54) of the $V_L$ region of mouse antibody 7C10;
the fifth column (Human germinal line DPK15/A19) represents the amino acid sequence (SEQ ID No. 59) of the kappa II human V light chain of the germinal line;
the sixth column (GM607) represents the amino acid sequence (SEQ ID No. 58) of the $V_L$ region of the human antibody GM607;
the seventh and eighth columns (remodeled human 7C10 1 and 2) represent the amino acid sequences of the humanized 1 and 2 antibody 7C10 VL (respectively SEQ ID Nos. 61 and 65).
"*" indicates the parts of the canonical structure of the CDR loop such as defined by Chothia et al. (Nature, 342, 877–883, 1989).

EXAMPLE 13

Process of Humanization by CDR Grafting of the Variable Region of the Heavy Chain of the Antibody 7C10 (7C10 VH)

a) Comparison of the Amino Acid Sequence of 7C10 VH with all of the Known Mouse VH Sequences As a preliminary stage in humanization by CDR grafting, the amino acid sequence of 7C10 VH was first compared with all the mouse VH sequences present in the Kabat databank (Internet address: ftp://ftp.ebi.ac.uk/pub/database/kabat/fasta_format/, last update of data dates from 1999). 7C10 VH has thus been identified as belonging to the subgroup I(A) of the heavy chains as defined by Kabat et al. (1991). VH regions of mouse monoclonal antibodies having a sequence identity ranging up to 90.5% were identified (AN03'CL (SEQ ID No. 70), see FIG. 22). In order to attempt to identify the out of the ordinary residues in the sequence of 7C10 Vh, we aligned the amino acid sequence of 7C10 VH (SEQ ID No. 69) with the consensus sequence (SEQ ID No. 71) of the subgroup I(A) of the mouse heavy chains as defined by Kabat (see FIG. 22).

Residue 17 (Kabat's numbering), Thr for the consensus sequence of subgroup I(A) and Ser in 7C10 VH, is located on the surface of the molecule with respect to the interface with the constant region. This residue does not seem to be important.

Residue 2/(Kabat's numbering), Asp for the consensus sequence of subgroup I(A) and Tyr in 7C10 VH, is a canonical residue for the CDR 1. Tyr in this position is now rare and is probably critical for maintaining CDR 1 in its good conformation.

Residue 84 (Kabat's numbering), Thr for the consensus sequence of the subgroup I(A) and Asn in 7C10 VH. Asn was found 93 times in mouse VH and 3 times in human VH. According to the molecular model, it is a surface residue remote from the paratope.

The numbering of the amino acids is that of Kabat et al. (1991). The residues in the framework regions (apart from CDRs) which, differ between 7C10 VH and Kabat mouse subgroup I(A) are underlined. AN03'CL represents the sequence of the heavy chain of a mouse antibody (access number in the Kabat databank is P001289).

b) Comparison of the Amino Acid Sequence of 7C10 VH with All of the Known Human VH Sequences In order to identify the best human candidate for the "CDR grafting", the VH region of human origin having the greatest possible homology with 7C10 VH was sought.

To this end, the amino acid sequence of mouse 7C10 VH was compared with all the human VH sequences present in the Kabat databank. Mouse 7C10 VH had the greatest sequence homology with the human VH regions of the subgroup II as defined by Kabat et al. (1991). VH regions of monoclonal antibodies of human origin were identified having a sequence identity ranging up to 67.3% (human VH FUR1'CL (SEQ ID No. 73), see FIG. 23) over the whole of the 98 amino acids encoded by the variable gene (that is to say apart from CDR3 and region J). A germinal line of human origin, 4.22 VH IV (Sanz et al., 1989), having a sequence identity of 68.4%, according to the same criteria as for VH FUR1'CL, was also identified (human Germ-line (SEQ ID No. 74), see FIG. 23) The sequence encoded by the germinal line 4.22 VH IV was chosen as a human sequence receptive of the CDRs (according to the definition of Kabat) of mouse 7C10 VH rather than VH FUR1'CL because in comparing the sequences of 4.22 VH IV and VH FUR1'CL with that of the consensus sequence of the human subgroup II (human Kabat sg II (SEQ ID No. 72), see FIG. 23 and table 6), no atypical residue in the framework regions (Rch) could be identified for 4.22 VH IV although the presence of two atypical residues (Gln and Arg in positions 81 and 82A according to the Nomenclature of Kabat, respectively) were identified in the sequence encoded by VH FUR1'CL.

c) Humanized Versions of 7C10 VH

The following stage in the humanization process consisted in joining the CDRs of mouse 7C10 VH to the framework regions (Rch) of the human germinal line 4.22 VH IV (Sanz et al., 1989). At this stage of the process, the molecular model of the mouse Fv regions of 7C10 is particularly useful in the choice of the mouse residues to be conserved as being able to play a role in the maintenance of the tridimensional structure of the molecule (canonical structure of the CDRs, VH/VL interface, etc.) or in the binding to the antigen (belonging to the paratope). In the Rchs, each difference between the mouse (7C10 VH) and human (4.22 VH IV) amino acids was examined scrupulously (see Table 6). In addition, the particular residues in the mouse 7C10 VH sequence which had been identified (see Example 8.a) were taken into account if needed.

In the first version of 7C10 VH humanized by "CDR grafting", humanized 1, four ranges in the framework regions (Rch) of 4.22 VH IV were carried out (see Table 6, FIG. 24 for the amino acid sequence (SEQ ID No. 75) and FIG. 25 for the DNA sequence (SEQ ID Nos. 76 and 78) and the amino acid sequence comprising the peptide signal (SEQ ID No. 77)). These four changes concern:

Residue 30 (Kabat's nomenclature) situated in Rch 1. This residue enters in effect into the structural composition of the CDR1 of 7C10 VH (as defined by Chothia et al., 1989) and could therefore be critical for maintaining this loop in its correct conformation. The Thr present in this position in the mouse sequence 7C10 VH is therefore conserved in this same position in the humanized form.

Residue 48 (Kabat's nomenclature) situated in Rch 2. This residue is close to the CDRs, although according to the molecular model not in direct contact with the latter, and could influence their ultimate conformation. The methionine present in this position in the mouse sequence 7C10 VH is therefore conserved in this same position in the humanized form 1.

Residue 67 (Kabat's nomenclature) situated in Rch 3. This residue is close to the CDRs and according to the molecular model could contact Lysine 60 (Kabat's nomenclature) in the CDR 2. The isoleucine present in this position in mouse sequence 7C10 VH is therefore conserved in this position in the humanized form 1.

Residue 71 (Kabat's nomenclature) situated in Rch 3. This residue is part of the canonical structure of the CDR 2 and should therefore be critical fur maintaining this loop in its correct conformation. The arginine present in this position in the mouse sequence 7C10 VH is therefore conserved in this position in the humanized form 1.

In the second version of 7C10 VH humanized by "CDR grafting", humanized 2, two changes in the framework regions (Rch) of 4.22 VH IV were carried out. These two changes concern the residues 30 and 71 (Kabat's nomenclature), already described in the humanized form 1 (see Table 6, FIG. 24 for the amino acid sequence (SEQ ID No. 79) and FIG. 26 for the DNA sequence (SEQ ID Nos. 80 and, 82) and the amino acid sequence comprising the peptide signal (SEQ ID No. 81)).

In the third form of 7C10 VH humanized by "CDR grafting", humanized 3, no change in the framework regions (Rch) of 4.22 VH IV was carried out. All the residues of the Rchs are therefore of human origin including the residues 30, 48, 67 and 71 (Kabat's nomenclature) which have been conserved (see Table 6, FIG. 24 for the amino acid sequence (SEQ ID No. 83) and FIG. 27 for tho DNA sequence (SEQ ID Nos. 84 and 86) and the amino acid sequence comprising the peptide signal (SEQ ID No. 85)). This humanized form 3 is therefore totally humanized (apart, of course, from the CDRs themselves as defined by Kabat) since all the residues of the Rchs are those encoded by the VH gene of the germinal line 4.22 VH IV.

TABLE 6

Alignment of the amino acid sequences leading to the design of the remodeled human 7C10 V$_H$ regions

| Kabnt | FR or CDR | Mouse heavy chain 7C10 | Germinal line 4.22 VH TV | Human FUR1'CL VR | Remodeled Human 7C10 H 1 | Remodeled Human 7C10 H 2 | Remodeled Human 7C10 H 3 | Comments |
|---|---|---|---|---|---|---|---|---|
| 1 | FR1 | D | Q | Q | Q | Q | Q | |
| 2 | | V | V | V | V | V | V | Vernier Zone |
| 3 | | Q | Q | Q | Q | Q | Q | |
| 4 | | L | L | L | L | L | L | |
| 5 | | Q | Q | Q | Q | Q | Q | |
| 6 | | E | E | E | E | E | E | |
| 7 | | S | S | S | S | S | S | |
| 8 | | G | G | G | G | G | G | |
| 9 | | P | P | P | P | P | P | |
| 10 | | G | G | G | G | G | G | |
| 11 | | L | L | L | L | L | L | |
| 12 | | V | V | V | V | V | V | |
| 13 | | K | K | K | K | K | K | |
| 14 | | P | P | P | P | P | P | |
| 15 | | S | S | S | S | S | S | |

TABLE 6-continued

Alignment of the amino acid sequences leading to the design of the remodeled human 7C10 V$_H$ regions

| Kabnt | FR or CDR | Mouse heavy chain 7C10 | Germinal line 4.22 VH TV | Human FUR1'CL VR | Remodeled Human 7C10 H 1 | Remodeled Human 7C10 H 2 | Remodeled Human 7C10 H 3 | Comments |
|---|---|---|---|---|---|---|---|---|
| 16 | | Q | E | E | E | E | E | |
| 17 | | S | T | T | T | T | T | |
| 18 | | L | L | L | L | L | L | |
| 19 | | S | S | S | S | S | S | |
| 20 | | L | L | L | L | L | L | |
| 21 | | T | T | T | T | T | T | |
| 22 | | C | C | C | C | C | C | |
| 23 | | S | T | T | T | T | T | |
| 24 | | V | V | V | V* | V* | V* | canonical H1 2(6) |
| 25 | | T | S | S | S | S | S | |
| 26 | | G* | G* | G* | G* | G* | G* | canonical H1 2(6) |
| 27 | | Y* | Y* | Y* | Y* | Y* | Y* | canonical H1 2(6) Vernier Zone |
| 28 | | S | S | S | S | S | S | Vernier Zone |
| 29 | | I* | I* | I* | I* | I* | I* | canonical H1 2(6) Vernier Zone |
| 30 | FR1 | T | S | S | t | T | S | Vernier Zone Close to the CDRs |
| 31 | CDR1 | G | S | S | g | G | g | |
| 32 | | G | G | G | G | G | G | |
| 33 | | Y | Y | Y | Y | Y | Y | |
| 34 | | L | Y | Y | I | L | I | |
| 35 | | W* | W* | W* | W* | W* | W* | canonical H1 2(6) VH/VL interface |
| 35A | CDR1 | N | G | G | n | N | n | |
| 36 | FR2 | W | W | W | W | W | W | |
| 37 | | I | I | I | I | I | I | VH/VL interface |
| 38 | | R | R | R | R | R | R | |
| 39 | | Q | Q | Q | Q | Q | Q | VH/VL interface |
| 40 | | F | P | P | P | P | P | |
| 41 | | P | P | P | P | P | P | |
| 42 | | G | G | G | G | G | G | |
| 43 | | N | K | K | K | K | K | |
| 44 | | K | G | G | G | G | G | |
| 45 | | L | L | L | L | L | L | VH/VL interface (+) |
| 46 | | E | E | E | E | E | E | |
| 47 | | W | W | W | W | W | W | VH/VL interface Vernier Zone |
| 48 | | M | I | I | m | I | I | Vernier Zone Close to the CDRs |
| 49 | FR2 | G | G | G | G | G | G | Vernier Zone |
| 50 | CDR2 | Y | S | S | y | Y | y | Vernier Zone |
| 51 | | I | I | M | I | L | I | |
| 52 | | S | Y | F | s | S | s | |
| 53 | | Y | H | H | y | Y | y | |
| 54 | | D | S | S | d | D | d | |
| 55 | | G* | G* | G* | G* | G* | G* | canonical H2 1(16) |
| 56 | | T | S | S | t | T | t | |
| 57 | | N | T | S | n | N | n | |
| 58 | | N | Y | Y | n | N | n | |
| 59 | | Y | Y | Y | Y | Y | Y | |
| 60 | | K | N | N | k | K | k | |
| 61 | | P | P | P | P | P | P | |
| 62 | | S | S | S | S | S | S | |
| 63 | | L | L | L | L | L | L | |
| 64 | | K | K | K | K | K | K | |
| 65 | CDR2 | D | S | S | d | d | d | |
| 66 | FR3 | R | R | R | R | R | R | |
| 67 | | I | V | V | j | V | V | Vernier Zone Close to the CDRs |
| 68 | | S | T | T | T | T | T | |
| 69 | | I | I | I | I | I | I | Vernier Zone |
| 70 | | T | S | S | S | S | S | |
| 71 | | R* | V* | V* | r* | r* | V* | canonical H2 1(16) Vernier Zone |
| 72 | | D | D | D | D | D | D | |
| 73 | | T | T | T | T | T | T | Vernier Zone |
| 74 | | S | S | S | S | S | S | |

TABLE 6-continued

Alignment of the amino acid sequences leading to the design of the remodeled human 7C10 V$_H$ regions

| Kabnt | FR or CDR | Mouse heavy chain 7C10 | Germinal line 4.22 VH IV | Human FUR1'CL VR | Remodeled Human 7C10 H 1 | Remodeled Human 7C10 H 2 | Remodeled Human 7C10 H 3 | Comments |
|---|---|---|---|---|---|---|---|---|
| 75 | I | K | K | K | K | K | K | |
| 76 | I | N | N | N | N | N | N | |
| 77 | I | Q | Q | Q | Q | Q | Q | |
| 78 | I | F | F | F | F | F | F | Vernier Zone |
| 79 | I | F | S | S | S | S | S | |
| 80 | I | L | L | L | L | L | L | |
| 81 | I | K | K | Q | K | K | K | |
| 82 | I | L | L | L | L | L | L | |
| 82A | I | N | S | R | S | S | S | |
| 82B | I | S | S | S | S | S | S | |
| 82C | I | V | V | V | V | V | V | |
| 83 | I | T | T | T | T | T | T | |
| 84 | I | N | A | A | A | A | A | |
| 85 | I | E | A | A | A | A | A | |
| 86 | I | D | D | D | D | D | D | |
| 87 | I | T | T | T | T | T | T | |
| 88 | I | A | A | A | A | A | A | |
| 89 | I | T | V | V | V | V | V | |
| 90 | I | Y | Y | Y | Y | Y | Y | |
| 91 | I | Y | Y | Y | Y | Y | Y | VH/VL interface |
| 92 | I | C | C | C | C | C | C | |
| 93 | I | A | A | A | A | A | A | VH/VL interface Vernier Zone |
| 94 | FR3 | R* | R* | R* | R* | R* | R* | canonical H1 2(6) Vernier Zone |
| 95 | CDR3 | Y | | G | y | y | y | VH/VL interface |
| 96 | I | G | | R | g | g | g | |
| 97 | I | R | | Y | r | r | r | |
| 98 | I | V | | C | v | v | v | |
| 99 | I | F | | S | f | f | f | |
| 100 | I | | | S | | | | |
| 100A | I | | | T | | | | |
| 100B | I | | | S | | | | |
| 100C | I | | | C | | | | |
| 100D | I | | | N | | | | |
| 100E | I | | | W | | | | |
| 100K | I | F | | F | f | f | f | VH/VL interface (+) |
| 101 | I | D | | D | d | d | d | |
| 102 | CDR3 | Y | | P | y | y | y | |
| 103 | FR4 | W | | W | W | W | W | VH/VL interface (+) Vernier Zone |
| 104 | I | G | | G | G | G | G | |
| 105 | I | Q | | Q | Q | Q | Q | |
| 106 | I | G | | G | G | G | G | |
| 107 | I | T | | T | T | T | T | |
| 108 | I | T | | L | L | L | L | |
| 109 | I | L | | V | V | V | V | |
| 110 | I | T | | T | T | T | T | |
| 111 | I | V | | V | V | V | V | |
| 112 | I | S | | S | S | S | S | |
| 113 | FR4 | S | | S | S | S | S | |

Legend:
The first column (Kabat) indicates the position of the amino acid residue according to Kabat et al. (1991);
the second column (FR or CDR) was made in order easily to identify the segments of the skeleton (FR1, FR2, FR3 and FR4) and the CDR segments (CDR1, CDR2 and CDR3) with the three CDRs seperating the four FRs;
the third column (Mouse heavy chain 7C10) represents the amino acid sequence (SEQ ID No. 69) of the V$_H$ region of the mouse antibody 7C10;
the fourth column (Germinal line 4.22 VH IV) represents the amino acid sequence of the gene 4.22 VH IV (Sanz et al., 1989) (SEQ ID No. 74);
the fifth column (human FUR1'CL VH, kabat accession number N020619) represents the amino acid sequence (SEQ ID No. 73) [lacuna] IgMK antilamin B of human origin (Mariette et al., 1993);
the sixth, seventh and eighth columns (remodeled human 7C10 1, 2 and 3) represent the amino acid sequences of the V$_H$ region of remodeled human 7C10 respectively for the versions 1 (SEQ ID No. 75), 2 (SEQ ID No. 79) and 3 (SEQ ID No. 83).
"*" indicates the parts of the canonical structure of the CDR loop such as defined by Chothia et al. (1989).

EXAMPLE 14

Construction of the Genes Coding for the Humanized Versions 1 of 7C10 VL and VH by Assembly of Oligonucleotides a) Principle The genes (leader peptide+variable regions VDJ for VH or VJ for VK) coding for the humanized variable regions were synthesized by solid-phase assembly on magnetic beads coated with streptavidin. The genes coding for humanized 7C10 VH (445 base pairs) and humanized 7C10 VL (433 base pairs) are constructed by fusing two fragments of DNA owing to the presence of a KpnI restriction site present in the two sequences and situated almost halfway along the gene (at 200 and 245 nucleotides with respect to the 5' end of the gene for VL and VH, respectively). The two fragments which are fused together are themselves assembled by an assembly technique which consists in using phosphorylated oligonucleotides (approximately 30–35 mer) hybridized two by two (one oligo sense and the other antisense, with a homology of approximately 50%) in such a way that they overlap during elongation. A first oligonucleotide biotinylated in the 5' position is attached to the magnetic beads and then the pairs of phosphorylated oligonucleotides are added one by one. The phosphodiester linkage between the juxtaposed phosphorylated oligonucleotides is produced by the enzyme T4 DNA ligase.

The genes thus synthesized de novo can be cloned directly (by digestion with restriction enzymes compatible with the expression vector chosen) or amplified by PCR in order to obtain more material as a prelude to directional cloning by enzymatic digestion. The sequence of the gene thus constructed by de novo assembly is then verified by automatic sequencing of the DNA.

b) Experimental Protocol of the De Novo Assembly Technique

Oligonucleotides phosphorylated in the 5' position or biotinylated in the 5' position whose concentration was adjusted to 100 μM were ordered from MWG Biotech (see the sequences of the oligonucleotides used in Table 7 for the construction of humanized 7C10 VL, and Table 8 for the construction of humanized 7C10 VH). The oligonucleotides were hybridized in pairs (an equimolar mixture, 500 pmol, of a sense oligo and of an antisense oligo in the buffer T4 DNA ligase is heated to 95° C. for 5 minutes and then allowed to cool on the bench to ambient temperature) according to a scheme described in Table 9.

The first biotinylated oligonucleotide is attached to magnetic beads coated with streptavidin (Dynaoeads M-280 streptavidin, Dynal product No. 112-05). For this, 500 pmol of the biotinylated oligonucleotide in a 15 mM NaCl solution are added to 50 μl of the decanted beads (use of a magnet holder) previously washed twice with 100 μl of TE 1× buffer (Tris-EDTA 100× buffer. 1M Tris-HCl, pH 8, 0.1 M EDTA, Sigma T-9285). After incubation at 37° C. for 15 min, the beads are washed twice with the wash buffer (10 mM Tris-HCl pH 7.6, 10 mM EDTA and 50 mM NaCl) and the pairs of hybridized oligo-nucleotides are then added one by one. On each readdition of a pair of oligonucleotides, the mixture is heated to 95° C. for 5 min and then allowed to cool on the bench to ambient temperature. Once ambient temperature is reached, 2 μl of 10 U/μl T4 DNA ligase (Biolabs) are added and the mixture is incubated for 20 min at 37° C. The beads are then washed (wash buffer) and the following pairs of oligonucleotides are then added in succession.

The last unpaired oligo (antisense) is assembled in the following fashion 5 μl of oligo (500 pmol and 43 μl of T4 DNA ligase buffer are added to the decanted beads, then the mixture is heated to 95° C. for 5 min and allowed to cool on the bench to ambient temperature. Once ambient temperature is reached, 2 μl of T4 DNA ligase are added and the mixture is incubated at 37° C. for 20 min. The beads are then washed twice with wash buffer and then twice with TE 1× buffer.

The beads can then be conserved at 4° C. before proceeding to the cloning and sequencing of the gene assembled de novo.

TABLE 7

DNA sequence of oligonucleotides used for the construction of humanized 7C10 VL 1 by de nova assembly

| | | |
|---|---|---|
| LeaderHluI.biotin | 5'-GTCAGAACGCGTGCCGCC | (SEQ ID No. 87) |
| 7C10Lresh.1sense | 5'-ACCATGAAGTTGCCTGTTAGGCTGTTGGTGCT | (SEQ ID No. 88) |
| 7C10Lresh.2sense | 5'-GATGTTCTGGTTTCCTGCTTCCAGCAGTGATG | (SEQ ID No. 89) |
| 7C10Lresh.3sense | 5'-TTGTCATGACTCAGTCTCCACTCTCCCTGCCC | (SEQ ID No. 90) |
| 7C10Lresh.4sense | 5'-GTCACCCCTGGAGAGCCGGCCTCCATCTCCTG | (SEQ ID No. 91) |
| 7C10Lresh.5sense | 5'-CAGGTCTAGTCAGACCATTATACATAGTAATG | (SEQ ID No. 92) |
| 7C10Lresh.6sense | 5'-GAAACACCTATTTGGAATGGTACCTGCAGA | (SEQ ID No. 93) |
| 7C10Lresh.7anti | 5'-GCCAACTTCATGGTGGCGGCACGCGTTCTCAC | (SEQ ID No. 94) |
| 7C10Lresh.8anti | 5'-GAAACCAGAACATCAGCACCAACAGCCTAACA | (SEQ ID No. 95) |
| 7C10Lresh.9anti | 5'-CTGAGTCATCACAACATCACTGCTGGAAGCAG | (SEQ ID No. 96) |
| 7C10Lresh.10anti | 5'-TCTCCAGGGGTGACGGGCAGGGAGAGTGGAGA | (SEQ ID No. 97) |

TABLE 7-continued

DNA sequence of oligonucleotides used for the
construction of humanized 7C10 VL 1 by de nova assembly

| | | |
|---|---|---|
| 7C10Lresh.11anti | 5'-TCTGACTAGACCTGCAGGAGATGGAGGCCGGC | (SEQ ID No. 98) |
| 7C10Lresh.12anti | 5'-AAATAGCTGTTTCCATTACTATGTACAATGC | (SEQ ID No. 99) |
| 7C10Lresh.13sense | 5'-CAGGGCAGTCTCCACAGCTCCTGATCTATAAA | (SEQ ID No. 100) |
| 7C10Lresh.14sense | 5'-GTTTCTAATCGGCTTTATGGGGTCCCTGACAG | (SEQ ID No. 101) |
| 7C10Lresh.15sense | 5'-GTTCAGTGGCAGTGGATCAGGCACAGATTTTA | (SEQ ID No. 102) |
| 7C10Lresh.16sense | 5'-CACTGAAAATCAGCAGAGTGGAGGCTGAGGAT | (SEQ ID No. 103) |
| 7C10Lresh.17sense | 5'-GTTGGGGTTTATTACTGCTTTCAAGGTTCACA | (SEQ ID No. 104) |
| 7C10Lresh.18sense | 5'-TGTTCCGTGGACCTTCGGCCAAGGGACCAAGG | (SEQ ID No. 105) |
| 7C10Lresh.19sense | 5'-TGGAAATCAAACGTGAGTGGATCCTCTGCG | (SEQ ID No. 106) |
| 7C10Lresh.KpnIREV | 5'-TCTCCAGGTACCATTGC | (SEQ ID No. 107) |
| 7C10Lresh.KpnIbiotin | 5'-TGCAATGGTACCTCCAGAAGC | (SEQ ID No. 108) |
| 7C10Lresh.20anti | 5'-AGACTGCCCTGGCTTCTGCAGGTACCATTGCA | (SEQ ID No. 109) |
| 7C10Lresh.21anti | 5'-CGATTAGAAACTTTATAGATCAGGAGCTGTGG | (SEQ ID No. 110) |
| 7C10Lresh.22anti | 5'-TCCCACTCAACCTGTCAGGGACCCCATAAAGC | (SEQ ID No. 111) |
| 7C10Lresh.23anti | 5'-GATTTTCAGTGTAAAATCTGTGCCTGATCCAC | (SEQ ID No. 112) |
| 7C10Lresh.24anti | 5'-TAAACCCCAACATCCTCAGCCTCCACTCTGCT | (SEQ ID No. 113) |
| 7C10Lresh.25anti | 5'-TCCACGGAACATGTGAACCTTGAAAGCAGTAA | (SEQ ID No. 114) |
| 7C10Lresh.26anti | 5'-TTTGATTTCCACCTTGGTCCCTTGGCCGAAC | (SEQ ID No. 115) |
| 7C10Lresh.BamHIantisense | 5'-CGCAGAGGATCCACTCACG | (SEQ ID No. 116) |

TABLE 8

DNA sequence of oligonucleotides used for the
construction of humanized 7C10 VE 1 by de nova assembly

| | | |
|---|---|---|
| LeaderMluI.biotin | 5'-GTCACAACCCGTGCCGCC | (SEQ ID No. 117) |
| 7C10Hresh.1sense | 5'-ACCATCAAAGTGTTGAGTCTGTTGTACCTCTTGA | (SEQ ID No. 118) |
| 7C10Hresh.2sense | 5'-CACCCATTCCTCCTATCCTGTCTCAGGTGCAGCT | (SEQ ID No. 119) |
| 7C10Hresh.3sense | 5'-TCAGGAGTCGGGCCCAGGACTGGTGAAGCCTTCG | (SEQ ID No. 120) |
| 7C10Hresh.4sense | 5'-GAGACCCTGTCCCTCACCTGCACTGTCTCTGGT | (SEQ ID No. 121) |
| 7C10Hresh.5sense | 5'-TACTCCATCACCGGTGGTTATTTATGGAACTGG | (SEQ ID No. 122) |
| 7C10Hresh.6sense | 5'-ATACGGCAGCCCCAGGGAAGGGACTGGAGTGG | (SEQ ID No. 123) |
| 7C10Hresh.7sense | 5'-ATGGGGTATATCAGCTACGACGGTACCAATAAC | (SEQ ID No. 124) |
| 7C10Hresh.8antisense | 5'-TCAACACTTTCATGGTGGCGCCACGCCTTCTGAC | (SEQ ID No. 125) |
| 7C10Hresh.9antisense | 5'-ATACCAGGAATGGCTGTCAAGAGGTACAACAGAC | (SEQ ID No. 126) |
| 7C10Hresh.10antisense | 5'-TGGGCCCGACTCCTGAAGCTGCACCTGAGACAGG | (SEQ ID No. 127) |
| 7C10Hresh.11antisense | 5'-TGAGGCACAGGGTCTCCGAAGGCTTCACCAGTCC | (SEQ ID No. 128) |
| 7C10Hresh.12antisense | 5'-CCACCCCTGATGGAGTAACCAGAGACAGTGCAGG | (SEQ ID No. 129) |

TABLE 8-continued

DNA sequence of oligonucleotides used for the construction of humanized 7C10 VE 1 by de nova assembly

| | | |
|---|---|---|
| 7C10Hresh.13antisense | 5'-CCCTGGGCGCTGCCGTATCCAGTTCCATAAATAA | (SEQ ID No. 130) |
| 7C10Hresh.14antisense | 5'-TAGCTGATATACCCCATCCACTCCAGTCCCTT | (SEQ ID No. 131) |
| 7C10Hresh.KpnIREV | 5'-GTTATTGGTACCGTCG | (SEQ ID No. 132) |
| 7C10Hresh.KpnIbiotin | 5'-TACGACGGTACCAATAACTAC | (SEQ ID No. 133) |
| 7C10Hresh.15sense | 5'-AAACCCTCCCTCAAGGATCGAATCACCATATC | (SEQ ID No. 134) |
| 7C10Hresh.16sense | 5'-ACGTGACACGTCCAAGAACCAGTTCTCCCTGA | (SEQ ID No. 135) |
| 7C10Hresh.17sense | 5'-AGCTGAGCTCTGTGACCGCTGCGGACACTGCA | (SEQ ID No. 136) |
| 7C10Hresh.18sense | 5'-GTGTATTACTCTGCGAGATACGGTAGGGTCTT | (SEQ ID No. 137) |
| 7C10Hresh.19sense | 5'-CTTTGACTACTGGGGCCAGGGAACCCTGGTCA | (SEQ ID No. 138) |
| 7C10Hresh.20sense | 5'-CCCTCTCCTCAGGTCAGTGGATCCTCTGCG | (SEQ ID No. 139) |
| 7C10Hresh.21antisense | 5'-ACCGAGGGTTTGTAGTTATTGGTACCGTCGTA | (SEQ ID No. 140) |
| 7C10Hresh.22antisense | 5'-ACGTGTCACCTGATATGGTGATTCGATCCTTG | (SEQ ID No. 141) |
| 7C10Hresh.23antisense | 5'-AGAGCTCAGCTTCAGGGAGAACTGCTTCTTCC | (SEQ ID No. 142) |
| 7C10Hresh.24antisense | 5'-CAGTAATACACTGCAGTGTCCGCAGCGGTCAC | (SEQ ID No. 143) |
| 7C10Hresh.25antisense | 5'-ACTAGTCAAAGAAGACCCTACCCTATCTCGCA | (SEQ ID No. 144) |
| 7C10Hresh.26antisense | 5'-CTGAGGAGACGGTGACCAGGGTTCCCTGGCCCC | (SEQ ID No. 145) |
| 7C10Hresh.BamHIantisense | 5'-CGCAGAGGATCCACTCAC | (SEQ ID No. 146) |

TABLE 9

Oligonucleotide pairing protocol for the de novo assembly of genes coding for the humanized forms of 7C10 VH and VL

| de novo assembly of the MlUI-KpnI fragment of 7C10 VL humanized 1 Biotinylated oligo leader MlUI 7C10 VL | de novo assembly of the KpnI-BamHI fragment of 7C10 VL humanized 1 Biotinylated oligo 7C10 L KpnI |
|---|---|
| Oligo pair 1 and 7 | Oligo pair 13 and 20 |
| Oligo pair 2 and 8 | Oligo pair 14 and 21 |
| Oligo pair 3 and 9 | Oligo pair 15 and 22 |
| Oligo pair 4 and 10 | Oligo pair 16 and 23 |
| Oligo pair 5 and 11 | Oligo pair 17 and 24 |
| Oligo pair 6 and 12 | Oligo pair 18 and 25 |
| Antisense oligo 7C10 VL KpnI | Oligo pair 19 and 26 Antisense oligo 7C10 L BamHI |
| de novo assembly of the MlUI-KpnI fragment of 7C10 VL humanized 1 Biotinylated oligo leader MlUI 7C10 VH | de novo assembly of the KpnI-BamHI fragment of 7C10 VL humanized 1 Biotinylated oligo 7C10 H KpnI |
| Oligo pair 1 and 8 | Oligo pair 15 and 21 |
| Oligo pair 2 and 9 | Oligo pair 16 and 22 |
| Oligo pair 3 and 10 | Oligo pair 17 and 23 |
| Oligo pair 4 and 11 | Oligo pair 18 and 24 |
| Oligo pair 5 and 12 | Oligo pair 19 and 25 |
| Oligo pair 6 and 13 | Oligo pair 20 and 26 |
| Oligo pair 7 and 14 | Antisense oligo 7C10 VH BamHI |
| Antisense oligo 7C10 VH KpnI | |

EXAMPLE 15

Construction of the Genes Coding for the Humanized Versions 2 of 7C10 VL and 7C10 VH and 3 of 7C10 VH by Directed Mutagenesis The humanized version 2 of 7C10 VH was obtained by directed mutagenesis of the residues 48 and 67 (according to Kabat's nomenclature) of version 1. This directed mutagenesis was carried out with the aid of the system QuikChange™ Site-directed mutagenesis of Stratagene (kit #200518) according to the protocol described by the manufacturer. The construction is carried out in two stages, first the residue 48 on version 1 was mutated with the aid of the pair or primers 7C10Hhumanized1QCM48 sense and antisense (see Table 10) and subsequently this version mutated at the residue 48 was itself mutated at the residue 67 with the aid of the pair of primers 7C10Hhumanized1QCI67 sense and antisense (see Table 10).

The humanized version 3 of 7C10 VH was obtained by site-directed mutation of tie residues 30 and 71 (according to Kabat's nomenclature) of version 2 likewise using the system QuikChange™. This construction is carried out in two stages. At first, the residue 30 on version 2 was mutated with the aid of the primers 7C10HhumanizedQCT30 sense and antisense (see Table 10). Subsequently, this version mutated at the residue 30 was itself mutated at the residue 71 by using the pair of primers 7C10Hhumanized1V67QCR71 sense and antisense (see Table 10).

The humanized version 2 of 7C10 VL was obtained by site-directed mutation of the residue 2 (according to Kabat's nomenclature) of version 1 by using the system QuikChange™. The residue 2 on version 1 was mutated by using the pair of primers 7C10Lhumanized1QCV2 sense and antisense (see Table 10).

TABLE 10

List of the oligonucleotides used for the
directed mutagenesis by the stratagene QuikChange ™ system

| | | |
|---|---|---|
| 7C10Hhumanized1QCT30. sense | 5'-CTGGTTACTCCATCAGCGGTCGTATTTATG | (SEQ ID No. 147) |
| 7C10Hhumanized1QCT30. antisense | 5'-CATAAATAACCACCGCTGATGGAGTAACCAG | (SEQ ID No. 148) |
| 7c10Hhumanized1QCM40. sense | 5'-GGGACTGGACTGGATCGGGTATATCACCTAC | (SEQ ID No. 149) |
| 7c10Hhumanizad1QCM48. antisense | 5'-GTAGCTGATATACCCGATCCACTCCAGTCCC | (SEQ ID No. 150) |
| 7c10Hhumanized1QCI67. sense | 5'-TCCCTCAAGGATCGAGTCACCATATCACGTG | (SEQ ID No. 151) |
| 7C10Hhumanized1QCI67. antisense | 5'-CACGTGATATGGTGACTCGATCCTTGAGGGA | (SEQ ID No. 152) |
| 7C10Hhumanized1V67QCH71. sense | 5'-GATCCAGTCACCATATCACTCGACACGTCCAAGAACCAG | (SEQ ID No. 153) |
| 7C10Hhumanized1V6QCH71. antisense | 5'-CTGGTTCTTGGACGTGTCCACTGATATGGTGACTCGATC | (SEQ ID No. 154) |
| 7C10Lhumanized1QCV2. sense | 5'-CCTTCCAGCAGTGATATTGTGATGACTCAGT | (SEQ ID No. 155) |
| 7C10Lhumanized1QCV2. antisense | 5'-ACTCACTCATCACAATATCACTCCTCCAAGC | (SEQ ID No. 156) |

EXAMPLE 16

Transfection of the Cos7 Cells by Electroporation

The mammalian expression vectors containing the chimeric or humanized versions of the heavy and light chains of the antibody 7C10 were tested in cos7 cells for the transitory expression of the recombinant antibodies 7C10. The DNA was introduced into the cos cells by electroporation with the aid of a BioRad instrument (Gene Pulsar). The DNA (10 μg of each vector) is added lo aliquots of 0.8 ml of cos cells at a concentration of 1×10$^7$ cells per ml in PBS buffer (without Ca++ and Mg++). A pulsation of 1900 volts and a capacity of 25 μF was delivered. The transfected cos cells are then added to 8 ml of DMEM medium containing 5% of calf serum and incubated at 37° C. for 72 hours. The supernatant is then collected, centrifuged in order to eliminate the cell debris and tested by ELISA for the measurement of its concentration of recombinant antibody 7C10 of IgG1/human Kappa type.

EXAMPLE 17

ELISA Method for Measuring the Concentrations of Recombinant Antibody IgG1/Human Kappa Present in the Supernatant of the Cos Transfectants The supernatants produced by transitory expression in cos7 cells were tested for the presence of 7C10 antibody of IgG1/human Kappa type. For the detection of the IgG1/human Kappa immunoglobulin, 96-well ELISA plates (Maxisorb, Nunc) were coated with a goat anti-human IgG polyclonal antibody (specific for the gamma, Fc fragment, Jackson Immuno-Research Laboratories; Inc., #109-005-098). The supernatants of cos cells were diluted in series and added to the coated wells. After incubation for one hour at 37° C. and washing, a goat anti-human light Kappa chain polyclonal antibody conjugated to peroxidase (HR, Sigma, A-7164) was added; After incubation for 45 minutes at 37° C. and washing, the TMB substrate (KPL #50-76-04) was added. After incubation for 10 minutes, the reaction was stopped by the addition of 1 M sulfuric acid and the optical density was read at 450 nm. A purified human IgG1/human Kappa immunoglobulin (Sigma, I-3389) of known concentration was used as a standard reference antibody.

EXAMPLE 18

ELISA Method for Determining the Recognition Activity of 7C10 Recombinant Antibodies of Human IgG1/Kappa Type on the Receptor for IGF-I (IGF-IR)

The cos7 culture supernatants were tested for their capacity to recognize IGF-I R by an ELISA method. 96-well ELISA plates (Dynex Immulon 2HB) were coated with 100 μl per well of a solution of PBS containing. 0.31 ng/μl of IGF-IR (Human Insulin-Like Growth Factor I soluble Receptor, R & D Systems, #391-GR) by incubation for one night at 4° C. After washing with PBS containing 0.05% Tween 20, the plates were saturated by the addition of a solution of PBS containing 0.5% gelatin solution and incubation at 37° C. for 1 hour. After three washes with PBS, the samples of cos supernatants to be tested, previously diluted in series in PBS containing 0.1% gelatin and 0.05% Tween 20, were added to the plates. After incubation at 37° C. for 1 hour followed by three washes (PBS containing 0.05% Tween 20), an anti-human IgG antibody (specific for the Fc fragment) conjugated to peroxidase (HRP, Jackson Immuno-Research Laboratories Inc., #109-035-098) was added (dilution, to 1/5000 in PBS containing 0.1 gelatin and 0.05% Tween 20). After incubation for 45 minutes at 37° C. and 3 washes (PBS containing 0.05% Tween 20), the TMB substrate (KPL #50-76-04) was added. After incubation for 10 minutes, the reaction was stopped by addition of 1 M sulfuric acid and the optical density was read at 450 nm.

EXAMPLE 19

Determination of the Recognition Activity of IGF1-R by Different Versions of the Humanized 7C10 Antibody by "CDR Grafting"

Figure 28:
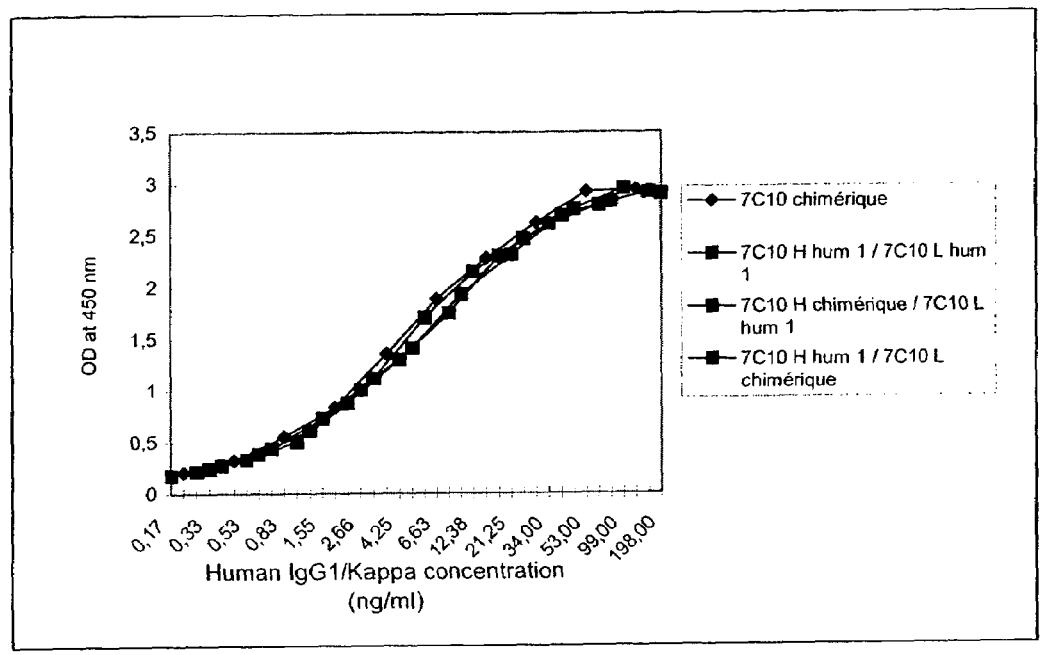

At first, we compared the recognition activity of humanized forms 1 of the heavy and light chains of 7C10 for the IGF-I receptor with respect to the chimeric form. FIG. 28 shows the results of an ELISA test of recognition of the IGF-IR (see Example 18) from supernatants of the cos7 cells whose concentration of IgG1/human Kappa had been previously determined by ELISA (see Example 17). The titration curves of the four recombinant antibodies tested overlap perfectly indicating that their relative affinities for IGF-IR are very similar. It is therefore concluded from this that the humanized form 1 of 7C10, composed of the humanized light chain 1 (1 single mouse residue present in the framework regions) in combination with the humanized heavy chain 1 (4 mouse residues present in the framework regions), specifically recognizes the IGF-I receptor and has an affinity very similar to that of the chimeric antibody (mouse variable regions).

Figure 29:
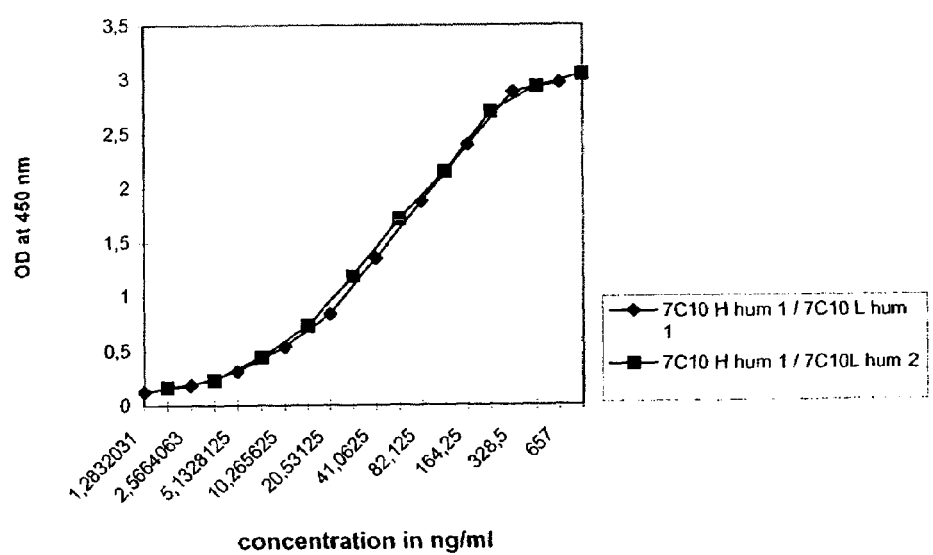

Subsequently, we looked at the influence of the residue 2 (according to Kabat's nomenclature) of the humanized light chain of 7C10 (humanized version 1 versus humanized 2, see FIG. 19) on the recognition of the IGF-IR. FIG. 29 shows the results of the ELISA test for recognition of the IGF-IR (see Example 18) from supernatants of cos7 cells whose concentration of IgG1/human Kappa had been previously determined by ELISA (see Example 17). The two humanized versions 1 and 2 of the light chain had been combined successively with humanized 7C10 VH 1. The titration curves of the two combinations are superimposed indicating that the mutation of residue 2 of the light chain, which has been changed from one valine in the humanized version 1 to an isoleucine in the humanized form 2, apparently has no influence on the relative affinity of recognition of the IGF1 receptor. The humanized form 2 of the light chain of 7C10 thus forms one version where no mouse residue (apart from CDRs) has been conserved. This version, totally humanized, represents the preferred version of 7C10 VL.

Figure 30:
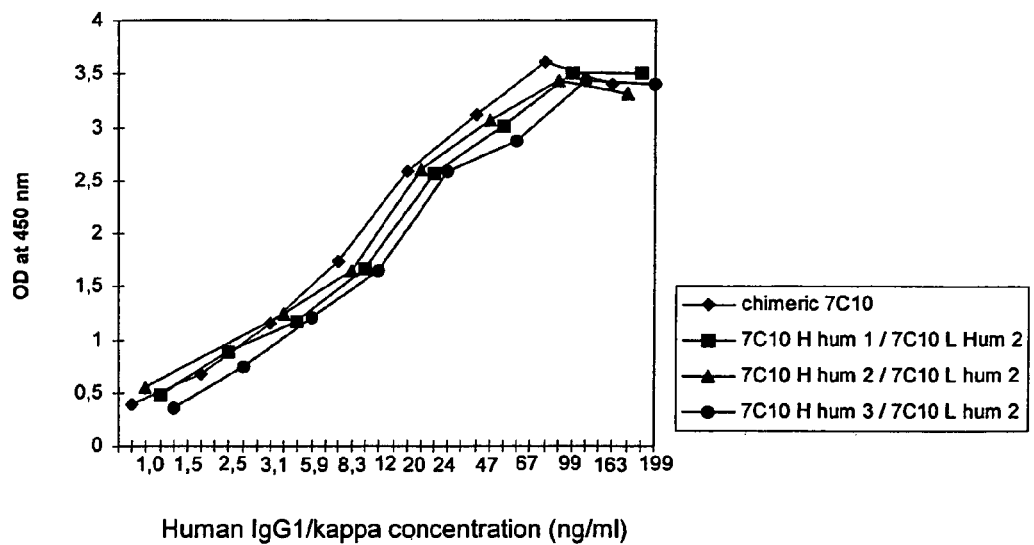

The totally humanized version of the 7C10 light chain (humanized version 2, see above) was tested in combination with the three humanized versions of the heavy chain of 7C10. FIG. 30 shows the results of the ELISA test for recognition of the IGF-IR from supernatants of cos7 cells whose concentration of IgG1/human Kappa had been previously determined by ELISA (see Example 17). The titration curves are very similar and virtually overlap with the reference curve corresponding to the chimeric antibody, indicating that the three humanized versions 1, 2 and 3 of 7C10 VH give an identical relative affinity for IGF-IR when they are combined with humanized 7C10 VL 2. Other ELISA tests conducted in parallel (results not shown) have however revealed that a point mutation of the residue 71 (Kabat's nomenclature) from an arginine (mouse) to a valine (human) involved a small loss of affinity of the corresponding antibody for IGF-IR. It is thus reasonable to think Chat humanized 7C10 VH 2 has the same relative affinity for IGF-IR as humanized 7C10 VH 1. This humanized form 2 will therefore be preferred with respect to the form 1 since it only has two mouse amino acids (residues 30 and 71, see FIG. 24). The humanized form 3 which does not have any mouse residue (apart from CDRs) will also be preferred since it only seems to involve a minimal loss of affinity.

In conclusion, it appears that two humanized forms of the antibody 7C10 according to the present invention are particularly preferred. A form constituted by the combination of humanized 7C10 VH 2 (2 conserved mouse residues) with humanized 7C10 VL 2 (no conserved mouse residue) and another form constituted by the combination of humanized 7C10 VH 3 (no conserved mouse residue) with humanized 7C10 VL 2 (no conserved mouse residue). This last form constitutes the ultimate humanized *version since no mouse residue is present at the same time in the heavy and light chains.

EXAMPLE 20

Expression of EGFR and of IGF-IR on the Surface of A549 Cells

The synergy of action obtained by the coadministration of two MAbs directed respectively against IGF-IR and EGFR was studied in nude mice carrying a non-small cell lung tumor established by subcutaneous injection (s.c.) of A549 cells (lung carcinoma cell line).

Figure 37A:
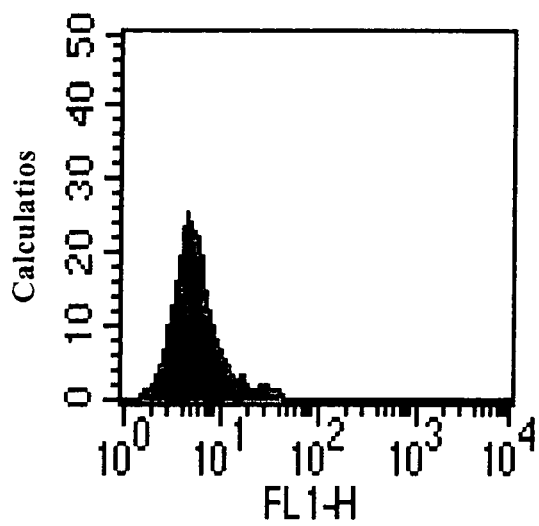
Figure 37B:
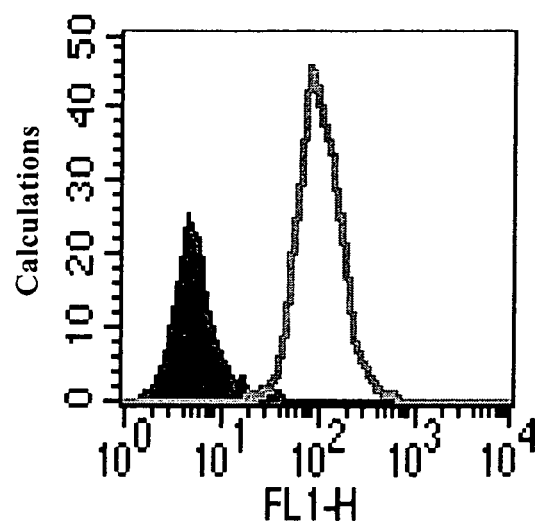
Figure 37C:
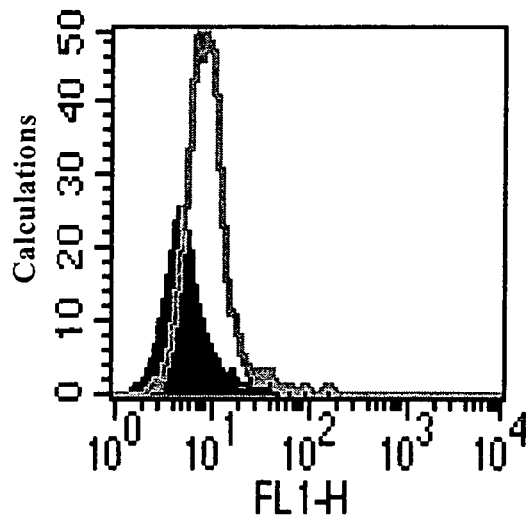
Figure 37D:
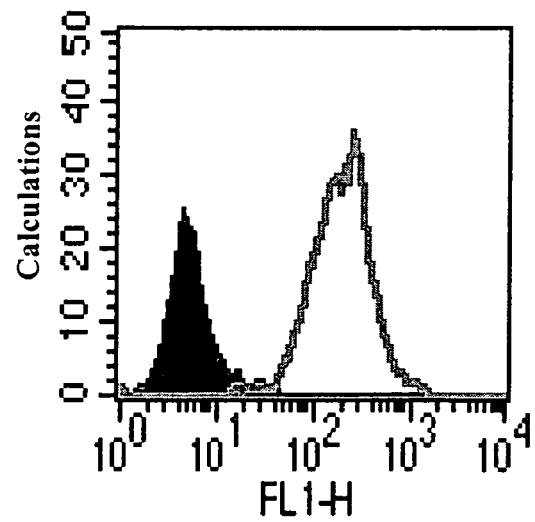

At first, and in order to ensure the presence of the two receptors IGF-IR and EGFR on the surface of the A549 cell before injecting this into the mouse, labeling for FACS reading of these cells was carried out with, respectively, the murine 7C10 anti-IGF-IR MAS (FIG. 37B) and the murine 225 anti-EGFR MAB (FIG. 37D). In order to do this, the cells were saturated for 30 min at 4° C. with a solution of PDS 10% FCS (fetal calf serum), washed and then incubated for 30 min at 4° C. with the MAB of interest. After 3 new washes, the secondary anti-species antibody coupled to FITC (fluorescein isothiocyanate) is added. After incubation for 30 min, reading on the FACS (Fluorescence Activated Cells Sorter) is carried out at 520 nm (excitation 488 nm).

The results presented in FIGS. 37A to 37D show that the A549 cells have on their surface a comparable number of receptors for EGF and IGF1. In the two cases, the population is homogeneous with respect to the distribution of each of the receptors. The specificity of the labeling is confirmed by the use of an isotype control (FIG. 37C) These results validate the use of the A549 cell as a model for the study of a synergy of action on two IGF-IR and EGFR receptors and for the study of a collaboration of these two receptors.

EXAMPLE 21

Synergy of Action of an Anti-IGF-IR MAD and of an Anti-EGFR MAB Coadministered In Vivo, in the Nude Mouse in the Context of an Antitumor Treatment For this study, nude mice are grafted s.c. with $5.10^6$ A549 cells. Five days after the cell graft, the tumors are measured and a homogeneous batch of mice in terms of tumor volume is formed. Starting from this batch, groups of 6 mice are generated at random. These mice will be treated intraperitoneally (i.p.), twice per week with each of the MAB 7C10 and 225 individually at the dose of 250 µg/mouse or with the two MAB in coadministration. The MAB 9G4 is administered as an experiment isotype control.

The results presented in FIG. 38 show that each of the antibodies 7C10 and 225 administered alone is capable of inducing a significant decrease in the tumor growth in vivo. It can be noted that the two MAB tested have a comparable activity on the growth of the tumor A549. In a surprising fashion with respect to the literature, a significant synergy is observed during simultaneous administration of the two MAB (p< or =0.01 at each of the times of the kinetics in a t-test) suggesting that a collaboration of tho two receptors exists for the optimum growth of a tumor in vivo and that, contrary to the data in the literature, the blockage of one of the two axes does not suffice to totally inhibit the growth mediated by the second.

EXAMPLE 22

Study of the Antitumor Activity of the Murine Antibodies 7C10 and 225 Coadministered in Mice Orthotopically Implanted with A549 Cells The use of orthotopic models for the evaluation of the antitumor activity presents a particular interest with respect to the process of metastatic dissemination of a tumor. In order to evaluate the antitumor activity of an antibody mixture directed respectively against IGF-IR and EGFR, $10^6$ A549 cells (non-small cell lung cancer) were implanted in the intrapleural cavity of nude mice. It is to be noted that the consequence of this type of tumor implantation is a metastatic dissemination similar to that observed in man and leads to the death of the animals. FIG. 39 shows that the administration of the antibodies 225 and 7C10 alone allows a comparable and a significant gain in survival to be observed. In a surprising fashion, the coadministration of these two antibodies increases in a considerable fashion the survival of the animals suggesting that this treatment could have an impact on the metastatic dissemination of the tumor cells.

EXAMPLE 23

7C10 and 7H2B24 Inhibit the Phosphorylation of the Tyrosine of the β Chain of IGF-IR and of IRS-I MCF7 cells are cultured for 24 hours at $5.10^4$ cells/cm$^2$ (75 cm$^2$ plates, COSTAR) in 20 ml of RPMI without phenol red, mixed with 5 mM of glutamine, penicillin/streptomycin (respectively, 100 U/100 µg/ml) and 10% of fetal calf serum. After three washes in PBS, the cells were incubated for 12 hours in medium (RPMI) without phenol red, devoid of fetal calf serum and mixed with 5 mM of glutamine, penicillin/streptomycin, bovine serum albumin at 0.5 µg/ml (Sigma A-8022) and transferring at 5 µg/ml (Sigma T8158).

For activation, the cells were first incubated at 37° C. for 2 minutes with blocking antibodies (10 µg/ml) and then IGF-I (Sigma I3769, 50 ng/ml) was added for two additional minutes. The reaction was stopped by aspiration of the incubation medium and the plates were laid on ice. The cells were solubilized by addition of 0.5 ml of lysis buffer (50 mM tris-HCl pH 7.5, 150 mM NaCl, 1% Nonidet P40, 0.5% sodium deoxycholate), mixed with protease inhibitors (1 tablet per 50 ml, Boehringer Ref.: 1697 498), and phosphatase inhibitors (Calbiochem Ref.: 524625 (1/100)). The cells were scraped off and the suspension was recovered and placed on a shaker at 4° C. for 1.5 hours. The solutions were centrifuged at 12,000 rpm for ten minutes (4° C.) and the protein concentrations of the supernatants were quantified by BCA.

500 µg of proteins of the cell lysate were mixed with the anti-IGF-IR (Santa cruz Ref.: sc-713) for immunoprecipitation and incubated on the shaker at 4° C. for 1.5 hours. The immunoprecipitates were recovered by addition of protein A-agarose (Boehringer Ref.: 1 134 515) and incubated all night on the shaker at 4° C. For the immunoprecipitation of IRS-1, anti-IRS-1 antibodies coupled to agarose beads (Santa cruz Ref.: 559Ac) were used. The agarose beads wore washed twice with 1 ml of lysis buffer, twice with a wash buffer 1 (50 mM tris-HCl pH 7.5; 500 mM NaCl; 0.1% Nonidet P40; 0.05% sodium deoxycholate (Boehringer 1 332 597), mixed with protease inhibitors and phosphatase inhibitors) and once with a wash butter 2 (50 mM tris-HCl; 0.1% Nonidet P40C; 0.05%, sodium deoxycholate (Boehringer Ref.: 1 332 597), mixed with protease inhibitors and phosphatase inhibitors 1/100). The immunoprecipitates were resuspended in a Laemmli buffer, heated to 100° C. for 5 minutes. The supernatants were analyzed by electrophoresis on polyacrylamide SDS gel (8% Novex EC6015). The proteins were transferred to a nitrocellulose membrane followed by either an immunoblot with anti-phosphotyrosine antibodies conjugated to IIRP (upstate Biotechnology 4G10) or beta anti-chain of IGF-IR or anti-IRS-1 (Santa Cruz Ref.: sc 8038) followed by an anti-rabbit antibody conjugated to IIRP. The imprints were revealed by chemiluminescence (Amersham RPN 2209) followed by autoradiography on Kodak X-mat AR films.

FIG. 40A represents MCF7 cells nonstimulated (0) or stimulated either with IGF-I (50 ng/ml) alone (0+IGF-I) or combined with monoclonal or humanized anti-IGF-IR antibodies (10 µg/ml) 7C10, 1H7, 7H2HM. The antibodies 9G4 or hIgG1 are murine or human immunoglobulins of isotype IgG1 used as an experiment negative control. The, beta chains of the IGF-IR were immunoprecipitated and blotted with phosphorylated anti-tyrosine antibodies. The results obtained show that the monoclonal or humanized anti-IGF-IR 7C10, 1H7 and 7H2HM antibodies inhibit the phosphorylation of the tyrosine of the beta chain of the IGF-IR.

FIG. 40B represents MCF7 cells nonstimulated (0) or stimulated either with IGF-I (50 ng/ml) alone (0+IGF-I) or combined with monoclonal or humanized anti-IGF-IR antibodies (10 µg/ml) 7C10, 1H7 , 7H2HM. As described above, the antibodies 9G4 or hIgG1 are murine or human immunoglobulins of isotype IgG1 used as an experiment negative control. The IRS-1 was immunoprecipitated and blotted with phosphorylated anti-tyrosine antibodies. The results obtained show that the monoclonal antibodies 7C10, 7H2HM and 1H7 inhibit the phosphorylation of the tyrosine of the IRS-1.

EXAMPLE 24

7C10 and 7H2HM Induces the Internalization of the IGF-IR

MCF7 and A549 cells were suspended to $1.10^7$ cells/ml in PBS with 10% of fetal calf serum (FACS buffer). $1.10^6$ cells were incubated for 30 minutes at 37° C. with the monoclonal antibodies at 10 µg/ml (7C10, 7G3, 9G4) or at 20 µg/ml for 7H2HM. After washing, the cells were labeled at 4° C. for 30 minutes with a biotinylated anti-IGF-IR (monoclonal antibody 12B1) and finally incubated at 4° C. for 30 minutes with a conjugate of streptavidin-488 alexa Fluor®. The cells were analyzed by FACScan (Becton-Dickinson, Enembogegem, Belgium) with the Cellquest software after elimination of debris.

FIG. 41 shows the A549 cells without coloration (1 peak), the A549 cells incubated with 7C10 or 7H2HM (2 peak) and the A549 cells incubated with an irrelevant mouse or rat IgG1 (3peak). A decrease by two of the surface expression of the IGF-IR by the cells is seen when the cells have been previously incubated with 7C10 or 7H2HM.

EXAMPLE 25

7C10 and 7H2HM Induce the Degradation of the IGF-IR

MCF-7 cells were cultured for 24 hours at $10.10^4$ cells/cm² (75 cm², Costar) in 15 ml of complete medium. Next, the cultures were washed three times with PBS and incubated for 12 hours with medium devoid of serum. Next, the cells were incubated with cycloheximide at 25 µg/ml alone or with 10 µg/ml of monoclonal antibody 7C10, 9G4, 7G3 or of IGF-I (50 ng/ml) In certain experiments, before incubation with the monoclonal antibodies, the cells were treated for 1 hour at 37° C. with MG-132 (10 µM, Calbiochem 474791) in order to inhibit the proteasome activities. After incubation, the cells were washed and solubilized by addition of a lysis buffer. 20 µg of proteins were analyzed by electrophoresis on polyacrylamide gel at 8% of SDS and transferred to a nitrocellulose membrane followed by a beta anti-chain immunoblot of the IGF-IR such as described further above.

The analysis by Western-blot (FIG. 42A) of the integrity of the IGF-IR shows that 7C10 and 7H2HM induce the degradation of the receptor while the natural ligand does not cause any degradation of the latter. No degradation of the receptor is observed with the 9G4, an irrelevant antibody used as an isotype control. FIG. 42B demonstrates, and with respect thereto, that the degradation is inhibited by a proteasome inhibitor MCG132 (incubation period of 2 hours).

Comparable results were obtained with the humanized antibody 7H2HM (FIG. 42C).

EXAMPLE 26

Evaluation of 7C10 and h7C10 Ability to Bind to IGF-IR and Insulin/IGF-I Hybrid

EXAMPLE 26.1

Evaluation of 7C10 and h7C10 Ability to Immunoprecipitate IGF-IR and IR/IGF-IR Receptors Purified from Transfected Cells Respectively with IGF-IR and IR-A or IGF-IR and IR-B (Thereafter Referred as R+/IR-A or R+/IR-B The goal of this study is to evaluate the ability of 7C10 and h7C10 to immunoprecipitate IGF-IR, IR or Hybrid-R. 7C10 and h7C10 are compared to 17-69 (which recognizes both IGF-IR well and Hybrid-R).

Method

The used cells for this study are listed thereafter

R+: R−fibroblasts stably transfected with the IGF-I receptor (IGF-IR) cDNA

R−/IR-A: R−fibroblasts stably transfected with the insulin receptor isoform A (IR-A) cDNA R−/IR-B: R−fibroblasts stably transfected with the insulin receptor isoform B (IR-B) cDNA R+/IR-A: R−fibroblasts stably co-transfected with the IGF-I and the insulin receptor isoform A cDNA and, therefore, expressing hybrid receptors A (Hybrid-RA)

R+/IR-B: R−fibroblasts stably co-transfected with the IGF-I and the insulin receptor isoform B cDNA and, therefore, expressing hybrid receptors A (Hybrid-RB)

For the obtention of cellular lysat, cells were solubilized in RIPA buffer and 4 mg protein used for immunoprecipitation.

Cell lysates were immuprecipitated as follows:
R+with either 7C10 or h7C10
R+/IR-A and R+/IR-B with either 7C10 or h7C10 or 17–69
R−/IR-A and R−/IR-B with either MA-20 (an anti-IR antibody) or 7C10 or h7C10

Following immunoprecipitation, the pellet was resuspended in 2× sample buffer and subjected to SDS-PAGE (7.5% polyacrylamide).

Filters were blotted as follows: Filters containing R+ lysates (and therefore only IGF-IR) with an anti-IGF-IR β-subunit (Santa Cruz). Filters containing lysates from all the remaining cells with an antibody anti-IR β-subunit (Santa Cruz).

Results

Two independent experiments are shown (FIG. 43A and FIG. 43B)

Comments
1) 7C10 and h7C10 are equally efficient in immunoprecipitating the IGF-IR (lanes 1 and 2)
2) Neither 7C10 nor h7c10 appreciably immunopreicipitate IR
3) Both 7C10 and h7C10 recognizes Hybrid-Rs.

EXAMPLE 26-2

Displacement Analysis of IGF-I on IGF-IR by 7C10, h7C10 and 1H7

IGF-IR frog R+ cell lysates were immunocaptured in Maxisorb plates coated with 17-69 antibody.

$^{125}$I-IGF-I (FIG. 44) was then allowed to bind to immunocaptured receptors in the absence or the presence of increasing concentrations of unlabeled ligand (IGF-I) or antibodies (7C10, h7C10, 1H7, 9G4). Results are plotted as percent of maximal binding.

Both 7C10 and h7C10 displace labeled IGF-I with a very similar efficiency. By comparison, 1H7 was much less effective (FIG. 44).

EXAMPLE 26-3

Displacement analysis of IGF-I on Hybrid-RA by 7C10, h7C10 and 1H7

Hybrid-RA from R−/IR-A cell lysates were immunocaptured in Maxisorb plates coated with anti IR antibody 83-7.

125I-IGF-I (FIG. 45) was then allowed to bind to immunocaptured receptors in the absence or the presence of increasing concentrations of unlabeled ligand (IGF-I) of antibodies (7C10, h7C10, 1H7, 9G4). Results are plotted as percent of maximal binding.

Both 7C10 and h7C10 displace labeled IGF-I with a very similar efficiency. By comparison, 1H7 was much lees effective (FIG. 45).

EXAMPLE 26-4

Displacement Analysis of IGF-I on Hybrid-RB by 7C10, h7C10 and 1H7

Hybrid-RB from R−/IR-B cell lysates were immunocaptured in Maxisorb plates coated with 83-7 antibody.

125I-IGF-I (FIG. 46) was then allowed to bind to immunocaptured receptors in the absence or the presence of increasing concentrations of IGF-1 or antibodies (7C10, h7C10, 1H7, 9G4). Results are plotted as percent of maximal binding.

Both 7C10 and h7C10 displace labeled IGF-I with a very similar efficiency. By comparison, 1H7 was much less effective (FIG. 46).

EXAMPLE 27

Internalization and Degradation Studies of the IGF-IR

Internalization and degradation studies were analyzed by FACS and western-blot analysis. Internalization studies were performed by FACS analysis using a murine biotinylated anti-IGF-IR monoclonal antibody (Mab) thereafter described as 12B1 MAb and binding to an epitope different from the one recognized by 7C10 and h7C10 antibodies. The 7G3 MAb, a non neutralizing anti-IGF-IR was introduced as negative control. Both antibodies were generated in our laboratory. Confluent MCF-7 cells were trypsinized and $1\times10^6$ cells from each cellular suspension was plated in 96-well plates in FACS buffer. Plates were incubated, either with or without 25 μg/ml of cycloheximide (Calbiochem), 30 min at 37° C. with either IGF1 (50 ng/ml) or with 10 μg/ml of 7C10, 7G3, h7C10, mIgG1, hIgG1. Cells incubated with FACS buffer alone were used to determine the basal level of expression of the IGF-IR. Then cells were washed twice and 12 μg/ml of biotinylated-12B1 MAb were added to the plate. After 30 min of incubation at 4° C. to avoid receptor internalization, cells were washed 3 times at 4° C. and stained by addition of a streptavidin Alexa Fluor® 488 conjugate (Molecular Probes Europe BV, Leiden, Netherlands).

Both 7C10 and h7C10 cause a rapid down regulation of the IGF-IR with a maximum after 4 hours of incubation with the antibodies (Table 11). No down regulation was observed when cells were incubated either with IGF1, 7G3 non neutralizing Mab, murine (mIgG1) or human (hIgG1) isotype control. The absence of internalization when cells were incubated with IGF-I is probably due to the rapid recycling of IGF-IR indeed this rapid recycling phenomenon is well known by the man skill in the art for this type of receptor. These results were observed either in presence or in absence of cyclohexemide. Observed results are shown in the following Table 11, Table 11 Study of Antibody Induced IGF-IR Internalization by FACS Analysis For immunoblotting experiments $7.5\times10^6$ cells were plated in 75 cm² flasks in 15 ml of complete medium (red phenol-free RPMI and Ham-F12K respectively for MCF-7 and A549 both supplemented with 10% FCS and 1% L-Glutamine). Twenty four hours after plating, cells were washed 3 times with PBS and incubated for 24 additional hours at 37° C. Then medium was removed and cells incubated either 1 h, 4 h or 16 h at 37° C. with 15 ml of serum-free medium with or without antibodies to be tested or with IGF-I Cells were then harvested and lysed in Tris HCl buffer pH 7.5, 15% NaCl 1M (Sigma), 10% detergent mix (10 mM Tris-HCl, 10% Igepal) (Sigma), 5% sodium deoxycholale (Sigmna), 1 protease inhibitor cocktail complete TM tablet (Roche) and 1% phosphatase inhibitor Cocktail Set II (Calbiochem). For Western blot analysis, equal amount of cell lysates were separated on 10% SDS-PAGE, transferred to nitrocellulose filters, probed with an anti-β IGF-IR rabbit polyclonal IgG (Santa Cruz Biotech), revelated with an anti rabbit IgG coupled to the HRP (Amersham Bioscience) and visualized by ECL (Amersham. Bioscience).

FIGS. 47A and 47B represent the study of antibody induced degradation of the IGF-IR.

For immuno-blotting analysis (FIGS. 47A and 47B), experiments were done without cyclohexemide as the above experiment shows that no difference was observed in presence or in absence of this compound. 7C10 and h7C10 cause a comparable internalization of the IGF-IR in both A549 (A) and MCF-7 (B) cells. In MCF-7 cells the maximal internalization was observed after four hours incubation with 7C10 and h7C10, whereas, for A549 the maximal internalization is observed as earlier as 1 hour. No degradation was observed when cells were incubated either with IGF-I, 7G3 or murine (mIgG1) or human (hIgG1) isotype control.

TABLE 11

| | | Cells incubated without Cyclohexemide | | | Cells incubated with Cyclohexemide | | |
|---|---|---|---|---|---|---|---|
| | | Buffer | mIgG1 Biotinylé | 12B1 Biotinylé | Buffer | mIgG1 Biotinylé | 12B1 Biotinylé |
| 5 min | Buffer | 8 | 8 | 135 | 8 | 8 | 90 |
| | IGF1 | 8 | 9 | 137 | 8 | 9 | 93 |
| 1 h | Buffer | 9 | 9 | 153 | 8 | 8 | 89 |
| | hIG1 | 8 | 9 | 150 | 8 | 9 | 92 |
| | h7C10 | 9 | 9 | 64 | 8 | 8 | 37 |
| | mIgG1 | 8 | 9 | 144 | 8 | 8 | 88 |
| | 7C10 | 9 | 9 | 61 | 8 | 9 | 36 |
| | 7G3 | 8 | 9 | 137 | 8 | 8 | 85 |
| 4 h | Buffer | 8 | 8 | 136 | 8 | 8 | 95 |
| | hIgG1 | 8 | 8 | 139 | 7 | 8 | 94 |
| | h7C10 | 8 | 8 | 39 | 8 | 8 | 29 |
| | mIgG1 | 9 | 9 | 130 | 8 | 8 | 78 |
| | 7C10 | 8 | 8 | 37 | 8 | 8 | 27 |
| | 7G | 8 | 8 | 109 | 8 | 8 | 72 |
| 16 h | Buffer | 8 | 9 | 135 | 8 | 8 | 85 |
| | HIgG1 | 9 | 9 | 144 | 8 | 8 | 85 |
| | H7C10 | 9 | 10 | 34 | 8 | 9 | 26 |
| | MIgG1 | 9 | 10 | 10 | 10 | 10 | 56 |
| | 7C10 | 9 | 9 | 31 | 9 | 9 | 25 |
| | 7G3 | 9 | 9 | 90 | 9 | 9 | 57 |

EXAMPLE 28

Study of the Degradation Pathway of IGF-IR $7.5 \times 10^6$ MCF-7 cells were plated in 75 cm$^2$ flasks in 15 ml of complete medium (red phenol-free RPMI supplemented with 10% FCS dald 1% L-Glutamine). Twenty four hours after plating, cells were washed 3 times with PBS and incubated for 24 additional hours at 37° C. in 15 ml serum-free medium Then medium was removed and cells incubated for two hours in 7.5 ml of serum-free medium either containing 30 µM MG115 or DMSO. Then, 7.5 ml of serum-free medium with or without h7C10, hIgC1 or IGF-I were added for 4 additional hours. Cells were then harvested and lysed in Tris HCl buffer pH 7.5, 15% NaCl 1M (Sigma), 10% detergent mix (10 mM Tris-HCl, 10% Igepal) (Sigma), 5% sodium dcoxycholate (Sigma), 1 protease inhibitor cocktail complete TM tablet (Roche) and 1% phosphatase inhibitor Cocktail Set II (Calbiochem). For Western blot analysis, equal amount of cell lysates were separated on 10% SDS-PAGE, transferred to nitrocellulose filters, probed with an anti-β IGF-IR rabbit polyclonal IgG (Santa Cruz Biotech), revelated with an anti rabbit IgG coupled to the HRP (Amersham Bioscience) and visualized by ECL (Amersham Bioscience). FIG. 48 shows the obtained results.

Figure 1:
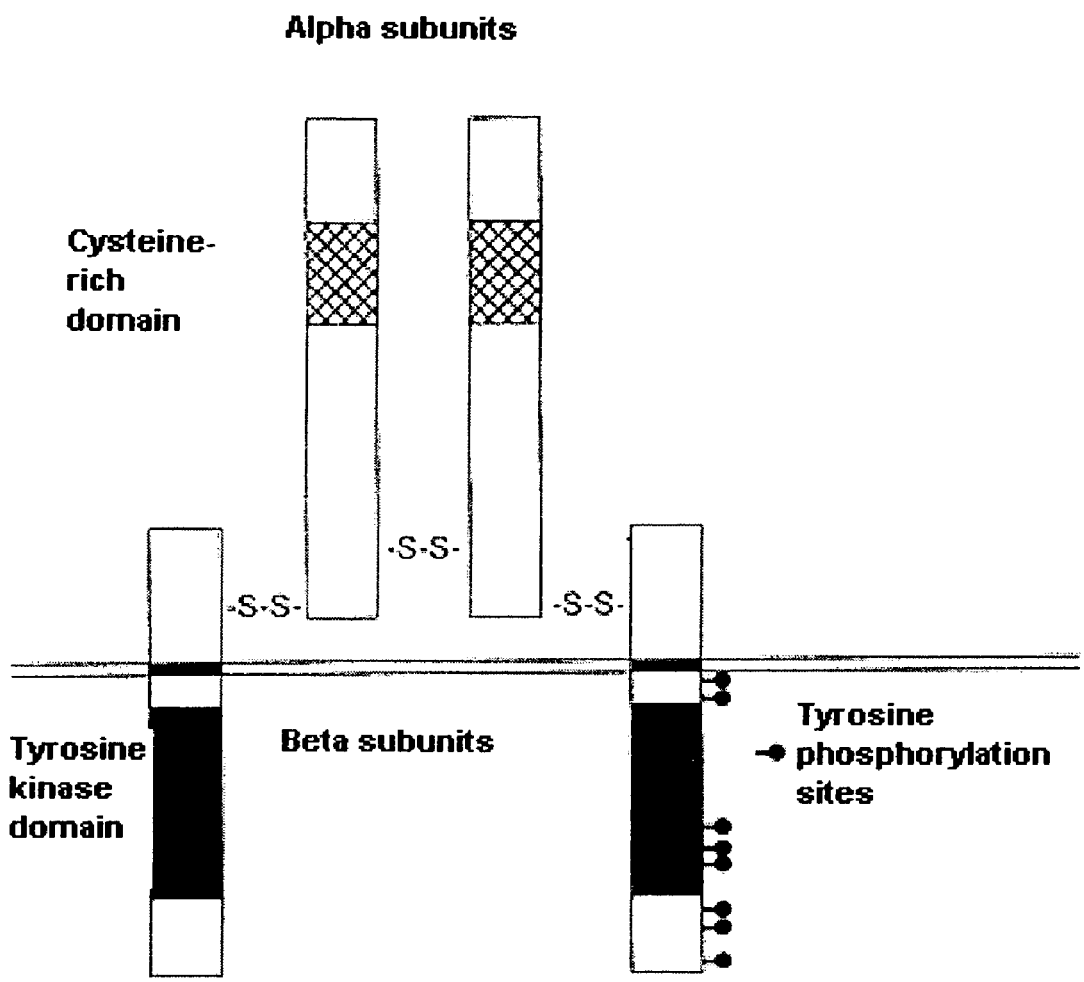
Figure 2:
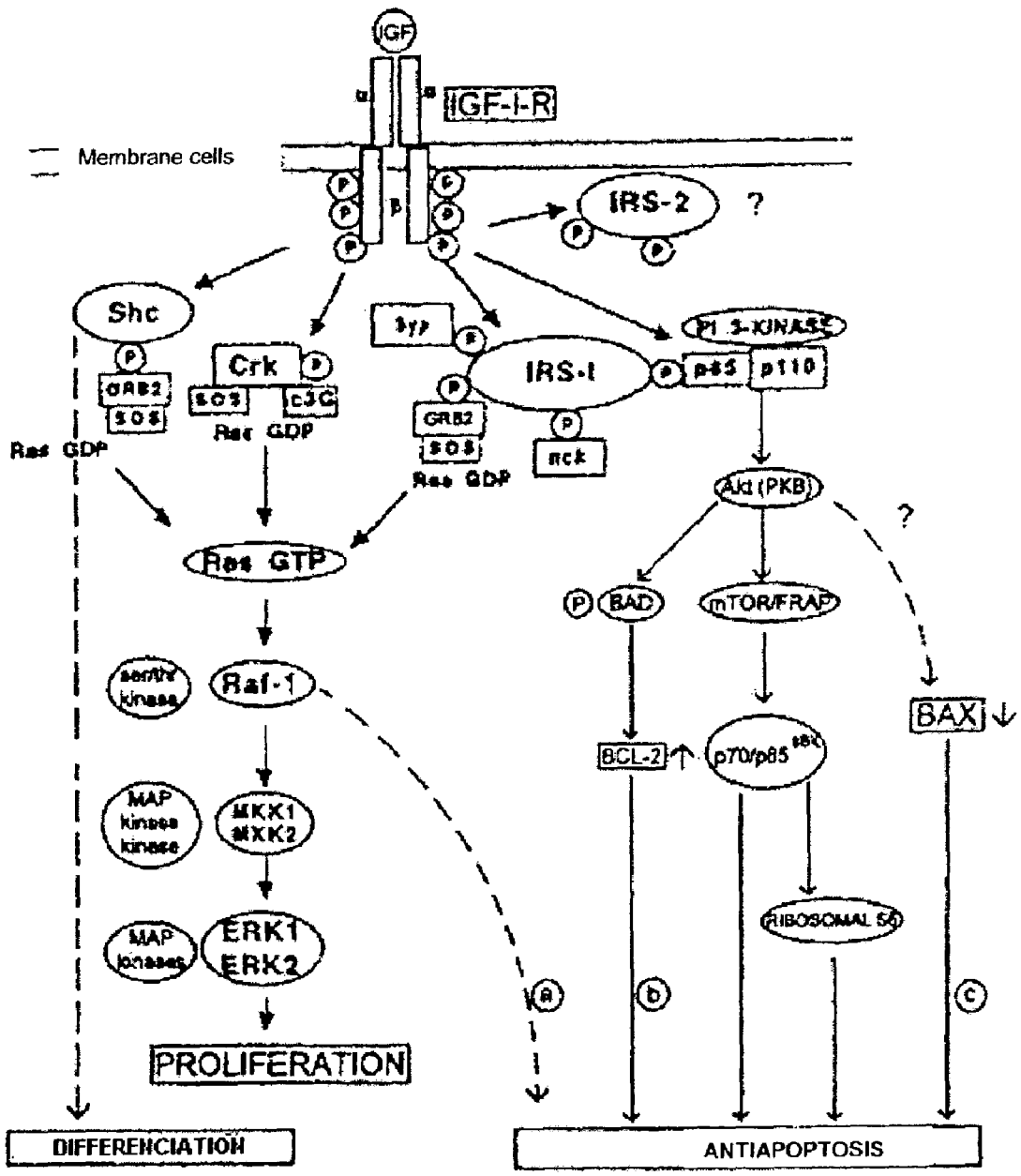

To further characterize the pathway of degration of the h7C10 antibody, cells were incubated 4 hours with either IGF-T or human isotype control (hIgG1) in presence or in absence of the proteasome inhibitor MG115. In the herein described experiment h7C10 induced, a dramatic degradation of the IGF-IR either in presence or in absence of DMSO. No degradation was observed when IGF-I or hIgG1 were added. When cells were incubates with 30 µM MG115, no down regulation of the IGF-IR was observed demonstrating that the down regulation of IGF-IR on MCF-7 observed in FIG. 2 occurs through the proteasome pathway. This property is surprising and of particular interest. Indeed none of the anti-IGF-IR antibody already described for inducing a degradation of the IGF-IR (Malauney EK and al, Cancer Research, 2003 ; Sachdev D and al, Cancer Research, 2003) involved the proteasome pathway for degradation. Actually, it has been reported that IGF-IR is internalized and degraded via a lysosome-dependent pathway (Alessi et. Al., B. Curr. Biol., 1997). In addition, both Mab391 (Hailey et Al., Molecular Cancer Therapeutics, 2002) and scFv-Fc (Sachdev et Al., Cancer Research, 2003) down regulate IGF-IR by the endocytic pathway As a consequence, regarding the present knowledge, it can *not be exclude that h7C10 also down regulate, in addition to the proteasome pathway as previously described, via other known and described pathways for anti-IGF-IR antibodies, i.e. lisosome-dependent and/or endocytic pathways.

Such a property, if validated, is of particular interest as it would demonstrate the capacity of the h7C10 to interact with different signalization/degradation pathways, and thus its therapeutic efficacy. Supplementary studies are in progress in order to validate this hypothesis.

EXAMPLE 29

Anti-tumoral Activity of the Murine Antibody 7C10 Co-Administrated with an Anti-VEGF Antibody on Mice Orthopically Implanted with A549 Cells One million of A549 NSCLC were implanted through the chest wall into the left pleural cavity space of 6 weeks old Swiss nude mice following the protocol described by Klaus-Berthier et al. (Kraus-Berthier, L., Jan, M., Guilbaud, N., Naze, M., Pierre, A., and Atassi, G. Histology and sensitivity to anticancer drugs of two human non-small cell lung carcinomas implanted in the pleural cavity of nude mice. Clin. Cancer Res. 6 (1): 297–304, 2000). Seven days after the cell injection, mice were treated i.p. with a loading dose of 250 µg of antibodies, and them, twice a week with 125 µg of antibodies. For the combined therapy, antibodies were mixed prior to the injection.

The anti-VEGF antibody used was an IgG2b, clone 26503.11 commercialized by SIGMA. It was described as a neutralizing antibody (Ferraca N. et al., Biochem. Res. Com. 161:351. 1999; Ferrara et al., Endocrinol. Review 13 :18.1992 Leung D. W. et al., Science 246 :1306.1989).

FIG. 48 shows that a combined therapy increase dramatically the time survival compared to untreated mice or to mice treated with single therapy.

The T/C % are calculated according the following formula, [MEDIAN OF TREATED MICE/MEDIAN OF CONTROL MICE×100]. The obtained T/C % are about 134% and 144% for the 7C10 and anti-VEF antibody respectively. For the combined treatment 7C10+anti-VEGF antibodies, the T/C % is 188%. As a conclusion, similarly to the co-administration of 7C10 225 (see example 22), the co-administration of 7C10+anti-VEGF antibodies increase the mice survival.

EXAMPLE 30

Production of Deoxyvinblastine

4'-R deoxyvinblastine (structure see below Scheme 1) is obtained by ionic reduction of anhydrovinblastine according to a process known to those skilled in the art (Lafitte C et al., Tetrahedron Letters, 1998, Volume 39, pp. 8281–8282).

4'-S deoxyvinblastine, or 4'-S deoxyleurosidine, is obtained by catalytic hydrogenation of anhydrovinblastine according to the technique also known to those skilled in the art (De-Bruyn A. et al., Bulletin of the Belgian Chemical Society, 1983, Volume 92, number 5, pp 485–494).

Scheme 1

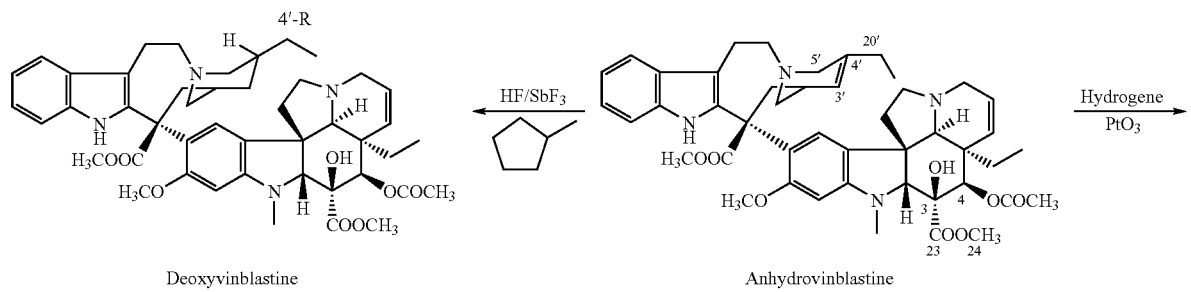

Deoxyvinblastine        Anhydrovinblastine

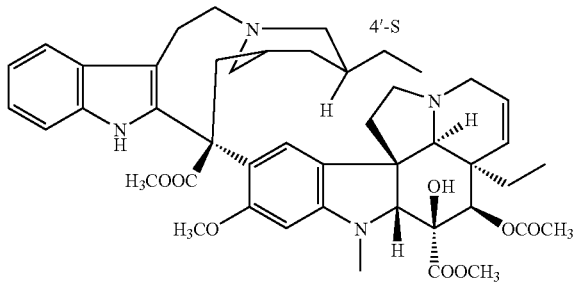

Deoxyleurosidine

EXAMPLE 31

Deacetylation of Vinca Dimeric Alkaloids

Deoxyvinblastine or deoxyleurosidine is dissolved and stirred for 4 hours at 50° C. in 30 ml of methanol containing 1.2 equivalents of sodium methoxide. This solution is then poured into ice-cold water in order to precipitate the compound formed. After filtration, washing with water and drying under vacuum at 40° C., 4-deacetyldeoxyvinblastine or 4-deacetyldeoxyleurosidine is obtained, with a purity of greater than 95%.

EXAMPLE 32

Direct Coupling of 4'-deoxyvinblastine (4' R) or 4'-deoxyleurosidine (4' S) by Reaction of a 4-caxboxyhydrazide Function on the Pre-Oxidized Anti-IGF-IR Antibodies The 4'-deoxyvinblastine or the 4'-deoxyleurosidine is treated with anhydrous hydrazine in solution in methanol end at ambient temperature. The reaction is monitored by Analytical High Performance Liquid Chromatography (HPLC) and, when 95% of the starting alkaloid has reacted, the reaction medium is treated with water in order for the 4'-deoxyvinblastine-3-deacetyl-4-carbohydrazide or the 4'-deoxyleurosidine-3-deacetyl-4-carbohydrazide to be separated by filtration.

After silica gel chromatography and then crystallization, the 4'-deoxyvinblastine-3-deacetyl-4-carbohydrazide or the 4'-deoxyleurosidine-3-deacetyl-4-carbohydrazide is greater than 96% pure.

The anti-IGF-IR antibody is oxidized under cold conditions in a sodium acetate buffer by treatment with sodium meta-periodate. After exclusion chromatography, the oxidized anti-ICF-IR antibody, in solution in an acetate buffer, is treated under cold conditions with the 4'-deoxyvinblastine-3-deacetyl-4-carbohydrazide or the 4'-deoxyleurosidine-3-deacetyl-4-carbohydrazide.

The immunoconjugate thus obtained is separated from the unconjugated residual Vinca alkaloid and purified by exclusion chromatography with a phosphate buffer at pH 7.4, and then intensive dialysis. The absence o free Vinca alkaloid is verified by analytical HPLC.

The immunoconjugate is characterized on an SDS PAGE-type electrophoresis gel (Coomassie blue and/or silver nitrate), by exclusion chromatography (SEC, UV at 280 nm) and by MALDI-TOF mass spectrometry. The mapping of the coupling sites is carried out by means of analysis by liquid chromatography coupled to mass spectrometry (LC MS), subsequent to enzyme digestion (trypsin and PNGase F) (Laguzza et al., J. MED. CM.1989, 32:548).

EXAMPLE 33

Coupling of the 4'-deoxyvinblastine (4' R) or the 4'-deoxyleurosidine (4' S) to the Anti-IGF-IR Antibodies by Virtue of Succinic Anhydride The 3-deacetyl-4'-deoxyvinblastine or the 3-deacetyl-4'-deoxyleurosidine is treated with succinic anhydride in pyridine for 24 hours at 20° C. The reaction is monitored by analytical HPLC and, when 95% of the starting alkaloid has reacted, the reaction medium is treated with water in order to precipitate the 3-deacetyl-4'-deoxyvinblastine hemisuccinate or the 3-deacetyl-4'-deoxyleurosidine hemisuccinate. After filtration and drying, the compound is purified by reverse-phase preparative HPLC using C18 grafted silica and an eluent made up of acetonitrile, methanol and ammonium acetate buffer.

The 3-deacetyl-4'-deoxyvinblastine hemisuccinate or the 3-deacetyl-4'-deoxyleurosidine hemisuccinate is treated with hydroxybenzotriazole and dicyclohexylcarbodiimide in dimethylformamide at ambient temperature for 24 hours and in the presence of a catalytic amount of dimethylaminopyridine. After filtration, the solution is mixed with the anti-IGF-IR monoclonal antibody at pH 8.6 for 4 hours. The immunoconjugate is separated from the unconjugated Vinca alkaloid by exclusion chromatography with a phosphate buffer at pH 7.4. Intensive dialysis makes it possible to eliminate the unconjugated vinca alkaloid. The immunoconjugate is characterized by SDS PAGE gel electrophoresis, by exclusion chromatography and by MALDI TOF mass spectrometry. The mapping of the coupling sites is carried out by means of liquid chromatography analysis coupled to mass spectrometry (LC MS), subsequent to enzyme (trypsin) digestion, compared to a reference tryptic man obtained for the non-derived monoclonal antibody (Schneck et al., Clin. Pharmacol. Ther., 1990, 47:36; Rowland et al., Cancer. Immunol. Immunother., 1985, 19:1).

EXAMPLE 34

Coupling of the 4'-deoxyvinblastine (4' R) or the 4'-deoxyleurosidine (4' S) on a Nitrogen-Containing Residue of the Anti-IGF-IR Antibodies by Virtue of a Disulphide Bridge Included in the Linkage The 3-deacetyl-4'-deoxyvinblastine or he 3-deacetyl-4'-deoxylcurosidine is treated, in methylene chloride, at ambient temperature for 24 hours, in the presence of a catalytic amount of dimethylaminopyridine, with a large excess of 3-methyldisulphanylpropanoic acid and a large excess of dicyclohexylcarbodiimide The reaction medium is treated conventionally and the 3-deacetyl-4'-deoxyvinblastine 3-methyldisulphanylpropanoate or the 3-deacetyl-4'-deoxyleurosidine 3-methyldisulphanylpropanoate is then purified by reverse-phase preparative HPLC using C18 grafted silica and an eluent made up of acetonitrile, methanol and ammonium acetate buffer.

The 3-deacetyl-4'-deoxyvinblastine 3-methyldisulphanylpropanoate or the 3-deacetyl-4'-deoxyleurosidine 3-methyldisulphanylpropanoate is treated with dithiothreitol in a mixture of water and methanol so au to obtain 3-deacetyl-4'-deoxyvinblastine 3-sulphanylpropanoate or 3-deacetyl-4'-deoxyleurosidine 3-sulphanylpropanoate, which is purified by reverse-phase preparative HPLC using C18 grafted silica and an eluent made up of acetonitrile, methanol and ammonium acetate buffer.

The anti-IGF-IR antibody is derivatized with N-succinimidyl 4-(2-pyridyldithio)propanoate (the trade name of which is SPDP) in a 50 mM potassium phosphate buffer, pH 6.5, containing 50 mM NaCl and 2 mM EDTA, for 90 minutes. Added to this solution of antibody thus derivatized is the 3-deacetyl-4'-deoxyvinblastine 3-sulphanylpropanoate or the 3-deacetyl-4'-deoxyleurosidine 3-sulphanylpropanoate dissolved in a minimum of DMSO. After contact for 24 hours, the immunoconjugate is isolated by exclusion chromatography and is characterized on an SDS PAGE electrophoresis gel, by exclusion chromatography and by MALDI TOF mass spectrometry (Ojima et al., J. Med. Chem., 2002, 45:5320).

EXAMPLE 35

Coupling of the 4'-deoxyvinblastine (4' R) or the 4'-deoxyleurosidine (4' S) to the Anti-IGF-IR Antibodies by Virtue of a Terminal Hydrazide Function Carried by a Linkage Connected to the Vinca Alkaloid The 3-deacetyl-4'-deoxyvinblastine or the 3-deacetyl-4'-deoxyleurosidine is treated, in methylene chloride at ambient temperature for 24 hours, in the presence of a catalytic amount of dimethylaminopyridine, with an excess of methyl monoester of 1,6-hexanedicarboxylic acid and an excess of dicyclohexylcarbodiimide. The reaction medium is treated conventionally and the 3-deacetyl-4'-deoxyvinblastine 3-methoxycarbonyl pentanoate or the 3-deacetyl-4'-deoxyleurosidine 3-methoxycarbonyl pentanoate is then purified by reverse-phase preparative HPLC using, C18 grafted silica and an eluent made up of acetonitrile, methanol and ammonium acetate buffer.

The 3-deacetyl-4'-deoxyvinblastine 3-methoxycarbonyl pentanoate or the 3-deacetyl-4'-deoxyleurosidine 3-methoxycarbonyl pentanoate is treated by default with anhydrous hydrazine in solution in methanol at ambient temperature. The reaction is monitored by analytical HPLC and, when 70% of the starting alkaloid has reacted, the reaction medium is evaporated and the 3-deacetyl-4'-deoxyvinblastine 3-hydrazinocarbonyl pentanoate or the 3-deacetyl-4'-deoxyleurosidine 3-hydrazinocarbonyl pentanoate is purified by reverse-phase preparative HPLC using C18 grafted silica and an eluent made up of acetonitrile, methanol and ammonium acetate buffer.

The oxidation of the anti-IGF-IF antibody, the coupling with 3-deacetyl-4'-deoxyvinbiastine 3-hydrazinocarbonyl pentanoate or 3-deacetyl-4'-deoxyleurosidine 3-hydrazinocarbonyl pentanoate, the purification and the identification are carried out according to the same techniques as those described in Example 32.

EXAMPLE 36

Activity, Compared In Vivo, of the 7C10 and h7C10 Antibodies on the A549 and MCF-7 Models In order to confirm the activity of the humanized antibody h7C10 in vivo, the latter was compared with 7C10 in the MCF-7 oestrogen-dependent breast tumour model and in the A549 non-small-cell lung tumour model.

To do this, $5.10^6$ A549 cells were implanted subcutaneously in nude mice. Five days after this implantation, the tumours were measured and groups of 6 mice were formed. These groups were treated, respectively, with 1) the 7C10 antibody injected ip (intraperitoreally) at a rate of 125 µg/dose twice a week; 2) the h7C10 antibody injected under the same conditions as its murine form; 3) PBS (it has been shown previously that murine and human control isotypes do not modify the tumour growth profile compared to treatment of the animals with PBS). In the MCF-7 breast tumour model, a sustained-release oestradiol granule (0.72 mg/tablet released over 60 days) is implanted subcutaneously 24 hours before implantation of the cells. This granule is essential to the establishment of any E2-dependent human tumour in this animal species.

FIGS. 50 and 51 show, as expected, that significant inhibition of tumour growth is observed with the 7C10 murine antibody. As regards the h7C10 humanized antibody, the activity observed is of exactly the same intensity as that observed with its murine counterpart, whatever the model used. This datum indicates that the humanization has not modified the properties of the antibody generated.

EXAMPLE 37

Demonstration of the Compared Activities of Vinblastine, of Vincristine, of 4' S deoxyvinblastine and of 4' R deoxyleurosidine The greater activity of the (4' R) deoxyvinblastine and of the (4' S) deoxyleurosidine was demonstrated in vivo against intravenously-grafted P388 murine leukaemia and compared with the activity of vinblastine and of vincristine tested under the same conditions. The protocol for this test is described by Kruczynski A. et al., Cancer Chemotherapy and Pharmacology, 1998, volume 41, pages 437 to 447.

To do this, a total of $10^6$ P388 murine leukaemia cells were implanted i.v. in COF1 mice on day 0. After randomization of the animals in cages for treatment with each alkaloid and control cages, the compounds were administered i.p. on day 1.

Conventionally, the in vivo activity of compounds is expressed by the increase in survival time. The survival time is expressed by the T/C at a dose expressed in mg per kg (mg/kg). The TIC corresponds to the ratio, multiplied by 100, of the median of the survival time of the treated animals to the median of the survival time of the control animals. In agreement with the standard criteria of the NCI, a T/C of 120 corresponds to a minimum level for concluding that activity is present.

A T/C of between 120 and 175 makes it possible to conclude that there is significant activity and a T/C above 175 makes it possible to conclude that there is a high level of anti-leukaemia activity. A T/C below 75 expresses toxicity of the test compound at the dose administered.

Table 12 below gives the results obtained with a minimum of 7 and a maximum of 15 treated mice for each group of animals treated with a Vinca alkaloid or for the control group.

Table 12 gives the results of T/C values obtained for each Vinca alkaloid tested.

FIGS. 52 and 53 show the greater anti-leukaemia activity of the 4'R and 4'S deoxyvinblastines compared to vinblastine and vincristine.

TABLE 12

| | Dose in mg/kg | | | | | | |
|---|---|---|---|---|---|---|---|
| | 0.63 | 1.25 | 2.5 | 5 | 10 | 20 | 40 |
| T/C for vinblastine | 114 | 114 | 129 | 143 | 57 | | |
| T/C for vincristine | 114 | 143 | 143 | 100 | 57 | | |
| T/C for 4'-S-deoxyvinblastine | 114 | 143 | 200 | 100 | 57 | | |
| T/C for 4'-R-deoxyvinblastine | 100 | 100 | 129 | 143 | 200 | 214 | 43 |

EXAMPLE 38

Demonstration of the In Vivo Antitumour Activity of 4' R- and 4' S-deoxyvinblastine Conjugated with IGR-IR Antibodies on Human Tumours of Various Origins In order to demonstrate the benefit of addressing the chemotherapy compounds (4' R) and (4' S) deoxyvinblastine (respectively called RDV and SDV in FIG. 5) with a humanized antibody directed against IGF-IR, $5.10^6$ A549 non-small-cell lung cancer cells were implanted in a subcutaneous position on the right flank of Swiss Nude mice. Seven days after implantation of the cells, the tumours can be measured and the animals are distributed randomly into 6 groups of 6 mice and treated according to the following protocol:

h7C10; twice a week at a rate of 250 µg/dose throughout the entire duration of the experiment;

RDV and SDV: 4 intraperitoneal injections 7 days apart at the dose of 0.35 mg/kg, which corresponds to the dose of each of the compounds present in the conjugates;

the groups of animals given the chemotherapy compounds coupled to the antibody receive respectively 0.35 mg/kg of each of the chemotherapy agents and 250 µg/dose of antibodies. These conjugates are administered according to the same modes as the groups given the chemotherapy compounds alone;

the animals of the control batch are given injections of PBS, administered according to the same frequency.

The weight of the Juice and the tumour volume are evaluated twice a week. The tumour volumes are calculated according to the formula; ½ (length·width·height).

The results are shown in FIG. 53.

The animals given only RDV or SDV evolve in the same manner as the control group, which seems coherent with respect to the optimum doses usually injected for these two compounds, which are respectively 20 mg/kg and 2.5 mg/kg. Surprisingly, when each of the compounds is coupled to the h7C10 antibody, a very significant inhibition of the tumour growth is observed. This inhibition is significantly greater than that observed with the antibody alone, administered at the same concentration.

All these results appear to indicate that targeting of the cells with the h7C10 antibody promotes concentration of the drug in the cell to be targeted and makes it possible to observe, as a result, significant inhibitions of tumour proliferation at low doses of chemotherapy product, and in particular at doses which are completely non-toxic in mice, as is demonstrated by the lack of weight loss of the animals (data not communicated).

SEQUENCE LISTING

<160> NUMBER OF SEQ ID NOS: 156

<210> SEQ ID NO 1
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 1 aga tct agt cag agc att gta cat agt aat gga aac acc tat tta caa    48
Arg Ser Ser Gln Ser Ile Val His Ser Asn Gly Asn Thr Tyr Leu Gln
 1               5                  10                  15

<210> SEQ ID NO 2
<211> LENGTH: 16
<212> TYPE: PRT
<213> ORGANISM: Mus musculus

<400> SEQUENCE: 2

Arg Ser Ser Gln Ser Ile Val His Ser Asn Gly Asn Thr Tyr Leu Gln
 1               5                  10                  15

<210> SEQ ID NO 3
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 3

```
aaa gtt tcc aac cga ctt tat                                          21
Lys Val Ser Asn Arg Leu Tyr
 1               5
```

<210> SEQ ID NO 4
<211> LENGTH: 7
<212> TYPE: PRT
<213> ORGANISM: Mus musculus

<400> SEQUENCE: 4

```
Lys Val Ser Asn Arg Leu Tyr
 1               5
```

<210> SEQ ID NO 5
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 5

```
ttt caa ggt tca cat gtt ccg tgg acg                                  27
Phe Gln Gly Ser His Val Pro Trp Thr
 1               5
```

<210> SEQ ID NO 6
<211> LENGTH: 9
<212> TYPE: PRT
<213> ORGANISM: Mus musculus

<400> SEQUENCE: 6

```
Phe Gln Gly Ser His Val Pro Trp Thr
 1               5
```

<210> SEQ ID NO 7
<211> LENGTH: 18
<212> TYPE: DNA
<213> ORGANISM: Mus musculus
<220> FEATURE:
<221> NAME/KEY: CDS
<222> LOCATION: (1)..(18)

<400> SEQUENCE: 7

```
ggt ggt tat tta tgg aac                                              18
Gly Gly Tyr Leu Trp Asn
 1               5
```

<210> SEQ ID NO 8
<211> LENGTH: 6
<212> TYPE: PRT
<213> ORGANISM: Mus musculus

<400> SEQUENCE: 8

```
Gly Gly Tyr Leu Trp Asn
 1               5
```

```
<210> SEQ ID NO 9
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 9 tac ata agc tac gac ggt acc aat aac tac aaa cca tct ctc aaa gat     48
Tyr Ile Ser Tyr Asp Gly Thr Asn Asn Tyr Lys Pro Ser Leu Lys Asp
 1               5                  10                  15

<210> SEQ ID NO 10
<211> LENGTH: 16
<212> TYPE: PRT
<213> ORGANISM: Mus musculus

<400> SEQUENCE: 10

Tyr Ile Ser Tyr Asp Gly Thr Asn Asn Tyr Lys Pro Ser Leu Lys Asp
 1               5                  10                  15

<210> SEQ ID NO 11
<211> LENGTH: 24
<212> TYPE: DNA
<213> ORGANISM: Mus musculus
<220> FEATURE:
<221> NAME/KEY: CDS
<222> LOCATION: (1)..(24)

<400> SEQUENCE: 11 tac ggt agg gtc ttc ttt gac tac                                     24
Tyr Gly Arg Val Phe Phe Asp Tyr
 1               5

<210> SEQ ID NO 12
<211> LENGTH: 8
<212> TYPE: PRT
<213> ORGANISM: Mus musculus

<400> SEQUENCE: 12

Tyr Gly Arg Val Phe Phe Asp Tyr
 1               5

<210> SEQ ID NO 13
<211> LENGTH: 26
<212> TYPE: DNA
<213> ORGANISM: Mus musculus

<400> SEQUENCE: 13
atgaaatgca gctgggtcat sttctt                                        26

<210> SEQ ID NO 14
<211> LENGTH: 26
<212> TYPE: DNA
<213> ORGANISM: Mus musculus

<400> SEQUENCE: 14
atgggatgga gctrtatcat sytctt                                        26

<210> SEQ ID NO 15
<211> LENGTH: 26
<212> TYPE: DNA
<213> ORGANISM: Mus musculus
```

```
<400> SEQUENCE: 15
atgaagwtgt ggttaaactg ggtttt                                        26

<210> SEQ ID NO 16
<211> LENGTH: 23
<212> TYPE: DNA
<213> ORGANISM: Mus musculus

<400> SEQUENCE: 16
atgractttg ggytcagctt grt                                           23

<210> SEQ ID NO 17
<211> LENGTH: 26
<212> TYPE: DNA
<213> ORGANISM: Mus musculus

<400> SEQUENCE: 17
atggactcca ggctcaattt agtttt                                        26

<210> SEQ ID NO 18
<211> LENGTH: 26
<212> TYPE: DNA
<213> ORGANISM: Mus musculus

<400> SEQUENCE: 18
atggctgtcy trgsgctrct cttctg                                        26

<210> SEQ ID NO 19
<211> LENGTH: 26
<212> TYPE: DNA
<213> ORGANISM: Mus musculus

<400> SEQUENCE: 19
atggratgga gckggrtctt tmtctt                                        26

<210> SEQ ID NO 20
<211> LENGTH: 23
<212> TYPE: DNA
<213> ORGANISM: Mus musculus

<400> SEQUENCE: 20
atgagagtgc tgattctttt gtg                                           23

<210> SEQ ID NO 21
<211> LENGTH: 26
<212> TYPE: DNA
<213> ORGANISM: Mus musculus

<400> SEQUENCE: 21
atggmttggg tgtggamctt gctatt                                        26

<210> SEQ ID NO 22
<211> LENGTH: 26
<212> TYPE: DNA
<213> ORGANISM: Mus musculus

<400> SEQUENCE: 22
atgggcagac ttacattctc attcct                                        26

<210> SEQ ID NO 23
<211> LENGTH: 28
<212> TYPE: DNA
<213> ORGANISM: Mus musculus
```

-continued

```
<400> SEQUENCE: 23
atggattttg ggctgatttt ttttattg                                      28

<210> SEQ ID NO 24
<211> LENGTH: 26
<212> TYPE: DNA
<213> ORGANISM: Mus musculus

<400> SEQUENCE: 24
atgatggtgt taagtcttct gtacct                                        26

<210> SEQ ID NO 25
<211> LENGTH: 29
<212> TYPE: DNA
<213> ORGANISM: Mus musculus

<400> SEQUENCE: 25
atgaagttgc ctgttaggct gttggtgct                                     29

<210> SEQ ID NO 26
<211> LENGTH: 29
<212> TYPE: DNA
<213> ORGANISM: Mus musculus

<400> SEQUENCE: 26
atggagwcag acacactcct gytatgggt                                     29

<210> SEQ ID NO 27
<211> LENGTH: 23
<212> TYPE: DNA
<213> ORGANISM: Mus musculus

<400> SEQUENCE: 27
atgagtgtgc tcactcaggt cct                                           23

<210> SEQ ID NO 28
<211> LENGTH: 26
<212> TYPE: DNA
<213> ORGANISM: Mus musculus

<400> SEQUENCE: 28
atgaggrccc ctgctcagwt tyttgg                                        26

<210> SEQ ID NO 29
<211> LENGTH: 29
<212> TYPE: DNA
<213> ORGANISM: Mus musculus

<400> SEQUENCE: 29
atggatttwc aggtgcagat twtcagctt                                     29

<210> SEQ ID NO 30
<211> LENGTH: 29
<212> TYPE: DNA
<213> ORGANISM: Mus musculus

<400> SEQUENCE: 30
atggatttwc argtgcagat twtcagctt                                     29

<210> SEQ ID NO 31
<211> LENGTH: 26
<212> TYPE: DNA
<213> ORGANISM: Mus musculus
```

```
<400> SEQUENCE: 31
atgaggtkcy ytgytsagyt yctgrg                                          26

<210> SEQ ID NO 32
<211> LENGTH: 23
<212> TYPE: DNA
<213> ORGANISM: Mus musculus

<400> SEQUENCE: 32
atgggcwtca agatggagtc aca                                             23

<210> SEQ ID NO 33
<211> LENGTH: 29
<212> TYPE: DNA
<213> ORGANISM: Mus musculus

<400> SEQUENCE: 33
atgtggggay ctktttycmm tttttcaat                                       29

<210> SEQ ID NO 34
<211> LENGTH: 24
<212> TYPE: DNA
<213> ORGANISM: Mus musculus

<400> SEQUENCE: 34
atggtrtccw casctcagtt cctt                                            24

<210> SEQ ID NO 35
<211> LENGTH: 26
<212> TYPE: DNA
<213> ORGANISM: Mus musculus

<400> SEQUENCE: 35
atgtatatat gtttgttgtc tatttc                                          26

<210> SEQ ID NO 36
<211> LENGTH: 26
<212> TYPE: DNA
<213> ORGANISM: Mus musculus

<400> SEQUENCE: 36
atggaagccc cagctcagct tctctt                                          26

<210> SEQ ID NO 37
<211> LENGTH: 26
<212> TYPE: DNA
<213> ORGANISM: Mus musculus

<400> SEQUENCE: 37
atgragtywc agacccaggt cttyrt                                          26

<210> SEQ ID NO 38
<211> LENGTH: 26
<212> TYPE: DNA
<213> ORGANISM: Mus musculus

<400> SEQUENCE: 38
atggagacac attctcaggt ctttgt                                          26

<210> SEQ ID NO 39
<211> LENGTH: 26
<212> TYPE: DNA
<213> ORGANISM: Mus musculus
```

```
<400> SEQUENCE: 39
atggattcac aggcccaggt tcttat                                  26

<210> SEQ ID NO 40
<211> LENGTH: 20
<212> TYPE: DNA
<213> ORGANISM: Mus musculus

<400> SEQUENCE: 40
actggatggt gggaagatgg                                         20

<210> SEQ ID NO 41
<211> LENGTH: 42
<212> TYPE: DNA
<213> ORGANISM: Mus musculus
<220> FEATURE:
<221> NAME/KEY: CDS
<222> LOCATION: (1)..(42)

<400> SEQUENCE: 41 gct gat gct gca cca act gta tcc atc ttc cca cca tcc agt      42
Ala Asp Ala Ala Pro Thr Val Ser Ile Phe Pro Pro Ser Ser
 1               5                  10

<210> SEQ ID NO 42
<211> LENGTH: 14
<212> TYPE: PRT
<213> ORGANISM: Mus musculus

<400> SEQUENCE: 42

Ala Asp Ala Ala Pro Thr Val Ser Ile Phe Pro Pro Ser Ser
 1               5                  10

<210> SEQ ID NO 43
<211> LENGTH: 20
<212> TYPE: DNA
<213> ORGANISM: Mus musculus

<400> SEQUENCE: 43
ccatcttccc accatccagt                                         20

<210> SEQ ID NO 44
<211> LENGTH: 18
<212> TYPE: DNA
<213> ORGANISM: Mus musculus

<400> SEQUENCE: 44
ccagtggata gacagatg                                           18

<210> SEQ ID NO 45
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 45 gcc aaa acg aca ccc cca tct gtc tat cca ctg                  33
Ala Lys Thr Thr Pro Pro Ser Val Tyr Pro Leu
 1               5                  10
```

```
<210> SEQ ID NO 46
<211> LENGTH: 11
<212> TYPE: PRT
<213> ORGANISM: Mus musculus

<400> SEQUENCE: 46

Ala Lys Thr Thr Pro Pro Ser Val Tyr Pro Leu
 1               5                  10

<210> SEQ ID NO 47
<211> LENGTH: 21
<212> TYPE: DNA
<213> ORGANISM: Mus musculus

<400> SEQUENCE: 47
cccccatctg tctatccact g                                                    21

<210> SEQ ID NO 48
<211> LENGTH: 438
<212> TYPE: DNA
<213> ORGANISM: Mus musculus
<220> FEATURE:
<221> NAME/KEY: CDS
<222> LOCATION: (28)..(393)

<400> SEQUENCE: 48
atgaagttgc ctgttaggct gttggtg ctg atg ttc tgg att cct gct tcc aga       54
                              Leu Met Phe Trp Ile Pro Ala Ser Arg
                                    1               5 agt gat gtt ttg atg acc caa att cca ctc tcc ctg cct gtc agt ctt        102
Ser Asp Val Leu Met Thr Gln Ile Pro Leu Ser Leu Pro Val Ser Leu
 10              15                  20                  25 gga gat caa gcc tcc atc tct tgc aga tct agt cag agc att gta cat        150
Gly Asp Gln Ala Ser Ile Ser Cys Arg Ser Ser Gln Ser Ile Val His
                 30                  35                  40 agt aat gga aac acc tat tta caa tgg tac ctg cag aaa cca ggt cag        198
Ser Asn Gly Asn Thr Tyr Leu Gln Trp Tyr Leu Gln Lys Pro Gly Gln
             45                  50                  55 tct cca aag ctc ctg atc tac aaa gtt tcc aac cga ctt tat ggg gtc        246
Ser Pro Lys Leu Leu Ile Tyr Lys Val Ser Asn Arg Leu Tyr Gly Val
         60                  65                  70 cca gac agg ttc agt ggc agt gga tca ggg aca gat ttc aca ctc aag        294
Pro Asp Arg Phe Ser Gly Ser Gly Ser Gly Thr Asp Phe Thr Leu Lys
     75                  80                  85 atc agc agc gtg gag gct gag gat ctg gga gtt tat tac tgc ttt caa        342
Ile Ser Ser Val Glu Ala Glu Asp Leu Gly Val Tyr Tyr Cys Phe Gln
 90                  95                 100                 105 ggt tca cat gtt ccg tgg acg ttc ggt gga ggc acc aag ctg gaa atc        390
Gly Ser His Val Pro Trp Thr Phe Gly Gly Gly Thr Lys Leu Glu Ile
                110                 115                 120 aaa cgg gctgatgctg caccaactgt atccatcttc ccaccatcca gt                 438
Lys

<210> SEQ ID NO 49
<211> LENGTH: 122
<212> TYPE: PRT
<213> ORGANISM: Mus musculus

<400> SEQUENCE: 49

Leu Met Phe Trp Ile Pro Ala Ser Arg Ser Asp Val Leu Met Thr Gln
 1               5                  10                  15

Ile Pro Leu Ser Leu Pro Val Ser Leu Gly Asp Gln Ala Ser Ile Ser
             20                  25                  30
```

```
Cys Arg Ser Ser Gln Ser Ile Val His Ser Asn Gly Asn Thr Tyr Leu
            35                  40                  45
Gln Trp Tyr Leu Gln Lys Pro Gly Gln Ser Pro Lys Leu Leu Ile Tyr
        50                  55                  60
Lys Val Ser Asn Arg Leu Tyr Gly Val Pro Asp Arg Phe Ser Gly Ser
 65                  70                  75                  80
Gly Ser Gly Thr Asp Phe Thr Leu Lys Ile Ser Ser Val Glu Ala Glu
                85                  90                  95
Asp Leu Gly Val Tyr Tyr Cys Phe Gln Gly Ser His Val Pro Trp Thr
            100                 105                 110
Phe Gly Gly Gly Thr Lys Leu Glu Ile Lys
        115                 120

<210> SEQ ID NO 50
<211> LENGTH: 438
<212> TYPE: DNA
<213> ORGANISM: Mus musculus

<400> SEQUENCE: 50
tacttcaacg  gacaatccga  caaccacgac  tacaagacct  aaggacgaag  gtcttcacta      60
caaaactact  gggtttaagg  tgagagggac  ggacagtcag  aacctctagt  tcggaggtag     120
agaacgtcta  gatcagtctc  gtaacatgta  tcattacctt  tgtggataaa  tgttaccatg     180
gacgtctttg  gtccagtcag  aggtttcgag  gactagatgt  ttcaaaggtt  ggctgaaata     240
ccccagggtc  tgtccaagtc  accgtcacct  agtccctgtc  taaagtgtga  gttctagtcg     300
tcgcacctcc  gactcctaga  ccctcaaata  atgacgaaag  ttccaagtgt  acaaggcacc     360
tgcaagccac  ctccgtggtt  cgacctttag  tttgcccgac  tacgacgtgg  ttgacatagg     420
tagaagggtg  gtaggtca                                                      438

<210> SEQ ID NO 51
<211> LENGTH: 438
<212> TYPE: DNA
<213> ORGANISM: Mus musculus
<220> FEATURE:
<221> NAME/KEY: CDS
<222> LOCATION: (25)..(405)

<400> SEQUENCE: 51
atgatggtgt taagtcttct gtac ctc ttg aca gcc att cct ggt atc ctg         51
                      Leu Leu Thr Ala Ile Pro Gly Ile Leu
                        1               5 tct gat gta cag ctt cag gag tca gga cct ggc ctc gtg aaa cct tct        99
Ser Asp Val Gln Leu Gln Glu Ser Gly Pro Gly Leu Val Lys Pro Ser
 10                  15                  20                  25 cag tct ctg tct ctc acc tgc tct gtc acc ggc tac tcc atc acc ggt       147
Gln Ser Leu Ser Leu Thr Cys Ser Val Thr Gly Tyr Ser Ile Thr Gly
                 30                  35                  40 ggt tat tta tgg aac tgg atc cgg cag ttt cca gga aac aaa ctg gag       195
Gly Tyr Leu Trp Asn Trp Ile Arg Gln Phe Pro Gly Asn Lys Leu Glu
            45                  50                  55 tgg atg ggc tac ata agc tac gac ggt acc aat aac tac aaa cca tct       243
Trp Met Gly Tyr Ile Ser Tyr Asp Gly Thr Asn Asn Tyr Lys Pro Ser
        60                  65                  70 ctc aaa gat cga atc tcc atc act cgt gac aca tct aag aac cag ttt       291
Leu Lys Asp Arg Ile Ser Ile Thr Arg Asp Thr Ser Lys Asn Gln Phe
 75                  80                  85
```

```
ttc ctg aag ttg aat tct gtg act aat gaa gac aca gct aca tat tac    339
Phe Leu Lys Leu Asn Ser Val Thr Asn Glu Asp Thr Ala Thr Tyr Tyr
 90              95                 100                 105 tgt gca aga tac ggt agg gtc ttc ttt gac tac tgg ggc caa ggc acc    387
Cys Ala Arg Tyr Gly Arg Val Phe Phe Asp Tyr Trp Gly Gln Gly Thr
            110                 115                 120 act ctc aca gtc tcc tca gccaaaacga cacccccatc tgtctatcca ctg       438
Thr Leu Thr Val Ser Ser
            125
```

<210> SEQ ID NO 52
<211> LENGTH: 127
<212> TYPE: PRT
<213> ORGANISM: Mus musculus

<400> SEQUENCE: 52

```
Leu Leu Thr Ala Ile Pro Gly Ile Leu Ser Asp Val Gln Leu Gln Glu
 1               5                  10                  15

Ser Gly Pro Gly Leu Val Lys Pro Ser Gln Ser Leu Ser Leu Thr Cys
             20                  25                  30

Ser Val Thr Gly Tyr Ser Ile Thr Gly Gly Tyr Leu Trp Asn Trp Ile
         35                  40                  45

Arg Gln Phe Pro Gly Asn Lys Leu Glu Trp Met Gly Tyr Ile Ser Tyr
     50                  55                  60

Asp Gly Thr Asn Asn Tyr Lys Pro Ser Leu Lys Asp Arg Ile Ser Ile
 65                  70                  75                  80

Thr Arg Asp Thr Ser Lys Asn Gln Phe Phe Leu Lys Leu Asn Ser Val
                 85                  90                  95

Thr Asn Glu Asp Thr Ala Thr Tyr Tyr Cys Ala Arg Tyr Gly Arg Val
            100                 105                 110

Phe Phe Asp Tyr Trp Gly Gln Gly Thr Thr Leu Thr Val Ser Ser
        115                 120                 125
```

<210> SEQ ID NO 53
<211> LENGTH: 438
<212> TYPE: DNA
<213> ORGANISM: Mus musculus

<400> SEQUENCE: 53

```
tactaccaca attcagaaga catggacaac tgtcggtaag gaccatagga cagactacat    60
gtcgaagtcc tcagtcctgg accggagcac tttggaagag tcagagacag agagtggacg   120
agacagtggc cgatgaggta gtggccacca ataaatacct tgacctaggc cgtcaaaggt   180
cctttgtttg acctcaccta cccgatgtat tcgatgctgc catggttatt gatgtttggt   240
agagagtttc tagcttagag gtagtgagca ctgtgtagat tcttggtcaa aaaggacttc   300
aacttaagac actgattact tctgtgtcga tgtataatga cacgttctat gccatcccag   360
aagaaactga tgaccccggt tccgtggtga gagtgtcaga ggagtcggtt ttgctgtggg   420
ggtagacaga taggtgac                                                  438
```

<210> SEQ ID NO 54
<211> LENGTH: 112
<212> TYPE: PRT
<213> ORGANISM: Mus musculus

<400> SEQUENCE: 54

```
Asp Val Leu Met Thr Gln Ile Pro Leu Ser Leu Pro Val Ser Leu Gly
 1               5                  10                  15
```

```
Asp Gln Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Ser Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 55
<211> LENGTH: 112
<212> TYPE: PRT
<213> ORGANISM: Mus musculus

<400> SEQUENCE: 55

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Asp Ile Lys
            100                 105                 110
```

<210> SEQ ID NO 56
<211> LENGTH: 112
<212> TYPE: PRT
<213> ORGANISM: Mus musculus

<400> SEQUENCE: 56

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110
```

<210> SEQ ID NO 57
<211> LENGTH: 112
<212> TYPE: PRT
<213> ORGANISM: Mus musculus

<400> SEQUENCE: 57

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Thr His Val Pro Tyr Thr Phe Gly Gly Gly Thr Lys Leu Glu Ile Lys
            100                 105                 110

<210> SEQ ID NO 58
<211> LENGTH: 112
<212> TYPE: PRT
<213> ORGANISM: Homo sapiens

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Val Glu Ile Lys
            100                 105                 110

<210> SEQ ID NO 59
<211> LENGTH: 100
<212> TYPE: PRT
<213> ORGANISM: Homo sapiens

<400> SEQUENCE: 59

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

-continued

Ser Arg Val Glu Ala Glu Asp Val Gly Val Tyr Tyr Cys Met Gln Ala
                85                  90                  95

Leu Gln Thr Pro
            100

<210> SEQ ID NO 60
<211> LENGTH: 112
<212> TYPE: PRT
<213> ORGANISM: Homo sapiens
<220> FEATURE:
<221> NAME/KEY: VARIANT
<222> LOCATION: 35, 36, 39, 99
<223> OTHER INFORMATION: Xaa = Any Amino Acid

<400> SEQUENCE: 60

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asp Gly Xaa Xaa Tyr Leu Xaa Trp Tyr Leu Gln Lys Pro Gly Gln Ser
            35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Xaa Pro Arg Thr Phe Gly Gln Gly Thr Lys Val Glu Ile Lys
            100                 105                 110

<210> SEQ ID NO 61
<211> LENGTH: 112
<212> TYPE: PRT
<213> ORGANISM: Homo sapiens

<400> SEQUENCE: 61

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
                20                  25                  30

Asn Gly Asn Thr Tyr Leu Gln Trp Tyr Leu Gln Lys Pro Gly Gln Ser
            35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 62
<211> LENGTH: 433
<212> TYPE: DNA
<213> ORGANISM: Homo sapiens
<220> FEATURE:
<221> NAME/KEY: CDS
<222> LOCATION: (22)..(414)

<400> SEQUENCE: 62

```
gtcagaacgc gtgccgccac c atg aag ttg cct gtt agg ctg ttg gtg ctg        51
                        Met Lys Leu Pro Val Arg Leu Leu Val Leu
                         1               5                  10 atg ttc tgg ttt cct gct tcc agc agt gat gtt gtg atg act cag tct        99
Met Phe Trp Phe Pro Ala Ser Ser Ser Asp Val Val Met Thr Gln Ser
             15                  20                  25 cca ctc tcc ctg ccc gtc acc cct gga gag ccg gcc tcc atc tcc tgc       147
Pro Leu Ser Leu Pro Val Thr Pro Gly Glu Pro Ala Ser Ile Ser Cys
         30                  35                  40 agg tct agt cag agc att gta cat agt aat gga aac acc tat ttg caa       195
Arg Ser Ser Gln Ser Ile Val His Ser Asn Gly Asn Thr Tyr Leu Gln
             45                  50                  55 tgg tac ctg cag aag cca ggg cag tct cca cag ctc ctg atc tat aaa       243
Trp Tyr Leu Gln Lys Pro Gly Gln Ser Pro Gln Leu Leu Ile Tyr Lys
     60                  65                  70 gtt tct aat cgg ctt tat ggg gtc cct gac agg ttc agt ggc agt gga       291
Val Ser Asn Arg Leu Tyr Gly Val Pro Asp Arg Phe Ser Gly Ser Gly
 75                  80                  85                  90 tca ggc aca gat ttt aca ctg aaa atc agc aga gtg gag gct gag gat       339
Ser Gly Thr Asp Phe Thr Leu Lys Ile Ser Arg Val Glu Ala Glu Asp
                 95                 100                 105 gtt ggg gtt tat tac tgc ttt caa ggt tca cat gtt ccg tgg acg ttc       387
Val Gly Val Tyr Tyr Cys Phe Gln Gly Ser His Val Pro Trp Thr Phe
             110                 115                 120 ggc caa ggg acc aag gtg gaa atc aaa cgt gagtggatcc tctgcg             433
Gly Gln Gly Thr Lys Val Glu Ile Lys
         125                 130
```

<210> SEQ ID NO 63
<211> LENGTH: 131
<212> TYPE: PRT
<213> ORGANISM: Homo sapiens

<400> SEQUENCE: 63

```
Met Lys Leu Pro Val Arg Leu Leu Val Leu Met Phe Trp Phe Pro Ala
 1               5                  10                  15

Ser Ser Ser Asp Val Val Met Thr Gln Ser Pro Leu Ser Leu Pro Val
             20                  25                  30

Thr Pro Gly Glu Pro Ala Ser Ile Ser Cys Arg Ser Ser Gln Ser Ile
         35                  40                  45

Val His Ser Asn Gly Asn Thr Tyr Leu Gln Trp Tyr Leu Gln Lys Pro
     50                  55                  60

Gly Gln Ser Pro Gln Leu Leu Ile Tyr Lys Val Ser Asn Arg Leu Tyr
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Val Gly Val Tyr Tyr Cys
             100                 105                 110

Phe Gln Gly Ser His Val Pro Trp Thr Phe Gly Gln Gly Thr Lys Val
         115                 120                 125

Glu Ile Lys
     130
```

<210> SEQ ID NO 64
<211> LENGTH: 433
<212> TYPE: DNA
<213> ORGANISM: Homo sapiens

```
<400> SEQUENCE: 64
cagtcttgcg cacggcggtg gtacttcaac ggacaatccg acaaccacga ctacaagacc      60
aaaggacgaa ggtcgtcact acaacactac tgagtcagag gtgagaggga cgggcagtgg     120
ggacctctcg gccggaggta gaggacgtcc agatcagtct cgtaacatgt atcattacct     180
ttgtggataa acgttaccat ggacgtcttc ggtcccgtca gaggtgtcga ggactagata     240
tttcaaagat tagccgaaat accccaggga ctgtccaagt caccgtcacc tagtccgtgt     300
ctaaaatgtg acttttagtc gtctcacctc cgactcctac aaccccaaat aatgacgaaa     360
gttccaagtg tacaaggcac ctgcaagccg gttccctggt tccaccttta gtttgcactc     420
acctaggaga cgc                                                         433

<210> SEQ ID NO 65
<211> LENGTH: 112
<212> TYPE: PRT
<213> ORGANISM: Homo sapiens

<400> SEQUENCE: 65

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Ile Val His Ser
            20                  25                  30

Asn Gly Asn Thr Tyr Leu Gln Trp Tyr Leu Gln Lys Pro Gly Gln Ser
        35                  40                  45

Pro Gln Leu Leu Ile Tyr Lys Val Ser Asn Arg Leu Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Val Glu Ile Lys
            100                 105                 110

<210> SEQ ID NO 66
<211> LENGTH: 433
<212> TYPE: DNA
<213> ORGANISM: Homo sapiens
<220> FEATURE:
<221> NAME/KEY: CDS
<222> LOCATION: (22)..(414)

<400> SEQUENCE: 66
gtcagaacgc gtgccgccac c atg aag ttg cct gtt agg ctg ttg gtg ctg        51
                         Met Lys Leu Pro Val Arg Leu Leu Val Leu
                          1               5                  10 atg ttc tgg ttt cct gct tcc agc agt gat att gtg atg act cag tct        99
Met Phe Trp Phe Pro Ala Ser Ser Ser Asp Ile Val Met Thr Gln Ser
                15                  20                  25 cca ctc tcc ctg ccc gtc acc cct gga gag ccg gcc tcc atc tcc tgc       147
Pro Leu Ser Leu Pro Val Thr Pro Gly Glu Pro Ala Ser Ile Ser Cys
            30                  35                  40 agg tct agt cag agc att gta cat agt aat gga aac acc tat ttg caa       195
Arg Ser Ser Gln Ser Ile Val His Ser Asn Gly Asn Thr Tyr Leu Gln
        45                  50                  55 tgg tac ctg cag aag cca ggg cag tct cca cag ctc ctg atc tat aaa       243
Trp Tyr Leu Gln Lys Pro Gly Gln Ser Pro Gln Leu Leu Ile Tyr Lys
    60                  65                  70
```

-continued

```
gtt tct aat cgg ctt tat ggg gtc cct gac agg ttc agt ggc agt gga    291
Val Ser Asn Arg Leu Tyr Gly Val Pro Asp Arg Phe Ser Gly Ser Gly
 75                  80                  85                  90 tca ggc aca gat ttt aca ctg aaa atc agc aga gtg gag gct gag gat    339
Ser Gly Thr Asp Phe Thr Leu Lys Ile Ser Arg Val Glu Ala Glu Asp
                 95                 100                 105 gtt ggg gtt tat tac tgc ttt caa ggt tca cat gtt ccg tgg acg ttc    387
Val Gly Val Tyr Tyr Cys Phe Gln Gly Ser His Val Pro Trp Thr Phe
            110                 115                 120 ggc caa ggg acc aag gtg gaa atc aaa cgt gagtggatcc tctgcg          433
Gly Gln Gly Thr Lys Val Glu Ile Lys
        125                 130
```

<210> SEQ ID NO 67
<211> LENGTH: 131
<212> TYPE: PRT
<213> ORGANISM: Homo sapiens

<400> SEQUENCE: 67

```
Met Lys Leu Pro Val Arg Leu Leu Val Leu Met Phe Trp Phe Pro Ala
 1               5                  10                  15

Ser Ser Ser Asp Ile Val Met Thr Gln Ser Pro Leu Ser Leu Pro Val
            20                  25                  30

Thr Pro Gly Glu Pro Ala Ser Ile Ser Cys Arg Ser Ser Gln Ser Ile
        35                  40                  45

Val His Ser Asn Gly Asn Thr Tyr Leu Gln Trp Tyr Leu Gln Lys Pro
     50                  55                  60

Gly Gln Ser Pro Gln Leu Leu Ile Tyr Lys Val Ser Asn Arg Leu Tyr
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Val Gly Val Tyr Tyr Cys
            100                 105                 110

Phe Gln Gly Ser His Val Pro Trp Thr Phe Gly Gln Gly Thr Lys Val
        115                 120                 125

Glu Ile Lys
    130
```

<210> SEQ ID NO 68
<211> LENGTH: 433
<212> TYPE: DNA
<213> ORGANISM: Homo sapiens

<400> SEQUENCE: 68

```
cagtcttgcg cacggcggtg gtacttcaac ggacaatccg acaaccacga ctacaagacc     60
aaaggacgaa ggtcgtcact acaacactac tgagtcagag gtgagaggga cgggcagtgg    120
ggacctctcg gccggaggta gaggacgtcc agatcagtct cgtaacatgt atcattacct    180
ttgtggataa acgttaccat ggacgtcttc ggtcccgtca gaggtgtcga ggactagata    240
tttcaaagat tagccgaaat accccaggga ctgtccaagt caccgtcacc tagtccgtgt    300
ctaaaatgtg acttttagtc gtctcacctc cgactcctac aacccaaat aatgacgaaa     360 gttccaagtg tacaaggcac ctgcaagccg gttccctggt tccacctta gtttgcactc    420 acctaggaga cgc                                                       433
```

```
<210> SEQ ID NO 69
<211> LENGTH: 117
<212> TYPE: PRT
<213> ORGANISM: Mus musculus

<400> SEQUENCE: 69

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Gly Gly
            20                  25                  30

Tyr Leu Trp Asn Trp Ile Arg Gln Phe Pro Gly Asn Lys Leu Glu Trp
        35                  40                  45

Met Gly Tyr Ile Ser Tyr Asp Gly Thr Asn Asn Tyr Lys Pro Ser Leu
 50                  55                  60

Lys Asp Arg Ile Ser Ile Thr Arg Asp Thr Ser Lys Asn Gln Phe Phe
 65                  70                  75                  80

Leu Lys Leu Asn Ser Val Thr Asn Glu Asp Thr Ala Thr Tyr Tyr Cys
                 85                  90                  95

Ala Arg Tyr Gly Arg Val Phe Phe Asp Tyr Trp Gly Gln Gly Thr Thr
            100                 105                 110

Leu Thr Val Ser Ser
        115

<210> SEQ ID NO 70
<211> LENGTH: 118
<212> TYPE: PRT
<213> ORGANISM: Mus musculus

<400> SEQUENCE: 70

Asp Val Gln Leu Gln Glu Ser Gly Pro Gly Leu Val Lys Pro Ser Gln
 1               5                  10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Asn Tyr Asp Gly Asn Asn Tyr Asn Pro Ser Leu
 50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Arg Glu Gly Tyr Gly Tyr Phe Phe Asp Tyr Trp Gly Gln Gly Thr
            100                 105                 110

Thr Leu Thr Val Ser Ser
        115

<210> SEQ ID NO 71
<211> LENGTH: 118
<212> TYPE: PRT
<213> ORGANISM: Mus musculus

<400> SEQUENCE: 71

Glu Val Gln Leu Gln Glu Ser Gly Pro Ser Leu Val Lys Pro Ser Gln
 1               5                  10                  15

Thr Leu Ser Leu Thr Cys Ser Val Thr Gly Asp Ser Ile Thr Ser Gly
            20                  25                  30

Tyr Trp Asn Asn Trp Ile Arg Gln Phe Pro Gly Asn Lys Leu Glu Trp
        35                  40                  45
```

```
Met Gly Tyr Ile Ser Tyr Ser Gly Ser Thr Tyr Tyr Asn Pro Ser Leu
         50                  55                  60

Lys Ser Arg Ile Ser Ile Thr Arg Asp Thr Ser Lys Asn Gln Tyr Phe
 65                  70                  75                  80

Leu Gln Leu Asn Ser Val Thr Thr Glu Asp Thr Ala Thr Tyr Tyr Cys
                 85                  90                  95

Ala Arg Gly Gly Tyr Gly Tyr Gly Phe Asp Tyr Trp Gly Gln Gly Thr
            100                 105                 110

Thr Val Thr Val Ser Ser
            115

<210> SEQ ID NO 72
<211> LENGTH: 117
<212> TYPE: PRT
<213> ORGANISM: Homo sapiens
<220> FEATURE:
<221> NAME/KEY: VARIANT
<222> LOCATION: 59
<223> OTHER INFORMATION: Xaa = Any Amino Acid

<400> SEQUENCE: 72

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Val Ser Ser Tyr
                 20                  25                  30

Trp Ser Trp Asn Trp Ile Arg Gln Pro Pro Gly Lys Gly Leu Glu Trp
             35                  40                  45

Ile Gly Arg Ile Tyr Tyr Ser Gly Ser Thr Xaa Tyr Asn Pro Ser Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Glu Leu Pro Gly Gly Tyr Asp Val Trp Gly Gln Gly Thr Leu
            100                 105                 110

Val Thr Val Ser Ser
            115

<210> SEQ ID NO 73
<211> LENGTH: 123
<212> TYPE: PRT
<213> ORGANISM: Homo sapiens

<400> SEQUENCE: 73

Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Ser Ser Gly
                 20                  25                  30

Tyr Tyr Trp Ser Trp Ile Arg Gln Pro Pro Gly Lys Gly Leu Glu Trp
             35                  40                  45

Ile Gly Ser Met Phe His Ser Gly Ser Tyr Tyr Asn Pro Ser Leu
         50                  55                  60

Lys Ser Arg Val Thr Ile Ser Val Asp Thr Ser Lys Asn Gln Phe Ser
 65                  70                  75                  80

Leu Gln Leu Arg Ser Val Thr Ala Ala Asp Thr Ala Val Tyr Tyr Cys
                 85                  90                  95
```

```
Ala Arg Gly Arg Tyr Cys Ser Ser Thr Ser Cys Asn Trp Phe Asp Pro
            100                 105                 110

Trp Gly Gln Gly Thr Leu Val Thr Val Ser Ser
        115                 120

<210> SEQ ID NO 74
<211> LENGTH: 98
<212> TYPE: PRT
<213> ORGANISM: Homo sapiens

<400> SEQUENCE: 74

Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Ser Ser Gly
             20                  25                  30

Tyr Tyr Trp Ser Trp Ile Arg Gln Pro Pro Gly Lys Gly Leu Glu Trp
         35                  40                  45

Ile Gly Ser Ile Tyr His Ser Gly Ser Thr Tyr Tyr Asn Pro Ser Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg

<210> SEQ ID NO 75
<211> LENGTH: 117
<212> TYPE: PRT
<213> ORGANISM: Homo sapiens

<400> SEQUENCE: 75

Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Thr Gly Gly
             20                  25                  30

Tyr Leu Trp Asn Trp Ile Arg Gln Pro Pro Gly Lys Gly Leu Glu Trp
         35                  40                  45

Met Gly Tyr Ile Ser Tyr Asp Gly Thr Asn Asn Tyr Lys Pro Ser Leu
     50                  55                  60

Lys Asp Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
            100                 105                 110

Val Thr Val Ser Ser
        115

<210> SEQ ID NO 76
<211> LENGTH: 445
<212> TYPE: DNA
<213> ORGANISM: Homo sapiens
<220> FEATURE:
<221> NAME/KEY: CDS
<222> LOCATION: (22)...(426)
```

```
<400> SEQUENCE: 76
gtcagaacgc gtgccgccac c atg aaa gtg ttg agt ctg ttg tac ctc ttg         51
                        Met Lys Val Leu Ser Leu Leu Tyr Leu Leu
                         1               5                  10 aca gcc att cct ggt atc ctg tct cag gtg cag ctt cag gag tcg ggc         99
Thr Ala Ile Pro Gly Ile Leu Ser Gln Val Gln Leu Gln Glu Ser Gly
             15                  20                  25 cca gga ctg gtg aag cct tcg gag acc ctg tcc ctc acc tgc act gtc        147
Pro Gly Leu Val Lys Pro Ser Glu Thr Leu Ser Leu Thr Cys Thr Val
         30                  35                  40 tct ggt tac tcc atc acc ggt ggt tat tta tgg aac tgg ata cgg cag        195
Ser Gly Tyr Ser Ile Thr Gly Gly Tyr Leu Trp Asn Trp Ile Arg Gln
     45                  50                  55 ccc cca ggg aag gga ctg gag tgg atg ggg tat atc agc tac gac ggt        243
Pro Pro Gly Lys Gly Leu Glu Trp Met Gly Tyr Ile Ser Tyr Asp Gly
 60                  65                  70 acc aat aac tac aaa ccc tcc ctc aag gat cga atc acc ata tca cgt        291
Thr Asn Asn Tyr Lys Pro Ser Leu Lys Asp Arg Ile Thr Ile Ser Arg
 75                  80                  85                  90 gac acg tcc aag aac cag ttc tcc ctg aag ctg agc tct gtg acc gct        339
Asp Thr Ser Lys Asn Gln Phe Ser Leu Lys Leu Ser Ser Val Thr Ala
                 95                 100                 105 gcg gac act gca gtg tat tac tgt gcg aga tac ggt agg gtc ttc ttt        387
Ala Asp Thr Ala Val Tyr Tyr Cys Ala Arg Tyr Gly Arg Val Phe Phe
             110                 115                 120 gac tac tgg ggc cag gga acc ctg gtc acc gtc tcc tca ggtgagtgga        436
Asp Tyr Trp Gly Gln Gly Thr Leu Val Thr Val Ser Ser
         125                 130                 135 tcctctgcg                                                               445

<210> SEQ ID NO 77
<211> LENGTH: 135
<212> TYPE: PRT
<213> ORGANISM: Homo sapiens

<400> SEQUENCE: 77

Met Lys Val Leu Ser Leu Leu Tyr Leu Leu Thr Ala Ile Pro Gly Ile
 1               5                  10                  15

Leu Ser Gln Val Gln Leu Gln Glu Ser Gly Pro Gly Leu Val Lys Pro
             20                  25                  30

Ser Glu Thr Leu Ser Leu Thr Cys Thr Val Ser Gly Tyr Ser Ile Thr
         35                  40                  45

Gly Gly Tyr Leu Trp Asn Trp Ile Arg Gln Pro Pro Gly Lys Gly Leu
     50                  55                  60

Glu Trp Met Gly Tyr Ile Ser Tyr Asp Gly Thr Asn Asn Tyr Lys Pro
 65                  70                  75                  80

Ser Leu Lys Asp Arg Ile Thr Ile Ser Arg Asp Thr Ser Lys Asn Gln
                 85                  90                  95

Phe Ser Leu Lys Leu Ser Ser Val Thr Ala Ala Asp Thr Ala Val Tyr
             100                 105                 110

Tyr Cys Ala Arg Tyr Gly Arg Val Phe Phe Asp Tyr Trp Gly Gln Gly
         115                 120                 125

Thr Leu Val Thr Val Ser Ser
     130                 135
```

<210> SEQ ID NO 78
<211> LENGTH: 445
<212> TYPE: DNA
<213> ORGANISM: Homo sapiens

<400> SEQUENCE: 78

```
cagtcttgcg cacggcggtg gtactttcac aactcagaca acatggagaa ctgtcggtaa      60
ggaccatagg acagagtcca cgtcgaagtc ctcagcccgg gtcctgacca cttcggaagc     120
ctctgggaca gggagtggac gtgacagaga ccaatgaggt agtggccacc aataaatacc     180
ttgacctatg ccgtcggggg tcccttccct gacctcacct accccatata gtcgatgctg     240
ccatggttat tgatgtttgg gagggagttc ctagcttagt ggtatagtgc actgtgcagg     300
ttcttggtca agagggactt cgactcgaga cactggcgac gcctgtgacg tcacataatg     360
acacgctcta tgccatccca aagaaactg atgaccccgg tcccttggga ccagtggcag     420
aggagtccac tcacctagga gacgc                                           445
```

<210> SEQ ID NO 79
<211> LENGTH: 117
<212> TYPE: PRT
<213> ORGANISM: Homo sapiens

<400> SEQUENCE: 79

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Thr Gly Gly
             20                  25                  30

Tyr Leu Trp Asn Trp Ile Arg Gln Pro Pro Gly Lys Gly Leu Glu Trp
         35                  40                  45

Ile Gly Tyr Ile Ser Tyr Asp Gly Thr Asn Asn Tyr Lys Pro Ser Leu
     50                  55                  60

Lys Asp Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
            100                 105                 110

Val Thr Val Ser Ser
        115
```

<210> SEQ ID NO 80
<211> LENGTH: 445
<212> TYPE: DNA
<213> ORGANISM: Homo sapiens
<220> FEATURE:
<221> NAME/KEY: CDS
<222> LOCATION: (22)...(426)

<400> SEQUENCE: 80

```
gtcagaacgc gtgccgccac c atg aaa gtg ttg agt ctg ttg tac ctc ttg        51
                        Met Lys Val Leu Ser Leu Leu Tyr Leu Leu
                          1               5                  10 aca gcc att cct ggt atc ctg tct cag gtg cag ctt cag gag tcg ggc        99
Thr Ala Ile Pro Gly Ile Leu Ser Gln Val Gln Leu Gln Glu Ser Gly
             15                  20                  25 cca gga ctg gtg aag cct tcg gag acc ctg tcc ctc acc tgc act gtc       147
Pro Gly Leu Val Lys Pro Ser Glu Thr Leu Ser Leu Thr Cys Thr Val
         30                  35                  40
```

```
tct ggt tac tcc atc acc ggt ggt tat tta tgg aac tgg ata cgg cag        195
Ser Gly Tyr Ser Ile Thr Gly Gly Tyr Leu Trp Asn Trp Ile Arg Gln
            45                  50                  55 ccc cca ggg aag gga ctg gag tgg atc ggg tat atc agc tac gac ggt        243
Pro Pro Gly Lys Gly Leu Glu Trp Ile Gly Tyr Ile Ser Tyr Asp Gly
    60                  65                  70 acc aat aac tac aaa ccc tcc ctc aag gat cga gtc acc ata tca cgt        291
Thr Asn Asn Tyr Lys Pro Ser Leu Lys Asp Arg Val Thr Ile Ser Arg
75                  80                  85                  90 gac acg tcc aag aac cag ttc tcc ctg aag ctg agc tct gtg acc gct        339
Asp Thr Ser Lys Asn Gln Phe Ser Leu Lys Leu Ser Ser Val Thr Ala
                95                  100                 105 gcg gac act gca gtg tat tac tgt gcg aga tac ggt agg gtc ttc ttt        387
Ala Asp Thr Ala Val Tyr Tyr Cys Ala Arg Tyr Gly Arg Val Phe Phe
            110                 115                 120 gac tac tgg ggc cag gga acc ctg gtc acc gtc tcc tca ggtgagtgga        436
Asp Tyr Trp Gly Gln Gly Thr Leu Val Thr Val Ser Ser
    125                 130                 135 tcctctgcg                                                              445
```

<210> SEQ ID NO 81
<211> LENGTH: 135
<212> TYPE: PRT
<213> ORGANISM: Homo sapiens

<400> SEQUENCE: 81

```
Met Lys Val Leu Ser Leu Leu Tyr Leu Leu Thr Ala Ile Pro Gly Ile
1               5                   10                  15

Leu Ser Gln Val Gln Leu Gln Glu Ser Gly Pro Gly Leu Val Lys Pro
                20                  25                  30

Ser Glu Thr Leu Ser Leu Thr Cys Thr Val Ser Gly Tyr Ser Ile Thr
            35                  40                  45

Gly Gly Tyr Leu Trp Asn Trp Ile Arg Gln Pro Pro Gly Lys Gly Leu
        50                  55                  60

Glu Trp Ile Gly Tyr Ile Ser Tyr Asp Gly Thr Asn Asn Tyr Lys Pro
65                  70                  75                  80

Ser Leu Lys Asp Arg Val Thr Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Tyr Gly Arg Val Phe Phe Asp Tyr Trp Gly Gln Gly
        115                 120                 125

Thr Leu Val Thr Val Ser Ser
    130                 135
```

<210> SEQ ID NO 82
<211> LENGTH: 445
<212> TYPE: DNA
<213> ORGANISM: Homo sapiens

<400> SEQUENCE: 82

```
cagtcttgcg cacggcggtg gtactttcac aactcagaca acatggagaa ctgtcggtaa      60
ggaccatagg acagagtcca cgtcgaagtc ctcagcccgg gtcctgacca cttcggaagc     120
ctctgggaca gggagtggac gtgacagaga ccaatgaggt agtcgccacc aataaatacc     180
ttgacctatg ccgtcggggg tcccttccct gacctcacct agcccatata gtcgatgctg     240
ccatggttat tgatgtttgg gagggagttc ctagctcagt ggtatagtgc actgtgcagg     300
```

```
ttcttggtca agagggactt cgactcgaga cactggcgac gcctgtgacg tcacataatg      360
acacgctcta tgccatccca gaagaaactg atgaccccgg tcccttggga ccagtggcag      420
aggagtccac tcacctagga gacgc                                            445
```

<210> SEQ ID NO 83
<211> LENGTH: 117
<212> TYPE: PRT
<213> ORGANISM: Homo sapiens

<400> SEQUENCE: 83

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Tyr Ser Ile Ser Gly Gly
             20                  25                  30

Tyr Leu Trp Asn Trp Ile Arg Gln Pro Pro Gly Lys Gly Leu Glu Trp
         35                  40                  45

Ile Gly Tyr Ile Ser Tyr Asp Gly Thr Asn Asn Tyr Lys Pro Ser Leu
     50                  55                  60

Lys Asp Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Tyr Gly Arg Val Phe Phe Asp Tyr Trp Gly Gln Gly Thr Leu
            100                 105                 110

Val Thr Val Ser Ser
            115
```

<210> SEQ ID NO 84
<211> LENGTH: 445
<212> TYPE: DNA
<213> ORGANISM: Homo sapiens
<220> FEATURE:
<221> NAME/KEY: CDS
<222> LOCATION: (22)...(426)

<400> SEQUENCE: 84

```
gtcagaacgc gtgccgccac c atg aaa gtg ttg agt ctg ttg tac ctc ttg       51
                        Met Lys Val Leu Ser Leu Leu Tyr Leu Leu
                          1               5                  10 aca gcc att cct ggt atc ctg tct cag gtg cag ctt cag gag tcg ggc       99
Thr Ala Ile Pro Gly Ile Leu Ser Gln Val Gln Leu Gln Glu Ser Gly
             15                  20                  25 cca gga ctg gtg aag cct tcg gag acc ctg tcc ctc acc tgc act gtc     147
Pro Gly Leu Val Lys Pro Ser Glu Thr Leu Ser Leu Thr Cys Thr Val
         30                  35                  40 tct ggt tac tcc atc agc ggt ggt tat tta tgg aac tgg ata cgg cag     195
Ser Gly Tyr Ser Ile Ser Gly Gly Tyr Leu Trp Asn Trp Ile Arg Gln
     45                  50                  55 ccc cca ggg aag gga ctg gag tgg atc ggg tat atc agc tac gac ggt     243
Pro Pro Gly Lys Gly Leu Glu Trp Ile Gly Tyr Ile Ser Tyr Asp Gly
 60                  65                  70 acc aat aac tac aaa ccc tcc ctc aag gat cga gtc acc ata tca gtg     291
Thr Asn Asn Tyr Lys Pro Ser Leu Lys Asp Arg Val Thr Ile Ser Val
 75                  80                  85                  90 gac acg tcc aag aac cag ttc tcc ctg aag ctg agc tct gtg acc gct     339
Asp Thr Ser Lys Asn Gln Phe Ser Leu Lys Leu Ser Ser Val Thr Ala
                 95                 100                 105
```

```
gcg gac act gca gtg tat tac tgt gcg aga tac ggt agg gtc ttc ttt    387
Ala Asp Thr Ala Val Tyr Tyr Cys Ala Arg Tyr Gly Arg Val Phe Phe
            110                 115                 120 gac tac tgg ggc cag gga acc ctg gtc acc gtc tcc tca ggtgagtgga     436
Asp Tyr Trp Gly Gln Gly Thr Leu Val Thr Val Ser Ser
        125                 130                 135 tcctctgcg                                                          445
```

<210> SEQ ID NO 85
<211> LENGTH: 135
<212> TYPE: PRT
<213> ORGANISM: Homo sapiens

<400> SEQUENCE: 85

```
Met Lys Val Leu Ser Leu Leu Tyr Leu Leu Thr Ala Ile Pro Gly Ile
 1               5                  10                  15

Leu Ser Gln Val Gln Leu Gln Glu Ser Gly Pro Gly Leu Val Lys Pro
                20                  25                  30

Ser Glu Thr Leu Ser Leu Thr Cys Thr Val Ser Gly Tyr Ser Ile Ser
            35                  40                  45

Gly Gly Tyr Leu Trp Asn Trp Ile Arg Gln Pro Pro Gly Lys Gly Leu
        50                  55                  60

Glu Trp Ile Gly Tyr Ile Ser Tyr Asp Gly Thr Asn Asn Tyr Lys Pro
65                  70                  75                  80

Ser Leu Lys Asp Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Tyr Gly Arg Val Phe Phe Asp Tyr Trp Gly Gln Gly
        115                 120                 125

Thr Leu Val Thr Val Ser Ser
    130                 135
```

<210> SEQ ID NO 86
<211> LENGTH: 445
<212> TYPE: DNA
<213> ORGANISM: Homo sapiens

<400> SEQUENCE: 86

```
cagtcttgcg cacggcggtg gtactttcac aactcagaca acatggagaa ctgtcggtaa    60
ggaccatagg acagagtcca cgtcgaagtc ctcagcccgg gtcctgacca cttcggaagc   120
ctctgggaca gggagtggac gtgacagaga ccaatgaggt agtcgccacc aataaatacc   180
ttgacctatg ccgtcggggg tcccttccct gacctcacct agcccatata gtcgatgctg   240
ccatggttat tgatgtttgg gagggagttc ctagctcagt ggtatagtca cctgtgcagg   300
ttcttggtca agaggggactt cgactcgaga cactggcgac gcctgtgacg tcacataatg   360
acacgctcta tgccatccca gaagaaactg atgacccccgg tcccttggga ccagtggcag   420
aggagtccac tcacctagga gacgc                                         445
```

<210> SEQ ID NO 87
<211> LENGTH: 18
<212> TYPE: DNA
<213> ORGANISM: Artificial sequence
<220> FEATURE:
<223> OTHER INFORMATION: Description de la Artificial sequence:
      Oligonucleotide

```
<400> SEQUENCE: 87
gtcagaacgc gtgccgcc                                                      18

<210> SEQ ID NO 88
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 88
accatgaagt tgcctgttag gctgttggtg ct                                      32

<210> SEQ ID NO 89
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 89
gatgttctgg tttcctgctt ccagcagtga tg                                      32

<210> SEQ ID NO 90
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 90
ttgtgatgac tcagtctcca ctctccctgc cc                                      32

<210> SEQ ID NO 91
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 91
gtcacccctg gagagccggc ctccatctcc tg                                      32

<210> SEQ ID NO 92
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 92
caggtctagt cagaccatta tacatagtaa tg                                      32

<210> SEQ ID NO 93
<211> LENGTH: 30
<212> TYPE: DNA
<213> ORGANISM: Artificial sequence
<220> FEATURE:
<223> OTHER INFORMATION: Description of artificial sequence:
      Oligonucleotide
```

<400> SEQUENCE: 93
gaaacaccta tttggaatgg tacctgcaga                               30

<210> SEQ ID NO 94
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 94
ggcaacttca tggtggcggc acgcgttctg ac                            32

<210> SEQ ID NO 95
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 95
gaaaccagaa catcagcacc aacagcctaa ca                            32

<210> SEQ ID NO 96
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 96
ctgagtcatc acaacatcac tgctggaagc ag                            32

<210> SEQ ID NO 97
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 97
tctccagggg tgacgggcag ggagagtgga ga                            32

<210> SEQ ID NO 98
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 98
tctgactaga cctgcaggag atggaggccg gc                            32

<210> SEQ ID NO 99
<211> LENGTH: 31
<212> TYPE: DNA
<213> ORGANISM: Artificial sequence
<220> FEATURE:
<223> OTHER INFORMATION: Description of artificial sequence:
      Oligonucleotide

```
<400> SEQUENCE: 99
aaataggtgt tccattact atgtacaatg c                              31

<210> SEQ ID NO 100
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 100
cagggcagtc tccacagctc ctgatctata aa                            32

<210> SEQ ID NO 101
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 101
gtttctaatc ggctttatgg ggtccctgac ag                            32

<210> SEQ ID NO 102
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 102
gttcagtggc agtggatcag gcacagattt ta                            32

<210> SEQ ID NO 103
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 103
cactgaaaat cagcagagtg gaggctgagg at                            32

<210> SEQ ID NO 104
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 104
gttggggttt attactgctt tcaaggttca ca                            32

<210> SEQ ID NO 105
<211> LENGTH: 32
<212> TYPE: DNA
<213> ORGANISM: Artificial sequence
<220> FEATURE:
<223> OTHER INFORMATION: Description of artificial sequence:
      Oligonucleotide
```

```
<400> SEQUENCE: 105
tgttccgtgg acgttcggcc aagggaccaa gg                              32

<210> SEQ ID NO 106
<211> LENGTH: 30
<212> TYPE: DNA
<213> ORGANISM: Artificial sequence
<220> FEATURE:
<223> OTHER INFORMATION: Description of artificial sequence:
      Oligonucleotide

<400> SEQUENCE: 106
tggaaatcaa acgtgagtgg atcctctgcg                                 30

<210> SEQ ID NO 107
<211> LENGTH: 17
<212> TYPE: DNA
<213> ORGANISM: Artificial sequence
<220> FEATURE:
<223> OTHER INFORMATION: Description of artificial sequence:
      Oligonucleotide

<400> SEQUENCE: 107
tctgcaggta ccattgc                                               17

<210> SEQ ID NO 108
<211> LENGTH: 21
<212> TYPE: DNA
<213> ORGANISM: Artificial sequence
<220> FEATURE:
<223> OTHER INFORMATION: Description of artificial sequence:
      Oligonucleotide

<400> SEQUENCE: 108
tgcaatggta cctgcagaag c                                          21

<210> SEQ ID NO 109
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 109
agactgccct ggcttctgca ggtaccattg ca                              32

<210> SEQ ID NO 110
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 110
cgattagaaa ctttatagat caggagctgt gg                              32

<210> SEQ ID NO 111
<211> LENGTH: 32
<212> TYPE: DNA
<213> ORGANISM: Artificial sequence
<220> FEATURE:
<223> OTHER INFORMATION: Description of artificial sequence:
      Oligonucleotide
```

```
<400> SEQUENCE: 111
tgccactgaa cctgtcaggg accccataaa gc                                32

<210> SEQ ID NO 112
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 112
gattttcagt gtaaaatctg tgcctgatcc ac                                32

<210> SEQ ID NO 113
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 113 taaacccaa catcctcagc ctccactctg ct                                 32

<210> SEQ ID NO 114
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 114
tccacggaac atgtgaacct tgaaagcagt aa                                32

<210> SEQ ID NO 115
<211> LENGTH: 31
<212> TYPE: DNA
<213> ORGANISM: Artificial sequence
<220> FEATURE:
<223> OTHER INFORMATION: Description of artificial sequence:
      Oligonucleotide

<400> SEQUENCE: 115
tttgatttcc accttggtcc cttggccgaa c                                 31

<210> SEQ ID NO 116
<211> LENGTH: 19
<212> TYPE: DNA
<213> ORGANISM: Artificial sequence
<220> FEATURE:
<223> OTHER INFORMATION: Description of artificial sequence:
      Oligonucleotide

<400> SEQUENCE: 116
cgcagaggat ccactcacg                                               19

<210> SEQ ID NO 117
<211> LENGTH: 18
<212> TYPE: DNA
<213> ORGANISM: Artificial sequence
<220> FEATURE:
<223> OTHER INFORMATION: Description of artificial sequence:
      Oligonucleotide
```

```
<400> SEQUENCE: 117
gtcagaacgc gtgccgcc                                               18

<210> SEQ ID NO 118
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 118
accatgaaag tgttgagtct gttgtacctc ttga                             34

<210> SEQ ID NO 119
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 119
cagccattcc tggtatcctg tctcaggtgc agct                             34

<210> SEQ ID NO 120
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 120
tcaggagtcg ggcccaggac tggtgaagcc ttcg                             34

<210> SEQ ID NO 121
<211> LENGTH: 33
<212> TYPE: DNA
<213> ORGANISM: Artificial sequence
<220> FEATURE:
<223> OTHER INFORMATION: Description of artificial sequence:
      Oligonucleotide

<400> SEQUENCE: 121
gagaccctgt ccctcacctg cactgtctct ggt                              33

<210> SEQ ID NO 122
<211> LENGTH: 33
<212> TYPE: DNA
<213> ORGANISM: Artificial sequence
<220> FEATURE:
<223> OTHER INFORMATION: Description of artificial sequence:
      Oligonucleotide

<400> SEQUENCE: 122
tactccatca ccggtggtta tttatggaac tgg                              33

<210> SEQ ID NO 123
<211> LENGTH: 33
<212> TYPE: DNA
<213> ORGANISM: Artificial sequence
<220> FEATURE:
<223> OTHER INFORMATION: Description of artificial sequence:
      Oligonucleotide
```

<210> SEQ ID NO 124
<211> LENGTH: 33
<212> TYPE: DNA
<213> ORGANISM: Artificial sequence
<220> FEATURE:
<223> OTHER INFORMATION: Description of artificial sequence:
      Oligonucleotide

<400> SEQUENCE: 124
atggggtata tcagctacga cggtaccaat aac                                   33

<210> SEQ ID NO 125
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 125
tcaacacttt catggtggcg gcacgcgttc tgac                                  34

<210> SEQ ID NO 126
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 126
ataccaggaa tggctgtcaa gaggtacaac agac                                  34

<210> SEQ ID NO 127
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 127
tgggcccgac tcctgaagct gcacctgaga cagg                                  34

<210> SEQ ID NO 128
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 128
tgagggacag ggtctccgaa ggcttcacca gtcc                                  34

<210> SEQ ID NO 129
<211> LENGTH: 34
<212> TYPE: DNA
<213> ORGANISM: Artificial sequence
<220> FEATURE:
<223> OTHER INFORMATION: Description of artificial sequence:
      Oligonucleotide

```
<400> SEQUENCE: 129
ccaccggtga tggagtaacc agagacagtg cagg                    34

<210> SEQ ID NO 130
<211> LENGTH: 34
<212> TYPE: DNA
<213> ORGANISM: Artificial sequence
<220> FEATURE:
<223> OTHER INFORMATION: Description of artificial sequence:
      Oligonucleotide

<400> SEQUENCE: 130
ccctgggggc tgccgtatcc agttccataa ataa                    34

<210> SEQ ID NO 131
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 131
tagctgatat accccatcca ctccagtccc tt                      32

<210> SEQ ID NO 132
<211> LENGTH: 16
<212> TYPE: DNA
<213> ORGANISM: Artificial sequence
<220> FEATURE:
<223> OTHER INFORMATION: Description of artificial sequence:
      Oligonucleotide

<400> SEQUENCE: 132
gttattggta ccgtcg                                        16

<210> SEQ ID NO 133
<211> LENGTH: 21
<212> TYPE: DNA
<213> ORGANISM: Artificial sequence
<220> FEATURE:
<223> OTHER INFORMATION: Description of artificial sequence:
      Oligonucleotide

<400> SEQUENCE: 133
tacgacggta ccaataacta c                                  21

<210> SEQ ID NO 134
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 134
aaaccctccc tcaaggatcg aatcaccata tc                      32

<210> SEQ ID NO 135
<211> LENGTH: 32
<212> TYPE: DNA
<213> ORGANISM: Artificial sequence
<220> FEATURE:
<223> OTHER INFORMATION: Description of artificial sequence:
      Oligonucleotide
```

```
<400> SEQUENCE: 135
acgtgacacg tccaagaacc agttctccct ga                              32

<210> SEQ ID NO 136
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 136
agctgagctc tgtgaccgct gcggacactg ca                              32

<210> SEQ ID NO 137
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 137
gtgtattact gtgcgagata cggtagggtc tt                              32

<210> SEQ ID NO 138
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 138
ctttgactac tggggccagg gaaccctggt ca                              32

<210> SEQ ID NO 139
<211> LENGTH: 30
<212> TYPE: DNA
<213> ORGANISM: Artificial sequence
<220> FEATURE:
<223> OTHER INFORMATION: Description of artificial sequence:
      Oligonucleotide

<400> SEQUENCE: 139
ccgtctcctc aggtgagtgg atcctctgcg                                 30

<210> SEQ ID NO 140
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 140
agggagggtt tgtagttatt ggtaccgtcg ta                              32

<210> SEQ ID NO 141
<211> LENGTH: 32
<212> TYPE: DNA
<213> ORGANISM: Artificial sequence
<220> FEATURE:
<223> OTHER INFORMATION: Description of artificial sequence:
      Oligonucleotide
```

<400> SEQUENCE: 141
acgtgtcacg tgatatggtg attcgatcct tg                32

<210> SEQ ID NO 142
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 142
agagctcagc ttcagggaga actggttctt gg                32

<210> SEQ ID NO 143
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 143
cagtaataca ctgcagtgtc cgcagcggtc ac                32

<210> SEQ ID NO 144
<211> LENGTH: 32
<212> TYPE: DNA
<213> ORGANISM: Artificial sequence
<220> FEATURE:
<223> OTHER INFORMATION: Description of artificial sequence:
      Oligonucleotide

<400> SEQUENCE: 144
agtagtcaaa gaagaccta ccgtatctcg ca                 32

<210> SEQ ID NO 145
<211> LENGTH: 33
<212> TYPE: DNA
<213> ORGANISM: Artificial sequence
<220> FEATURE:
<223> OTHER INFORMATION: Description of artificial sequence:
      Oligonucleotide

<400> SEQUENCE: 145
ctgaggagac ggtgaccagg gttccctggc ccc                33

<210> SEQ ID NO 146
<211> LENGTH: 18
<212> TYPE: DNA
<213> ORGANISM: Artificial sequence
<220> FEATURE:
<223> OTHER INFORMATION: Description of artificial sequence:
      Oligonucleotide

<400> SEQUENCE: 146
cgcagaggat ccactcac                                18

<210> SEQ ID NO 147
<211> LENGTH: 31
<212> TYPE: DNA
<213> ORGANISM: Homo sapiens

```
<400> SEQUENCE: 147
ctggttactc catcagcggt ggttatttat g                              31

<210> SEQ ID NO 148
<211> LENGTH: 31
<212> TYPE: DNA
<213> ORGANISM: Homo sapiens

<400> SEQUENCE: 148
cataaataac caccgctgat ggagtaacca g                              31

<210> SEQ ID NO 149
<211> LENGTH: 31
<212> TYPE: DNA
<213> ORGANISM: Homo sapiens

<400> SEQUENCE: 149
gggactggag tggatcgggt atatcagcta c                              31

<210> SEQ ID NO 150
<211> LENGTH: 31
<212> TYPE: DNA
<213> ORGANISM: Homo sapiens

<400> SEQUENCE: 150
gtagctgata tacccgatcc actccagtcc c                              31

<210> SEQ ID NO 151
<211> LENGTH: 31
<212> TYPE: DNA
<213> ORGANISM: Homo sapiens

<400> SEQUENCE: 151
tccctcaagg atcgagtcac catatcacgt g                              31

<210> SEQ ID NO 152
<211> LENGTH: 31
<212> TYPE: DNA
<213> ORGANISM: Homo sapiens

<400> SEQUENCE: 152
cacgtgatat ggtgactcga tccttgaggg a                              31

<210> SEQ ID NO 153
<211> LENGTH: 39
<212> TYPE: DNA
<213> ORGANISM: Homo sapiens

<400> SEQUENCE: 153
gatcgagtca ccatatcagt ggacacgtcc aagaaccag                      39

<210> SEQ ID NO 154
<211> LENGTH: 39
<212> TYPE: DNA
<213> ORGANISM: Homo sapiens

<400> SEQUENCE: 154
ctggttcttg gacgtgtcca ctgatatggt gactcgatc                      39

<210> SEQ ID NO 155
<211> LENGTH: 31
<212> TYPE: DNA
<213> ORGANISM: Homo sapiens
```

```
-continued

<400> SEQUENCE: 155
gcttccagca gtgatattgt gatgactcag t                                31

<210> SEQ ID NO 156
<211> LENGTH: 31
<212> TYPE: DNA
<213> ORGANISM: Homo sapiens

<400> SEQUENCE: 156
actgagtcat cacaatatca ctgctggaag c                                31
```

The invention claimed is:

1. An isolated antibody, or binding fragment thereof, comprising:
 a light chain complementarity determining region (CDR) comprising SEQ ID Nos. 2, 4 and 6; and
 a heavy chain complementarity determining region (CDR) comprising SEQ ID Nos. 8, 10 and 12, wherein the antibody, or binding fragment thereof, binds to human insulin-like growth factor I receptor (IGF-IR) and inhibits binding of IGF1 and/or IGF2 to said IGF-IR.

2. A composition comprising the antibody or binding fragment thereof of claim 1, in a pharmaceutically acceptable carrier.

3. An isolated antibody or binding fragment thereof of claim 1, wherein said binding fragment is selected from the group consisting of Fv, Fab, F(ab')$_2$, Fab', scFv, scFv-Fc and diabodies.

4. A murine hybridoma, deposited with the CNCM Institut Pasteur, under accession number I-2717.

5. The antibody or binding fragment thereof of claim 1, wherein the antibody comprises an immunoglobulin light chain comprising the amino acid sequence of SEQ ID No. 54 and an immunoglobulin heavy chain comprising the amino acid sequence of SEQ ID No. 69.

6. The antibody or binding fragment thereof of claim 1, wherein said antibody is a chimeric antibody comprising the light chain and heavy chain constant regions derived from an antibody of a species heterologous to the mouse.

7. The antibody or binding fragment thereof of claim 6, wherein the heterologous species is human.

8. The antibody or binding fragment thereof of claim 7, wherein the light chain and heavy chain constant regions derived from a human antibody are respectively the kappa and gamma-1, gamma-2 or gamma-4 region.

9. The antibody or binding fragment thereof of claim 1, wherein said antibody is a humanized antibody and comprises a light chain and/or a heavy chain in which the skeleton segments FR1 to FR4 of said light chain and/or heavy chain are respectively derived from skeleton segments FR1 to FR4 of human antibody light chain and/or heavy chain.

10. The antibody or binding fragment thereof of claim 1, wherein the antibody comprises an immunoglobulin light chain comprising the amino acid sequence of SEQ ID No. 61 or 65, and an immunoglobulin heavy chain comprising the amino acid sequence of SEQ ID No. 75, 79 or 83.

11. The antibody or binding fragment thereof of claim 10, wherein said antibody comprises the immunoglobulin light chain comprising the amino acid sequence of SEQ ID No. 65 and the immunoglobulin heavy chain comprising the amino acid sequence of SEQ ID No. 79 or 83.

12. The antibody or binding fragment thereof of claim 11, wherein said antibody comprises the immunoglobulin light chain comprising the amino acid sequence of SEQ ID No. 65, and the immunoglobulin heavy chain comprising the amino acid sequence of SEQ ID No. 83.

13. A method of producing an antibody, comprising the steps of:
 a) culturing the hybridoma of claim 4 in a medium for production of an antibody; and
 b) recovering said antibody from the culture medium or said cultured hybridoma.

14. A kit for carrying out a method of diagnosis of a cancer induced by an overexpression of the IGF-IR receptor, wherein said kit comprises:
 a) the antibody or the binding fragment thereof, of claim 1;
 b) optionally, reagents for the formation of the medium favorable to the immunological reaction; and
 c) optionally, reagents allowing the demonstration of IGF-IR/antibody complexes produced by the immunological reaction.

15. A kit for carrying out a process for the detection or the quantification of IGF-IR receptor expression in a biological sample, wherein said kit comprises:
 a) the antibody or the binding fragment thereof, of claim 1;
 b) optionally, reagents for the formation of the medium favorable to the immunological reaction; and
 c) optionally, reagents allowing the demonstration of IGF-IR/antibody complexes produced by the immunological reaction.

16. The kit according to claim 15 for the detection or the quantification of an overexpression of the IGF-IR receptor in a biological sample.

17. An in vitro method for diagnosis of cancer induced by an overexpression of the IGF-IR receptor the method comprising: contacting a biological sample obtained from a patient in needed of diagnosis with a conjugated antibody or a binding fragment thereof wherein the antibody or binding fragment thereof of claim 1 is labeled with a detectable label; detecting the binding thereof and quantifying the overexpression of IGF-IR receptor in said sample which is indicative of cancer in said biological sample.

* * * * *